(12) United States Patent
Martin et al.

(10) Patent No.: US 8,133,884 B2
(45) Date of Patent: Mar. 13, 2012

(54) COMPOUNDS FOR THE TREATMENT OF HEPATITIS C

(75) Inventors: Scott W. Martin, Middletown, CT (US);
Carl P. Bergstrom, Madison, CT (US);
Min Ding, Glastonbury, CT (US);
Xiaofan Zheng, Cheshire, CT (US);
Robert G. Gentles, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 332 days.

(21) Appl. No.: 12/434,748

(22) Filed: May 4, 2009

(65) Prior Publication Data
US 2009/0280083 A1 Nov. 12, 2009

Related U.S. Application Data

(60) Provisional application No. 61/050,743, filed on May 6, 2008.

(51) Int. Cl.
*A61P 31/00* (2006.01)
*A61K 31/55* (2006.01)
*C07D 223/14* (2006.01)

(52) U.S. Cl. .................................. 514/214.01; 540/576

(58) Field of Classification Search ............. 514/214.01; 540/576
See application file for complete search history.

(56) References Cited

U.S. PATENT DOCUMENTS

| | | | |
|---|---|---|---|
| 7,153,848 B2 | 12/2006 | Hudyma et al. |
| 7,399,758 B2 | 7/2008 | Meanwell et al. |
| 7,452,876 B2 | 11/2008 | Yeung et al. |
| 7,456,165 B2 | 11/2008 | Bergstrom et al. |
| 7,456,166 B2 | 11/2008 | Bender et al. |
| 7,456,167 B2 | 11/2008 | Bergstrom |
| 7,473,688 B2 | 1/2009 | Bergstrom et al. |
| 7,517,872 B2 | 4/2009 | Nickel et al. |
| 7,521,441 B2 | 4/2009 | Gentles et al. |
| 7,521,442 B2 | 4/2009 | Gentles et al. |
| 7,521,444 B2 | 4/2009 | Bender et al. |
| 7,538,102 B2 | 5/2009 | Yeung et al. |
| 7,538,103 B2 | 5/2009 | Hewawasam et al. |
| 7,541,351 B2 | 6/2009 | Bender et al. |
| 7,541,353 B2 | 6/2009 | Gentles et al. |
| 7,547,690 B2 | 6/2009 | Gentles et al. |
| 2009/0018163 A1 | 1/2009 | Schmitz et al. |
| 2009/0042860 A1 | 2/2009 | Bergstrom et al. |
| 2009/0074715 A1 | 3/2009 | Martin et al. |
| 2009/0130056 A1 | 5/2009 | Bender et al. |
| 2009/0130057 A1 | 5/2009 | Hewawasam et al. |

FOREIGN PATENT DOCUMENTS

| | | |
|---|---|---|
| WO | WO 2005/080399 | 9/2005 |
| WO | WO 2006/046030 | 5/2006 |
| WO | WO 2006/046039 | 5/2006 |
| WO | WO 2007/029029 | 3/2007 |
| WO | WO 2007/092888 | 8/2007 |
| WO | WO 2007/129119 | 11/2007 |
| WO | WO 2009/029384 | 3/2009 |

OTHER PUBLICATIONS

U.S. Appl. No. 60/894,881, filed Mar. 14, 2007, Yeung et al.
U.S. Appl. No. 61/039,961, filed Mar. 27, 2008, Bender et al.
U.S. Appl. No. 61/039,973, filed Mar. 27, 2008, Yang et al.
U.S. Appl. No. 61/039,976, filed Mar. 27, 2008, Yeung et al.
U.S. Appl. No. 12/369,222, filed Feb. 11, 2009, Martin et al.
Ikegashira, K. et al., "Discovery of Conformationally Constrained Tetracyclic Compounds as Potent Hepatitis C Virus NS5B RNA Polymerase Inhibitors", Journal of Medicinal Chemistry, vol. 49, No. 24, pp. 6950-6953 (2006).

*Primary Examiner* — Brenda Coleman
(74) *Attorney, Agent, or Firm* — James Epperson

(57) ABSTRACT

The invention encompasses compounds of formula I as well as compositions and methods of using the compounds. The compounds have activity against hepatitis C virus (HCV) and are useful in treating those infected with HCV.

13 Claims, No Drawings

COMPOUNDS FOR THE TREATMENT OF HEPATITIS C

CROSS-REFERENCE TO RELATED APPLICATIONS

This application claims the benefit of U.S. provisional application Ser. No. 61/050,743 filed May 6, 2008.

BACKGROUND OF THE INVENTION

The disclosure generally relates to the novel compounds of formula I, including their salts, which have activity against hepatitis C virus (HCV) and are useful in treating those infected with HCV. The disclosure also relates to compositions and methods of using these compounds.

Hepatitis C virus (HCV) is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma (Lauer, G. M. et al., N. Engl. J. Med., 345:41-52 (2001)).

HCV is a positive-stranded RNA virus. Based on a comparison of the deduced amino acid sequence and the extensive similarity in the 5'-untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to as HCV polymerase) is a RNA-dependent RNA polymerase that is involved in the replication of HCV. The HCV NS5B protein is described in "Structural Analysis of the Hepatitis C Virus RNA Polymerase in Complex with Ribonucleotides" (Bressanelli, S. et al., J. Virology, 3482-3492 (2002); and Defrancesco et al., Clinics in Liver Disease, 7:211-242 (2003).

Currently, the most effective HCV therapy employs a combination of alpha-interferon and ribavirin, leading to sustained efficacy in 40% of patients (Poynard, T. et al., Lancet, 352:1426-1432 (1998)). Recent clinical results demonstrate that pegylated alpha-interferon is superior to unmodified alpha-interferon as monotherapy (Zeuzem, S. et al., N. Engl. J. Med., 343:1666-1672 (2000)). However, even with experimental therapeutic regimens involving combinations of pegylated alpha-interferon and ribavirin, a substantial fraction of patients do not have a sustained reduction in viral load. Thus, there is a clear and important need to develop effective therapeutics for treatment of HCV infection.

The invention provides technical advantages, for example, the compounds are novel and are effective against hepatitis C. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The invention encompasses compounds of formula I, including pharmaceutically acceptable salts, and compositions and methods of treatment using these compounds.

One aspect of the invention is a compound of formula I

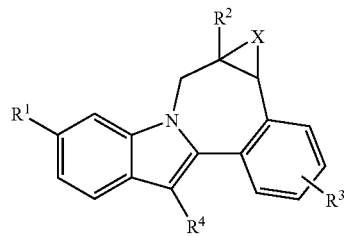

where:
$R^1$ is $CO_2R^5$ or $CONR^6R^7$;
$R^2$ is furanyl, pyrrolyl, thienyl, pyrazolyl, isoxazolyl, isothiazolyl, imidazolyl, oxazolyl, thiazolyl, oxadiazolyl, triazolyl, or tetrazolyl; and $R^2$ is substituted with 1 substituent selected from the group consisting of cycloalkyl, tetrahydrofuranyl, tetrahydropyranyl, phenyl, pyrimidinyl, pyrazinyl, pyridinonyl, benzimidazolyl, piperidinyl substituted with 0-1 alkyl substituents, and pyridinyl substituted with 0-1 alkyl substituents; and $R^2$ is substituted with 1 substituent selected from $CO_2R^5$, $CON(R^{12})_2$, and $COR^{13}$; and $R^2$ is substituted with 0-1 substituents selected from oxo, amino, alkyl, and haloalkyl;
$R^3$ is hydrogen, halo, alkyl, alkenyl, hydroxy, benzyloxy, or alkoxy;
$R^4$ is cycloalkyl;
$R^5$ is hydrogen or alkyl;
$R^6$ is hydrogen, alkyl, alkylSO$_2$, cycloalkylSO$_2$, haloalkylSO$_2$, $(R^9)(R^{10})NSO_2$, or $(R^{11})SO_2$;
$R^7$ is hydrogen or alkyl;
$R^8$ is hydrogen, alkyl, cycloalkyl, (cycloalkyl)alkyl, alkylcarbonyl, cycloalkylcarbonyl, haloalkylcarbonyl, alkoxycarbonyl, alkylSO$_2$, cycloalkylSO$_2$, haloalkylSO$_2$, aminocarbonyl, (alkylamino)carbonyl, (dialkylamino)carbonyl, benzyl, benzyloxycarbonyl, or pyridinyl;
$R^9$ is hydrogen or alkyl;

$R^{10}$ is hydrogen or alkyl;

$R^{11}$ is azetidinyl, pyrrolidinyl, piperidinyl, piperazinyl, morpholinyl, thiomorpholinyl, homopiperidinyl, homopiperazinyl, or homomorpholinyl, and is substituted with 0-1 alkyl substituents;

$R^{12}$ is hydrogen, alkyl, alkoxyalkyl, aminoalkyl, (alkylamino)alkyl, (dialkylamino)alkyl, or $(R^{11})$alkyl;

$R^{13}$ is azetidinyl, pyrrolidinyl, piperidinyl, piperazinyl, morpholinyl, thiomorpholinyl, homopiperidinyl, homopiperazinyl, or homomorpholinyl, and is substituted with 0-3 substituents selected from halo, alkyl, cycloalkyl, alkoxyalkyl, amino, alkylamino, dialkylamino, $R^{11}$, aminoalkyl, (alkylamino)alkyl, (dialkylamino)alkyl, $(R^{11})$alkyl, or $CO_2R^5$;

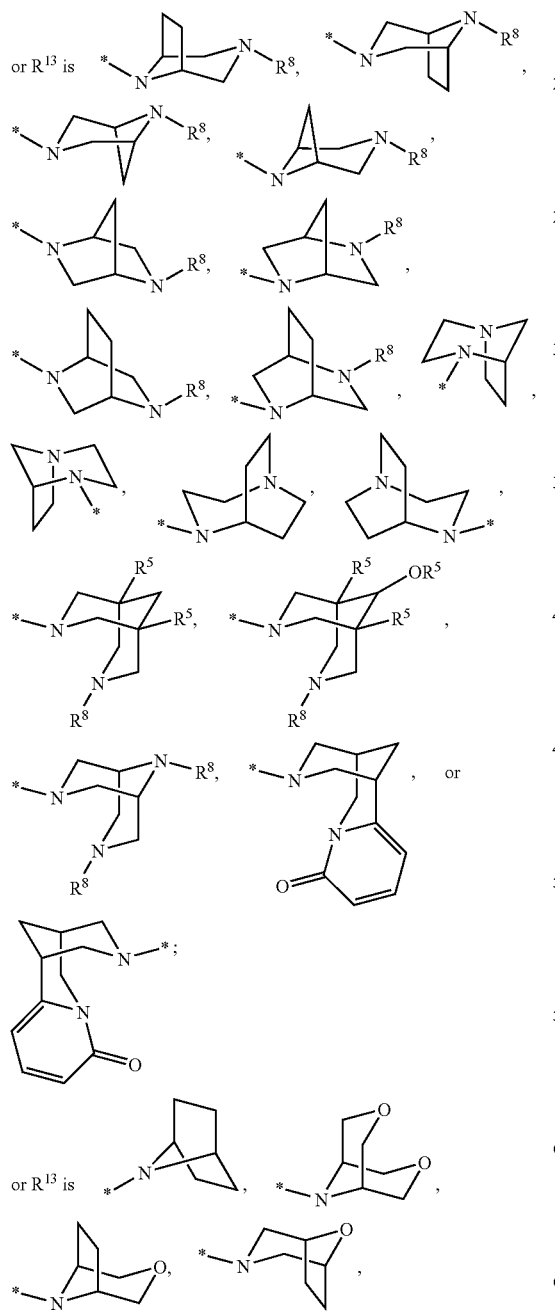

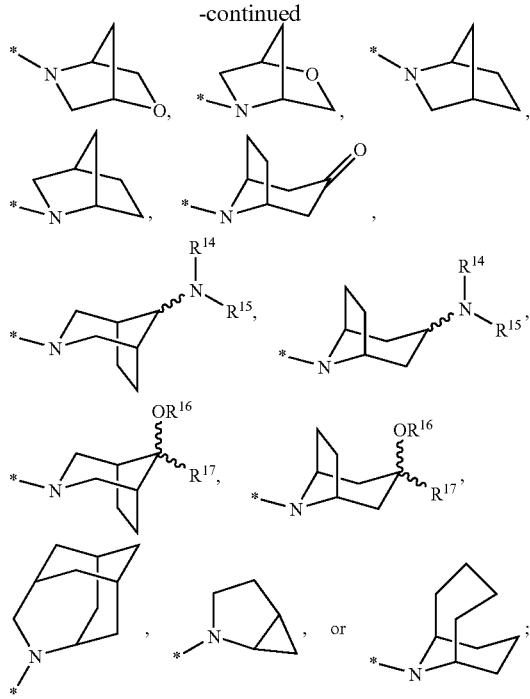

or $R^{13}$ is a [4.3.0] or [3.3.0] bicyclic diamine attached to the carbonyl through one nitrogen, and is substituted with 0-2 $R^8$ substituents;

or $R^{13}$ is 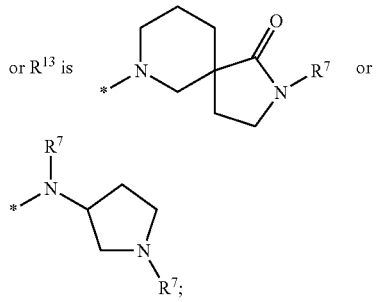

$R^{14}$ is hydrogen, alkyl, cycloalkyl, (cycloalkyl)alkyl, aminoalkyl, (alkylamino)alkyl, (dialkylamino)alkyl, or benzyl;

$R^{15}$ is hydrogen, alkyl, cycloalkyl, (cycloalkyl)alkyl, aminoalkyl, (alkylamino)alkyl, (dialkylamino)alkyl, or benzyl;

or $NR^{14}R^{15}$ taken together is azetidinyl, pyrrolidinyl, piperidinyl, piperazinyl, N-(alkyl)piperazinyl, morpholinyl, thiomorpholinyl, homopiperidinyl, or homomorpholinyl;

$R^{16}$ is hydrogen or alkyl;

$R^{17}$ is hydrogen, alkyl, or cycloalkyl; and

X is methylene, a bond, or absent;

or a pharmaceutically acceptable salt thereof.

Another aspect of the invention is a compound of formula I where:

$R^1$ is $CO_2R^5$ or $CONR^6R^7$;

$R^2$ is pyrazolyl, isoxazolyl, or imidazolyl, and is substituted with 1 substituent selected from the group consisting of cycloalkyl, tetrahydropyranyl, phenyl, pyrimidinyl, pyrazinyl, pyridinonyl, benzimidazolyl, piperidinyl substituted with 1 alkyl substituent, and pyridinyl substituted with 0-1 alkyl substituents; and $R^2$ is substituted with 1 substituent selected from $CO_2R^5$, $CON(R^{12})_2$, and $COR^{13}$; and $R^2$ is substituted with 0-1 alkyl substituents;

R³ is alkoxy;
R⁴ is cycloalkyl;
R⁵ is hydrogen or alkyl;
R⁶ is alkylSO₂, cycloalkylSO₂, or (R⁹)(R¹⁰)NSO₂;
R⁷ is hydrogen;
R⁸ is hydrogen, alkyl, or (cycloalkyl)alkyl;
R¹² is alkyl or alkoxyalkyl;
R¹³ is azetidinyl, piperidinyl, piperazinyl, morpholinyl, homopiperazinyl, or homomorpholinyl, and is substituted with 0-3 substituents selected from halo, alkyl, cycloalkyl, or alkoxyalkyl;

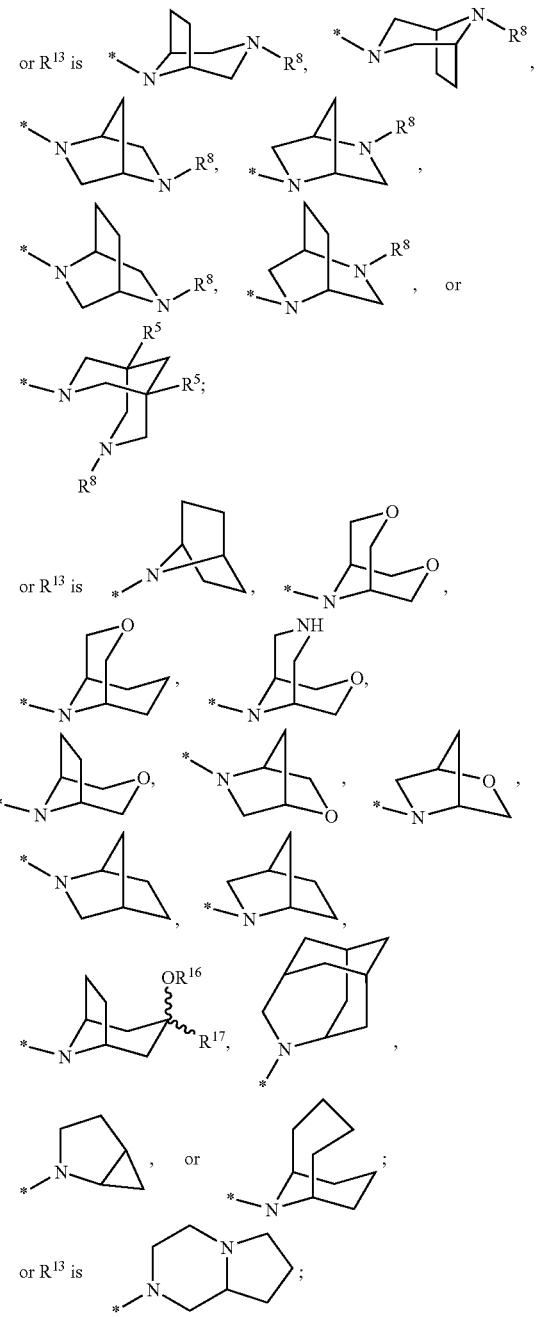

R¹⁶ is hydrogen;
R¹⁷ is alkyl; and
X is a bond;

or a pharmaceutically acceptable salt thereof.

Another aspect of the invention is a compound of formula I where:

R¹ is CO₂R⁵ or CONR⁶R⁷;
R² is pyrazolyl, isoxazolyl, or imidazolyl, and is substituted with 1 substituent selected from cyclopropyl, cyclobutyl, tetrahydropyranyl, phenyl, pyrimidinyl, pyrazinyl, pyridinonyl, benzimidazolyl, N-methylpiperidinyl, pyridinyl or methylpyridinyl; and R² is substituted with 1 substituent selected from CO₂R⁵, CON(R¹²)₂, and COR¹³; and R² is substituted with 0-1 methyl substituent;
R³ is methoxy;
R⁴ is cyclohexyl;
R⁵ is hydrogen or alkyl;
R⁶ is isopropylSO₂, isobutylSO₂, cyclopropylSO₂, or Me₂NSO₂;
R⁷ is hydrogen;
R⁸ is hydrogen, methyl, ethyl, or (cyclopropyl)methyl;
R¹² is isopropyl or methoxyethyl;
R¹³ is difluoroazetidinyl, difluoropiperidinyl, methylpiperazinyl, cyclopentylpiperazinyl, trimethylpiperazinyl, morpholinyl, dimethylmorpholinyl, (methoxymethyl)morpholinyl, N-methylhomopiperazinyl, or homomorpholinyl;

or R¹³ is

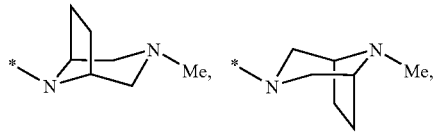

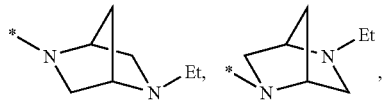

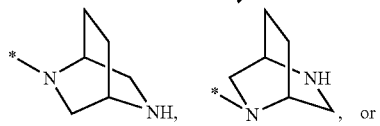

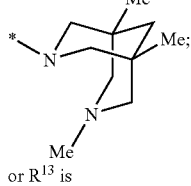

or R¹³ is

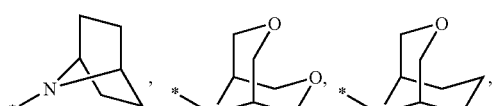

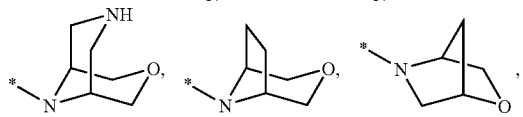

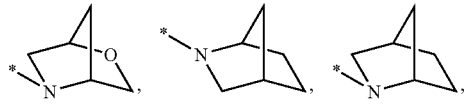

-continued

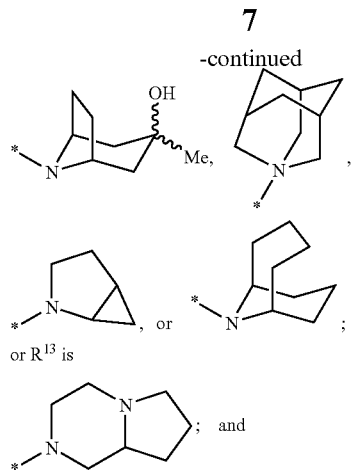

or $R^{13}$ is

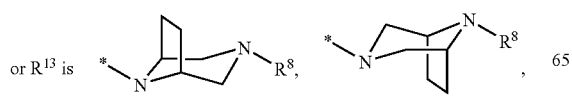
; and

X a bond;
or a pharmaceutically acceptable salt thereof.

Another aspect of the invention is a compound of formula I where:

$R^1$ is $CO_2R^5$ or $CONR^6R^7$;

$R^2$ is furanyl, pyrrolyl, thienyl, pyrazolyl, isoxazolyl, isothiazolyl, imidazolyl, oxazolyl, thiazolyl, oxadiazolyl, triazolyl, or tetrazolyl; and $R^2$ is substituted with 1 substituent selected from cycloalkyl, tetrahydrofuranyl, tetrahydropyranyl, piperidinyl substituted with 0-1 alkyl substituents, and pyridinyl substituted with 0-1 alkyl substituents; and $R^2$ is substituted with 1 substituent selected from $CO_2R^5$, CON$(R^{12})_2$, and $COR^{13}$; and $R^2$ is substituted with 0-1 substituents selected from oxo, amino, alkyl, and haloalkyl;

$R^3$ is hydrogen, halo, alkyl, alkenyl, hydroxy, benzyloxy, or alkoxy;

$R^4$ is cycloalkyl;

$R^5$ is hydrogen or alkyl;

$R^6$ is hydrogen, alkyl, alkylSO$_2$, cycloalkylSO$_2$, haloalkylSO$_2$, $(R^9)(R^{10})NSO_2$, or $(R^{11})SO_2$;

$R^7$ is hydrogen or alkyl;

$R^8$ is hydrogen, alkyl, cycloalkyl, (cycloalkyl)alkyl, alkylcarbonyl, cycloalkylcarbonyl, haloalkylcarbonyl, alkoxycarbonyl, alkylSO$_2$, cycloalkylSO$_2$, haloalkylSO$_2$, aminocarbonyl, (alkylamino)carbonyl, (dialkylamino)carbonyl, benzyl, benzyloxycarbonyl, or pyridinyl;

$R^9$ is hydrogen or alkyl;

$R^{10}$ is hydrogen or alkyl;

$R^{11}$ is azetidinyl, pyrrolidinyl, piperidinyl, piperazinyl, morpholinyl, thiomorpholinyl, homopiperidinyl, homopiperazinyl, or homomorpholinyl, and is substituted with 0-1 alkyl substituents;

$R^{12}$ is hydrogen, alkyl, alkoxyalkyl, aminoalkyl, (alkylamino)alkyl, (dialkylamino)alkyl, or $(R^{11})$alkyl;

$R^{13}$ is azetidinyl, pyrrolidinyl, piperidinyl, piperazinyl, morpholinyl, thiomorpholinyl, homopiperidinyl, homopiperazinyl, or homomorpholinyl, and is substituted with 0-3 substituents selected from alkyl, alkoxyalkyl, amino, alkylamino, dialkylamino, $R^{11}$, aminoalkyl, (alkylamino)alkyl, (dialkylamino)alkyl, $(R^{11})$alkyl, or $CO_2R^5$;

or $R^{13}$ is

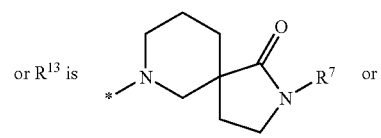

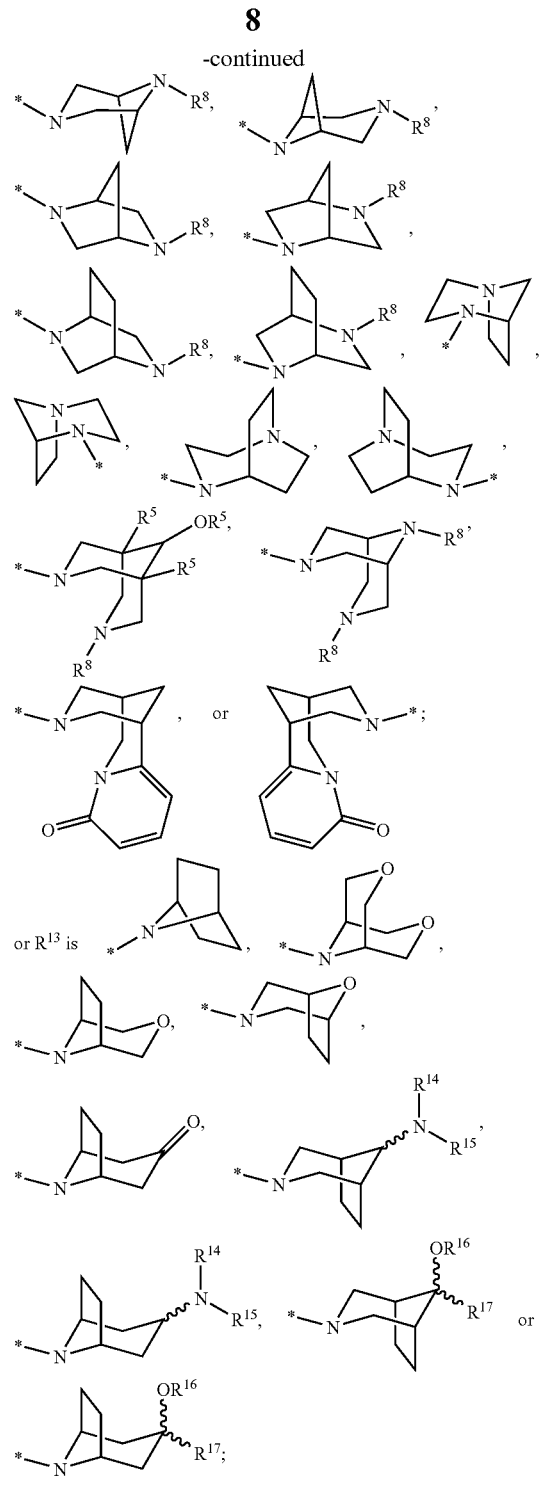

or $R^{13}$ is a [4.3.0] or [3.3.0] bicyclic diamine attached to the carbonyl through one nitrogen, and is substituted with 0-2 $R^8$ substituents;

-continued

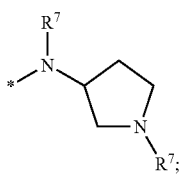

$R^{14}$ is hydrogen, alkyl, cycloalkyl, (cycloalkyl)alkyl, aminoalkyl, (alkylamino)alkyl, (dialkylamino)alkyl, or benzyl;

$R^{15}$ is hydrogen, alkyl, cycloalkyl, (cycloalkyl)alkyl, aminoalkyl, (alkylamino)alkyl, (dialkylamino)alkyl, or benzyl;

or $NR^{14}R^{15}$ taken together is azetidinyl, pyrrolidinyl, piperidinyl, piperazinyl, N-(alkyl)piperazinyl, morpholinyl, thiomorpholinyl, homopiperidinyl, or homomorpholinyl;

$R^{16}$ is hydrogen or alkyl;

$R^{17}$ is hydrogen, alkyl, or cycloalkyl; and

X is methylene, a bond, or absent;

or a pharmaceutically acceptable salt thereof.

Another aspect of the invention is a compound of formula I where $R^1$ is $CONR^6R^7$; $R^6$ is alkyl$SO_2$, cycloalkyl$SO_2$, haloalkyl$SO_2$, $(R^9)_2NSO_2$, or $(R^{10})SO_2$; and $R^7$ is hydrogen.

Another aspect of the invention is a compound of formula I where $R^2$ is pyrazolyl substituted with 1 substituent selected from cyclopropyl, cyclobutyl, N-alkylpiperidin-4-yl, 3-alkylpyridin-4-yl, and tetrahydropyran-4-yl, 1 substituent selected from $CON(R^{12})_2$ and $COR^{13}$, and 0-1 alkyl substituent.

Another aspect of the invention is a compound of formula I where $R^3$ is hydrogen.

Another aspect of the invention is a compound of formula I where $R^3$ is methoxy.

Another aspect of the invention is a compound of formula I where $R^4$ is cyclohexyl.

Another aspect of the invention is a compound of formula I where $R^6$ is $(R^9)(R^{10})NSO_2$ or $(R^{13})SO_2$.

Another aspect of the invention is a compound of formula I where X is methylene

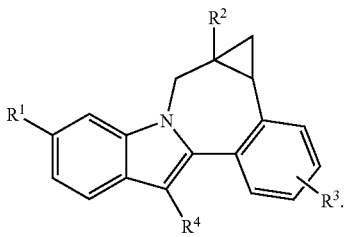

Another aspect of the invention is a compound of formula I where X is a bond

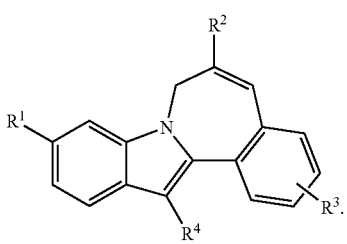

Another aspect of the invention is a compound of formula I where X is absent

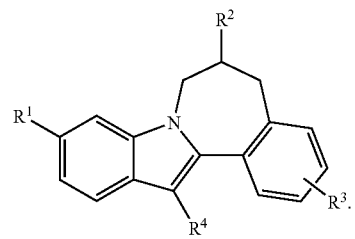

Another aspect of the invention is a compound of formula I according to the following stereochemistry

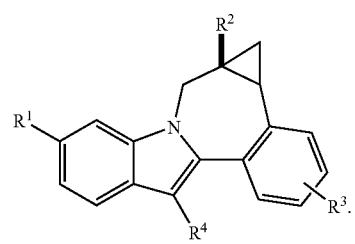

Another aspect of the invention is a compound of formula I according to the following stereochemistry

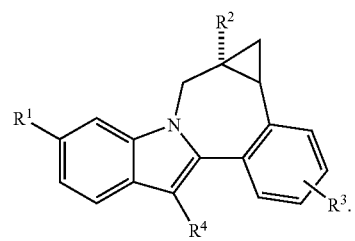

Another aspect of the invention is a compound of formula I according to the following stereochemistry

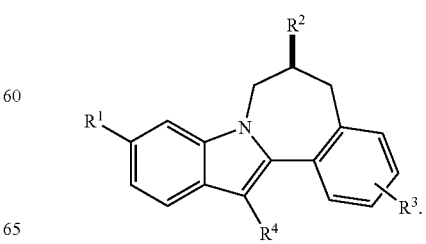

Another aspect of the invention is a compound of formula I according to the following stereochemistry

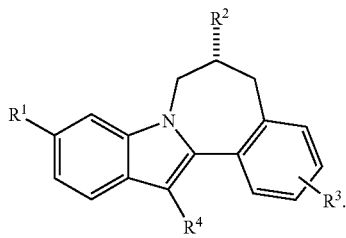

For a compound of formula I, the scope of any instance of a variable substituent, including $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and X, can be used independently with the scope of any other instance of a variable substituent. As such, the invention includes combinations of the different aspects.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons. "Haloalkyl" and "haloalkoxy" include all halogenated isomers from monohalo to perhalo. Terms with a hydrocarbon moiety (e.g., alkoxy) include straight and branched isomers for the hydrocarbon portion. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention possess asymmetric carbon atoms (see, for example, the compound below). The invention includes all stereoisomeric forms, including enantiomers and diastereomers as well as mixtures of stereoisomers such as racemates. Some stereoisomers can be made using methods known in the art. Stereoisomeric mixtures of the compounds and related intermediates can be separated into individual isomers according to methods commonly known in the art

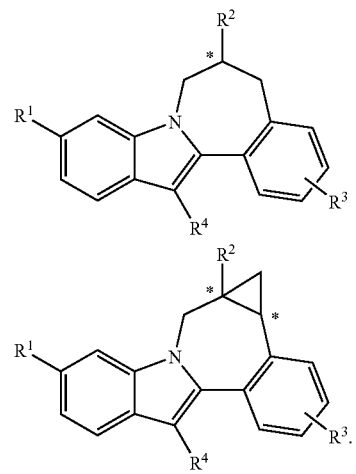

Synthetic Methods

The compounds may be made by methods known in the art including those described below and including variations within the skill of the art. Some reagents and intermediates are known in the art. Other reagents and intermediates can be made by methods known in the art using readily available materials. The variables (e.g., numbered "R" substituents) used to describe the synthesis of the compounds are intended only to illustrate how to make the compounds and are not to be confused with variables used in the claims or in other sections of the specification. The following methods are for illustrative purposes and are not intended to limit the scope of the invention.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC", "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for $CF_3(CF_2)_3SO_2$—; and "TMOF" for trimethylorthoformate.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "¹H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

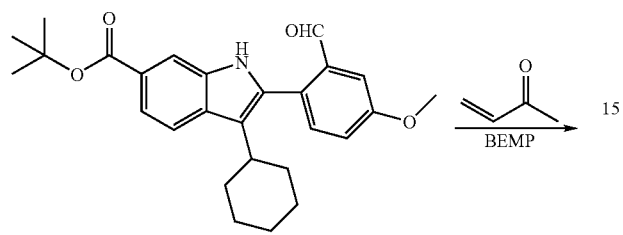

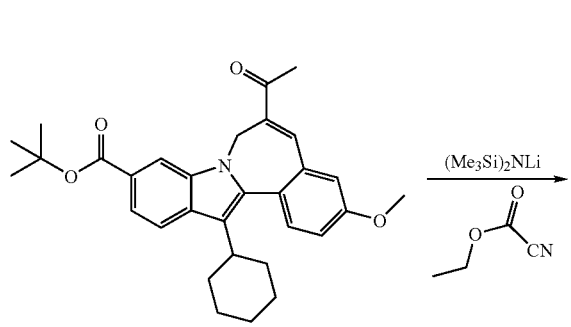

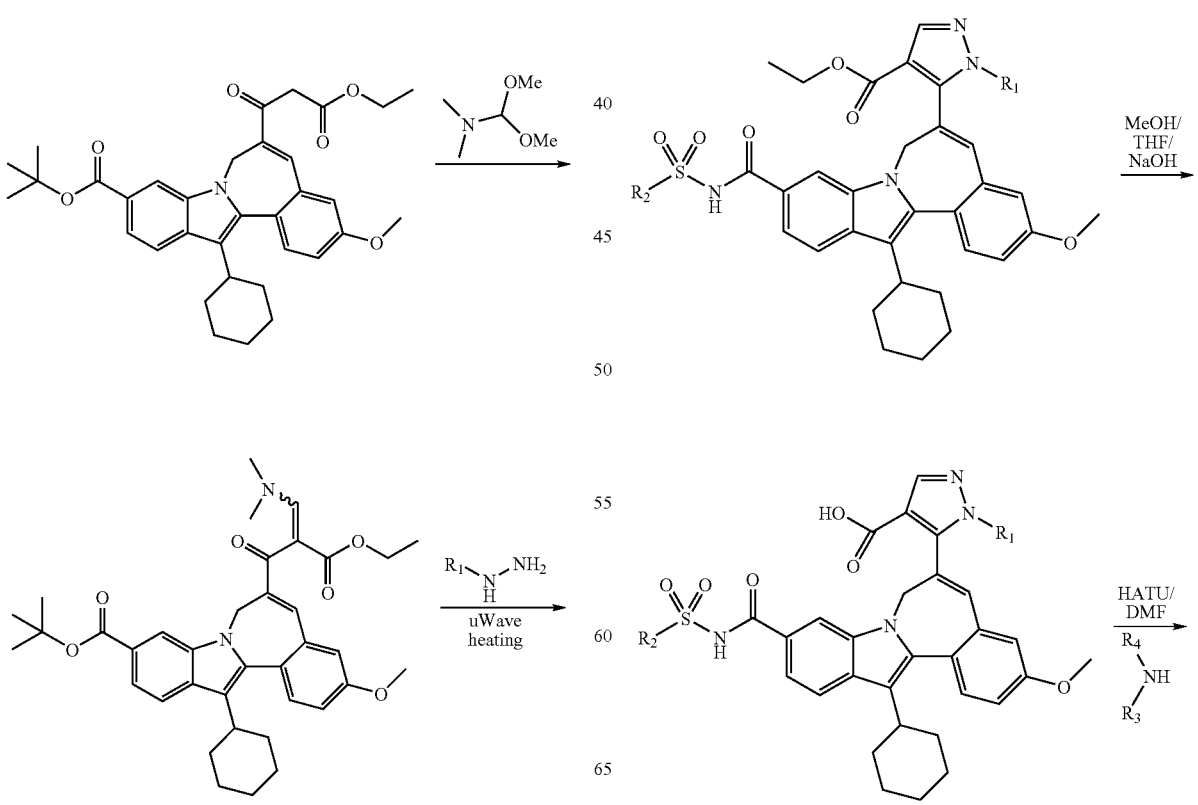

-continued

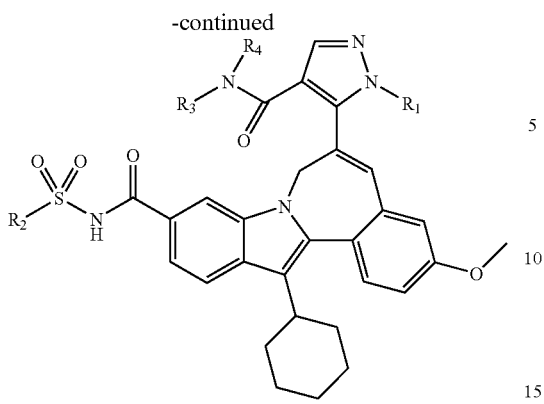

tert-Butyl 13-cyclohexyl-6-((2E,Z)-3-(dimethylamino)-2-(ethoxycarbonyl)-2-propenoyl)-3-methoxy-7H-indolo[2,1-a][2]benzazepine-10-carboxylate

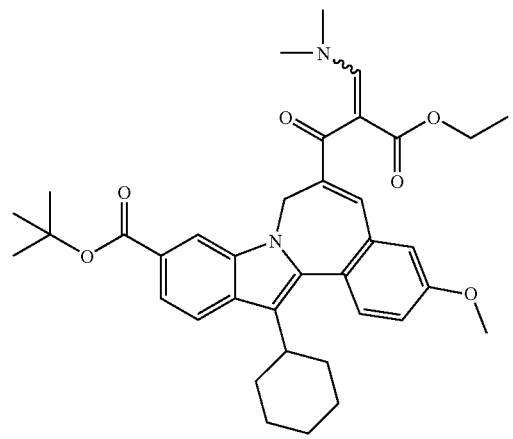

Dissolve tert-butyl 13-cyclohexyl-6-(3-ethoxy-3-oxopropanoyl)-3-methoxy-7H-indolo[2,1-a][2]benzazepine-10-carboxylate (1.63 g, 2.92 mmol) in N,N-dimethylformamide dimethyl acetal (7.0 mL, 52.7 mmol) in a 50 ml round bottom flask. Place the reaction under a nitrogen atmosphere and heat in oil bath to refluxing (110° C.) for 2.75 hrs. Cool reaction under a nitrogen atmosphere then remove volatiles in vacuo using a rotovap to obtain an orange foam. TLC analysis (SiO2 plate, elution-50% diethyl ether in hexanes) confirmed that the reaction is complete. Sample was dried in vacuo at room temperature overnight to yield 1.87 g of the enamine intermediate an orange amber foam which was used in the next step without any further purification.

LC-MS of Intermediate Enamine:

LC-MS retention time 2.81 min; 613 m/z (MH+). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 10% MeOH/90% H$_2$O/0.1% trifluoroacetic acid and solvent B was 10% H$_2$O/90% MeOH/0.1% trifluoroacetic acid. MS data was determined using a MICROMASS® Platform for LC in electrospray mode.

7H-Indolo[2,1-a][2]benzazepine-10-carboxylic acid, 13-cyclohexyl-6-[4-(ethoxycarbonyl)-1-(1-methyl-4-piperidinyl)-1H-pyrazol-5-yl]-3-methoxy-, 1,1-dimethylethyl ester

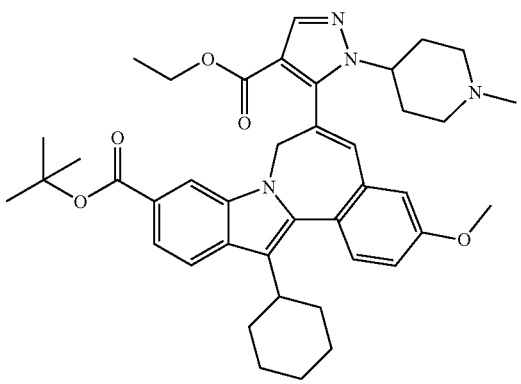

In a 5 ml microwave vessel suspend tert-butyl 13-cyclohexyl-6-((2E,Z)-3-(dimethylamino)-2-(ethoxycarbonyl)-2-propenoyl)-3-methoxy-7H-indolo[2,1-a][2]benzazepine-10-carboxylate (500 mg, 0.816 mmol) in ethanol (2.5 ml) and 1,4-dioxane (0.65 ml). To the reaction was added 4-hydrazinyl-1-methylpiperidine dihydrochloride (173.6 mg, 0.859 mmol) and triethylamine (0.341 ml, 2.448 mmol). The microwave vessel was capped under an inert atmosphere of nitrogen and the reaction heated at 160° C. for 40 minutes. The reaction was combined with previous experiments run under identical experimental conditions. The mixture was diluted with ethyl acetate and washed with 1.0N aqueous hydrochloric acid. The acidic aqueous phases were combined and back extracted one time using ethyl acetate. The ethyl acetate fractions were combined and washed sequentially with saturated aqueous sodium bicarbonate and brine. The organic phase was dried over MgSO$_4$, filtered and solvent removed in vacuo to obtain an orange-amber foam. The crude product was adsorbed onto 3.1 g of silica gel using dichloromethane then chromatograph on 34.7 g of silica gel slurry packed in 2% methanol in dichloromethane solvent mixture. The product was eluted using a gradient of 2% methanol in dichloromethane to 5% methanol in dichloromethane.

The pure product fractions were combined and the solvent removed in vacuo using a rotary evaporator. The product was then dried in vacuo at room temperature to obtain 753 mg (62%) of the title compound as a yellow amorphous solid.

$^1$H NMR (500 MHz, CHLOROFORM-D) δ ppm 1.23-1.30 (m, 1H) 1.31-1.36 (m, 3H) 1.36-1.53 (m, 5H) 1.56 (s, 9H) 1.58-1.74 (m, 4H) 1.78 (d, J=10.99 Hz, 2H) 1.91-2.00 (m, 5H) 2.00-2.14 (m, 4H) 2.18 (d, J=10.99 Hz, 1H) 2.61 (d, J=10.68 Hz, 1H) 2.83-2.92 (m, 1H) 2.97 (t, J=11.60 Hz, 1H) 3.90 (s, 3H) 4.30 (d, J=5.80 Hz, 2H) 4.68 (d, J=14.65 Hz, 1H) 4.92 (d, J=14.95 Hz, 1H) 6.67 (s, 1H) 6.93 (d, J=2.44 Hz, 1H) 7.07 (dd, J=8.55, 2.75 Hz, 1H) 7.52 (d, J=8.55 Hz, 1H) 7.64 (dd, J=8.55, 1.22 Hz, 1H) 7.79 (s, 1H) 7.82 (d, J=8.55 Hz, 1H) 7.92 (s, 1H).

LC-MS retention time 2.77 min; 679 m/z (MH+). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% $H_2O$/10 mM ammonium acetate and solvent B was 5% $H_2O$/95% acetonitrile/10 mM ammonium acetate. MS data was determined using a MICROMASS® Platform for LC in electrospray mode.

7H-Indolo[2,1-a][2]benzazepine-10-carboxylic acid, 13-cyclohexyl-6-[4-(ethoxycarbonyl)-1-(1-methyl-4-piperidinyl)-1H-pyrazol-5-yl]-3-methoxy-

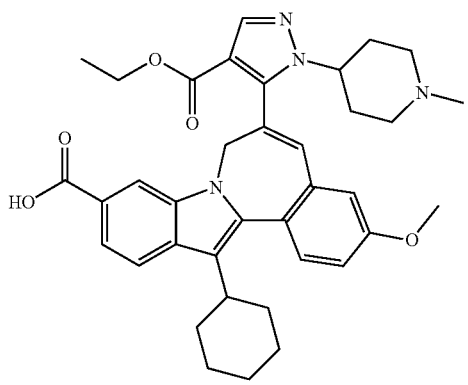

7H-Indolo[2,1-a][2]benzazepine-10-carboxylic acid, 13-cyclohexyl-6-[4-(ethoxycarbonyl)-1-(1-methyl-4-piperidinyl)-1H-pyrazol-5-yl]-3-methoxy-, 1,1-dimethylethyl ester (744 mg, 1.096 mmol) in 1,2-dichloroethane (5.5 ml) then add TFA (5.50 ml) to the reaction. The reaction was stirred under a nitrogen atmosphere at room temperature for 2 hours. Volatiles were removed in vacuo from the reaction using a rotary evaporator. The resulting product as an amber foam was dissolved in dichloromethane and benzene added. The volatiles were removed in vacuo using a rotary evaporator. The process of dissolution in dichloromethane/benzene and removal was repeated to aid in removal of free TFA in the reaction. The product as an amber foam was dried in vacuo at room temperature overnight of yield 920 mg of the title compound as an amorphous yellow solid.

$^1$H NMR (500 MHz, CHLOROFORM-D) δ ppm 0.58-0.68 (m, 0.4H) 0.75 (d, J=14.04 Hz, 0.6H) 1.03-1.14 (m, 1.0H) 1.16-1.27 (m, 0.8H) 1.28-1.41 (m, 4.6H) 1.42-1.54 (m, 2.4H) 1.64 (d, J=14.04 Hz, 0.6H) 1.73-1.87 (m, 2.2H) 1.88-2.25 (m, 6.5H) 2.26-2.39 (m, 0.6H) 2.43-2.56 (m, 2.1H) 2.69 (s, 1.2H) 2.82 (t, J=12.36 Hz, 0.5H) 2.94 (q, J=11.90 Hz, 1.6H) 3.06 (d, J=10.07 Hz, 0.6H) 3.26 (d, J=9.77 Hz, 0.4H) 3.51 (d, J=10.99 Hz, 1.1H) 3.64 (s, 0.4H) 3.85-3.98 (m, 3.2H) 4.25-4.40 (m, 2.0H) 4.73 (d, J=14.95 Hz, 0.9H) 4.95 (d, J=15.26 Hz, 0.9H) 5.98 TFA/$H_2O$ (s, 4.3H) 6.67-6.76 (m, 1.0H) 6.94 (d, J=2.14 Hz, 0.4H) 6.97 (d, J=2.44 Hz, 0.6H) 7.06-7.13 (m, 1.0H) 7.52 (dd, J=8.70, 3.20 Hz, 1.0H) 7.75 (d, J=8.85 Hz, 0.5H) 7.81 (d, J=8.55 Hz, 0.6H) 7.85 (s, 0.5H) 7.88-7.94 (m, 1.4H) 7.96 (d, J=6.41 Hz, 1.2H) 11.20 (s, 0.4H) 11.60 (s, 0.5H).

LC-MS retention time 1.57 min; 621 m/z (MH−). LC data was recorded on a Shimadzu LC-10AS liquid chromatograph equipped with a Waters XTERRA® MS 7u C18 30.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% $H_2O$/10 mM ammonium acetate and solvent B was 5% $H_2O$/95% acetonitrile/10 mM ammonium acetate. MS data was determined using a MICROMASS® Platform for LC in electrospray mode.

1H-Pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-(1-methyl-4-piperidinyl)-, ethyl ester

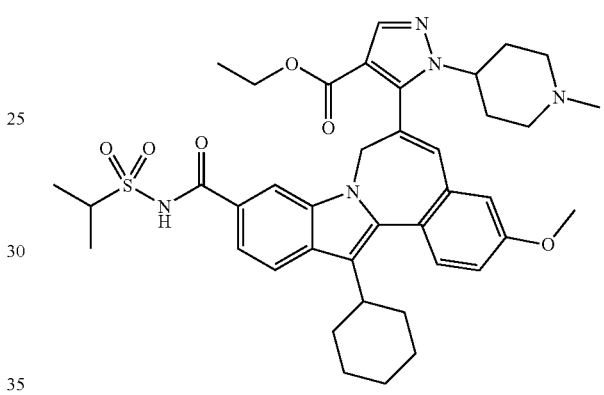

In a 50 ml round bottom flask dissolve 7H-indolo[2,1-a][2]benzazepine-10-carboxylic acid, 13-cyclohexyl-6-[4-(ethoxycarbonyl)-1-(1-methyl-4-piperidinyl)-1H-pyrazol-5-yl]-3-methoxy-*TFA (730 mg, 0.991 mmol) in THF (10 mL). To the reaction add CDI (406 mg, 2.507 mmol) and stir reaction at room temperature under a nitrogen atmosphere for 1 hour. Heat reaction to reflux under a nitrogen atmosphere for one hour the cool and add propane-2-sulfonamide (648 mg, 5.26 mmol) followed by DBU (450 µL, 2.99 mmol). The reaction was again placed under a nitrogen atmosphere and heated at 70° C. overnight.

The reaction was diluted with ethyl acetate (approx 150 ml) and washed sequentially with 1.0N aqueous hydrochloric acid (2×50 ml) and brine. The organic phase was dried magnesium sulfate then filtered. To ensure complete hydrochloride salt formation, approximately 10 ml of 2.0N hydrogen chloride in diethyl ether was added to the filtrate then volatiles removed in vacuo using a rotary evaporator. The residue was dissolved in benzene and volatiles removed in vacuo. The crude product was dried in vacuo to give 1.07 g of product as a yellow foam/amorphous film. The crude product was used as is in further synthesis.

LC-MS retention time 1.68 min; 726 m/z (MH−). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H₂O/10 mM ammonium acetate and solvent B was 5% H₂O/95% acetonitrile/10 mM ammonium acetate. MS data was determined using a MICROMASS® Platform for LC in electrospray mode. Sample exhibits a small peak (~6%) at 220 nm with m/e=744 (MH+) this may be an oxidation impurity (parent MW+16 mass units), retention time=1.50 minutes.

Characterization of title compound isolated from small scale reaction run under similar conditions as above: Isolation by reverse phase HPLC: purified on a Shimadzu high pressure liquid chromatography system employing DISCOVERY VP® software interfaced with a SCL-10A controller, SIL-10A autosampler and FRC-10A fraction collector. The sample was dissolved in acetonitrile/DMF (1:1) (4 ml) purified using a PHENOMENEX® Luna C18 30×100 mm 10u column and monitored using a SPD-10AV UV-Vis detector at a detector wave length of 220 nM. The elution conditions employed a flow rate of 40 mL/min, a gradient of 80% solvent A/20% solvent B to 0% solvent A/100% solvent B, a gradient time of 20 minutes with a run time of 20 minutes using % A=10 mM Ammonium Acetate in 95:5 Water/Acetonitrile % B=10 mM Ammonium Acetate in 5:95 Water/Acetonitrile solvent system. The title compound was collected between 10.4 and 11.4 minutes. The product fraction were combined and volatiles removed in vacuo. The trifluoroacetic acid salt was formed by dissolving the product in dichloromethane (~12 ml) and filtering using Whatman autovial 0.45 uM filter, then adding TFA (35 µL, 0.454 mmol) then remove volatiles in vacuo using a rotary evaporator. The final product was dried in vacuo at room temperature. The ¹H NMR exhibited characteristics of restricted rotation and/or salt formation with broadening and splitting of spectra peaks.

¹H NMR (500 MHz, CHLOROFORM-D) δ ppm 0.43-0.65 (m, 1.4H) 0.75-0.98 (m, 1.5H) 1.02-1.32 (m, 6.2H) 1.30-1.57 (m, 12.8H) 1.59-1.87 (m, 2.7H) 1.89-2.19 (m, 6.3H) 2.34-2.58 (m, 2.4H) 2.68 (s, 1.7H) 2.74-3.09 (m, 2.7H) 3.23 (d, J=8.55 Hz, 0.8H) 3.53 (m, 1.8H) 3.66-3.87 (m, 2.8H) 3.88-3.93 (m, 3.8H) 3.94-4.04 (m, 1.6H) 4.22-4.41 (m, 2.0H) 4.72 (d, J=14.95 Hz, 1.0H) 4.94 (dd, J=14.65, 5.80 Hz, 1.0H) 6.70 (d, J=7.63 Hz, 1.1H) 6.88-7.01 (m, 1.1H) 7.04-7.15 (m, 1.1H) 7.37 (d, J=8.24 Hz, 0.6H) 7.48-7.59 (m, 1.5H) 7.73 (s, 0.6H) 7.85-7.94 (m, 2.6H) 8.87 (s, 0.5H) 11.13-12.06 (m, 0.9H).

LC-MS retention time 1.71 min; 726 m/z (MH−). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H₂O/10 mM ammonium acetate and solvent B was 5% H₂O/95% acetonitrile/10 mM ammonium acetate. MS data was determined using a MICROMASS® Platform for LC in electrospray mode.

1H-Pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-(1-methyl-4-piperidinyl)-

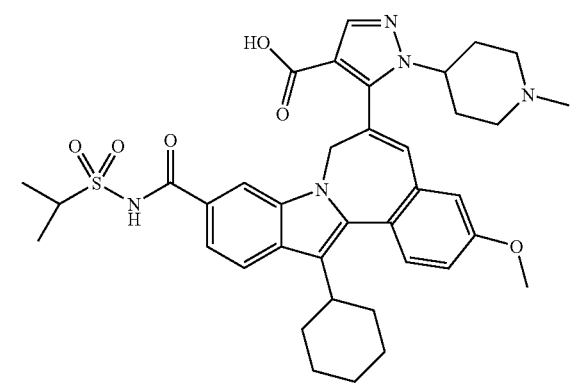

1H-Pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-(1-methyl-4-piperidinyl)-, ethyl ester*hydrochloride salt (0.87 g, 1.138 mmol) was dissolved in THF (12 mL) and methanol (12 mL) added to the reaction followed by 1N aqueous sodium hydroxide (12 mL, 12.00 mmol). The reaction was capped under a nitrogen atmosphere and stirred at room temperature for 19 hrs. The reaction was diluted with ethyl acetate (400 ml) and washed with 1.0N aqueous hydrochloric acid (2×60 ml). The aqueous layers were combined and back extracted with ethyl acetate (2×75 ml). The organic phases were combined and washed with brine and dried over magnesium sulfate and filtered. To the yellow filtrate was added 10 ml of 2.0M hydrogen chloride in diethyl ether, volatiles were then removed in vacuo using a rotary evaporator. The product was dissolved in dichloromethane and benzene then volatiles were removed in vacuo to give a reddish-orange oil. The product was again dissolved in dichloromethane and solvent removed in vacuo to give an orange foam which yielded 799 mg after drying in vacuo at room temperature.

LC-MS retention time 1.14 min; 698 m/z (MH−). LC data was recorded on a Shimadzu LC-10AS liquid chromatograph equipped with a [LC COLUMN] column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H₂O/10 mM ammonium acetate and solvent B was 5% H₂O/95% acetonitrile/10 mM ammonium acetate. MS data was determined using a MICROMASS® Platform for LC in electrospray mode.

7H-Indolo[2,1-a][2]benzazepine-10-carboxamide, 13-cyclohexyl-6-[4-(3,7-dioxa-9-azabicyclo[3.3.1]non-9-ylcarbonyl)-1-(1-methyl-4-piperidinyl)-1H-pyrazol-5-yl]-3-methoxy-N-[(1-methylethyl)sulfonyl]-

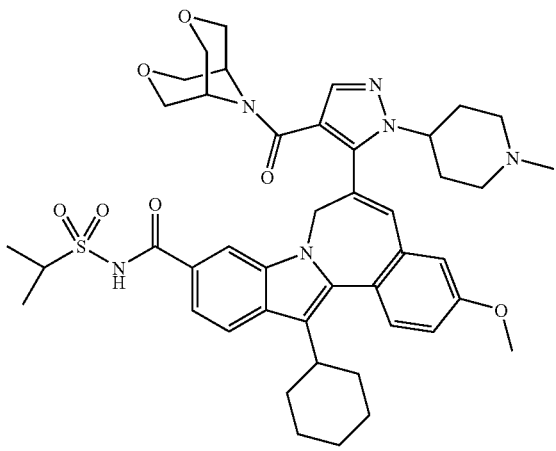

1H-Pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-(1-methyl-4-piperidinyl)-*HCl salt (64 mg, 0.087 mmol) was dissolved in DMF (869 µL) and HATU (111 mg, 0.292 mmol) added to the reaction. The reaction was capped under a nitrogen atmosphere and stirred at room temperature for 1.3 hours. DMAP (55.9 mg, 0.458 mmol) was added to the reaction followed by the amine reagent, 3,7-dioxa-9-azabicyclo[3.3.1]nonane hydrochloride (37.5 mg, 0.226 mmol). The reaction was again capped under a nitrogen atmosphere and stirred at room temperature overnight (16 hr).

The product was purified on a Shimadzu high pressure liquid chromatography system employing DISCOVERY VP® software interfaced with a SCL-10A controller, SIL-10A autosampler and FRC-10A fraction collector. The reaction mixture was dissolved in acetonitrile/DMF mixture (total volume-4 ml) and purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 80% solvent A/20% solvent B to 0% solvent A 100% solvent B, a gradient time of 15 minutes with a run time of 20 minutes using % A=10% acetonitrile, 90% water, 0.1% TFA % B=90% acetonitrile, 10% water, 0.1% TFA solvent system. Retention time of product=6.5 minutes. Volatiles were removed from the product fractions in vacuo and the sample transferred to a vial using dichloromethane and volatiles removed under a nitrogen sweep. The product was dried in vacuo at room temperature to yield a yellow amorphous solid. Preliminary HPLC analysis indicated further purification would be desirable. The sample was further purified on a Shimadzu high pressure liquid chromatography system employing DISCOVERY VP® software interfaced with a SCL-10A controller, SIL-10A autosampler and FRC-10A fraction collector. The sample was dissolved in acetonitrile/DMF (1:1) (2 mL) purified using a PHENOMENEX® Luna C18 30×100 mm 10u column and monitored using a SPD-10AV UV-Vis detector at a detector wave length of 220 nM. The elution conditions employed a flow rate of 40 mL/min, a gradient of 80% solvent A/20% solvent B to 0% solvent A/100% solvent B, a gradient time of 20 minutes with a run time of 20 minutes using % A=10 mM Ammonium Acetate in 95:5 Water/Acetonitrile % B=10 mM Ammonium Acetate in 5:95 Water/Acetonitrile solvent system. The product exhibited rotomeric peaks with retention time of 8.5 minutes and a shoulder peak at 8.9 minutes. The product fractions were combined and the volatiles removed in vacuo using a rotary evaporator. Place the off white pale yellow product on vacuum pump and dry in vacuo for approximately 1 hr, then dissolve in dichloromethane and transfer to a 25 ml pear shaped flask, add TFA (30 µL, 0.389 mmol), then remove volatiles in vacuo using a rotary evaporator. Transfer product to a CMDD vial using dichloromethane then concentrate using a nitrogen sweep and finally remove remainder of solvent in vacuo using a rotary evaporator. The sample was dried in vacuo at room temperature to yield 32.4 mg (40%) as a yellow amorphous film.

$^1$H NMR (500 MHz, CHLOROFORM-D) δ ppm 1.13-1.30 (m, 1.4H) 1.33-1.47 (m, 5.9H) 1.50 (d, J=6.41 Hz, 2.7H) 1.69-1.86 (m, 2.4H) 1.89-2.02 (m, 2.6H) 2.02-2.17 (m, 2.6H) 2.24-2.77 (m, 4.5H) 2.77-3.04 (m, 3.8H) 3.09-3.54 (m, J=110.48 Hz, 5.5H) 3.64 (d, J=46.08 Hz, 4.7H) 3.93 (s, 3.0H) 3.96-4.21 (m, 3.3H) 4.43 (s, 4.7H) 4.55-4.73 (m, 1.9H) 4.75-4.94 (m, 1.7H) 5.05 (s, 0.8H) 6.81 (s, 1.0H) 6.87-6.96 (m, 1.1H) 7.09-7.17 (m, 1.1H) 7.50-7.64 (m, 2.2H) 7.64-7.78 (m, 1.6H) 7.88-7.99 (m, 1.1H) 10.20 (s, 0.8H) 11.46 (s, 1.1H).

LC-MS retention time 1.46 min; 809 m/z (MH−). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% $H_2O$/10 mM ammonium acetate and solvent B was 5% $H_2O$ i 95% acetonitrile/10 mM ammonium acetate. MS data was determined using a MICROMASS® Platform for LC in electrospray mode.

7H-Indolo[2,1-a][2]benzazepine-10-carboxamide, 13-cyclohexyl-3-methoxy-N-[(1-methylethyl)sulfonyl]-6-[1-(1-methyl-4-piperidinyl)-4-(4-morpholinylcarbonyl)-1H-pyrazol-5-yl]-

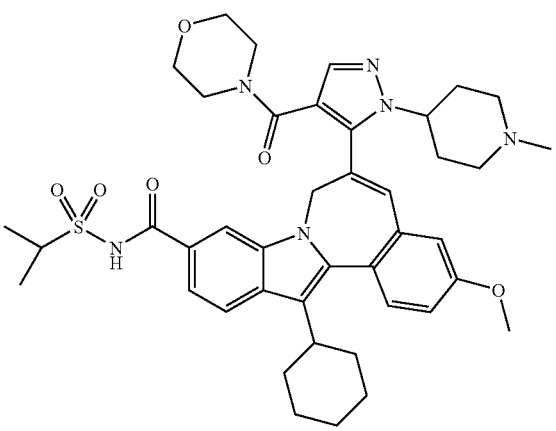

1H-Pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-(1-methyl-4-piperidinyl)-*HCl salt (68 mg, 0.092 mmol) was dissolved in DMF (924 μL) and HATU (72.7 mg, 0.191 mmol) added to the reaction. The reaction was capped under a nitrogen atmosphere and stirred at room temperature for 1 hour. DMAP (45.9 mg, 0.376 mmol) was added to the reaction followed by the amine reagent, morpholine (24.2 μL, 0.277 mmol). The reaction was again capped under a nitrogen atmosphere and stirred at room temperature overnight (18 hr). The reaction was purified on a Shimadzu high pressure liquid chromatography system employing DISCOVERY VP® software interfaced with a SCL-10A controller, SIL-10A autosampler and FRC-10A fraction collector. The sample was dissolved in acetonitrile/DMF (1:1) (2 ml) purified using a PHENOMENEX® Luna C18 30×100 mm 10u column and monitored using a SPD-10AV UV-Vis detector at a detector wave length of 220 nM. The elution conditions employed a flow rate of 40 mL/min, a gradient of 80% solvent A/20% solvent B to 0% solvent A/100% solvent B, a gradient time of 20 minutes with a run time of 20 minutes using % A=10 mM Ammonium Acetate in 95:5 Water/Acetonitrile % B=10 mM Ammonium Acetate in 5:95 Water/Acetonitrile solvent system. Retention time of product is 8.8 minutes. Combine product fractions and remove volatiles in vacuo using rotary evaporator connected to a vacuum pump.

The product was dried in vacuo at room temperature for approximately 45 min then transfer to a 25 ml pear flask using dichloromethane and TFA (60 μL, 0.779 mmol) added. Volatiles were then removed in vacuo on rotary evaporator and dry in vacuo at room temperature for approximately 1 hr before re-dissolving in approximately 3 ml of dichloromethane (cloudy) then filtering through a 0.45 uM syringe filter and transferring into a vial. The solution was concentrated using a nitrogen sweep and TFA (15 μL, 0.195 mmol) added then volatiles removed in vacuo on rotary evaporator to yield a orange solid which was dried in vacuo at room temperature overnight to give 34.9 mg (55%) of the title compound. The proton NMR of the title compound exhibits broadening of peaks along with characteristics of restricted rotation/confirmation.

$^1$H NMR (500 MHz, CHLOROFORM-D) δ ppm 1.11-1.30 (m, 2.4H) 1.32-1.54 (m, 10.1H) 1.79 (d, J=9.77 Hz, 2.4H) 1.87-2.18 (m, 6.5H) 2.78-2.98 (m, 5.3H) 3.05-3.21 (m, 1.6H) 3.43 (s, 2.2H) 3.59 (s, 2.5H) 3.90-3.95 (m, 4.1H) 3.96-4.14 (m, 5.4H) 4.60 (d, J=14.95 Hz, 1.0H) 4.87 (d, J=17.09 Hz, 0.9H) 5.02 (s, 0.2H) 6.71-6.85 (m, 1.0H) 6.90-6.97 (m, 1.0H) 7.08-7.16 (m, 1.0H) 7.50-7.63 (m, 2.2H) 7.67 (d, J=6.10 Hz, 1.5H) 7.94 (d, J=8.24 Hz, 0.3H) 10.13 (s, 1H) 11.41 (s, 0.6H).

LC-MS retention time 1.49 min; 767 m/z (MH−). LC data was recorded on a Shimadzu LC-10AS liquid chromatograph equipped with a PHENOMENEX® Luna 10u C18 30.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H$_2$O/10 mM ammonium acetate and solvent B was 5% H$_2$O/95% acetonitrile/10 mM ammonium acetate. MS data was determined using a MICROMASS® Platform for LC in electrospray mode.

7H-Indolo[2,1-a][2]benzazepine-10-carboxamide, 13-cyclohexyl-3-methoxy-6-[4-[(3-methyl-3,8-diazabicyclo[3.2.1]oct-8-yl)carbonyl]-1-(1-methyl-4-piperidinyl)-1H-pyrazol-5-yl]-N-[(1-methylethyl)sulfonyl]-

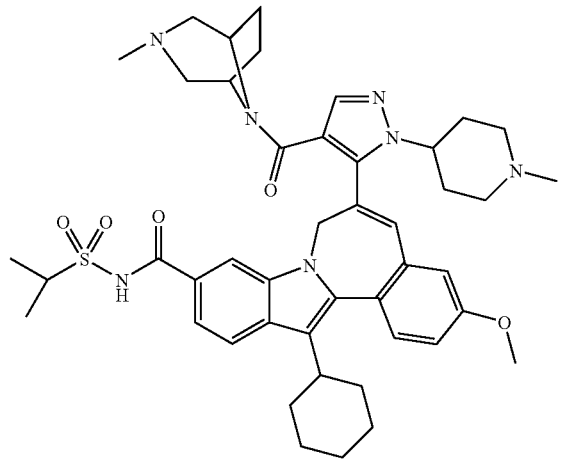

1H-Pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-(1-methyl-4-piperidinyl)-*HCl salt (71.2 mg, 0.097 mmol) was dissolved in DMF (967 μL) and HATU (82.2 mg, 0.216 mmol) added to the reaction. The reaction was capped under a nitrogen atmosphere and stirred at room temperature for 1 hour. DMAP (64.5 mg, 0.528 mmol) was added to the reaction followed by the amine reagent, 3-methyl-3,8-diazabicyclo[3.2.1]octane dihydrochloride (82.4 mg, 0.414 mmol). Note: excess amine was added to reaction therefore an additional amount of DMAP (50 mg, 0.409 mmol) was added to compensate for the dihydrochloride salt of the amine. The reaction was capped under a nitrogen atmosphere and stirred at room temperature (17 hrs).

The reaction was purified on a Shimadzu high pressure liquid chromatography system employing DISCOVERY VP® software interfaced with a SCL-10A controller, SIL-10A autosampler and FRC-10A fraction collector. The sample was dissolved in acetonitrile/DMF (3:1) (4 ml) purified using a PHENOMENEX® Luna C18 30×100 mm 10u column and monitored using a SPD-10AV UV-Vis detector at a detector wave length of 220 nM. The elution conditions employed a flow rate of 40 mL/min, a gradient of 80% solvent A/20% solvent B to 0% solvent A/100% solvent B, a gradient time of 20 minutes with a run time of 20 minutes using % A=10 mM Ammonium Acetate in 95:5 Water/Acetonitrile % B=10 mM Ammonium Acetate in 5:95 Water/Acetonitrile solvent system. The retention time of product is 9.3 minutes. Combine product fractions and remove volatiles in vacuo using a rotary evaporator using a vacuum pump. The product was briefly dried in vacuo at room temperature and the TFA salt made by dissolving in dichloromethane and adding TFA (60 μL, 0.779 mmol). The volatiles were removed in vacuo and the sample re-dissolved in dichloromethane, filtered through a 0.45 uM syringe filter and the solution concentrated. An additional amount of TFA (15.0 μL, 0.195 mmol) was added to the product solution and the volatiles were removed in vacuo using a rotary evaporator to obtain an orange solid. The title compound was dried in vacuo at room temperature overnight to yield 35.8 mg (34%) as an amorphous orange solid.

$^1$H NMR (500 MHz, CHLOROFORM-D) δ ppm 0.68-1.29 (m, 3.6H) 1.28-1.53 (m, 9.3H) 1.61 (s, 1.2H) 1.79 (d, J=11.29 Hz, 2.2H) 1.87-2.35 (m, 8.4H) 2.38-2.74 (m, 4.1H) 2.75-3.48 (m, 9.1H) 3.73 (d, J=54.32 Hz, 2.6H) 3.85-4.03 (m, 3.7H) 4.46-4.98 (m, 3.3H) 4.97-5.52 (m, 3.2H) 6.75 (s, 0.6H) 6.89-6.98 (m, 1.2H) 7.06-7.16 (m, 1.0H) 7.37-7.81 (m, 3.4H) 7.94 (dd, J=25.48, 8.09 Hz, 1.0H) 8.10 (s, 0.4H) 10.16 (s, 0.7H) 11.53 (s, 0.9H) 11.73 (s, 0.9H).

LC-MS retention time 1.59 min; 806 m/z (MH−). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H$_2$O/10 mM ammonium acetate and solvent B was 5% H$_2$O/95% acetonitrile/10 mM ammonium acetate. MS data was determined using a MICROMASS® Platform for LC in electrospray mode.

7H-Indolo[2,1-a][2]benzazepine-10-carboxamide, 13-cyclohexyl-6-[4-[[(2R,6S)-2,6-dimethyl-4-morpholinyl]carbonyl]-1-(1-methyl-4-piperidinyl)-1H-pyrazol-5-yl]-3-methoxy-N-[(1-methylethyl)sulfonyl]-

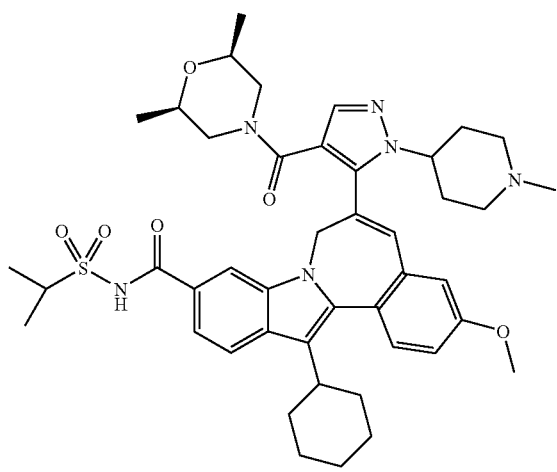

1H-Pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-(1-methyl-4-piperidinyl)-*HCl salt (73.6 mg, 0.100 mmol) in was dissolved in DMF (1.000 mL) and HATU (84 mg, 0.220 mmol) added to the reaction. The reaction was capped under a nitrogen atmosphere and stirred at room temperature for 1.3 hours. DMAP (50.3 mg, 0.412 mmol) was added to the reaction followed by the amine reagent, (2R,6S)-2,6-dimethylmorpholine (37.1 µL, 0.300 mmol). The reaction was again capped under a nitrogen atmosphere and stirred at room temperature overnight (16 hr).

The reaction was purified on a Shimadzu high pressure liquid chromatography system employing DISCOVERY VP® software interfaced with a SCL-10A controller, SIL-10A autosampler and FRC-10A fraction collector. The reaction was diluted in acetonitrile/DMF (1:1) (2 ml) purified using a PHENOMENEX® Luna C18 30×100 mm 10u column and monitored using a SPD-10AV UV-Vis detector at a detector wave length of 220 nM. The elution conditions employed a flow rate of 40 mL/min, a gradient of 80% solvent A/20% solvent B to 0% solvent A/1.00% solvent B, a gradient time of 20 minutes with a run time of 20 minutes using % A=10 mM Ammonium Acetate in 95:5 Water/Acetonitrile % B=10 mM Ammonium Acetate in 5:95 Water/Acetonitrile solvent system. The product fractions were combined and the volatiles were removed in vacuo using a rotary evaporator. The product was briefly dried in vacuo and then dissolved in dichloromethane and TFA (30 µL, 0.389 mmol) was added. The volatiles were removed in vacuo using a rotary evaporator. The sample was re-dissolved in approximately 2 ml of dichloromethane and filtered through a 0.45 uM syringe filter into a vial. The product solution was concentrated under a nitrogen sweep then TFA (15 µL, 0.195 mmol) was added and the volatiles removed in vacuo using a rotary evaporator resulting in an orange foam. The title compound was dried in vacuo at room temperature to give 33.1 mg of an orange solid.

$^1$H NMR (500 MHz, CHLOROFORM-D) δ ppm 0.47-1.01 (m, 4.5H) 1.00-1.33 (m, 3.5H) 1.33-1.63 (m, 8.0H) 1.79 (d, J=10.68 Hz, 1.9H) 1.85-2.19 (m, 5.5H) 2.20 (s, 1.0H) 2.38 (s, 1.1H) 2.58 (s, 1.4H) 2.69-3.02 (m, 4.8H) 3.14 (s, 2.1H) 3.52 (d, J=75.38 Hz, 3.8H) 3.84-3.98 (m, 2.7H) 3.98-4.15 (m, 1.7H) 4.21-4.71 (m, 5.1H) 4.72-5.19 (m; 2.0H) 6.78 (s, 1.0H) 6.85-6.97 (m, 0.9H) 7.07-7.19 (m, 0.9H) 7.49-7.75 (m, 3.2H) 7.92 (d, J=8.24 Hz, 1.0H) 10.40 (s, 0.8H) 11.66 (s, 1.0H).

LC-MS retention time 1.65 min; 795 m/z (MH−). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H$_2$O/10 mM ammonium acetate and solvent B was 5% H$_2$O/95% acetonitrile/10 mM ammonium acetate. MS data was determined using a MICROMASS® Platform for LC in electrospray mode.

13-Cyclohexyl-6-(4-((3-hydroxy-3-methyl-8-azabicyclo[3.2.1]oct-8-yl)carbonyl)-1-(1-methyl-4-piperidinyl)-1H-pyrazol-5-yl)-N-(isopropylsulfonyl)-3-methoxy-7H-indolo[2,1-a][2]benzazepine-10-carboxamide

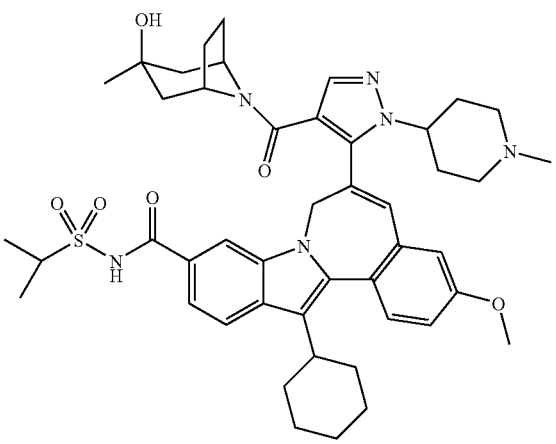

1H-Pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-(1-methyl-4-piperidinyl)-*HCl salt (72 mg, 0.098 mmol) in was dissolved in DMF (0.5 ml) and HATU (82 mg, 0.215 mmol) added to the reaction. The reaction was capped under a nitrogen atmosphere and stirred at room temperature for 1 hour. DMAP (49.7 mg, 0.407 mmol), was added to the reaction followed by the amine reagent, 3-methyl-8-azabicyclo[3.2.1]octan-3-ol (37.7 mg, 0.267 mmol) dissolved in DMF (0.5 ml). The reaction was again capped under a nitrogen atmosphere and stirred at room temperature overnight (16 hr). The product was purified on a Shimadzu high pressure liquid chromatography system employing DISCOVERY VP® software interfaced with a SCL-10A controller, SIL-10A autosampler and FRC-10A fraction collector. The reaction mixture was diluted with acetonitrile and a small amount of water to effect solubilization of the sample to a total volume of 2 ml and purified using a Waters XTERRA® Prep MS C18 OBD, 5 uM, 30 mm×100 mm column and monitored using a SPD-10AV UV-Vis detector at a detector wave length of 220 nM. The elution conditions employed a flow rate of 40 mL/min, a gradient of 80% solvent A/20% solvent B to 0% solvent A/100% solvent B, a gradient time of 20 minutes with a run time of 20 minutes using % A=10 mM Ammonium Acetate in 95:5 Water/Acetonitrile % B=10 mM Ammonium Acetate in 5:95 Water/Acetonitrile solvent system. The product exhibited rotomeric like peak splitting with retention time s of 9.2 and 9.4 minutes. The product fractions were combined and volatiles removed in vacuo using a rotary evaporator. The product was dried in vacuo for ~1 hr then dissolved in dichloromethane (~3 ml) and filtered through an ACRODISC® 0.45 uM syringe filter using a norm jet syringe which was pre-rinsed using dichloromethane in to a 35 ml flask. TFA (30 μL, 0.389 mmol) was added to the solution and the volatiles were removed in vacuo using a rotary evaporator. The sample was redissolved in dichloromethane and transferred into a vial. The solution was concentrated using a nitrogen sweep and final volatiles were removed in vacuo using a rotary evaporator. The title compound was dried in vacuo to give 40.0 mg (43.7% isolated yield) as an amorphous orange solid.

$^1$H NMR (500 MHz, CHLOROFORM-D) δ ppm –0.25 (s, 0.6H) 0.51 (s, 0.7H) 1.04 (s, 2.7H) 1.11-1.30 (m, 2.5H) 1.30-1.60 (m, 13.1H) 1.68-2.04 (m, 7.5H) 2.03-2.13 (m, 2.3H) 2.41-2.58 (m, 1.7H) 2.76 (d, J=21.67 Hz, 1.2H) 2.81-2.89 (m, 1.3H) 2.93 (s, 1.9H) 3.17-3.31 (m, J=9.16 Hz, 0.9H) 3.42 (d, J=10.68 Hz, 0.8H) 3.46-3.56 (m, 1.1H) 3.62 (d, J=23.19 Hz, 1.4H) 3.87-3.96 (m, 3.1H) 3.97-4.11 (m, 1.6H) 4.51-4.75 (m, 1.2H) 4.84 (s, 0.8H) 4.94 (d, J=15.56 Hz, 0.8H) 4.98-5.17 (m, 1.3H) 5.18-5.50 (m, 3.6H) 6.65-6.90 (m, 1.0H) 6.92 (d, J=2.14 Hz, 1.0H) 7.03-7.16 (m, 1.0H) 7.44-7.60 (m, 1.3H) 7.61-7.80 (m, 2.5H) 7.90 (d, J=8.24 Hz, 1.2H) 10.45 (s, 0.5H) 11.21 (s, 0.6H).

LC-MS retention time 1.59 min; 821 m/z (MH–). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was ~5% acetonitrile/95% H$_2$O/10 mM ammonium acetate and solvent B was 5% H$_2$O/95% acetonitrile/10 mM ammonium acetate. MS data was determined using a MICROMASS® Platform for LC in electrospray mode.

7H-Indolo[2,1-a][2]benzazepine-10-carboxamide, 13-cyclohexyl-3-methoxy-N-[(1-methylethyl)sulfonyl]-6-[1-(1-methyl-4-piperidinyl)-4-(3-oxa-9-azabicyclo[3.3.1]non-9-ylcarbonyl)-1H-pyrazol-5-yl]-

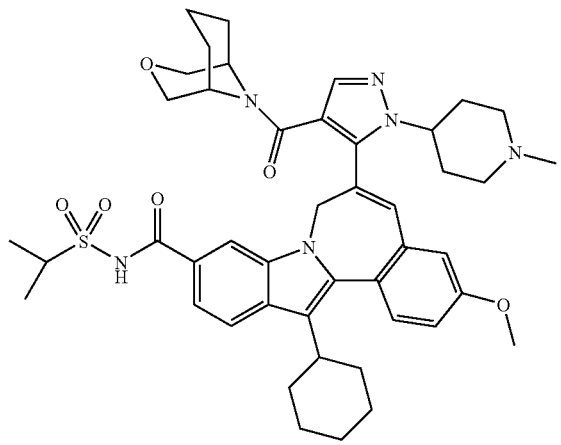

1H-Pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-(1-methyl-4-piperidinyl)-*HCl salt (71.9 mg, 0.098 mmol) in was dissolved in DMF (1.0 ml) and HATU (82 mg, 0.215 mmol) added to the reaction. The reaction was capped under a nitrogen atmosphere and stirred at room temperature for 2 hours. DMAP (49.7 mg, 0.407 mmol), was added to the reaction followed by the amine reagent, 3-oxa-9-azabicyclo[3.3.1]nonane hydrochloride (35.2 mg, 0.215 mmol). The reaction was again capped under a nitrogen atmosphere and stirred at room temperature overnight (16 hr).

The product was purified on a Shimadzu high pressure liquid chromatography system employing DISCOVERY VP® software interfaced with a SCL-10A controller, SIL-10A autosampler and FRC-10A fraction collector. The reaction mixture was diluted with acetonitrile to 2 ml and purified using a Waters XTERRA® Prep MS C18 OBD, 5 uM, 30 mm×100 mm column and monitored using a SPD-10AV UV-V is detector at a detector wave length of 220 nM. The elution conditions employed a flow rate of 40 mL/min, a gradient of 80% solvent A/20% solvent B to 0% solvent A/100% solvent B, a gradient time of 20 minutes with a run time of 20 minutes using % A=10 mM Ammonium Acetate in 95:5 Water/Acetonitrile % B=10 mM Ammonium Acetate in 5:95 Water/Acetonitrile solvent system. The product exhibited rotomeric like splitting with retention time s of 10.5 and 10.8 minutes. The product fractions were combined and volatiles removed in vacuo using a rotary evaporator. The product was transferred to a 25 ml flask with dichloromethane then TFA (30 μL, 0.389 mmol) was added via pipet. The product solution went from a yellow color to a darker orange-reddish color. The volatiles were removed in vacuo and the product transferred to a vial in dichloromethane. The product solution was concentrated using a nitrogen sweep then the remaining volatiles were removed in vacuo using rotary evaporator. The title compound was dried in vacuo at room temperature to yield 46.7 mg (51.8%) as a reddish-orange amorphous solid. HPLC analysis indicated that further purification was desirable.

The sample was further purified on a Shimadzu high pressure liquid chromatography system employing DISCOVERY VP® software interfaced with a SCL-10A controller, SIL-10A autosampler and FRC-10A fraction collector. The sample was dissolved in acetonitrile (1 mL) and purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 80% solvent A/20% solvent B to 0% solvent A/100% solvent B, a gradient time of 15 minutes with a run time of 20 minutes using % A=10% acetonitrile, 90% water, 0.1% TFA % B=90% acetonitrile, 10% water, 0.1% TFA solvent system. Retention time of product is 8.4 minutes. Volatiles were removed from the product fraction in vacuo using a rotary evaporator. The product was transferred to a vial using dichloromethane, concentrated with a nitrogen sweep and the remainder of volatile solvent was removed in vacuo using a rotary evaporator. The title compound was dried in vacuo at room temperature to yield 26.0 mg (29%) as a pale yellow amorphous solid.

$^1$H NMR (500 MHz, CHLOROFORM-D) δ ppm 1.09-1.28 (m, 2.7H) 1.29-1.40 (m, 3.2H) 1.45 (d, J=7.02 Hz, 5.5H) 1.47-1.55 (m, 3.8H) 1.77 (d, J=9.16 Hz, 3.0H) 1.87 (d, J=15.87 Hz, 1.0H) 1.97 (dd; J=10.99, 8.85 Hz, 2.4H) 2.01-2.14 (m, 2.7H) 2.21 (s, 1.0H) 2.39 (d, J=26.55 Hz, 1.6H) 2.56 (s, 1.4H) 2.68-2.98 (m, 4.7H) 3.05 (d, J=7.32 Hz, 0.9H) 3.18 (d, J=28.08 Hz, 1.5H) 3.38 (dd, J=55.39, 11.14 Hz, 2.4H) 3.58 (s, 2.6H) 3.94 (s, 3.4H) 3.97-4.13 (m, 1.9H) 4.44-5.19 (m, 6.5H) 6.75-6.84 (m, 1.0H) 6.86-6.96 (m, 1.0H) 7.13 (d, J=8.24 Hz, 1.0H) 7.50-7.78 (m, 4.0H) 7.91 (d, J=8.24 Hz, 1.2H) 10.50 (s, 0.6H) 11.72 (s, 0.7H).

LC-MS retention time 1.71 min; 807 m/z (MH−). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% $H_2O$/10 mM ammonium acetate and solvent B was 5% $H_2O$/95% acetonitrile/10 mM ammonium acetate. MS data was determined using a MICROMASS® Platform for LC in electrospray mode.

7H-Indolo[2,1-a][2]benzazepine-10-carboxamide, 13-cyclohexyl-3-methoxy-6-[4-[[(2S)-2-(methoxymethyl)-4-morpholinyl]carbonyl]-1-(1-methyl-4-piperidinyl)-1H-pyrazol-5-yl]-N-[(1-methylethyl)sulfonyl]-

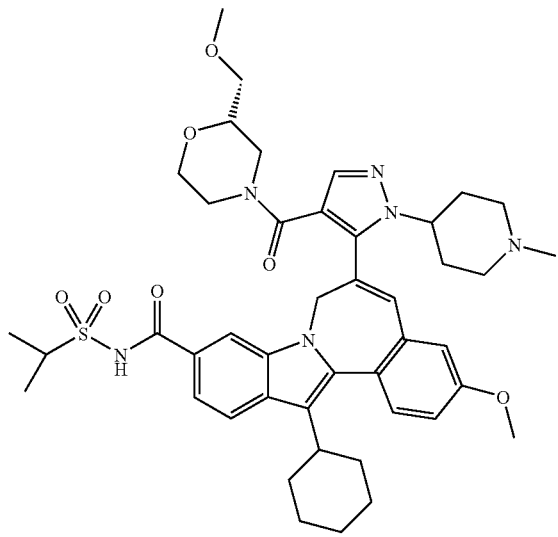

1H-Pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-(1-methyl-4-piperidinyl)-*HCl salt (71.9 mg, 0.098 mmol) in was dissolved in DMF (1.0 ml) and HATU (82 mg, 0.215 mmol) added to the reaction. The reaction was capped under a nitrogen atmosphere and stirred at room temperature for 2 hours. DMAP (46.6 mg, 0.381 mmol), was added to the reaction followed by the amine reagent, (S)-2-(methoxymethyl)morpholine hydrochloride (35.4 mg, 0.211 mmol). The reaction was again capped under a nitrogen atmosphere and stirred at room temperature overnight (16 hr).

The product was purified on a Shimadzu high pressure liquid chromatography system employing DISCOVERY VP® software interfaced with a SCL-10A controller, SIL-10A autosampler and FRC-10A fraction collector. The reaction mixture was diluted with acetonitrile to 2 ml and purified using a Waters XTERRA® Prep MS C18 OBD, 5 uM, 30 mm×100 mm column and monitored using a SPD-10AV UV-Vis detector at a detector wave length of 220 nM. The elution conditions employed a flow rate of 40 mL/min, a gradient of 80% solvent A/20% solvent B to 0% solvent A/100% solvent B, a gradient time of 20 minutes with a run time of 20 minutes using % A=10 mM Ammonium Acetate in 95:5 Water/Acetonitrile % B=10 mM Ammonium Acetate in 5:95 Water/Acetonitrile solvent system. The product exhibited rotomeric like splitting with retention time s of 9.3 and 9.6 minutes. The product fractions were combined and volatiles removed in vacuo using a rotary evaporator. The product was dried in vacuo for approximately 1 hr then dissolved in dichloromethane (~4 ml) and filtered through an ACRODISC® 0.45 uM syringe filter using a norm jet syringe which was pre-rinsed using dichloromethane. TFA (30 µL, 0.389 mmol) was added to the solution and the volatiles were removed in vacuo using a rotary evaporator. The product was dried in vacuo at room temperature yielding 40.9 mg (45.2%) as an amorphous orange solid.

$^1$H NMR (500 MHz, CHLOROFORM-D) δ ppm 1.00-1.30 (m, 2.7H) 1.30-1.61 (m, 8.9H) 1.79 (d, J=9.16 Hz, 2.3H) 1.88-2.16 (m, 5.8H) 2.24-2.65 (m, 3.9H) 2.66-2.99 (m, 6.3H) 2.98-3.53 (m, 9.3H) 3.61 (s, 3.0H) 3.90-3.95 (m, 3.0H) 3.96-4.14 (m, 2.1H) 4.59 (d, J=118.62 Hz, 2.0H) 4.68-5.09 (m, 6.1H) 6.75-6.85 (m, 1.1H) 6.87-6.99 (m, 1.2H) 7.12 (t, J=7.02 Hz, 1.1H) 7.46-7.77 (m, 3.9H) 7.82-8.01 (m, 1.3H) 10.24 (s, 0.8H) 11.30 (s, 1.1H).

LC-MS retention time 1.60 min; 811 m/z (MH−). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% $H_2O$/10 mM ammonium acetate and solvent B was 5% $H_2O$/95% acetonitrile/10 mM ammonium acetate. MS data was determined using a MICROMASS® Platform for LC in electrospray mode.

7H-Indolo[2,1-a][2]benzazepine-10-carboxamide, 13-cyclohexyl-3-methoxy-N-[(1-methylethyl)sulfonyl]-6-[1-(1-methyl-4-piperidinyl)-4-[[(3R,5S)-3,4,5-trimethyl-1-piperazinyl]carbonyl]-1H-pyrazol-5-yl]-

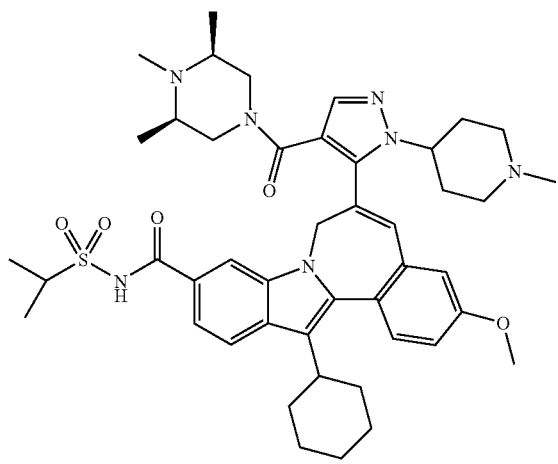

1H-Pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-(1-methyl-4-piperidinyl)-*HCl salt (71.7 mg, 0.097 mmol) in was dissolved in DMF (1.0 ml) and HATU (82 mg, 0.215 mmol) added to the reaction. The reaction was capped under a nitrogen atmosphere and stirred at room temperature for 2 hours. DMAP (64.3 mg, 0.526 mmol), was added to the reaction followed by the amine reagent, (2R,6S)-1,2,6-trimethylpiperazine dihydrochloride (42 mg, 0.209 mmol). The clear orange reaction solution was capped under a nitrogen atmosphere and the reaction stirred at room temperature overnight (16 hrs).

The product was purified on a Shimadzu high pressure liquid chromatography system employing DISCOVERY VP® software interfaced with a SCL-10A controller, SIL-10A autosampler and FRC-10A fraction collector. The reaction mixture was diluted with acetonitrile to 2 ml and purified using a Waters XTERRA® Prep MS C18 OBD, 5 uM, 30 mm×100 mm column and monitored using a SPD-10AV UV-Vis detector at a detector wave length of 220 nM. The elution conditions employed a flow rate of 40 mL/min, a gradient of 80% solvent A/20% solvent B to 0% solvent A/100% solvent B, a gradient time of 20 minutes with a run time of 20 minutes using %A=10 mM Ammonium Acetate in 95:5 Water/Acetonitrile % B=10 mM Ammonium Acetate in 5:95 Water/Acetonitrile solvent system. The product exhibited an asymmetric peak with retention time of 9.0 minutes. The product fractions were combined and volatiles removed in vacuo using a rotary evaporator. The product was dried in vacuo for ~1 hr then dissolved in dichloromethane (~3 ml) and filtered through an ACRODISC® 0.45 uM syringe filter using a norm jet syringe which was pre-rinsed using dichloromethane in to a 35 ml flask. TFA (60 µL, 0.779 mmol) was added to the solution and the volatiles were removed in vacuo using a rotary evaporator. The title compound was dried in vacuo at room temperature to yield 41.4 mg (41%) of amorphous yellow-orange solid.

$^1$H NMR (500 MHz, CHLOROFORM-D) δ ppm 0.79-1.19 (m, 1H) 1.24 (s, 1H) 1.28-1.73 (m, 11H) 1.81 (s, 2H) 1.90-2.18 (m, 5H) 2.20-2.71 (m, 5H) 2.78-2.99 (m, 3H) 2.98-3.79 (m, 7H) 3.87-3.97 (m, 3H) 4.00 (s, 1H) 4.54-4.73 (m, 2H) 4.92 (s, 4H) 5.10 (d, J=15.26 Hz, 1H) 6.74-6.89 (m, 1H) 6.94 (d=2.14 Hz, 1H) 6.98-7.17 (m, 2H) 7.39-7.63 (m, 2H) 7.69 (d, J=7.93 Hz, 1H) 7.82-8.14 (m, 2H) 11.12 (s, 1H) 11.45 (s, 1H).

LC-MS retention time 1.74 min; 808 m/z (MH−). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H$_2$O/10 mM ammonium acetate and solvent B was 5% H$_2$O/95% acetonitrile/10 mM ammonium acetate. MS data was determined using a MICROMASS® Platform for LC in electrospray mode.

7H-Indolo[2,1-a][2]benzazepine-10-carboxylic acid, 13-cyclohexyl-6-[4-(ethoxycarbonyl)-1-(3-methyl-4-pyridinyl)-1H-pyrazol-5-yl]-3-methoxy-, 1,1-dimethylethyl ester

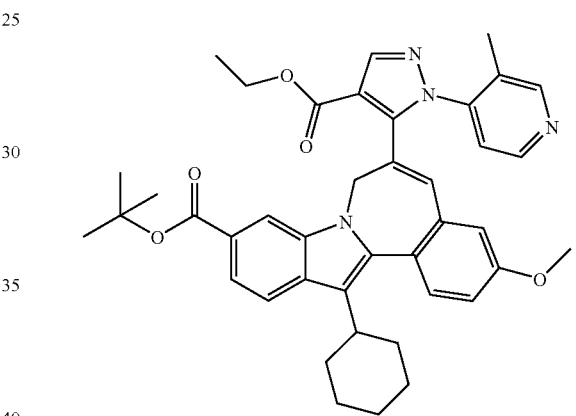

tert-Butyl 13-cyclohexyl-6-((2E,Z)-3-(dimethylamino)-2-(ethoxycarbonyl)-2-propenoyl)-3-methoxy-7H-indolo[2,1-a][2]benzazepine-10-carboxylate (98.5 mg, 0.161 mmol) was suspended in ethanol (504 µL) and dioxane (126 µL). Triethylamine (68.2 µL, 0.489 mmol) was added to the reaction followed by 4-hydrazinyl-3-methylpyridine hydrochloride, 0.4H$_2$O (27.6 mg, 0.165 mmol). The reaction was capped under a nitrogen atmosphere and heated in a microwave to 140° C. for 40 minutes. The reaction was diluted with ethyl acetate and washed with 1.0N aqueous hydrochloric acid. The aqueous phase was back extracted one time using ethyl acetate. The organic phases were combined and sequentially washed with saturated sodium bicarbonate and brine. The organic phase was dried over sodium sulfate, filtered and solvent removed in vacuo.

The product was transferred to a vial using dichloromethane and the solvent removed using a nitrogen sweep. The product was dried in vacuo at room temperature to yield 0.114 g of an orange amorphous film.

$^1$H NMR (500 MHz, CHLOROFORM-D) δ ppm 1.18 (d, J=11.29 Hz, 1H) 1.25 (t, J=7.17 Hz, 2H) 1.39 (t, J=7.02 Hz, 5H) 1.45-1.58 (m, 3H) 1.60 (s, 9H) 1.62-1.66 (m, 1H) 1.69-1.86 (m, 3H) 1.86-2.02 (m, 3H) 2.02-2.08 (m, 5H) 2.09 (s, 1H) 2.68-2.77 (m, 1H) 3.83 (s, 3H) 4.37 (q, J=7.02 Hz, 2H) 4.67 (d, J=14.95 Hz, 1H) 5.17 (d, J=14.65 Hz, 1H) 5.67 (d, J=4.58 Hz, 1H) 6.29 (s, 1H) 6.73 (d, J=2.44 Hz, 1H) 6.98 (dd, J=8.55, 2.75 Hz, 1H) 7.41 (d, J=8.85 Hz, 1H) 7.54 (d, J=5.19 Hz, 1H) 7.71 (dd, J=8.39, 1.37 Hz, 1H) 7.89 (d, J=8.55 Hz, 1H) 7.95 (s, 1H) 8.16 (s, 1H) 8.30 (s, 1H).

LC-MS retention time 2.75 min; 673 m/z (MH+). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H$_2$O/10 mM ammonium acetate and solvent B was 5% H$_2$O/95% acetonitrile/10 mM ammonium acetate. MS data was determined using a MICROMASS® Platform for LC in electrospray mode.

7H-Indolo[2,1-a][2]benzazepine-10-carboxylic acid, 13-cyclohexyl-6-[4-(ethoxycarbonyl)-1-(3-methyl-4-pyridinyl)-1H-pyrazol-5-yl]-3-methoxy-

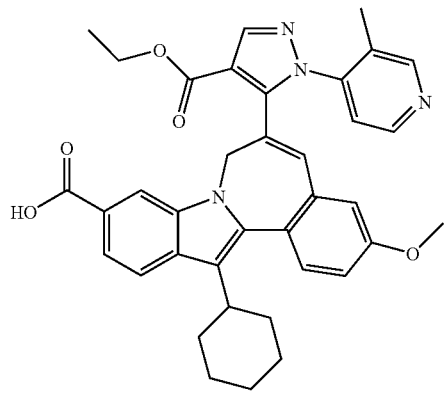

Dissolve 7H-indolo[2,1-a][2]benzazepine-10-carboxylic acid, 13-cyclohexyl-6-[4-(ethoxycarbonyl)-1-(3-methyl-4-pyridinyl)-1H-pyrazol-5-yl]-3-methoxy-, 1,1-dimethylethyl ester (1.233 g, 1.833 mmol) in 1,2-dichloroethane (10 mL) then add trifluoroacetic acid (10.00 mL). The reaction was placed under an inert nitrogen atmosphere and stirred at room temperature for 2 hours. The volatiles were removed from the reaction in vacuo using a rotary evaporator. The product was dissolved in approximately 125 ml of ethyl acetate and washed two times with 75 ml of aqueous 1.0N hydrochloric acid. The aqueous layers were combined and backed extracted with ethyl acetate. The organic extracts were combined and washed with brine and dried over magnesium sulfate, filtered and the solvent removed in vacuo to give an amorphous orange solid. To aid in trace water removal, the product was dissolved in dichloromethane and benzene added to the solution. The volatiles were removed in vacuo using a rotary evaporator. The product was re-dissolved in dichloromethane and solvent removed in vacuo to give a amorphous orange foam (1.28 g).

Analytical grade sample was purified by reverse phase HPLC: The sample was purified on a Shimadzu high pressure liquid chromatography system employing DISCOVERY VP® software interfaced with a SCL-10A controller, SIL-10A autosampler and FRC-10A fraction collector. The sample (40 mg) was dissolved in acetonitrile/DMF (1:1) (2 ml) purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 80% solvent A/20% solvent B to 0% solvent A/100% solvent B, a gradient time of 20 minutes with a run time of 25 minutes using % A=10% acetonitrile, 90% water, 0.1% TFA % B=90% acetonitrile, 10% water, 0.1% TFA solvent system.

Retention time of product is 11.5 minutes. Remove volatiles from product in vacuo using a rotary evaporator then transfer to a vial in dichloromethane. Dichloromethane was removed using a nitrogen sweep. The yellow amorphous solid was dried in vacuo at room temperature overnight to give 24.7 mg of the title compound.

$^1$H NMR (500 MHz, CHLOROFORM-D) δ ppm 1.10-1.23 (m, 1H) 1.34-1.48 (m, 6H) 1.77 (d, J=6.71 Hz, 1H) 1.82 (d, J=13.12 Hz, 1H) 1.88-2.01 (m, 2H) 2.01-2.15 (m, 2H) 2.36 (s, 3H) 2.71-2.80 (m, 1H) 3.87 (s, 3H) 4.41 (q, J=7.12 Hz, 2H) 4.72 (d, J=15.56 Hz, 1H) 5.05 (d, J=15.26 Hz, 1H) 6.14 (d, J=5.80 Hz, 1H) 6.55 (s, 1H) 6.84 (d, J=2.44 Hz, 1H) 7.05 (dd, J=8.55, 2.75 Hz, 1H) 7.44 (d, J=8.55 Hz, 1H) 7.54 (d, J=5.80 Hz, 1H) 7.83 (dd, J=8.39, 1.37 Hz, 1H) 7.88 (s, 1H) 7.94 (d, J=8.54 Hz, 1H) 8.22 (s, 1H) 8.56 (s, 1H).

LC-MS retention time 1.90 min; 615 m/z (MH−). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H$_2$O/10 mM ammonium acetate and solvent B was 5% H$_2$O/95% acetonitrile/10 mM ammonium acetate. MS data was determined using a MICROMASS® Platform for LC in electrospray mode.

1H-Pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-(3-methyl-4-pyridinyl)-, ethyl ester

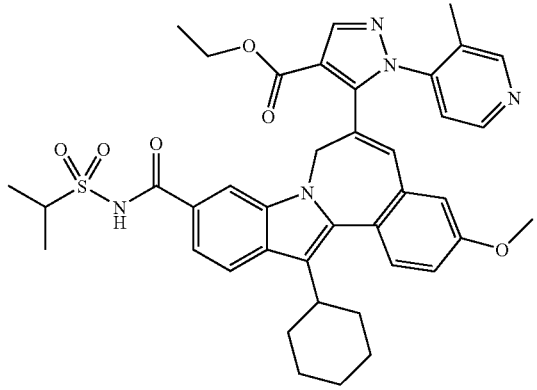

In a 50 ml round bottom flask dissolve starting acid 7H-indolo[2,1-a][2]benzazepine-10-carboxylic acid, 13-cyclohexyl-6-[4-(ethoxycarbonyl)-1-(3-methyl-4-pyridinyl)-1H-pyrazol-5-yl]-3-methoxy-*HCl (776 mg, 1.188 mmol) in THF (11.9 mL). To the reaction add CDI (487 mg, 3.01 mmol) then stir the reaction under a nitrogen atmosphere at room temperature for 1 hour. The reaction was then heated at reflux for 45 minutes. The reaction was cooled under a nitrogen atmosphere and propane-2-sulfonamide (766 mg, 6.22 mmol) was added followed by DBU (0.537 mL, 3.56 mmol) and the reaction was again heated to 70° C. under a nitrogen atmosphere for 17 hrs. The reaction was cooled and diluted with ethyl acetate, washed with 1.0N aqueous hydrochloric acid. Upon sitting material is precipitating out of the organic phase, Drain off aqueous layer and decant mostly solid from separatory funnel. Attempts to complete solubilize material by addition of dichloromethane and THF was not successful. Combine organic layers and remove solvents in vacuo to obtain 1.25 g as a paste like yellow brownish solid. The material was purified by trituration. The solid reaction residue was heated to reflux in 20 ml of methanol then 7 ml of de-ionized water added. The material was allowed to cool and stand for 1.5 hours then filtered. The mustard colored precipitate was rinsed with a small amount of 15% water in methanol (% v/v). The product was dried in vacuo at room temperature to give 445 mg of a mustard yellow solid. A second crop of product was obtained from the mother liquor by dissolving with the addition of methanol and the subsequent concentration in vacuo using a rotary evaporator. The mustard yellow precipitate formed was filtered and rinsed with a small amount of 30% methanol/70% water (v/v) mixture then dried in vacuo at room temperature to yield 238 mg of a second crop of product.

$^1$H NMR (500 MHz, DMSO-D6) δ ppm 0.66-0.90 (m, 1H) 0.92-1.18 (m, 3H) 1.18-1.27 (m, 5H) 1.27-1.46 (m, 10H) 1.65-1.78 (m, 3H) 1.81-1.91 (m, 2H) 1.93-2.09 (m, 6H) 2.60-2.70 (m, 1H) 3.82 (s, 3H) 3.84-3.91 (m, 1H) 4.10-4.35 (m, 2H) 4.50 (d, J=14.65 Hz, 1H) 5.05 (s, 2H) 5.22 (d, J=14.34 Hz, 2H) 6.26 (s, 1H) 6.80 (s, 1H) 7.01 (s, 1H) 7.14 (dd, J=8.55, 2.75 Hz, 1H) 7.41 (d, J=8.55 Hz, 1H) 7.62 (d, J=8.55 Hz, 2H) 7.89 (d, J=8.55 Hz, 1H) 8.18 (s, 1H) 8.28 (s, 2H) 11.62 (s, 1H).

LC-MS retention time 1.95 min; 720 m/z (MH−). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H$_2$O/10 mM ammonium acetate and solvent B was 5% H$_2$O/95% acetonitrile/10 mM ammonium acetate. MS data was determined using a MICROMASS® Platform for LC in electrospray mode.

1H-Pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-(3-methyl-4-pyridinyl)-

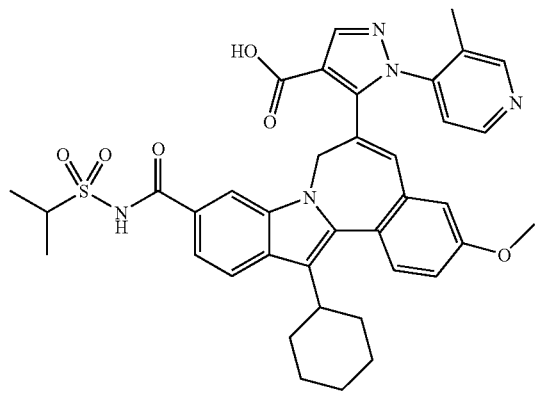

1H-Pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-(3-methyl-4-pyridinyl)-, ethyl ester* HCl (238 mg, 0.314 mmol) was dissolved in THF (3.3 mL) then methanol (3.3 mL) and sodium hydroxide (3.3 mL, 3.30 mmol) was added to the reaction. The reaction was capped under a nitrogen atmosphere and stirred at room temperature for 19 hrs. The reaction was diluted with ethyl acetate (125 ml) and washed with 1.0N aqueous hydrochloric acid. The aqueous layers were combined and back extracted 1× with ethyl acetate. The organic layers were combined and washed sequentially with 1.0N aqueous hydrochloric acid and brine. The organic phase was dried over MgSO$_4$, filtered and solvent removed in vacuo. The sample was dried in vacuo at room temperature to give 232 mg of product as a amorphous orange/amber solid.

A small analytical grade sample was purified by reverse phase HPLC. The 89 mg of product was purified on a Shimadzu high pressure liquid chromatography system employing DISCOVERY VP® software interfaced with a SCL-10A controller, SIL-10A autosampler and FRC-10A fraction collector. The sample was dissolved in acetonitrile/DMF (1:1) (2 mL) and purified using a Waters Sunfire Prep C18 OBD, 5 uM 19 mm×100 mm column and monitored using a SPD-10AV Uv-V is detector at a detector wave length of 220 nM. The elution conditions employed a flow rate of 25 mL/min, a gradient of 80% solvent A/20% solvent B to 0% solvent A/100% solvent B, a gradient time of 20 minutes with a run time of 20 minutes using % A=10% acetonitrile, 90% water, 0.1% TFA % B=90% acetonitrile, 10% water, 0.1% TFA solvent system. Product peak eluted as broad peak collected from 9.97 min to 11.18 min. Remove volatiles for product fractions in vacuo using a SPEED VAC® with heat on low setting. The purified title compound was isolated (49.8 mg) as a amorphous yellow solid. The remainder of the reaction product was carried forward into amide coupling reactions without further purification. The $^1$H NMR sample was prepared by dissolution in CDCl$_3$ (1.5 ml) then the addition of CD3OD (6 drops) to achieve complete solubilization.

$^1$H NMR (500 MHz, CHLOROFORM-D/CD3OD) δ ppm 1.06-1.20 (m, 1H) 1.27-1.36 (m, 2H) 1.36-1.44 (m, 7H) 1.65-1.77 (m, 2H) 1.81-1.94 (m, 2H) 1.95-2.07 (m, 5H) 2.60-2.73 (m, 1H) 3.31-3.48 (m, 9H) 3.78 (s, 3H) 3.92-4.01 (m, 1H) 4.60 (d, J=14.95 Hz, 1H) 5.12 (d, J=14.65 Hz, 1H) 5.74 (d, J=5.19 Hz, 1H) 6.32 (s, 1H) 6.71 (d, J=2.44 Hz, 1H) 6.94 (dd, J=8.70, 2.59 Hz, 1H) 7.34 (d, J=8.55 Hz, 1H) 7.41 (d, J=5.19 Hz, 1H) 7.54 (dd, J=8.55, 1.22 Hz, 1H) 7.83-7.89 (m, 2H) 8.12 (s, 1H) 8.20 (s, 1H).

LC-MS retention time 1.23 min; 692 m/z (MH−). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H$_2$O/10 mM ammonium acetate and solvent B was 5% H$_2$O/95% acetonitrile/10 mM ammonium acetate. MS data was determined using a MICROMASS® Platform for LC in electrospray mode.

7H-Indolo[2,1-a][2]benzazepine-10-carboxamide, 13-cyclohexyl-3-methoxy-N-[(1-methylethyl)sulfonyl]-6-[1-(3-methyl-4-pyridinyl)-4-(4-morpholinylcarbonyl)-1H-pyrazol-5-yl]-

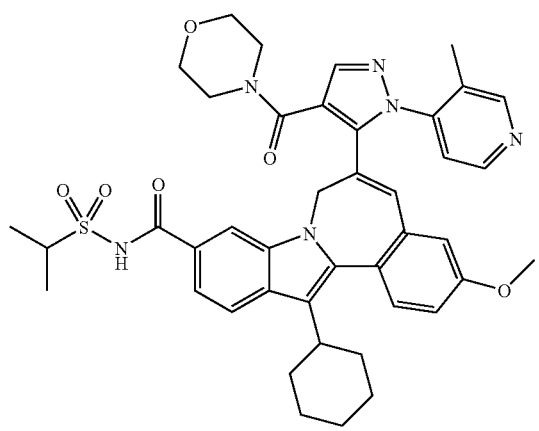

1H-Pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-(3-methyl-4-pyridinyl)-*HCl (69.1 mg, 0.095 mmol) was dissolved in DMF (946 μL) and HATU (81 mg, 0.213 mmol) added to the reaction. The reaction was capped under a nitrogen atmosphere and stirred at room temperature for 1 hr. DMAP (48.5 mg, 0.397 mmol) was added to the reaction followed by the amine reagent, morpholine (25.0 μL, 0.287 mmol). The reaction was capped under a nitrogen atmosphere and stirred at room temperature for 36 hrs. The product was purified on a Shimadzu high pressure liquid chromatography system employing DISCOVERY VP® software interfaced with a SCL-10A controller, SIL-10A autosampler and FRC-10A fraction collector. The reaction was diluted to 2 ml with acetonitrile and purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 80% solvent A/20% solvent B to 0% solvent A/100% solvent B, a gradient time of 20 minutes with a run time of 20 minutes using % A=10% acetonitrile, 90% water, 0.1% TFA % B=90% acetonitrile, 10% water, 0.1% TFA solvent system. Retention time is 10.2 minutes. Remove volatiles for product fractions in vacuo using a SPEED VAC® with heat on low setting. The title compound (48.9 mg) was isolated as a amorphous yellow solid trifluoroacetic acid salt.

$^1$H NMR (500 MHz, CHLOROFORM-D) δ ppm 1.15-1.29 (m, 1H) 1.33-1.45 (m, 2H) 1.50 (d, J=6.71 Hz, 3H) 1.54 (d, J=6.71 Hz, 3H) 1.72-1.87 (m, 2H) 1.88-2.11 (m, 4H) 2.77-2.87 (m, 1H) 3.33 (s, 6H) 3.53 (s, 2H) 3.87 (s, 3H) 3.99-4.07 (m, 1H) 4.49 (d, J=15.26 Hz, 1H) 4.80 (d, J=14.95 Hz, 1H) 6.25 (s, 2H, TFA/H$_2$O) 6.71 (s, 1H) 6.83 (s, 1H) 6.97 (d, J=4.88 Hz, 1H) 7.07 (dd, J=8.55, 2.75 Hz, 1H) 7.40-7.51 (m, 3H) 7.84 (d, J=8.55 Hz, 1H) 7.87-7.95 (m, 2H) 8.55 (s, 1H) 9.86 (s, 1H).

LC-MS retention time 1.19 min; 761 m/z (MH−). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H$_2$O/10 mM ammonium acetate and solvent B was 5% H$_2$O/95% acetonitrile/10 mM ammonium acetate. MS data was determined using a MICROMASS® Platform for LC in electrospray mode.

7H-Indolo[2,1-a][2]benzazepine-10-carboxamide, 13-cyclohexyl-3-methoxy-6-[4-[(8-methyl-3,8-diazabicyclo[3.2.1]oct-3-yl)carbonyl]-1-(3-methyl-4-pyridinyl)-1H-pyrazol-5-yl]-N-[(1-methylethyl)sulfonyl]-

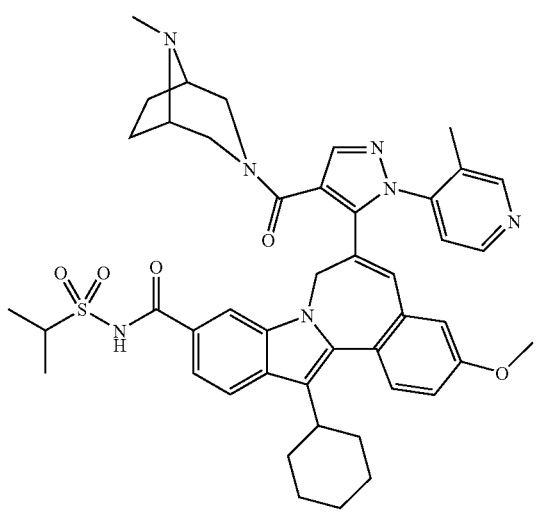

1H-Pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-(3-methyl-4-pyridinyl)-*HCl (71.0 mg, 0.097 mmol) was dissolved in DMF (972 μL) and HATU (81.5 mg, 0.214 mmol) added to the reaction. The reaction was capped under a nitrogen atmosphere and stirred at room temperature for 1 hr. DMAP (62.0 mg, 0.507 mmol) was added to the reaction followed by the amine reagent, 8-methyl-3,8-diazabicyclo[3.2.1]octane dihydrochloride (40.1 mg, 0.201 mmol). The reaction was capped under a nitrogen atmosphere and stirred at room temperature for 36 hrs. The product was purified on a Shimadzu high pressure liquid chromatography system employing DISCOVERY VP® software interfaced with a SCL-10A controller, SIL-10A autosampler and FRC-10A fraction collector. The reaction was diluted to 2 ml with acetonitrile and purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 80% solvent A/20% solvent B to 0% solvent A/100% solvent B, a gradient time of 20 minutes with a run time of 20 minutes using % A=10% acetonitrile, 90% water, 0.1% TFA % B=90% acetonitrile, 10% water, 0.1% TFA solvent system. The product peak appears to be rotomeric with splitting and broadening, retention time is 6.18 to 7.33 minutes. Remove volatiles for product fractions in vacuo using a SPEED VAC® with heat on low setting. The title compound (61.9 mg) was isolated as a amorphous yellow solid trifluoroacetic acid salt.

¹H NMR (500 MHz, CHLOROFORM-D) δ ppm 1.07-1.28 (m, 2H) 1.37 (s, 3H) 1.44-1.64 (m, 6H) 1.79 (d, J=17.40 Hz, 3H) 1.85-2.23 (m, 6H) 2.47 (s, 3H) 2.66-3.16 (m, 4H) 3.49 (s, 3H) 3.85 (s, 3H) 3.94 (s, 1H) 4.39 (s, 2H) 4.91 (s, 2H) 6.86 (s, 2H) 6.94-7.19 (m, 2H) 7.29-7.49 (m, 2H) 7.64-8.13 (m, 3H) 8.29 (s, 1H).

LC-MS retention time 1.26 min; 800 m/z (MH−). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H₂O/10 mM ammonium, acetate and solvent B was 5% H₂O/95% acetonitrile/10 mM ammonium acetate. MS data was determined using a MICROMASS® Platform for LC in electrospray mode.

7H-Indolo[2,1-a][2]benzazepine-10-carboxamide, 13-cyclohexyl-3-methoxy-6-[4-[[(2S)-2-(methoxymethyl)-4-morpholinyl]carbonyl]-1-(3-methyl-4-pyridinyl)-1H-pyrazol-5-yl]-N-[(1-methylethyl)sulfonyl]-

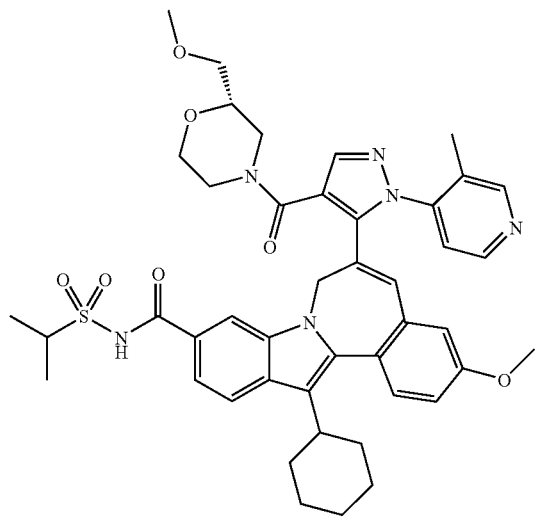

1H-Pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-(3-methyl-4-pyridinyl)-*HCl (65.0 mg, 0.089 mmol) was dissolved in DMF (890 μL) and HATU (77 mg, 0.203 mmol) added to the reaction. The reaction was capped under a nitrogen atmosphere and stirred at room temperature for 2 hr. DMAP (49.4 mg, 0.404 mmol) was added to the reaction followed by the amine reagent, (S)-2-(methoxymethyl)morpholine hydrochloride (34.7 mg, 0.207 mmol). The reaction was capped under a nitrogen atmosphere and stirred at room temperature over weekend (65 hrs). The product was purified on a Shimadzu high pressure liquid chromatography system employing DISCOVERY VP® software interfaced with a SCL-10A controller, SIL-10A autosampler and FRC-10A fraction collector. The reaction was diluted to 2 ml with acetonitrile and purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 80% solvent A/20% solvent B to 0% solvent A/100% solvent B, a gradient time of 20 minutes with a run time of 20 minutes using % A=10% acetonitrile, 90% water, 0.1% TFA % B=90% acetonitrile, 10% water, 0.1% TFA solvent system. Retention time of product was 10.4 minutes. Remove volatiles for product fractions in vacuo using a SPEED VAC® with heat on low setting. The title compound (56.2 mg) was isolated as a amorphous yellow solid trifluoroacetic acid salt.

¹H NMR (500 MHz, CHLOROFORM-D) δ ppm 1.10-1.29 (m, 1H) 1.32-1.44 (m, 2H) 1.52 (dd, J=21.82, 6.87 Hz, 6H) 1.73-1.87 (m, 2H) 1.88-2.12 (m, 4H) 2.32-2.45 (m, 3H) 2.82 (t, J=11.75 Hz, 2H) 3.12-3.42 (m, 5H) 3.50 (s, 1H) 3.68 (s, 1H) 3.86 (s, 3H) 3.99-4.12 (m, 1H) 4.48 (d, J=14.95 Hz, 1H) 4.72-4.92 (m, 1H) 5.66 (d, J=1.53 Hz, 2H) 6.41-6.89 (m, 2H) 6.96 (s, 1H) 7.05 (dd, J=8.70, 2.59 Hz, 1H) 7.45 (d, J=8.55 Hz, 2H) 7.53 (s, 1H) 7.80-7.92 (m, 2H) 8.56 (s, 1H) 9.90 (s, 1H).

LC-MS retention time 1.61 min; 805 m/z (MH−). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H₂O/10 mM ammonium acetate and solvent B was 5% H₂O/95% acetonitrile/10 mM ammonium acetate. MS data was determined using a MICROMASS® Platform for LC in electrospray mode.

7H-Indolo[2,1-a][2]benzazepine-10-carboxamide, 13-cyclohexyl-6-[4-(3,7-dioxa-9-azabicyclo[3.3.1]non-9-ylcarbonyl)-1-(3-methyl-4-pyridinyl)-1H-pyrazol-5-yl]-3-methoxy-N-[(1-methylethyl)sulfonyl]-

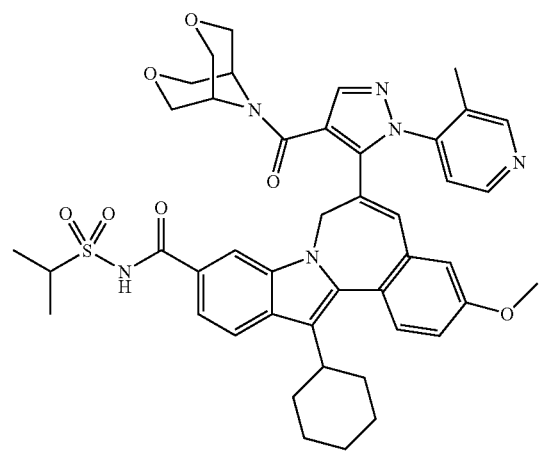

1H-Pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-(3-methyl-4-pyridinyl)-*HCl (66.9 mg, 0.092 mmol) was dissolved in DMF (916 μL) and HATU (103 mg, 0.271 mmol) added to the reaction. The reaction was capped under a nitrogen atmosphere and stirred at room temperature for 2 hr. DMAP (46.1 mg, 0.377 mmol) was added to the reaction followed by the amine reagent, 3,7-dioxa-9-azabicyclo[3.3.1]nonane hydrochloride (38.0 mg, 0.229 mmol). The reaction was capped under a nitrogen atmosphere and stirred at room temperature over weekend (65 hrs). The reaction appeared heterogeneous and an LCMS assay of the reaction indicated an incomplete reaction. HATU (70 mg, 0.184 mmol) was added and the reaction was capped under a nitrogen atmosphere and stirred at room temperature for 24 hrs. The reaction was again assayed using LCMS and the hydroxyazabenztriazole adduct of the acid starting material was observed. DMF (100 uL) was added to the reaction followed by 3,7-dioxa-9-azabicyclo[3.3.1]nonane hydrochloride (16.4 mg, 0.099 mmol) then DMAP (14.6 mg, 0.120 mmol). The reaction was capped under a nitrogen atmosphere and stirred at room temperature for 42 hrs. The product was purified on a Shimadzu high pressure liquid chromatography system employing DISCOVERY VP® software interfaced with a SCL-10A controller, SIL-10A autosampler and FRC-10A fraction collector. The reaction was diluted to 4 ml with acetonitrile and a few drops of water were added to completely solubilize the mixture. The reaction solution was filtered through a 0.45 uM syringe filter and filtrate solution was purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 80% solvent A/20% solvent B to 0% solvent A/100% solvent B, a gradient time of 20 minutes with a run time of 20 minutes using % A=10% acetonitrile, 90% water, 0.1% TFA % B=90% acetonitrile, 10% water, 0.1% TFA solvent system. Remove solvent-volatiles from product fractions in vacuo using SPEED VAC® on medium heat setting. The title compound (51.6 mg) was isolated as a amorphous yellow solid trifluoroacetic acid salt.

¹H NMR (500 MHz, CHLOROFORM-D) δ ppm 1.13-1.30 (m, 1H) 1.32-1.45 (m, 2H) 1.51 (dd, J=20.91, 6.87 Hz, 6H) 1.73-1.86 (m, 2H) 1.89-2.09 (m, 4H) 2.44 (s, 3H) 2.77-2.86 (m, 1H) 3.68 (s, 3H) 3.88 (s, 3H) 3.91-4.11 (m, 5H) 4.34 (s, 1H) 4.51 (d, J=14.95 Hz, 1H) 4.81 (d, J=14.95 Hz, 1H) 6.77 (s, 1H) 6.86-6.99 (m, 2H) 7.08 (dd, J=8.70, 2.59 Hz, 1H) 7.39-7.49 (m, 3H) 7.78 (s, 1H) 7.83 (d, J=8.24 Hz, 1H) 7.87 (s, 1H) 8.50 (s, 1H) 9.80 (s, 1H).

LC-MS retention time 1.55 min; 803 m/z (MH−). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H₂O/10 mM ammonium acetate and solvent B was 5% H₂O/95% acetonitrile/10 mM ammonium acetate. MS data was determined using a MICROMASS® Platform for LC in electrospray mode.

13-Cyclohexyl-N-(isopropylsulfonyl)-3-methoxy-6-(1-(3-methyl-4-pyridinyl)-4-(3-oxa-9-azabicyclo[3.3.1]non-9-ylcarbonyl)-1H-pyrazol-5-yl)-7H-indolo[2,1-a][2]benzazepine-10-carboxamide

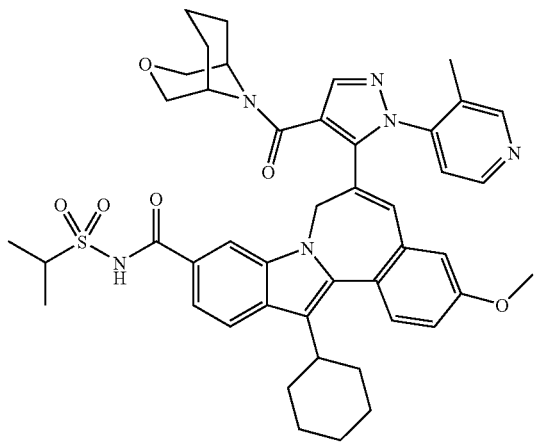

1H-Pyrazolecarboxylic acid, 5-[13-cyclohexyl-3-methoxy-10-[[[(1-methylethyl)sulfonyl]amino]carbonyl]-7H-indolo[2,1-a][2]benzazepin-6-yl]-1-(3-methyl-4-pyridinyl)-*HCl (65.6 mg, 0.090 mmol) was dissolved in DMF (898 μL) and HATU (76.4 mg, 0.201 mmol) added to the reaction. The reaction was capped under a nitrogen atmosphere and stirred at room temperature for 2 hr. DMAP (51.5 mg, 0.422 mmol) was added to the reaction followed by the amine reagent, 3-oxa-9-azabicyclo[3.3.1]nonane hydrochloride (32.8 mg, 0.200 mmol). The reaction was capped under a nitrogen atmosphere and stirred at room temperature over weekend (65 hrs). The product was purified on a Shimadzu high pressure liquid chromatography system employing DISCOVERY VP® software interfaced with a SCL-10A controller, SIL-10A autosampler and FRC-10A fraction collector. The reaction was diluted to 2 ml with acetonitrile and purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 80% solvent A/20% solvent B to 0% solvent A/100% solvent B, a gradient time of 20 minutes with a run time of 20 minutes using % A=10% acetonitrile, 90% water, 0.1% TFA % B=90% acetonitrile, 10% water, 0.1% TFA solvent system. Retention time of product was approximately 12.0 minutes. Remove volatiles from the product fraction in vacuo using a SPEED VAC® set on low heat. The title compound (58.2 mg) was isolated as a amorphous yellow solid trifluoroacetic acid salt. ¹H NMR spectrum exhibits characteristics of restricted rotation with broadening of peaks and splitting of peaks.

¹H NMR (500 MHz, CHLOROFORM-D) δ ppm 1.12-1.30 (m, 1H) 1.29-1.67 (m, 11H) 1.79 (s, 4H) 1.86-2.13 (m, 5H) 2.41 (d, J=16.48 Hz, 4H) 2.77-2.89 (m, 1H) 3.31-3.81 (m, 4H) 3.86 (d, J=12.82 Hz, 3H) 3.92 (d, J=11.90 Hz, 0.6H) 4.01-4.09 (m, 1H) 4.37-4.56 (m, 1H) 4.87 (dd, J=32.96, 14.65 Hz, 1H) 5.82 (s, 2H) 6.42-6.78 (m, 1H) 6.83-6.97 (m, 1H) 7.02-7.10 (m, 1H) 7.41-7.62 (m, 3H) 7.79-7.90 (m, 2H) 8.55 (d, J=30.21 Hz, 1H) 9.95 (s, 0.3H) 10.21 (s, 0.4H).

LC-MS retention time 1.80 min; 801 m/z (MH−). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H$_2$O/10 mM ammonium acetate and solvent B was 5% H$_2$O/95% acetonitrile/10 mM ammonium acetate. MS data was determined using a MICROMASS® Platform for LC in electrospray mode.

7H-Indolo[2,1-a][2]benzazepine-10-carboxamide, 13-cyclohexyl-6-[4-[[(2R,6S)-2,6-dimethyl-4-morpholinyl]carbonyl]-1-(3-methyl-4-pyridinyl)-1H-pyrazol-5-yl]-3-methoxy-N-[(1-methylethyl)sulfonyl]-

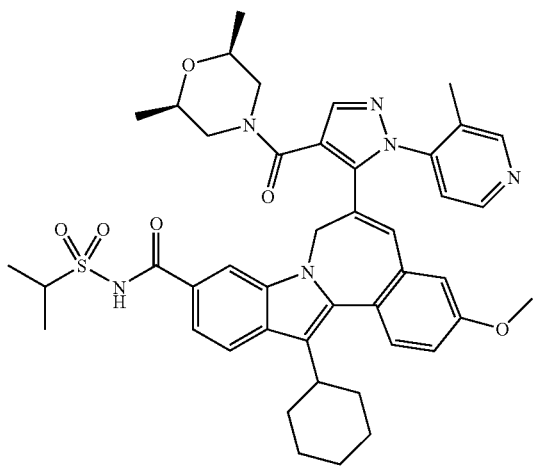

1H-Pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-(3-methyl-4-pyridinyl)-*HCl (65.5 mg, 0.090 mmol) was dissolved in DMF (897 µL) and HATU (77.3 mg, 0.203 mmol) added to the reaction. The reaction was capped under a nitrogen atmosphere and stirred at room temperature for 2 hr. DMAP (43.5 mg, 0.356 mmol) was added to the reaction followed by the amine reagent, (2R,6S)-2,6-dimethylmorpholine (33.3 µL, 0.269 mmol). The reaction was capped under a nitrogen atmosphere and stirred at room temperature over weekend (65 hrs). The product was purified on a Shimadzu high pressure liquid chromatography system employing DISCOVERY VP® software interfaced with a SCL-10A controller, SIL-10A autosampler and FRC-10A fraction collector. The reaction was diluted to 2 ml with acetonitrile and purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 80% solvent A/20% solvent B to 0% solvent A/100% solvent B, a gradient time of 20 minutes with a run time of 20 minutes using % A=10% acetonitrile, 90% water, 0.1% TFA % B=90% acetonitrile, 10% water, 0.1% TFA solvent system. Retention time of product was 11.8 min.

Remove volatiles from the product fraction in vacuo using a SPEED VAC® set on low heat. The title compound (56.9 mg) was isolated as a amorphous yellow solid trifluoroacetic acid salt. $^1$H NMR spectrum exhibits characteristics of restricted rotation with broadening of peaks and splitting of peaks.

$^1$H NMR (500 MHz, CHLOROFORM-D) δ ppm 0.79-0.98 (m, 2H) 1.07 (s, 3H) 1.14-1.30 (m, 2H) 1.32-1.46 (m, 2H) 1.52 (dd, J=21.67, 6.71 Hz, 6H) 1.73-1.87 (m, 2H) 1.88-2.12 (m, 4H) 2.33 (s, 1H) 2.50 (s, 3H) 2.78-2.90 (m, 1H) 3.39 (s, 0.1H) 3.56 (s, 1H) 3.88 (s, 3H) 3.98-4.10 (m, 1H) 4.48 (s, 1H) 4.76 (s, 1H) 6.40 (s, 3H) 6.70 (s, 1H) 6.80 (s, 1H) 6.97 (s, 1H) 7.08 (dd, J=8.85, 2.75 Hz, 1H) 7.35-7.50 (m, 2H) 7.53 (s, 0.5H) 7.69 (s, 0.4H) 7.83 (d, J=5.19 Hz, 1H) 7.88 (s, 1H) 8.56 (d, J=48.83 Hz, 1H) 9.82 (s, 1H).

LC-MS retention time 1.75 min; 789 m/z (MH−). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H$_2$O/10 mM ammonium acetate and solvent B was 5% H$_2$O/95% acetonitrile/10 mM ammonium acetate. MS data was determined using a MICROMASS® Platform for LC in electrospray mode.

7H-Indolo[2,1-a][2]benzazepine-10-carboxamide, 13-cyclohexyl-3-methoxy-N-[(1-methylethyl)sulfonyl]-6-[1-(3-methyl-4-pyridinyl)-4-[[(3R,5S)-3,4,5-trimethyl-1-piperazinyl]carbonyl]-1H-pyrazol-5-yl]-

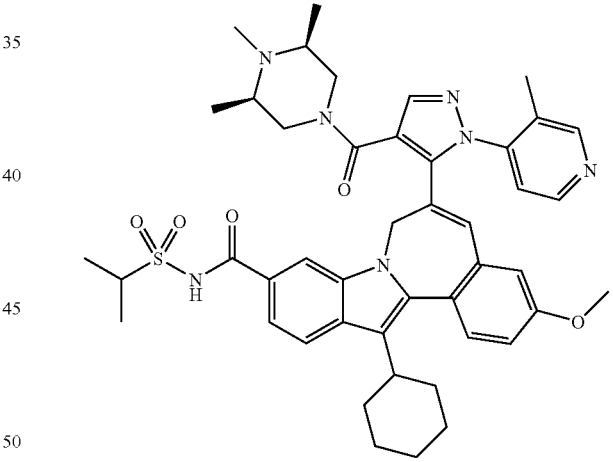

1H-Pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-(3-methyl-4-pyridinyl)-*HCl (66.4 mg, 0.091 mmol) was dissolved in DMF (909 µL) and HATU (78.4 mg, 0.206 mmol) added to the reaction. The reaction was capped under a nitrogen atmosphere and stirred at room temperature for 2 hr. DMAP (61.4 mg, 0.503 mmol) was added to the reaction followed by the amine reagent, (2R,6S)-1,2,6-trimethylpiperazine dihydrochloride (40.4 mg, 0.201 mmol). The reaction was capped under a nitrogen atmosphere and stirred at room temperature over weekend (65 hrs). The product was purified on a Shimadzu high pressure liquid chromatography system employing DISCOVERY VP® software interfaced with a SCL-10A controller, SIL-10A autosampler and FRC-10A fraction collector. The reaction was diluted to 4 ml with acetonitrile with the addition of 1.0N aqueous hydrochloric acid. The reaction solution was filtered through a 0.45 uM syringe filter and purified using a Waters Sunfire Prep C18 OBD, 5 uM 19 mm×100 nm column and monitored using a SPD-10AV UV-Vis detector at a detector wave length of 220 nM. The elution conditions employed a flow rate of 25 mL/min, a gradient of 80% solvent A/20% solvent B to 0% solvent A/100% solvent B, a gradient time of 20 minutes with a run time of 20 minutes using % A=10% acetonitrile, 90% water, 0.1% TFA % B=90% acetonitrile, 10% water, 0.1% TFA solvent system.

Two 2 ml injection were performed for purification. Retention time of product was 6.0 min. Remove volatiles from the product fractions in vacuo using a SPEED VAC® set on low heat. The title compound (60.4 mg) was isolated as a amorphous yellow solid trifluoroacetic acid salt. $^1$H NMR spectrum exhibits characteristics of restricted rotation\salt formation with broadening of peaks and splitting of peaks.

$^1$H NMR (500 MHz, CHLOROFORM-D) δ ppm 1.12-1.29 (m, 1H) 1.29-1.67 (m, 9H) 1.72-1.87 (m, 1H) 1.87-2.10 (m, 3H) 2.31 (s, 2H) 2.68-2.85 (m, 1H) 2.91 (s, 2H) 3.14 (s, 1H) 3.42 (s, 1H) 3.86 (s, 3H) 3.92-4.09 (m, 1H) 4.47 (d, J=13.73 Hz, 1H) 4.72-4.91 (m, 1H) 6.58-6.93 (m, 2H) 7.03 (d, J=8.24 Hz, 1H) 7.33-7.72 (m, 4H) 7.82 (d, J=7.93 Hz, 1H) 7.89 (s, 1H) 8.43 (s, 1H) 9.72 (s, 1H) 11.69 (s, 2H).

LC-MS retention time 1.61 min; 802 m/z (MH−). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H$_2$O/10 mM ammonium acetate and solvent B was 5% H$_2$O/95% acetonitrile/10 mM ammonium acetate. MS data was determined using a MICROMASS® Platform for LC in electrospray mode.

7H-Indolo[2,1-a][2]benzazepine-10-carboxamide, 13-cyclohexyl-6-[4-[(3-hydroxy-3-methyl-8-azabicyclo[3.2.1]oct-8-yl)carbonyl]-1-(3-methyl-4-pyridinyl)-1H-pyrazol-5-yl]-3-methoxy-N-[(1-methylethyl)sulfonyl]-

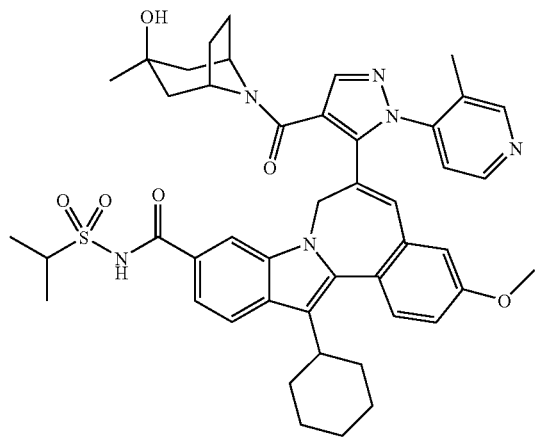

1H-Pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-(3-methyl-4-pyridinyl)-*HCl (69.2 mg, 0.095 mmol) was dissolved in DMF (474 μL) and HATU (90 mg, 0.237 mmol) added to the reaction. The reaction was capped under a nitrogen atmosphere and stirred at room temperature for 2 hr. DMAP (52.8 mg, 0.432 mmol) was added to the reaction followed by the amine reagent, 3-methyl-8-azabicyclo[3.2.1]octan-3-ol hydrochloride (44 mg, 0.248 mmol) dissolved in DMF (474 μL). The reaction was capped under a nitrogen atmosphere and stirred at room temperature for 45 hr. Reaction became heterogeneous. Acetonitrile and a small amount of water were added to the reaction to achieve solubility. The 2 ml reaction mixture was filtered through a 0.45 uM syringe filter and the product filtrate solution was purified by reverse phase HPLC. The product was purified on a Shimadzu high pressure liquid chromatography system employing DISCOVERY VP® software interfaced with a SCL-10A controller, SIL-10A autosampler and FRC-10A fraction collector. Product purification was accomplished using a Waters Sunfire Prep C18 OBD, 5 uM 19 mm×100 mm column monitored using a SPD-10AV UV-Vis detector at a detector wave length of 220 nM. The elution conditions employed a flow rate of 25 mL/min, a gradient of 80% solvent A/20% solvent B to 0% solvent A/100% solvent B, a gradient time of 15 minutes with a run time of 20 minutes using % A=10% acetonitrile, 90% water, 0.1% TFA % B=90% acetonitrile, 10% water, 0.1% TFA solvent system. Retention time of product was 8.63 minutes. Remove solvent-volatiles from product fraction in vacuo using SPEED VAC® on medium heat setting. The title compound (42.8 mg) was isolated as a amorphous yellow solid trifluoroacetic acid salt. $^1$H NMR spectrum peakshape is rather broad, exhibiting splitting of peaks characteristic of restricted rotation and/or salt formation.

$^1$H NMR (500 MHz, CHLOROFORM-D) δ ppm 1.04 (s, 2H) 1.08-1.30 (m, 3H) 1.31-1.47 (m, 3H) 1.45-1.66 (m, 7H) 1.77 (d, J=10.68 Hz, 4H) 1.87-2.15 (m, 5H) 2.27 (s, 1H) 2.37 (s, 2H) 2.74-2.87 (m, 1H) 3.77-3.91 (m, 3H) 3.98-4.19 (m, 2H) 4.41-4.83 (m, 3H) 4.95 (s, 2H) 6.22-6.85 (m, 3H) 6.99-7.10 (m, 1H) 7.40-7.49 (m, 1H) 7.52-7.73 (m, 2H) 7.77-7.91 (m, 1H) 7.92-8.01 (m, 1H) 8.39-8.78 (m, 2H) 9.82 (s, 1H) 10.55 (s, 1H).

LC-MS retention time 1.68 min; 815 m/z (MH−). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H$_2$O/10 mM ammonium acetate and solvent B was 5% H$_2$O/95% acetonitrile/10 mM ammonium acetate. MS data was determined using a MICROMASS® Platform for LC in electrospray mode.

7H-Indolo[2,1-a][2]benzazepine-10-carboxylic acid, 13-cyclohexyl-6-[4-(ethoxycarbonyl)-1-(tetrahydro-2H-pyran-4-yl)-1H-pyrazol-5-yl]-3-methoxy-, 1,1-dimethylethyl ester

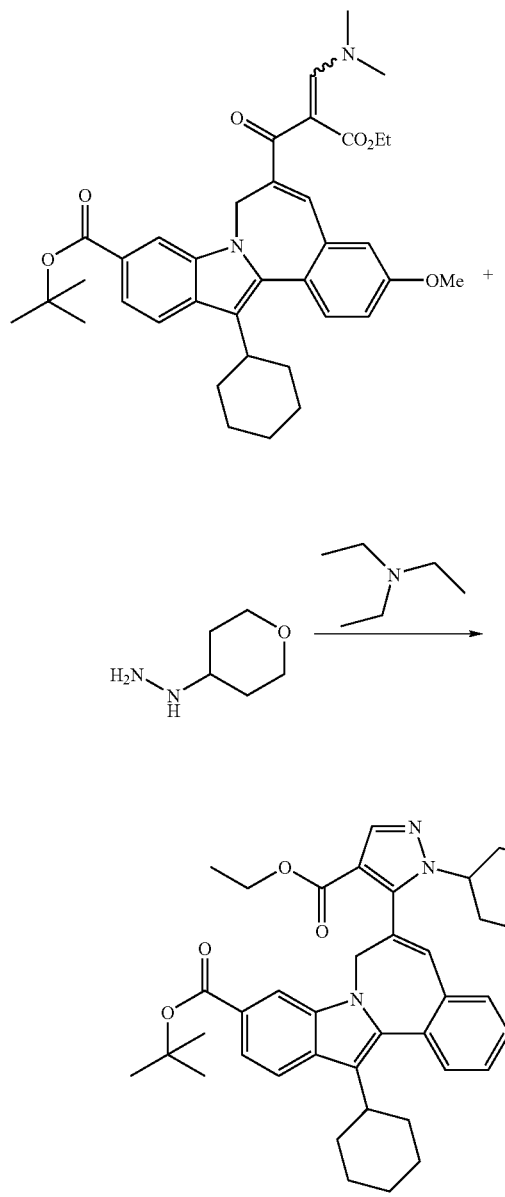

TEA (0.136 mL, 0.979 mmol) and (tetrahydro-2H-pyran-4-yl)hydrazine, HCl (49.8 mg, 0.326 mmol) were added sequentially to a mixture of starting compound (200 mg, 0.326 mmol) in EtOH (1 mL) and 1,4-dioxane (0.25 mL) in microwave process tube. The resulting suspension was heated at 160° C. for 60 min. The reaction was monitored by LC/MS. The crude was diluted with EtOAc and washed with H$_2$O. The aq. layer was extracted with EtOAc (20 mL×2) and the combined organic layer was washed with brine and dried over Na$_2$SO$_4$. Concentrated and the residue was purified via BIOTAGE® (4:1 Hex/EtOAc; 25+M column) to afford the title compound as light yellow solid (0.56 g, 86%). ESI-MS m/e 666 (MH$^+$). $^1$H NMR (500 MHz, CHLOROFORM-D) δ ppm 1.20-1.86 (m, 24H) 1.91-2.15 (m, 2H) 2.75-2.94 (m, 2H) 3.14-3.25 (m, 1H) 3.28-3.39 (m, 1H) 3.70-3.80 (m, 1H) 3.88-3.94 (m, 3H) 4.12 (q, J=7.02 Hz, 1H) 4.31 (d, J=4.58 Hz, 2H) 4.70 (d, J=14.65 Hz, 1H) 4.93 (d, J=14.65 Hz, 1H) 6.69 (s, 1H) 6.94 (d, J=2.75 Hz, 1H) 7.08 (dd, J=8.70, 2.59 Hz, 1H) 7.53 (d, J=8.54 Hz, 1H) 7.63 (dd, J=8.39, 1.37 Hz, 1H) 7.77-7.86 (m, 2H) 7.94 (s, 1H).

7H-Indolo[2,1-a][2]benzazepine-10-carboxylic acid, 13-cyclohexyl-6-[4-(ethoxycarbonyl)-1-(tetrahydro-2H-pyran-4-yl)-1H-pyrazol-5-yl]-3-methoxy-

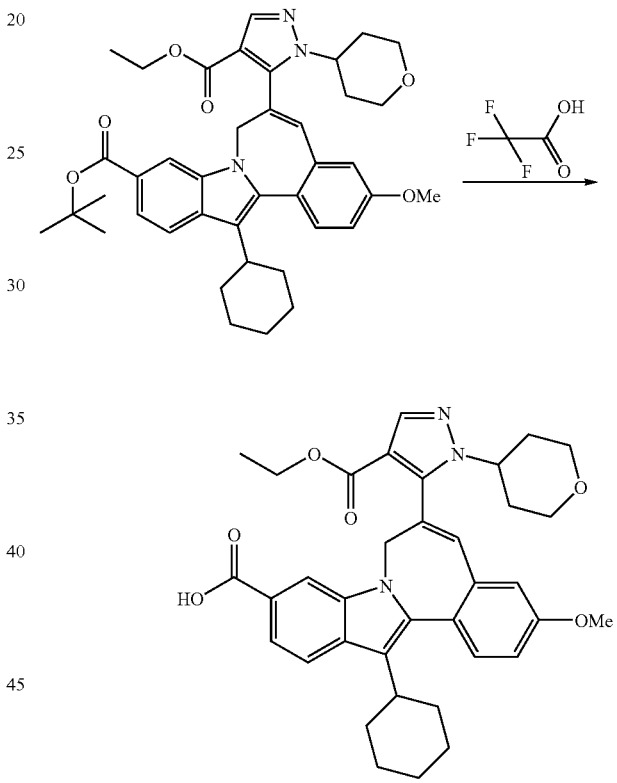

The CH$_2$Cl$_2$ (10 mL) solution of 7H-indolo[2,1-a][2]benzazepine-10-carboxylic acid, 13-cyclohexyl-6-[4-(ethoxycarbonyl)-1-(tetrahydro-2H-pyran-4-yl)-1H-pyrazol-5-yl]-3-methoxy-, 1,1-dimethylethyl ester (1.12 g, 1.682 mmol) was added TFA (8 mL, 104 mmol) and let it stirred at r.t. for 2 h. The reaction was monitored by LC/MS. The solvent was removed in vacuo to afford the title compound as light yellow powder. ESI-MS m/e 610 (MH$^+$). $^1$H NMR (500 MHz, DMSO-D6) δ ppm 1.12-1.59 (m, 9H) 1.68-2.15 (m, 8H) 2.64 (d, J=1.83 Hz, 1H) 2.78-2.88 (m, 1H) 2.99-3.13 (m, 2H) 3.14-3.24 (m, 1H) 3.62-3.70 (m, 1H) 3.88 (s, 3H) 4.51 (d, J=14.65 Hz, 1H) 5.22 (d, J=15.56 Hz, 1H) 6.96 (s, 1H) 7.13 (d, J=2.44 Hz, 1H) 7.22 (dd, J=8.55, 2.44 Hz, 1H) 7.54-7.62 (m, 2H) 7.90 (d, J=8.55 Hz, 1H) 7.96 (s, 1H) 8.01 (s, 1H).

1H-Pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-(tetrahydro-2H-pyran-4-yl)-, ethyl ester

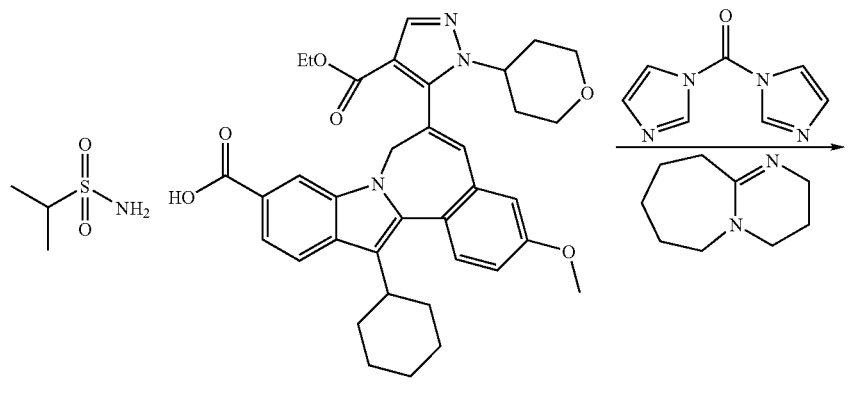

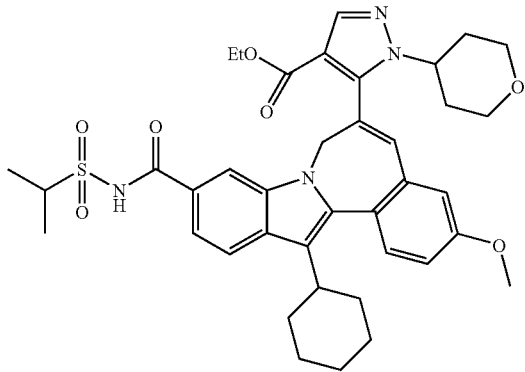

The THF (8 mL) solution of 7H-indolo[2,1-a][2]benzazepine-10-carboxylic acid, 13-cyclohexyl-6-[4-(ethoxycarbonyl)-1-(tetrahydro-2H-pyran-4-yl)-1H-pyrazol-5-yl]-3-methoxy-(450 mg, 0.738 mmol) was added CDI (239 mg, 1.476 mmol) and let it stirred at 60° C. for 1 h. Cooled to r.t. and propane-2-sulfonamide (273 mg, 2.214 mmol) and DBU (0.222 mL, 1.476 mmol) was added. Let it heated at 60° C. for 3 h. The reaction was monitored by LC/MS. The solvent was removed and the residue was redissolved in EtOAc. The organic layer was washed with HCl (1N) (20 mL×3), Brine (20 mL x3) and dried over $Na_2SO_4$. The solvent was removed in vacuo and the crude was purified using Shimadzu prep HPLC employing ACN/water and 0.1% TFA buffer with a XTERRA® column, 30 mm×100 mm, Gradient over 15 min; Starting conc: 10% B; Ending conc: 100% B. The solvent was removed by SPEEDVAC® to afford the title compound as light yellow solid (350 mg, 66%). ESI-MS m/e 715 (MH$^+$). $^1$H NMR (500 MHz, CHLOROFORM-D) δ ppm 1.19-1.89 (m, 15H) 1.25 (t, J=7.02 Hz, 3H) 1.44 (d, J=7.02 Hz, 6H) 1.93-2.25 (m, 2H) 2.83-2.95 (m, 2H) 3.21-3.55 (m, 2H) 3.76-3.85 (m, 1H) 3.98-4.17 (m, 4H) 4.66-4.75 (m, 1H) 4.96 (d, J=14.95 Hz, 1H) 6.72 (s, 1H) 6.96 (d, J=2.44 Hz, 1H) 7.09 (dd, J=8.55, 2.75 Hz, 1H) 7.39-7.44 (m, 1H) 7.52 (d, J=8.55 Hz, 1H) 7.79 (s, 1H) 7.90 (d, J=8.54 Hz, 1H) 7.99 (s, 1H) 8.47-8.61 (m, 1H).

51

1H-Pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-(tetrahydro-2H-pyran-4-yl)-

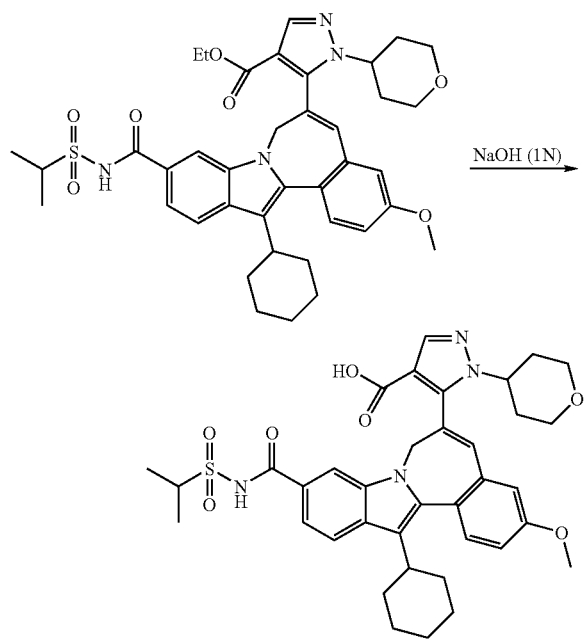

52

The EtOH/THF solution of 1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-(tetrahydro-2H-pyran-4-yl)-, ethyl ester (350 mg, 0.490 mmol) was added NaOH (1N, 5 mL) and let it shake at r.t. for overnight. The reaction was monitored by LC/MS. HCl (1N, 4 mL) was added and the solvent was removed by vacuo. The residue was redissolved in EtOAc and washed with brine (20 mL x3) and dried over $Na_2SO_4$. The solvent was removed in vacuo to afford the title product as yellow solid (175 mg, 52%). ESI-MS m/e 687 (MH$^+$). $^1$H NMR (500 MHz, CHLOROFORM-D) δ ppm 1.21-1.87 (m, 12H) 1.45 (d, J=6.71 Hz, 6H) 1.91-2.17 (m, 2H) 2.82-2.95 (m, 2H) 3.18-3.28 (m, 1H) 3.34 (d, J=10.68 Hz, 1H) 3.80 (d, J=12.21 Hz, 1H) 3.92 (s, 3H) 3.97-4.07 (m, 1H) 4.32 (d, J=6.71 Hz, 1H) 4.73 (d, J=14.65 Hz, 1H) 4.95 (d, J=14.34 Hz, 1H) 6.71 (s, 1H) 6.96 (d, J=2.75 Hz, 1H) 7.10 (dd, J=8.70, 2.59 Hz, 1H) 7.38 (dd, J=8.55, 1.22 Hz, 1H) 7.53 (d, J=8.55 Hz, 1H) 7.76 (d, J=1.22 Hz, 1H) 7.90 (d, J=8.55 Hz, 1H) 7.96 (s, 1H) 8.32 (s, 1H).

1H-Pyrazole-4-carboxylic acid, 5-[13-cyclohexyl-3-methoxy-10-[[[(1-methylpropyl)sulfonyl]amino]carbonyl]-7H-indolo[2,1-a][2]benzazepin-6-yl]-1-(tetrahydro-2H-pyran-4-yl)-, ethyl ester

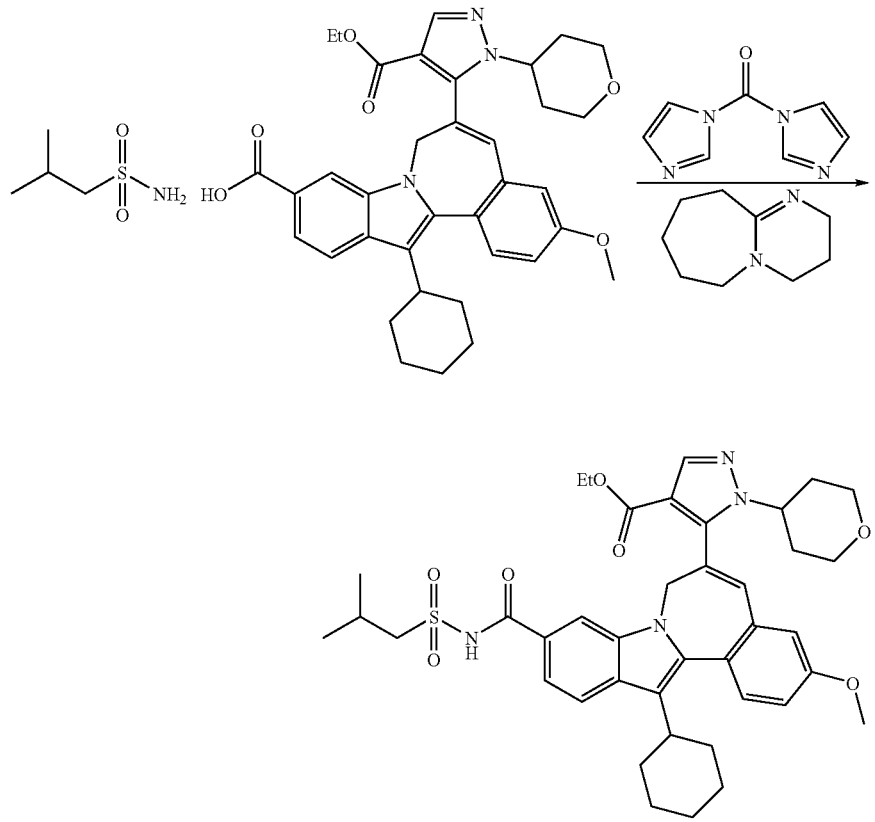

The THF (10 mL)/EtOH (10.00 mL) solution of 7H-indolo[2,1-a][2]benzazepine-10-carboxylic acid, 13-cyclohexyl-6-[4-(ethoxycarbonyl)-1-(tetrahydro-2H-pyran-4-yl)-1H-pyrazol-5-yl]-3-methoxy- (700 mg, 1.148 mmol) was added CDI (372 mg, 2.296 mmol) and let it stirred at 60° C. for 1 h. Cooled to r.t. and 2-methylpropane-1-sulfonamide (473 mg, 3.44 mmol) and DBU (0.346 mL, 2.296 mmol) was added. Let it heated at 60° C. for overnight. The reaction was completed monitored by LC/MS. The solvent was removed and redissolved in EtOAc. The organic layer was washed with HCl (1N) (20 mL×3), Brine (20 mL x3) and dried over Na$_2$SO$_4$. The solvent was removed in vacuo and the crude was purified using Shimadzu prep HPLC employing ACN/water and 0.1% TFA buffer with a XTERRA® column, 30 mm×100 mm, Gradient over 20 min; Starting conc: 20% B; Ending conc: 100% B. The solvent was removed by SPEEDVAC® to afford the title compound as light yellow solid (750 mg, 90%). ESI-MS m/e 729 (MH$^+$). $^1$H NMR (500 MHz, CHLOROFORM-D) δ ppm 1.12 (d, J=6.71 Hz, 6H) 1.24 (t, J=7.02 Hz, 3H) 1.33-1.86 (m, 11H) 1.93-2.15 (m, 2H) 2.33-2.40 (m, 1H) 2.85-2.93 (m, 2H) 3.19-3.36 (m, 2H) 3.51 (d, J=6.41 Hz, 2H) 3.73 (q, J=7.02 Hz, 2H) 3.76-3.83 (m, 1H) 3.92 (s, 3H) 4.32 (d, J=7.63 Hz, 2H) 4.74 (d, J=14.65 Hz, 1H) 4.94 (d, J=14.34 Hz, 1H) 6.70 (s, 1H) 6.96 (d, J=2.75 Hz, 1H) 7.10 (dd, J=8.70, 2.59 Hz, 1H) 7.32-7.37 (m, 1H) 7.53 (d, J=8.55 Hz, 1H) 7.75 (s, 1H) 7.90 (d, J=8.55 Hz, 1H) 7.95 (s, 1H) 8.30-8.38 (m, 1H).

1H-Pyrazole-4-carboxylic acid, 5-[13-cyclohexyl-3-methoxy-10-[[[(2-methylpropyl)sulfonyl]amino]carbonyl]-7H-indolo[2,1-a][2]benzazepin-6-yl]-1'-(tetrahydro-2H-pyran-4-yl)-

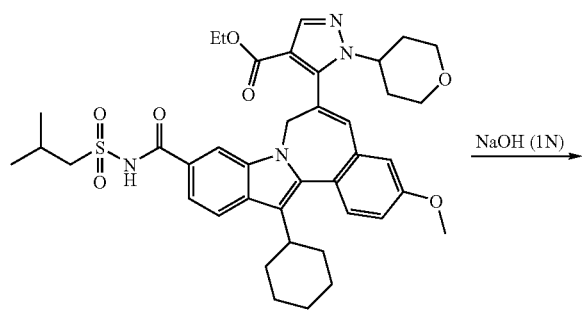

NaOH (1N) →

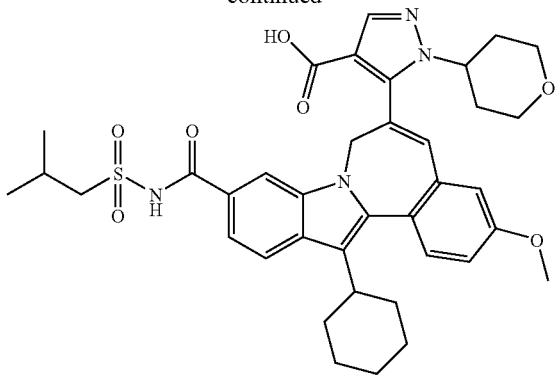

The EtOH/THF solution of 1H-pyrazole-4-carboxylic acid, 5-[13-cyclohexyl-3-methoxy-10-[[[(1'-methylpropyl)sulfonyl]amino]carbonyl]-7H-indolo[2,1-a][2]benzazepin-6-yl]-1-(tetrahydro-2H-pyran-4-yl)-, ethyl ester (750 mg, 1.029 mmol) was added NaOH (1N, 5 mL) and let it shake at r.t. for overnight. The reaction was monitored by LC/MS. HCl (1N, 5 mL) was added and the solvent was removed by vacuo. The residue was redissolved in EtOAc and washed with HCl, brine and dried over Na$_2$SO$_4$. The solvent was removed in vacuo to afford the title product as yellow solid (670 mg, 93%). ESI-MS m/e 701 (MH$^+$). $^1$H NMR (500 MHz, CHLOROFORM-D) δ ppm 1.10 (d, J=6.71 Hz, 6H) 1.19-1.87 (m, 12H) 1.92-2.18 (m, 2H) 2.29-2.40 (m, 1H) 2.82-2.94 (m, 2H) 3.18-3.42 (m, 2H) 3.50 (dd, J=6.71, 2.44 Hz, 2H) 3.75-3.85 (m, 2H) 3.91 (s, 3H) 4.71 (d, J=14.95 Hz, 1H) 4.96 (d, J=14.04 Hz, 1H) 6.72 (s, 1H) 6.96 (d, J=2.44 Hz, 1H) 7.09 (dd, J=8.55, 2.44 Hz, 1H) 7.42 (dd, J=8.55, 1.53 Hz, 1H) 7.52 (d, J=8.55 Hz, 1H) 7.78 (s, 1H) 7.90 (d, J=8.54 Hz, 1H) 8.00 (s, 1H) 8.74 (s, 1H).

7H-Indolo[2,1-a][2]benzazepine-10-carboxamide, 13-cyclohexyl-6-[4-[[(2R,6S)-2,6-dimethyl-4-morpholinyl]carbonyl]-1-(tetrahydro-2H-pyran-4-yl)-1H-pyrazol-5-yl]-3-methoxy-N-[(1-methylethyl)sulfonyl]-

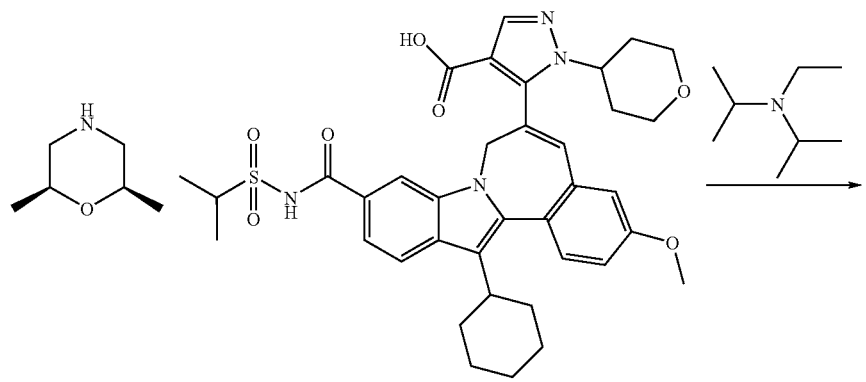

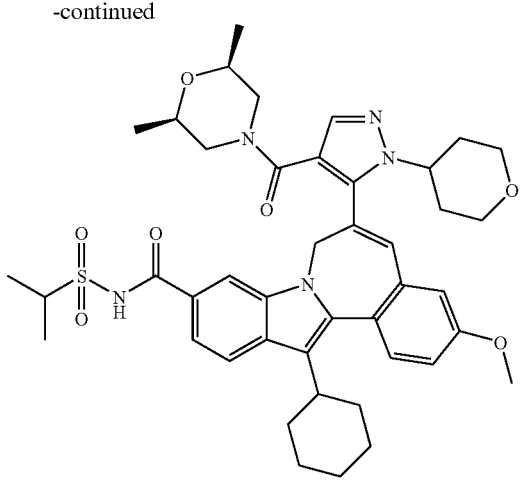

The DMF solution of 74809-037 (50 mg, 0.073 mmol) was added TBTU (46.7 mg, 0.146 mmol), DIPEA (0.038 mL, 0.218 mmol) and (2S,6R)-2,6-dimethylmorpholine (16.77 mg, 0.146 mmol). The solution was shaked at r.t. for 1 h. The reaction was monitored by LC/MS. The crude was purified by Prep HPLC employed Shimadzu prep HPLC employing ACN/water and 0.1% TFA buffer with a XTERRA® column, 30 mm×100 mm, Gradient over 15 min; Starting conc: 10% B; Ending conc: 90% B. The solvent was removed by SPEEDVAC® to afford the title product as light yellow solid (37 mg, 62%). ESI-MS m/e 784 (MH+). $^1$H NMR (300 MHz, CHLOROFORM-D) δ ppm 0.81-1.66 (m, 16H) 1.68-2.54 (m, 16H) 2.86 (dd, J=11.71, 7.32 Hz, 1H) 3.09-3.61 (m, 3H) 3.85-3.91 (m, 1H) 3.92 (s, 3H) 3.96-4.14 (m, 2H) 4.60 (d, J=15.37 Hz, 1H) 4.91 (d, J=16.10 Hz, 1H) 6.73 (s, 1H) 6.89 (d, J=2.20 Hz, 1H) 7.07-7.15 (m, 1H) 7.51-7.62 (m, 2H) 7.66 (s, 1H) 7.72 (s, 1H) 7.90 (d, J=8.42 Hz, 1H).

7H-Indolo[2,1-a][2]benzazepine-10-carboxamide, 13-cyclohexyl-3-methoxy-N-[(1-methylethyl)sulfonyl]-6-[4-(4-morpholinylcarbonyl)-1-(tetrahydro-2H-pyran-4-yl)-1H-pyrazol-5-yl]-

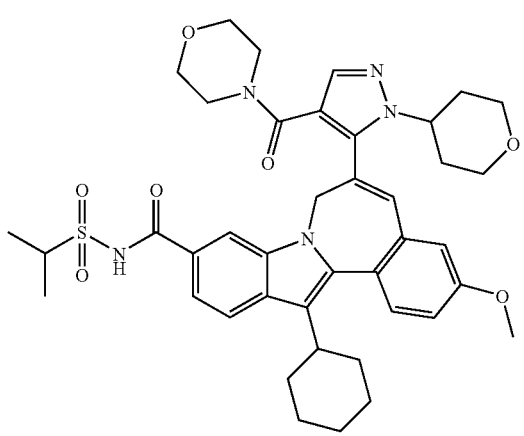

ESI-MS m/e 756 (MH+). $^1$H NMR (300 MHz, CHLOROFORM-D) δ ppm 1.11-2.38 (m, 20H) 2.42-3.51 (m, 12H) 3.80-4.12 (m, 3H) 3.92 (s, 3H) 4.54-4.68 (m, 1H) 4.86-5.00 (m, 1H) 6.75 (s, 1H) 6.89 (s, 1H) 7.10 (d, J=7.68 Hz, 1H) 7.55 (d, J=8.05 Hz, 2H) 7.67 (s, 1H) 7.73 (s, 1H) 7.91 (d, J=8.42 Hz, 1H).

7H-Indolo[2,1-a][2]benzazepine-10-carboxamide, 13-cyclohexyl-3-methoxy-6-[4-[(3-methyl-3,8-diazabicyclo[3.2.1]oct-8-yl)carbonyl]-1-(tetrahydro-2H-pyran-4-yl)-1H-pyrazol-5-yl]-N-[(1-methylethyl)sulfonyl]-

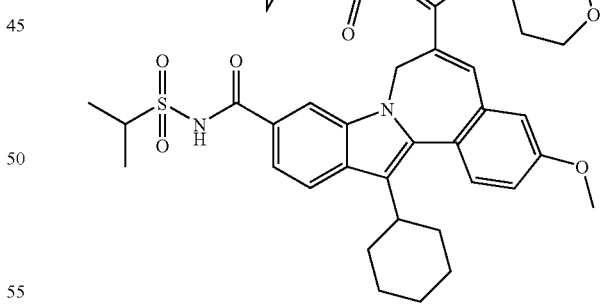

ESI-MS m/e 796 (MH+). $^1$H NMR (300 MHz, CHLOROFORM-D) δ ppm 1.12-1.62 (m, 8H) 1.46 (d, J=6.95 Hz, 6H) 1.62-2.28 (m, 11H) 2.57-2.76 (m, 4H) 2.78-3.00 (m, 3H) 3.34-3.64 (m, 4H) 3.71-3.88 (m, 3H) 3.91 (s, 3H) 3.94-4.09 (m, 1H) 4.54-5.01 (m, 2H) 6.77 (s, 1H) 6.87-6.93 (m, 1H) 7.10 (dd, J=8.42, 2.20 Hz, 1H) 7.46-7.61 (m, 2H) 7.63-7.74 (m, 2H) 7.90 (d, J=8.42 Hz, 1H).

57

7H-Indolo[2,1-a][2]benzazepine-10-carboxamide, 13-cyclohexyl-3-methoxy-N-[(1-methylethyl)sulfonyl]-6-[1-(tetrahydro-2H-pyran-4-yl)-4-[[(3R,5S)-3,4,5-trimethyl-1-piperazinyl]carbonyl]-1H-pyrazol-5-yl]-

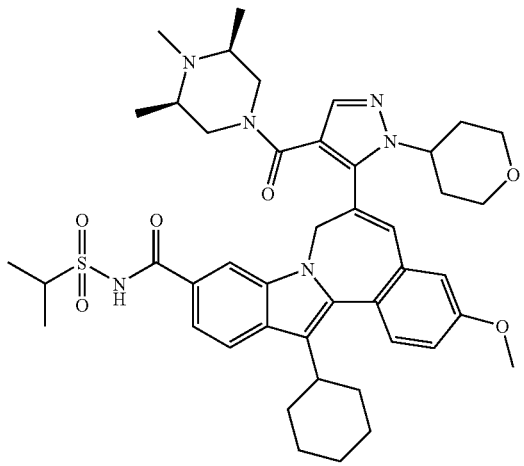

ESI-MS m/e 798 (MH+). ¹H NMR (300 MHz, CHLOROFORM-D) δ ppm 1.13-1.66 (m, 18H) 1.69-2.17 (m, 8H) 2.54-2.66 (m, 1H) 2.69-3.08 (m, 6H) 3.32-3.65 (m, 3H) 3.78-4.30 (m, 6H) 3.89 (s, 3H) 4.51-4.72 (m, 1H) 4.84-5.06 (m, 1H) 6.76 (s, 1H) 6.94 (d, J=2.56 Hz, 1H) 7.07 (dd, J=8.42, 2.56 Hz, 1H) 7.50 (d, J=8.78 Hz, 2H) 7.55-7.64 (m, 1H) 7.83 (s, 1H) 7.90 (d, J=8.42 Hz, 1H).

7H-Indolo[2,1-a][2]benzazepine-10-carboxamide, 13-cyclohexyl-6-[4-[[(1S,4S)-5-ethyl-2,5-diazabicyclo[2.2.1]hept-2-yl]carbonyl]-1-(tetrahydro-2H-pyran-4-yl)-1H-pyrazol-5-yl]-3-methoxy-N-[(1-methylethyl)sulfonyl]-

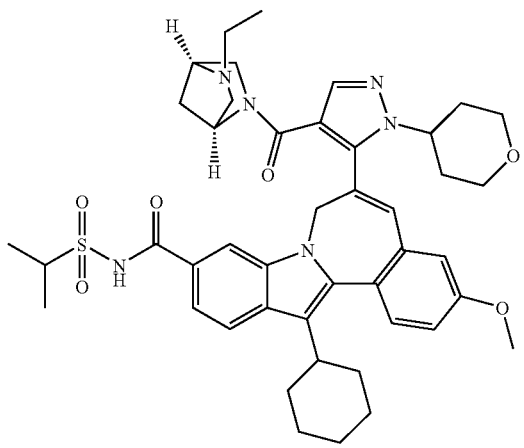

ESI-MS m/e 796 (MH+). ¹H NMR (300 MHz, CHLOROFORM-D) δ ppm 1.09-1.49 (m, 16H) 1.51-2.28 (m, 9H) 2.80-3.49 (m, 14H) 3.89 (s, 3H) 3.91-4.04 (m, 1H) 4.25-4.40 (m, 1H) 4.65-4.87 (m, 1H) 6.68 (d, J=2.20 Hz, 1H) 6.96 (s, 1H) 7.06 (dd, J=8.42, 2.20 Hz, 1H) 7.48-7.61 (m, 2H) 7.62-7.93 (m, 3H).

58

7H-Indolo[2,1-a][2]benzazepine-10-carboxamide, 13-cyclohexyl-3-methoxy-6-[4-[(8-methyl-3,8-diazabicyclo[3.2.1]oct-3-yl)carbonyl]-1-(tetrahydro-2H-pyran-4-yl)-1H-pyrazol-5-yl]-N-[(1-methylethyl)sulfonyl]-

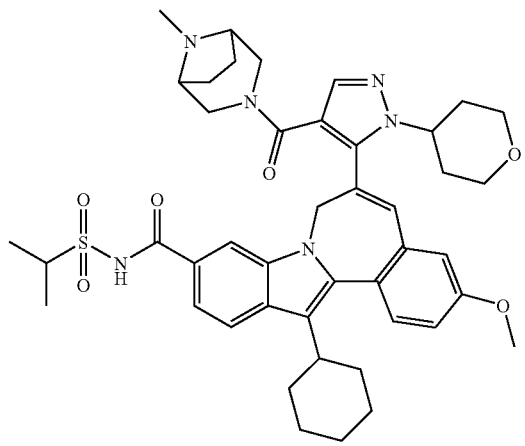

ESI-MS m/e 796 (MH+). ¹H NMR (300 MHz, CHLOROFORM-D) δ ppm 1.02-1.57 (m, 15H) 1.64-2.17 (m, 9H) 2.48-3.10 (m, 7H) 3.14-3.94 (m, 6H) 3.87-3.93 (m, 3H) 3.94-4.11 (m, 2H) 4.52-4.72 (m, 2H) 4.80-5.01 (m, 1H) 6.69-6.85 (m, 1H) 6.89 (d, J=2.56 Hz, 1H) 7.10 (dd, J=8.60, 2.01 Hz, 1H) 7.46-7.61 (m, 2H) 7.62-7.82 (m, 2H) 7.91 (d, J=8.78 Hz, 1H).

7H-Indolo[2,1-a][2]benzazepine-10-carboxamide, 13-cyclohexyl-6-[4-[[(2R,6S)-2,6-dimethyl-4-morpholinyl]carbonyl]-1-(tetrahydro-2H-pyran-4-yl)-1H-pyrazol-5-yl]-3-methoxy-N-[(2-methylpropyl)sulfonyl]-

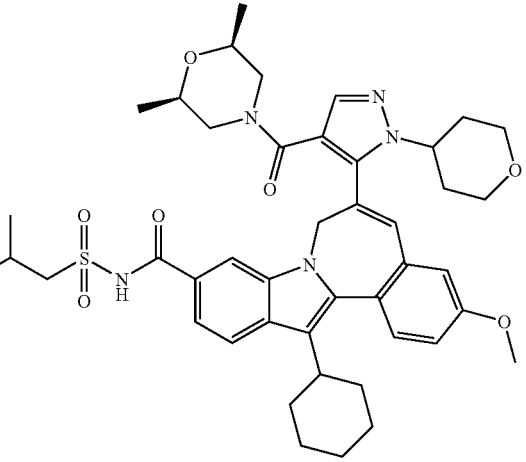

ESI-MS m/e 799 (MH+). ¹H NMR (300 MHz, CHLOROFORM-D) δ ppm 0.45-1.44 (m, 12H) 1.45 (d, J=6.95 Hz, 6H) 1.59-2.24 (m, 9H) 2.51-3.02 (m, 6H) 3.39-3.88 (m, 5H) 3.91 (s, 3H) 3.94-4.07 (m, 1H) 4.35-5.08 (m, 4H) 6.78 (s, 1H) 6.90

(d, J=2.20 Hz, 1H) 7.10 (dd, J=8.78, 2.56 Hz, 1H) 7.54 (t, J=8.78 Hz, 2H) 7.69 (s, 2H) 7.90 (d, J=8.42 Hz, 1H).

7H-Indolo[2,1-a][2]benzazepine-10-carboxamide, 13-cyclohexyl-3-methoxy-N-[(2-methylpropyl)sulfonyl]-6-[4-(4-morpholinylcarbonyl)-1-(tetrahydro-2H-pyran-4-yl)-1H-pyrazol-5-yl]-

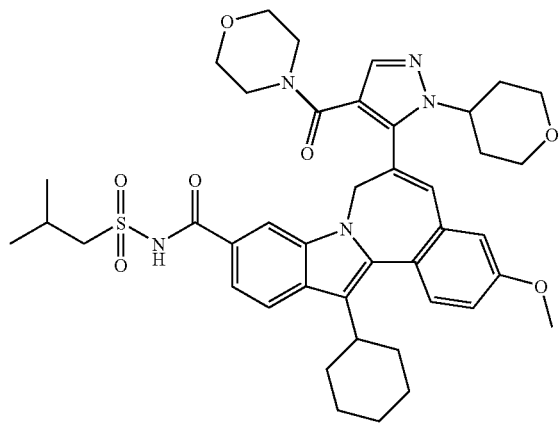

ESI-MS m/e 770 (MH+). ¹H NMR (300 MHz, CHLOROFORM-D) δ ppm 1.13 (d, J=6.59 Hz, 6H) 1.17-1.68 (m, 6H) 1.69-2.29 (m, 9H) 2.31-2.47 (m, 1H) 2.48-2.73 (m, 6H) 2.80-2.97 (m, 1H) 2.95-3.36 (m, 3H) 3.50 (d, J=6.59 Hz, 2H) 3.82-4.07 (m, 3H) 3.92 (s, 3H) 4.52-4.73 (m, 1H) 4.83-5.02 (m, 1H) 6.75 (s, 1H) 6.89 (t, J=3.11 Hz, 1H) 7.10 (dd, J=8.42, 2.56 Hz, 1H) 7.54 (t, J=8.78 Hz, 2H) 7.66 (s, 1H) 7.72 (s, 1H) 7.91 (d, J=8.42 Hz, 1H).

7H-Indolo[2,1-a][2]benzazepine-10-carboxamide, 13-cyclohexyl-3-methoxy-6-[4-[(3-methyl-3,8-diazabicyclo[3.2.1]oct-8-yl)carbonyl]-1-(tetrahydro-2H-pyran-4-yl)-1H-pyrazol-5-yl]-N-[(2-methylpropyl)sulfonyl]-

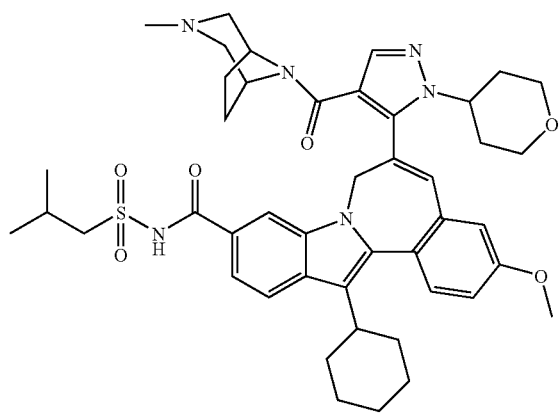

ESI-MS m/e 810 (MH+). ¹H NMR (500 MHz, CHLOROFORM-D) δ ppm 0.85-1.19 (m, 8H) 1.19-1.51 (m, 4H) 1.51-1.62 (m, 1H) 1.63-2.38 (m, 12H) 2.39-2.80 (m, 2H) 2.81-3.37 (m, 6H) 3.37-3.65 (m, 4H) 3.64-3.85 (m, 1H) 3.86-4.00 (m, 3H) 4.02-4.79 (m, 2H) 4.80-5.73 (m, 4H) 6.63-6.81 (m, 1H) 6.85-6.98 (m, 1H) 7.05-7.20 (m, 1H) 7.48-7.63 (m, 2H) 7.65 (d, J=8.55 Hz, 1H) 7.74-7.91 (m, 1H) 7.94 (d, J=8.55 Hz, 1H).

7H-Indolo[2,1-a][2]benzazepine-10-carboxamide, 13-cyclohexyl-3-methoxy-N-[(2-methylpropyl)sulfonyl]-6-[1-(tetrahydro-2H-pyran-4-yl)-4-[[(3R,5S)-3,4,5-trimethyl-1-piperazinyl]carbonyl]-1H-pyrazol-5-yl]-

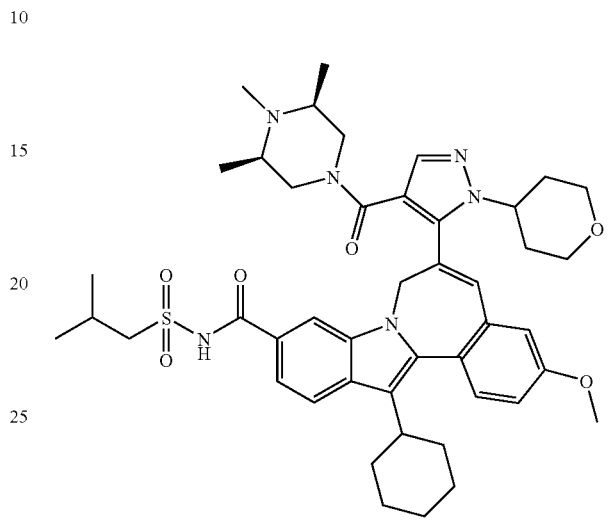

ESI-MS m/e 812 (MH+). ¹H NMR (500 MHz, CHLOROFORM-D) δ ppm 1.03-1.17 (m, 7H) 1.17-1.62 (m, 11H) 1.65-2.14 (m, 8H) 2.35 (d, J=7.02 Hz, 1H) 2.75-3.05 (m, 4H) 3.15-3.66 (m, 6H) 3.70-3.94 (m, 2H) 3.87-3.93 (m, 3H) 3.98-4.44 (m, 2H) 4.61 (d, J=14.04 Hz, 1H) 5.03-5.68 (m, 4H) 6.77 (s, 1H) 6.88-7.16 (m, 2H) 7.40-7.53 (m, 1H) 7.55-7.80 (m, 2H) 7.91 (d, J=8.55 Hz, 1H) 7.97-8.18 (m, 1H) 9.50-9.76 (m, 1H).

7H-Indolo[2,1-a][2]benzazepine-10-carboxamide, 13-cyclohexyl-6-[4-[[(1S,4S)-5-ethyl-2,5-diazabicyclo[2.2.1]hept-2-yl]carbonyl]-1-(tetrahydro-2H-pyran-4-yl)-1H-pyrazol-5-yl]-3-methoxy-N-[(2-methylpropyl)sulfonyl]-

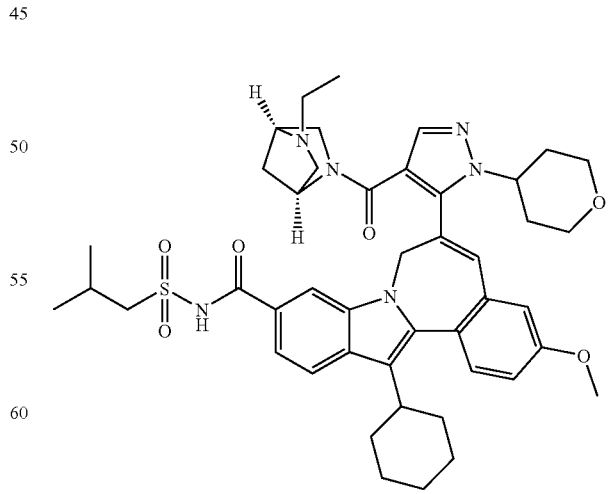

ESI-MS m/e 810 (MH+). ¹H NMR (500 MHz, CHLOROFORM-D) δ ppm 1.10 (d, J=6.10 Hz, 7H) 1.19-1.64 (m, 8H) 1.65-2.14 (m, 8H) 2.15-2.51 (m, 3H) 2.80-3.68 (m, 8H) 3.69-

3.85 (m, 1H) 3.90 (s, 3H) 4.22-4.76 (m, 8H) 4.88-4.98 (m, 1H) 6.59-6.74 (m, 1H) 6.90-7.18 (m, 2H) 7.41-7.97 (m, 5H).

7H-Indolo[2,1-a][2]benzazepine-10-carboxamide, 13-cyclohexyl-3-methoxy-6-[4-[(8-methyl-3,8-diazabicyclo[3.2.1]oct-3-yl)carbonyl]-1-(tetrahydro-2H-pyran-4-yl)-1H-pyrazol-5-yl]-N-[(2-methylpropyl)sulfonyl]-

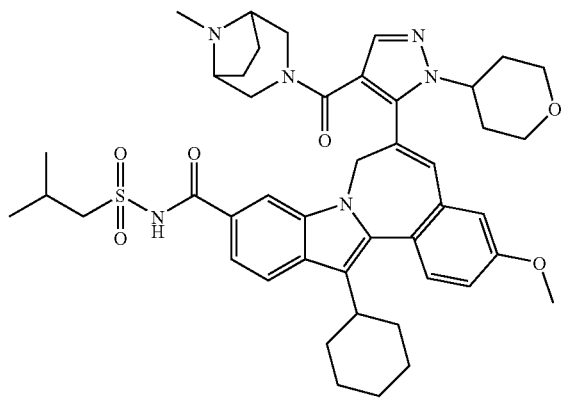

ESI-MS m/e 810 (MH⁺). ¹H NMR (500 MHz, CHLOROFORM-D) δ ppm 1.05-1.20 (m, 7H) 1.20-1.63 (m, 6H) 1.65-2.13 (m, 9H) 2.28-2.68 (m, 3H) 2.81-2.97 (m, 2H) 3.02-3.31 (m, 4H) 3.36-3.64 (m, 4H) 3.69-4.31 (m, 10H) 4.57-4.75 (m, 1H) 4.79-5.10 (m, 1H) 6.61-6.80 (m, 1H) 6.92 (s, 1H) 7.06-7.18 (m, 1H) 7.49-7.71 (m, 3H) 7.77-7.88 (m, 1H) 7.94 (d, J=8.85 Hz, 1H).

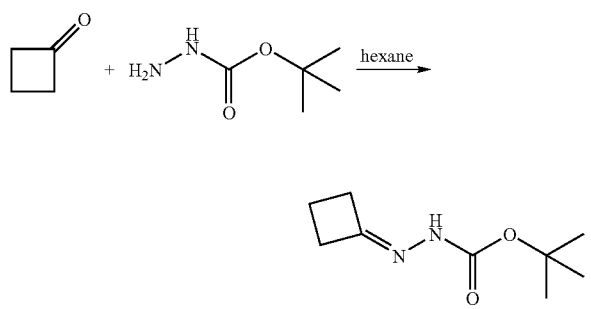

A reaction mixture of cyclobutanone (7.01 g, 100 mmol) and tert-butyl hydrazinecarboxylate (13.22 g, 100 mmol) in hexane (100 mL) was heated under reflux for 2 hours. After cooling down, a precipitate was formed and collected. It was then triturated with isopropanol (5 mL) and hexane (50 mL) to give a white solid as final product tert-butyl 2-cyclobutylidenehydrazinecarboxylate (13.5 g, 73.3 mmol, 73.3% yield). ¹H NMR (500 MHz, CHLOROFORM-D) δ ppm 1.50 (s, 9H) 1.96-2.08 (m, 2H) 2.75-2.84 (m, 2H) 2.93-3.05 (m, 2H). MS m/z 207 (M+Na⁺), Retention time: 1.420 min. (acid).

7H-Indolo[2,1-a][2]benzazepine-10-carboxylic acid, 6-[1-cyclobutyl-4-(ethoxycarbonyl)-1H-pyrazol-5-yl]-13-cyclohexyl-3-methoxy-, 1,1-dimethylethyl ester

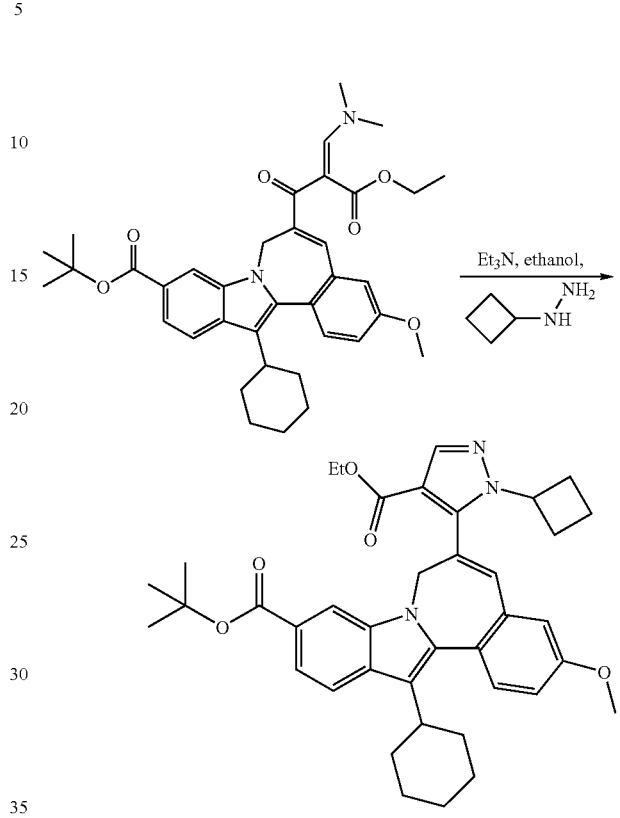

A 2M solution of BH3.DMS (6.92 mL, 13.84 mmol) in tetrahydrofuran was added to tert-butyl 2-cyclobutylidenehydrazinecarboxylate (1.5 g, 8.14 mmol). The reaction mixture was stirred at RT for 1 hr. Then it was evaporated and a white foam solid was obtained as cyclobutylhydrazine (0.45 g, 5.22 mmol, 64.2% yield). It was used in the next step without further purification.

In a microwave tube, tert-butyl 13-cyclohexyl-6-((2E,Z)-3-(dimethylamino)-2-(ethoxycarbonyl)-2-propenoyl)-3-methoxy-7H-indolo[2,1-a][2]benzazepine-10-carboxylate (1900 mg, 3.10 mmol) was dissolved in ethanol (20 mL). Cyclobutylhydrazine (267 mg, 3.10 mmol) and triethylamine (1.426 mL, 10.23 mmol) were added. The reaction mixture was then heated at 160° C. under microwave condition for 2 hr. All the volatiles were evaporated and the residue was triturated with acetonitrile and a few drops of DMSO. A light yellow solid was collected as title compound (1.127 g, 1.773 mmol, 57.2% yield) which was pure. MS m/z 636 (MH⁺), Retention time: 2.961 min. (basic). ¹H NMR (500 MHz, CHLOROFORM-D) δ ppm 1.11-2.20 (m, 27H) 2.48 (s, br, 1H) 2.79-2.94 (m, 1H) 3.90 (s, 3H) 3.92-4.03 (m, br, 1H) 4.18-4.41 (m, br, 2H) 4.61-4.75 (m, br, 1H) 4.89-5.04 (m, br, 1H) 6.68 (s, 1H) 6.93 (d, J=2.44 Hz, 1H) 7.06 (dd, J=8.70, 2.59 Hz, 1H) 7.52 (d, J=8.55 Hz, 1H) 7.64 (d, J=8.55 Hz, 1H) 7.79 (s, 1H) 7.82 (d, J=8.54 Hz, 1H) 7.95 (s, 1H).

7H-Indolo[2,1-a][2]benzazepine-10-carboxylic acid, 6-[1-cyclobutyl-4-(ethoxycarbonyl)-1H-pyrazol-5-yl]-13-cyclohexyl-3-methoxy-

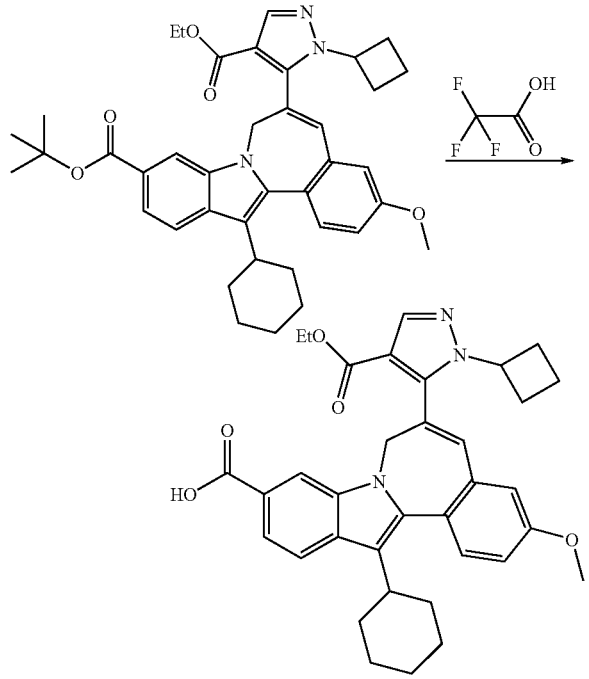

To a solution of 7H-indolo[2,1-a][2]benzazepine-10-carboxylic acid, 6-[1-cyclobutyl-4-(ethoxycarbonyl)-1H-pyrazol-5-yl]-13-cyclohexyl-3-methoxy-, 1,1-dimethylethyl ester (0.94 g, 1.478 mmol) in ClCH₂CH₂Cl (10 mL), TFA (5 mL, 64.9 mmol) was added. The reaction mixture was stirred at RT for overnight. Solvent and TFA were evaporated and the residue was added benzene (20 mL). All the volatiles were evaporated again and the residue was dried under vacuum to give a brownish solid as title compound (0.97 g, 1.673 mmol, 113% yield). It still contained some TFA. It was used in the next step without further purification. MS m/z 580 (MH⁺), Retention time: 3.263 min. (acid). ¹H NMR (500 MHz, MeOD) δ ppm 1.07-2.23 (m, 18H) 2.39 (s, br, 1H) 2.84-2.97 (m, 1H) 3.79-3.93 (m, 4H) 4.15-4.38 (m, br, 2H) 4.58-4.67 (m, 1H) 4.94-5.03 (m, 1H) 6.80 (s, 1H) 7.07 (d, J=2.75 Hz, 1H) 7.15 (dd, J=8.54, 2.75 Hz, 1H) 7.57 (d, J=8.55 Hz, 1H) 7.67 (dd, J=8.55, 1.22 Hz, 1H) 7.83 (s, 1H) 7.88 (d, J=8.55 Hz, 1H) 7.93 (s, 1H).

1H-Pyrazole-4-carboxylic acid, 1-cyclobutyl-5-[13-cyclohexyl-3-methoxy-10-[[[(2-methylpropyl)sulfonyl]amino]carbonyl]-7H-indolo[2,1-a][2]benzazepin-6-yl]-, ethyl ester

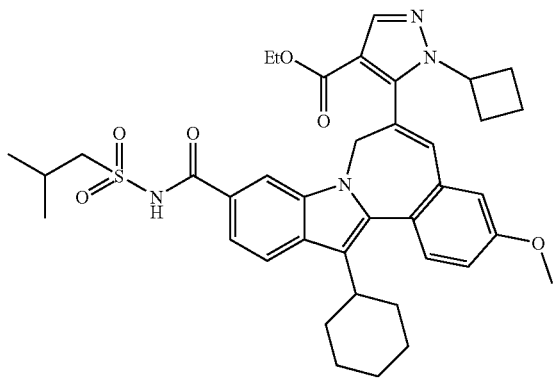

To a solution of 7H-indolo[2,1-a][2]benzazepine-10-carboxylic acid, 6-[1-cyclobutyl-4-(ethoxycarbonyl)-1H-pyrazol-5-yl]-13-cyclohexyl-3-methoxy- (480 mg, 0.828 mmol) in tetrahydrofuran (20 mL), CDI (201 mg, 1.242 mmol) was added. The reaction mixture was heated at 60° C. for one hour. Then it was cooled down. 2-Methylpropane-1-sulfonamide (341 mg, 2.484 mmol) and DBU (0.250 mL, 1.656 mmol) were added. The reaction mixture was then heated at 60° C. for 4 hours. The reaction mixture was quenched with 1N HCl solution and extracted with ethyl acetate (2×50 mL). The organic layers were combined, washed with 1N HCl solution, brine and dried (MgSO₄). Evaporation of solvents gave an orange thick oil as crude product. It was then triturated with acetonitrile and hexanes. A light yellow solid was collected which was quiet pure (390 mg). The filtrate from above was concentrated and the residue was purified by Prep. HPLC column using CH₃CN—H₂O-TFA as solvent system. Fractions were collected and concentrated to afford a yellow solid as title compound. (11.5 mg) Total weight of compound was 401.5 mg (69.4% yield). MS m/z 699 (MH⁺), Retention time: 3.250 min. (basic). ¹H NMR (500 MHz, CHLOROFORM-D) δ ppm 1.03-2.18 (m, 24H) 2.28-2.42 (m, 1H) 2.51 (s, br, 1H) 2.81-2.95 (m, 1H) 3.51 (d, J=5.80 Hz, 2H) 3.91 (s, 3H) 3.93-4.04 (m, br, 1H) 4.16-4.40 (m, br, 2H) 4.62-4.78 (m, br, 1H) 4.88-5.02 (m, br, 1H) 6.69 (s, 1H) 6.94 (d, J=2.44 Hz, 1H) 7.08 (dd, J=8.55, 2.44 Hz, 1H) 7.37 (dd, J=8.55, 1.22 Hz, 1H) 7.52 (d, J=8.85 Hz, 1H) 7.72 (s, 1H) 7.89 (d, J=8.55 Hz, 1H) 7.94 (s, 1H) 8.46 (s, 1H).

1H-Pyrazole-4-carboxylic acid, 1-cyclobutyl-5-[13-cyclohexyl-3-methoxy-10-[[[(1-methylethyl)sulfonyl]amino]carbonyl]-7H-indolo[2,1-a][2]benzazepin-6-yl]-, ethyl ester

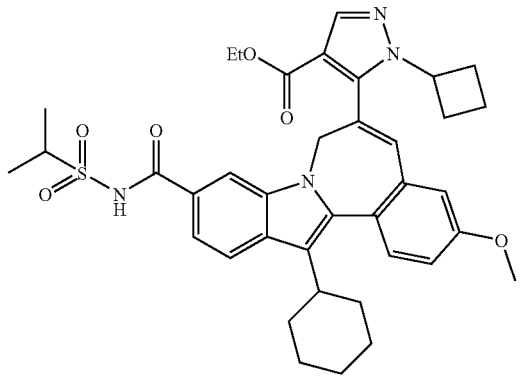

To a solution of 7H-indolo[2,1-a][2]benzazepine-10-carboxylic acid, 6-[1-cyclobutyl-4-(ethoxycarbonyl)-1H-pyrazol-5-yl]-13-cyclohexyl-3-methoxy- (480 mg, 0.828 mmol) in tetrahydrofuran (20 mL), CDI (201 mg, 1.242 mmol) was added. The reaction mixture was heated at 60° C. for one hour. Then it was cooled down. Propane-2-sulfonamide (306 mg, 2.484 mmol) and DBU (0.250 mL, 1.656 mmol) were added. The reaction mixture was then heated at 60° C. for 4 hours. The reaction mixture was quenched with 1N HCl solution and extracted with ethyl acetate (2×50 mL). The organic layers were combined, washed with 1N HCl solution, brine and dried (MgSO₄). Evaporation of solvents gave an orange thick oil as crude product. It was then triturated with acetonitrile and hexanes. A light yellow solid was collected which was quiet pure (350 mg). The filtrate from above was concentrated and the residue was purified by Prep. HPLC column using CH₃CN—H₂O-TFA as solvent system. Fractions were collected and concentrated to afford a yellow solid. (10 mg) Total weight of title compound was 360 mg (63.5% yield). MS m/z 685 (MH⁺), Retention time: 2.162 min. (basic). ¹H NMR (500 MHz, CHLOROFORM-D) δ ppm 1.16-2.16 (m, 25H) 2.52 (s, br, 1H) 2.82-2.94 (m, 1H) 3.91 (s, 3H) 3.93-4.09 (m, 2H) 4.19-4.37 (m, br, 2H) 4.65-4.77 (m, 1H) 4.87-5.02 (m, 1H) 6.70 (s, 1H) 6.94 (d, J=2.75 Hz, 1H) 7.08 (dd, J=8.55, 2.75 Hz, 1H) 7.37 (dd, J=8.55, 1.53 Hz, 1H) 7.53 (d, J=8.55 Hz, 1H) 7.71 (d, J=1.53 Hz, 1H) 7.90 (d, J=8.55 Hz, 1H) 7.95 (s, 1H).

1H-Pyrazole-4-carboxylic acid, 1-cyclobutyl-5-[13-cyclohexyl-3-methoxy-10-[[[(2-methylpropyl)sulfonyl]amino]carbonyl]-7H-indolo[2,1-a][2]benzazepin-6-yl]-

To a solution of 1H-pyrazole-4-carboxylic acid, 1-cyclobutyl-5-[13-cyclohexyl-3-methoxy-10-[[[(2-methylpropyl)sulfonyl]amino]carbonyl]-7H-indolo[2,1-a][2]benzazepin-6-yl]-, ethyl ester (385 mg, 0.551 mmol) in tetrahydrofuran (10.00 mL) and ethanol (10 mL), 1N sodium hydroxide (4.41 mL, 4.41 mmol) solution was added. The reaction mixture was stirred at RT for 4 days. The reaction mixture was concentrated at RT and the residue was acidified with 1N HCl solution. A light yellow solid was collected as title compound (360 mg, 0.537 mmol, 97% yield). MS m/z 671 (MH⁺), Retention time: 1.535 min. (basic). ¹H NMR (500 MHz, MeOD) δ ppm 1.12 (t, J=6.71 Hz, 6H) 1.17-2.22 (m, 15H) 2.22-2.33 (m, 1H) 2.36-2.52 (m, 1H) 2.87-3.01 (m, 1H) 3.45 (dd, J=6.41, 1.22 Hz, 2H) 3.82-3.99 (m, 4H) 4.58-4.73 (m, 1H) 5.02-5.17 (m, 1H) 6.85 (s, 1H) 7.12 (d, J=2.75 Hz, 1H) 7.18 (dd, J=8.70, 2.59 Hz, 1H) 7.58-7.64 (m, 2H) 7.90 (d, J=1.22 Hz, 1H) 7.94-7.99 (m, 2H).

1H-Pyrazole-4-carboxylic acid, 1-cyclobutyl-5-[13-cyclohexyl-3-methoxy-10-[[[(1-methylethyl)sulfonyl]amino]carbonyl]-7H-indolo[2,1-a][2]benzazepin-6-yl]-

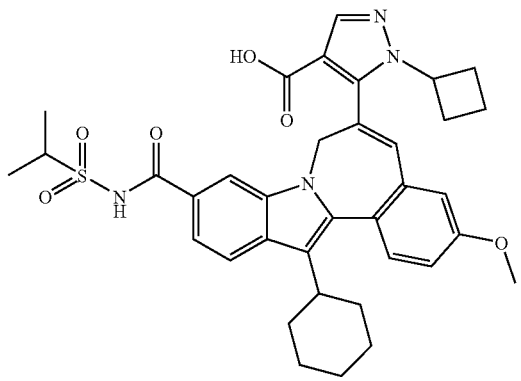

To a solution of 1H-pyrazole-4-carboxylic acid, 1-cyclobutyl-5-[13-cyclohexyl-3-methoxy-10-[[[(1-methylethyl)sulfonyl]amino]carbonyl]-7H-indolo[2,1-a][2]benzazepin-6-yl]-, ethyl ester (350 mg, 0.511 mmol) in tetrahydrofuran (10.00 mL) and ethanol (10 mL), 1N sodium hydroxide (4.09 mL, 4.09 mmol) solution was added. The reaction mixture was stirred at RT for 3 days. The reaction mixture was concentrated at RT and the residue was acidified with 1N HCl solution. A light yellow solid was collected as title compound (330 mg, 0.502 mmol, 98% yield). MS m/z 657 (MH⁺), Retention time: 1.467 min. (basic). ¹H NMR (500 MHz, MeOD) δ ppm 1.14-2.25 (m, 21H) 2.36-2.53 (m, 1H) 2.85-3.03 (m, 1H) 3.89-3.96 (m, 5H) 4.67 (d, J=14.34 Hz, 1H) 5.07 (d, J=14.95 Hz, 1H) 6.86 (s, 1H) 7.12 (d, J=2.75 Hz, 1H) 7.18 (dd, J=8.54, 2.75 Hz, 1H) 7.58-7.65 (m, 2H) 7.90 (s, 1H) 7.94-7.99 (m, 2H).

7H-Indolo[2,1-a][2]benzazepine-10-carboxamide, 6-[1-cyclobutyl-4-[(3-methyl-3,8-diazabicyclo[3.2.1]oct-8-yl)carbonyl]-1H-pyrazol-5-yl]-13-cyclohexyl-3-methoxy-N-[(2-methylpropyl)sulfonyl]-

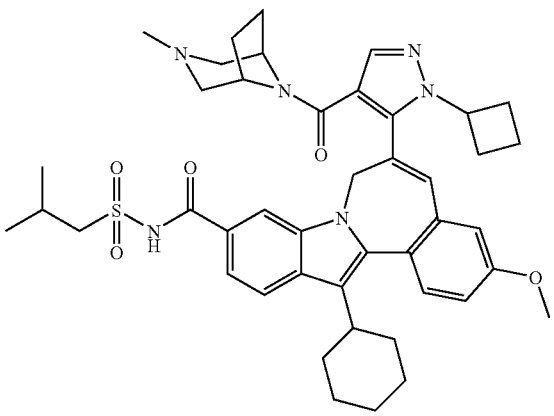

To a solution of 1H-pyrazole-4-carboxylic acid, 1-cyclobutyl-5-[13-cyclohexyl-3-methoxy-10-[[[(2-methylpropyl)sulfonyl]amino]carbonyl]-7H-indolo[2,1-a][2]benzazepin-6-yl]-(30 mg, 0.045 mmol) in DMSO (1 mL), TBTU (21.54 mg, 0.067 mmol) and DIPEA (0.039 mL, 0.224 mmol) were added. The reaction mixture was stirred at RT for 15 min. Then 3-methyl-3,8-diazabicyclo[3.2.1]octane, 2HCl (13.36 mg, 0.067 mmol) was added. The solution was stirred at RT for overnight. The reaction mixture was then purified by Prep. HPLC column using $CH_3CN-H_2O$-TFA as solvent system. Fractions were collected and concentrated under SPEED VAC® for overnight. A yellow solid was obtained as title compound as TFA salt (28.3 mg, 0.032 mmol, 70.9% yield). MS m/z 777 (M−H⁻), Retention time: 2.177 min. (basic). $^1$H NMR (500 MHz, MeOD) δ ppm 1.15 (d, J=6.71 Hz, 6H) 1.21-2.39 (m, 20H) 2.54 (s, br, 1H) 2.75-3.02 (m, 5H) 3.15-3.59 (m, 7H) 3.95 (s, 3H) 4.56-4.66 (m, 2H) 4.94-5.04 (m, 1H) 7.00 (s, 1H) 7.12 (s, 1H) 7.21 (dd, J=8.55, 2.44 Hz, 1H) 7.57-7.63 (m, 2H) 7.81 (s, 1H) 7.90 (s, 1H) 7.97 (d, J=8.55 Hz, 1H).

7H-Indolo[2,1-a][2]benzazepine-10-carboxamide, 6-[1-cyclobutyl-4-(3,7-dioxa-9-azabicyclo[3.3.1]non-9-ylcarbonyl)-1H-pyrazol-5-yl]-13-cyclohexyl-3-methoxy-N-[(2-methylpropyl)sulfonyl]-

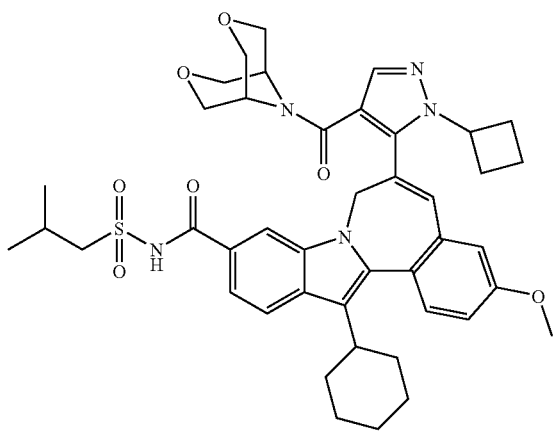

To a solution of 1H-pyrazole-4-carboxylic acid, 1-cyclobutyl-5-[13-cyclohexyl-3-methoxy-10-[[[(2-methylpropyl)sulfonyl]amino]carbonyl]-7H-indolo[2,1-a][2]benzazepin-6-yl]-(30 mg, 0.045 mmol) in DMSO (1 mL), TBTU (21.54 mg, 0.067 mmol) and DIPEA (0.039 mL, 0.224 mmol) were added. The reaction mixture was stirred at RT for 15 min. Then 3,7-dioxa-9-azabicyclo[3.3.1]nonane (8.66 mg, 0.067 mmol) was added. The solution was stirred at RT for overnight. LC/MS shown incompletion of reaction. One more equivalent of TBTU and DIPEA were added. The reaction mixture was continued stirring at RT for 2 days. The reaction mixture was then purified by Prep. HPLC column using $CH_3CN-H_2O$-TFA as solvent system. Fractions were collected and concentrated under SPEED VAC® for over the weekend. A yellow solid was obtained as title compound (27.4 mg, 0.032 mmol, 78% yield). MS m/z 780 (M−H⁻), Retention time: 1.990 min. (basic). $^1$H NMR (500 MHz, MeOD) δ ppm 1.14 (d, J=6.71 Hz, 6H) 1.20-2.68 (m, 17H) 2.87-3.00 (m, 1H) 3.22-3.99 (m, 16H) 4.64 (d, J=14.95 Hz, 1H) 5.00 (d, J=14.04 Hz, 1H) 7.02 (s, 1H) 7.13 (d, J=2.44 Hz, 1H) 7.21 (dd, J=8.70, 2.59 Hz, 1H) 7.55-7.65 (m, 2H) 7.78 (s, 1H) 7.86 (s, 1H) 7.97 (d, J=8.24 Hz, 1H).

7H-Indolo[2,1-a][2]benzazepine-10-carboxamide, 6-[1-cyclobutyl-4-[[3,5-cis-3,4,5-trimethyl-1-piperazinyl]carbonyl]-1H-pyrazol-5-yl]-13-cyclohexyl-3-methoxy-N-[(2-methylpropyl)sulfonyl]-

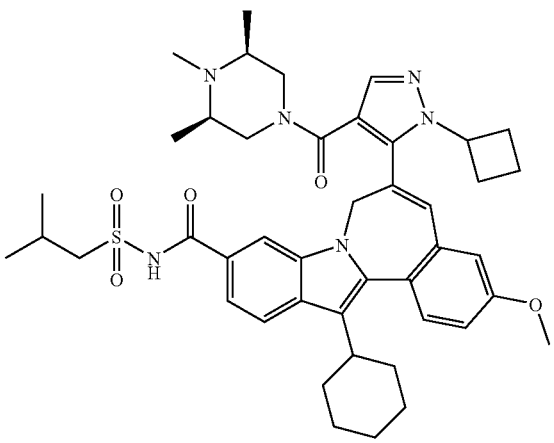

To a solution of 1H-pyrazole-4-carboxylic acid, 1-cyclobutyl-5-[13-cyclohexyl-3-methoxy-10-[[[(2-methylpropyl)sulfonyl]amino]carbonyl]-7H-indolo[2,1-a][2]benzazepin-6-yl]-(30 mg, 0.045 mmol) in DMSO (1 mL), TBTU (21.54 mg, 0.067 mmol) and DIPEA (0.039 mL, 0.224 mmol) were added. The reaction mixture was stirred at RT for 15 min. Then (2R,6S)-1,2,6-trimethylpiperazine, 2 HCl (13.49 mg, 0.067 mmol) was added. The solution was stirred at RT for overnight. The reaction mixture was then purified by Prep. HPLC column using $CH_3CN-H_2O$-TFA as solvent system. Fractions were collected and concentrated under SPEED VAC® for overnight. A yellow solid was obtained as title compound as TFA salt (32.7 mg, 0.037 mmol, 82% yield). MS m/z 779 (M−H⁻), Retention time: 2.080 min. (basic). $^1$H NMR (500 MHz, MeOD) δ ppm 1.14 (d, J=6.71 Hz, 6H) 1.19-2.38 (m, 22H) 2.54 (s, br, 1H) 2.70-3.19 (m, 8H) 3.48 (d, J=6.41 Hz, 2H) 3.95 (s, 3H) 4.36 (s, br, 3H) 4.53-4.66 (m, 1H) 4.97-5.08 (m, 1H) 6.97 (s, 1H) 7.11 (d, J=2.75 Hz, 1H) 7.20 (dd, J=8.55, 2.75 Hz, 1H) 7.54-7.64 (m, 2H) 7.79 (s, 1H) 7.86 (s, 1H) 7.98 (d, J=8.24 Hz, 1H).

7H-Indolo[2,1-a][2]benzazepine-10-carboxamide, 6-[1-cyclobutyl-4-[[(1S,4S)-5-ethyl-2,5-diazabicyclo[2.2.1]hept-2-yl]carbonyl]-1H-pyrazol-5-yl]-13-cyclohexyl-3-methoxy-N-[(2-methylpropyl)sulfonyl]-

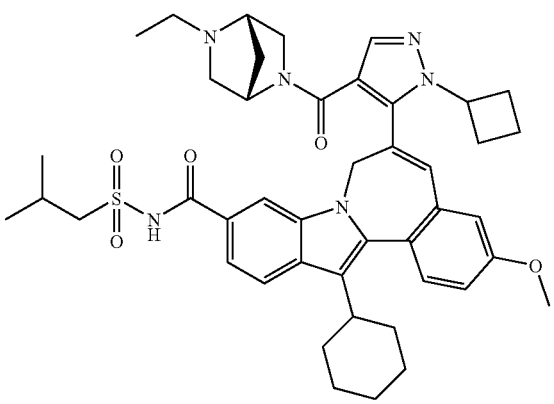

To a solution of 1H-pyrazole-4-carboxylic acid, 1-cyclobutyl-5-[13-cyclohexyl-3-methoxy-10-[[[(2-methylpropyl)sulfonyl]amino]carbonyl]-7H-indolo[2,1-a][2]benzazepin-6-yl]-(30 mg, 0.045 mmol) in DMSO (1 mL), TBTU (21.54 mg, 0.067 mmol) and DIPEA (0.039 mL, 0.224 mmol) were added. The reaction mixture was stirred at RT for 15 min. Then (1S,4S)-2-ethyl-2,5-diazabicyclo[2.2.1]heptane, TFA (23.76 mg, 0.067 mmol) was added. The solution was stirred at RT for overnight. The reaction mixture was then purified by Prep. HPLC column using CH$_3$CN—H$_2$O-TFA as solvent system. Fractions were collected and concentrated under SPEED VAC® for overnight. A yellow solid was obtained as title compound (22.1 mg, 0.025 mmol, 55.3% yield) as TFA salt. MS m/z 777 (M–H⁻), Retention time: 1.960 min. (basic). $^1$H NMR (500 MHz, MeOD) δ ppm 1.13 (d, J=6.71 Hz, 6H) 1.19-2.61 (m, 22H) 2.87-3.03 (m, 1H) 3.08-4.55 (m, 14H) 4.57-4.69 (m, 1H) 5.03-5.13 (m, 1H) 6.85 (s, 1H) 7.04-7.15 (m, 1H) 7.20 (dd, J=8.55, 2.44 Hz, 1H) 7.61 (d, J=8.85 Hz, 2H) 7.75-7.91 (m, 2H) 7.97 (d, J=8.55 Hz, 1H).

7H-Indolo[2,1-a][2]benzazepine-10-carboxamide, 6-[1-cyclobutyl-4-(4-morpholinylcarbonyl)-1H-pyrazol-5-yl]-13-cyclohexyl-3-methoxy-N-[(2-methylpropyl)sulfonyl]-

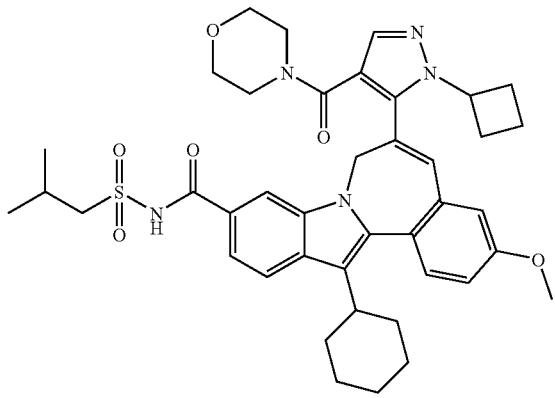

To a solution of 1H-pyrazole-4-carboxylic acid, 1-cyclobutyl-5-[13-cyclohexyl-3-methoxy-10-[[[(2-methylpropyl)sulfonyl]amino]carbonyl]-7H-indolo[2,1-a][2]benzazepin-6-yl]-(30 mg, 0.045 mmol) in DMSO (1 mL), TBTU (21.54 mg, 0.067 mmol) and DIPEA (0.039 mL, 0.224 mmol) were added. The reaction mixture was stirred at RT for 15 min. Then morpholine (5.84 mg, 0.067 mmol) was added. The solution was stirred at RT for overnight.

The reaction mixture was then purified by Prep. HPLC column using CH$_3$CN—H$_2$O-TFA as solvent system. Fractions were collected and concentrated under SPEED VAC® for overnight. A yellow solid was obtained as title compound (26.8 mg, 0.036 mmol, 81% yield).

MS m/z 738 (M–H⁻), Retention time: 2.015 min. (basic).

$^1$H NMR (500 MHz, MeOD) δ ppm 1.14 (d, J=6.71 Hz, 6H) 1.19-2.69 (m, 17H) 2.88-3.57 (m, 11H) 3.95 (s, 3H) 4.46-4.60 (m, br, 1H) 4.65 (d, J=14.95 Hz, 1H) 5.03 (d, J=14.95 Hz, 1H) 6.98 (s, 1H) 7.13 (d, J=2.44 Hz, 1H) 7.20 (dd, J=8.55, 2.75 Hz, 1H) 7.58-7.64 (m, 2H) 7.72 (s, 1H) 7.86 (d, J=1.22 Hz, 1H) 7.98 (d, J=8.55 Hz, 1H).

7H-Indolo[2,1-a][2]benzazepine-10-carboxamide, 6-[1-cyclobutyl-4-[[cis-2,6-dimethyl-4-morpholinyl]carbonyl]-1H-pyrazol-5-yl]-13-cyclohexyl-3-methoxy-N-[(2-methylpropyl)sulfonyl]-

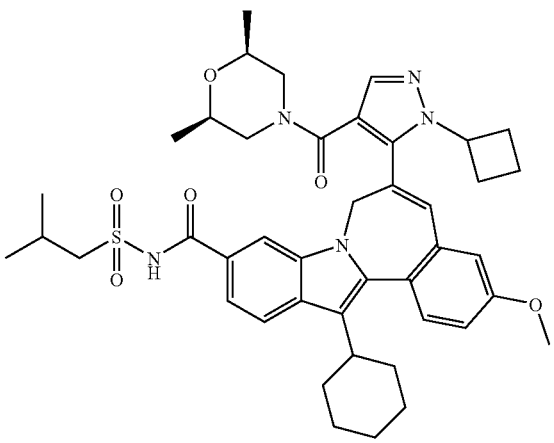

To a solution of 1H-pyrazole-4-carboxylic acid, 1-cyclobutyl-5-[13-cyclohexyl-3-methoxy-10-[[[(2-methylpropyl)sulfonyl]amino]carbonyl]-7H-indolo[2,1-a][2]benzazepin-6-yl]-(30 mg, 0.045 mmol) in DMSO (1 mL), TBTU (21.54 mg, 0.067 mmol) and DIPEA (0.039 mL, 0.224 mmol) were added. The reaction mixture was stirred at RT for 15 min. Then cis-2,6-dimethylmorpholine (7.73 mg, 0.067 mmol) was added. The solution was stirred at RT for overnight. The reaction mixture was then purified by Prep. HPLC column using CH$_3$CN—H$_2$O-TFA as solvent system. Fractions were collected and concentrated under SPEED VAC® for overnight. A yellow solid was obtained as title compound (26.9 mg, 0.035 mmol, 78% yield). MS m/z 766 (M–H⁻), Retention time: 2.270 min. (basic). $^1$H NMR (500 MHz, MeOD) δ ppm 0.51-2.76 (m, 29H) 2.88-3.02 (m, 1H) 3.22-3.67 (m, 9H) 3.96 (s, 3H) 4.63 (d, J=14.96 Hz, 1H) 5.00 (d, J=15.26 Hz, 1H) 7.03 (s, 1H) 7.14 (d, J=1.83 Hz, 1H) 7.20 (dd, 1H) 7.57-7.63 (m, J=8.55, 1.53 Hz, 2H) 7.70 (s, 1H) 7.87 (d, J=1.22 Hz, 1H) 7.97 (d, J=8.55 Hz, 1H).

7H-Indolo[2,1-a][2]benzazepine-10-carboxamide, 6-[1-cyclobutyl-4-[(8-methyl-3,8-diazabicyclo[3.2.1]oct-3-yl)carbonyl]-1H-pyrazol-5-yl]-13-cyclohexyl-3-methoxy-N-[(2-methylpropyl)sulfonyl]-

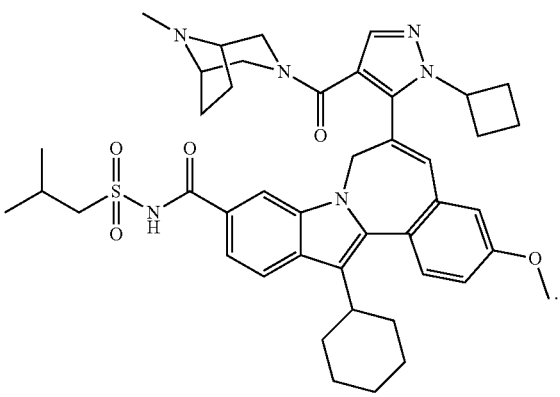

To a solution of 1H-pyrazole-4-carboxylic acid, 1-cyclobutyl-5-[13-cyclohexyl-3-methoxy-10-[[[(2-methylpropyl)sulfonyl]amino]carbonyl]-7H-indolo[2,1-a][2]benzazepin-6-yl]-(30 mg, 0.045 mmol) in DMSO (1 mL), TBTU (21.54 mg, 0.067 mmol) and DIPEA (0.039 mL, 0.224 mmol) were added. The reaction mixture was stirred at RT for 15 min. Then 8-methyl-3,8-diazabicyclo[3.2.1]octane, 2HCl (13.36 mg, 0.067 mmol) was added. The solution was stirred at RT for overnight. The reaction mixture was then purified by Prep. HPLC column using CH$_3$CN—H$_2$O-TFA as solvent system. Fractions were collected and concentrated under SPEED VAC® for overnight. A yellow solid was obtained as title compound (31.5 mg, 0.035 mmol, 79% yield) as TFA salt. MS m/z 779 (MH$^+$), Retention time: 2.778 min. (acid).
$^1$H NMR (500 MHz, MeOD) δ ppm 1.15 (d, J=6.71 Hz, 6H) 1.20-2.41 (m, 20H) 2.55 (s, br, 1H) 2.71-3.05 (m, 5H) 3.11-3.59 (m, 7H) 3.96 (s, 3H) 4.54-4.70 (m, 2H) 4.95-5.04 (m, 1H) 7.00 (s, 1H) 7.12 (s, 1H) 7.21 (dd, J=8.55, 2.44 Hz, 1H) 7.57-7.64 (m, 2H) 7.81 (s, 1H) 7.90 (s, 1H) 7.97 (d, J=8.54 Hz, 1H).

7H-Indolo[2,1-a][2]benzazepine-10-carboxamide, 6-[1-cyclobutyl-4-[(3-hydroxy-3-methyl-8-azabicyclo[3.2.1]oct-8-yl)carbonyl]-1H-pyrazol-5-yl]-13-cyclohexyl-3-methoxy-N-[(2-methylpropyl)sulfonyl]-

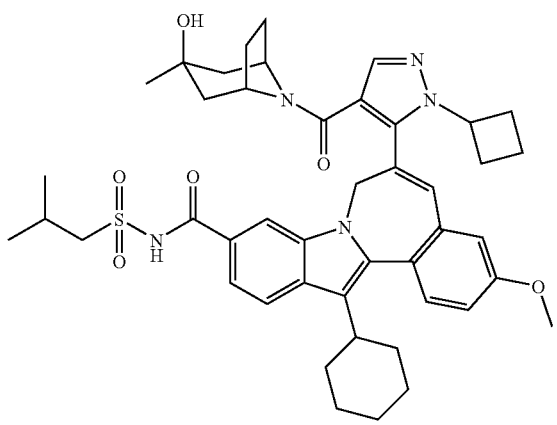

To a solution of 1H-pyrazole-4-carboxylic acid, 1-cyclobutyl-5-[13-cyclohexyl-3-methoxy-10-[[[(2-methylpropyl)sulfonyl]amino]carbonyl]-7H-indolo[2,1-a][2]benzazepin-6-yl]-(30 mg, 0.045 mmol) in DMSO (1 mL), TBTU (28.7 mg, 0.089 mmol) and DIPEA (0.039 mL, 0.224 mmol) were added. The reaction mixture was stirred at RT for 15 min. Then 3-methyl-8-azabicyclo[3.2.1]octan-3-ol, HCl (11.92 mg, 0.067 mmol) was added. The solution was stirred at RT for overnight. The reaction mixture was then purified by Prep. HPLC column using CH$_3$CN—H$_2$O-TFA as solvent system. Fractions were collected and concentrated under SPEED VAC® for overnight. A yellow solid was obtained as title compound (20.5 mg, 0.025 mmol, 56.6% yield). MS m/z 792 (M–H$^-$), Retention time: 2.152 min. (basic). $^1$H NMR (500 MHz, MeOD) δ ppm 0.95-2.72 (m, 34H) 2.88-3.03 (m, 1H) 3.43-3.65 (m, 3H) 3.96 (s, 3H) 4.12 (s, br, 1H) 4.51-4.70 (m, 2H) 4.95-5.03 (m, 1H) 6.87-7.15 (m, 2H) 7.19 (d, J=7.93 Hz, 1H) 7.58-7.66 (m, 2H) 7.78 (s, 1H) 7.86 (m, 1H) 7.96 (d, J=8.54 Hz, 1H).

7H-Indolo[2,1-a][2]benzazepine-10-carboxamide, 6-[1-cyclobutyl-4-[(3-methyl-3,8-diazabicyclo[3.2.1]oct-8-yl)carbonyl]-1H-pyrazol-5-yl]-13-cyclohexyl-3-methoxy-N-[(1-methylethyl)sulfonyl]-

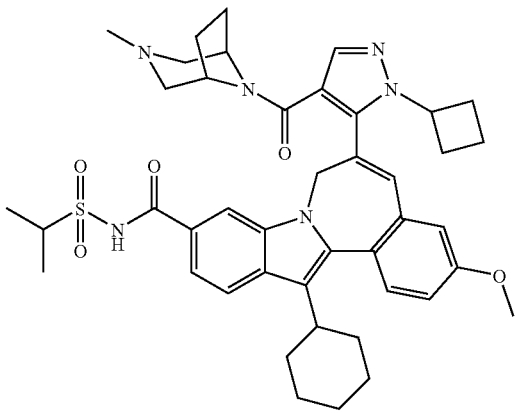

To a solution of 1H-pyrazole-4-carboxylic acid, 1-cyclobutyl-5-[13-cyclohexyl-3-methoxy-10-[[[(1-methylethyl)sulfonyl]amino]carbonyl]-7H-indolo[2,1-a][2]benzazepin-6-yl]-(30 mg, 0.046 mmol) in DMSO (1 mL), TBTU (22.00 mg, 0.069 mmol) and DIPEA (0.040 mL, 0.228 mmol) were added. The reaction mixture was stirred at RT for 15 min. Then 3-methyl-3,8-diazabicyclo[3.2.1]octane, 2HCl (13.64 mg, 0.069 mmol) was added. The solution was stirred at RT for overnight. The reaction mixture was then purified by Prep. HPLC column using CH$_3$CN—H$_2$O-TFA as solvent system. Fractions were collected and concentrated under SPEED VAC® for overnight. A yellow solid was obtained as title compound (34.6 mg, 0.039 mmol, 86% yield) as TFA salt. MS m/z 763 (M–H$^-$), Retention time: 2.125 min. (basic).
$^1$H NMR (500 MHz, MeOD) δ ppm 1.16-2.36 (m, 25H) 2.41-2.65 (m, br, 1H) 2.70-3.65 (m, 10H) 3.90-4.02 (m, 5H) 4.60 (d, J=14.65 Hz, 1H) 4.97 (d, J=15.26 Hz, 1H) 7.00 (s, br, 1H) 7.12 (s, 1H) 7.20 (dd, J=8.70, 2.59 Hz, 1H) 7.60 (d, J=8.85 Hz, 2H) 7.80 (s, 1H) 7.89 (s, 1H) 7.97 (d, J=8.55 Hz, 1H).

7H-Indolo[2,1-a][2]benzazepine-10-carboxamide, 6-[1-cyclobutyl-4-(3,7-dioxa-9-azabicyclo[3.3.1]non-9-ylcarbonyl)-1H-pyrazol-5-yl]-13-cyclohexyl-3-methoxy-N-[(1-methylethyl)sulfonyl]-

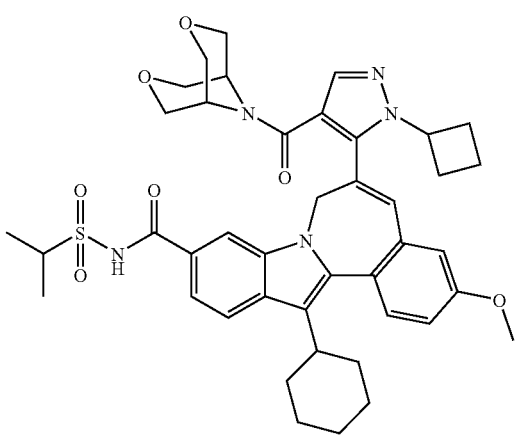

To a solution of 1H-pyrazole-4-carboxylic acid, 1-cyclobutyl-5-[13-cyclohexyl-3-methoxy-10-[[[(1-methylethyl)sulfonyl]amino]carbonyl]-7H-indolo[2,1-a][2]benzazepin-6-yl]- (30 mg, 0.046 mmol) in DMSO (1 mL), TBTU (22.00 mg, 0.069 mmol) and DIPEA (0.040 mL, 0.228 mmol) were added. The reaction mixture was stirred at RT for 15 min. Then 3,7-dioxa-9-azabicyclo[3.3.1]nonane (8.85 mg, 0.069 mmol) was added. The solution was stirred at RT for overnight. LC/MS shown incompletion of reaction. One more equivalent of TBTU and DIPEA were added. The reaction mixture was continued stirring at RT for overnight. The reaction mixture was then purified by Prep. HPLC column using $CH_3CN$—$H_2O$-TFA as solvent system. Fractions were collected and concentrated under SPEED VAC® for over the weekend. A yellow solid was obtained as title compound (29.9 mg, 0.039 mmol, 85% yield). MS m/z 766 (M–H⁻), Retention time: 1.868 min. (basic). $^1$H NMR (500 MHz, MeOD) δ ppm 1.18-2.66 (m, 22H) 2.90-3.05 (m, 1H) 3.21-4.05 (m, 15H) 4.60-4.71 (m, 1H) 4.98-5.08 (m, 1H) 7.03 (s, 1H) 7.13 (d, J=2.44 Hz, 1H) 7.22 (dd, J=8.55, 2.75 Hz, 1H) 7.56-7.71 (m, 2H) 7.78 (s, 1H) 7.88 (s, 1H) 7.98 (d, J=8.24 Hz, 1H).

7H-Indolo[2,1-a][2]benzazepine-10-carboxamide, 6-[1-cyclobutyl-4-[[3,5-cis-3,4,5-trimethyl-1-piperazinyl]carbonyl]-1H-pyrazol-5-yl]-13-cyclohexyl-3-methoxy-N-[(1-methylethyl)sulfonyl]-

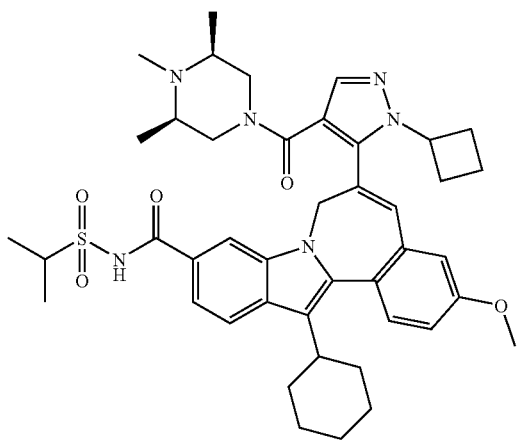

To a solution of 1H-pyrazole-4-carboxylic acid, 1-cyclobutyl-5-[13-cyclohexyl-3-methoxy-10-[[[(1-methylethyl)sulfonyl]amino]carbonyl]-7H-indolo[2,1-a][2]benzazepin-6-yl]-(30 mg, 0.046 mmol) in DMSO (1 mL), TBTU (22.00 mg, 0.069 mmol) and DIPEA (0.040 mL, 0.228 mmol) were added. The reaction mixture was stirred at RT for 15 min. Then cis-1,2,6-trimethylpiperazine, 2HCl (13.78 mg, 0.069 mmol) was added. The solution was stirred at RT for 3 hr. The reaction mixture was then purified by Prep. HPLC column using $CH_3CN$—$H_2O$-TFA as solvent system. Fractions were collected and concentrated under SPEED VAC® for overnight. A yellow solid was obtained as title compound (34.5 mg, 0.039 mmol, 86% yield) as TFA salt. MS m/z 765 (M–H), Retention time: 1.970 min. (basic). $^1$H NMR (500 MHz, MeOD) δ ppm 1.14-2.34 (m, 27H) 2.54 (s, br, 1H) 2.69-3.24 (m, 8H) 3.87-3.99 (m, 4H) 4.36 (s, br, 3H) 4.51-4.66 (m, 1H) 4.97-5.06 (m, br, 1H) 6.96 (s, 1H) 7.11 (d, J=2.75 Hz, 1H) 7.19 (dd, J=8.55, 2.75 Hz, 1H) 7.53-7.65 (m, J=10.68, 8.55 Hz, 2H) 7.78 (s, 1H) 7.82-7.87 (m, 1H) 7.98 (d, J=8.55 Hz, 1H).

7H-Indolo[2,1-a][2]benzazepine-10-carboxamide, 6-[1-cyclobutyl-4-[[(1S,4S)-5-ethyl-2,5-diazabicyclo[2.2.1]hept-2-yl]carbonyl]-1H-pyrazol-5-yl]-13-cyclohexyl-3-methoxy-N-[(1-methylethyl)sulfonyl]

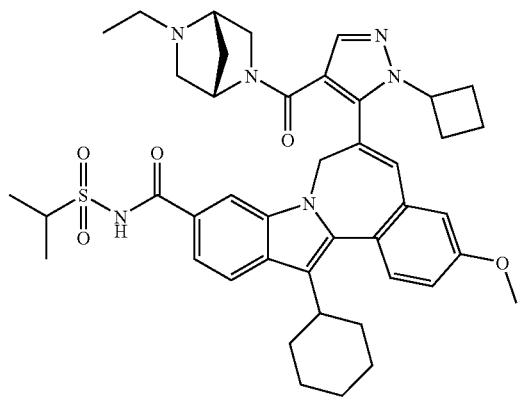

To a solution of 1H-pyrazole-4-carboxylic acid, 1-cyclobutyl-5-[13-cyclohexyl-3-methoxy-10-[[[(1-methylethyl)sulfonyl]amino]carbonyl]-7H-indolo[2,1-a][2]benzazepin-6-yl]-(30 mg, 0.046 mmol) in DMSO (1 mL), TBTU (22.00 mg, 0.069 mmol) and DIPEA (0.040 mL, 0.228 mmol) were added. The reaction mixture was stirred at RT for 15 min. Then (1S,4S)-2-ethyl-2,5-diazabicyclo[2.2.1]heptane, TFA (24.27 mg, 0.069 mmol) was added. The solution was stirred at RT for 3 hr. The reaction mixture was then purified by Prep. HPLC column using $CH_3CN$—$H_2O$-TFA as solvent system. Fractions were collected and concentrated under SPEED VAC® for overnight.

A yellow solid was obtained as title compound (33.9 mg, 0.039 mmol, 84% yield) as TFA salt.

MS m/z 763 (M–H–), Retention time: 1.883 min. (basic). $^1$H NMR (500 MHz, MeOD) δ ppm 1.15-2.62 (m, 27H) 2.84-3.02 (m, 1H) 3.07-4.69 (m, 14H) 5.01-5.11 (m, 1H) 6.84 (s, 1H) 7.03-7.11 (m, 1H) 7.19 (dd, J=8.55, 2.44 Hz, 1H) 7.59 (d, J=8.55 Hz, 2H) 7.72-7.92 (m, 2H) 7.97 (d, J=8.24 Hz, 1H).

7H-Indolo[2,1-a][2]benzazepine-10-carboxamide, 6-[1-cyclobutyl-4-(4-morpholinylcarbonyl)-1H-pyrazol-5-yl]-13-cyclohexyl-3-methoxy-N-[(1-methylethyl)sulfonyl]-

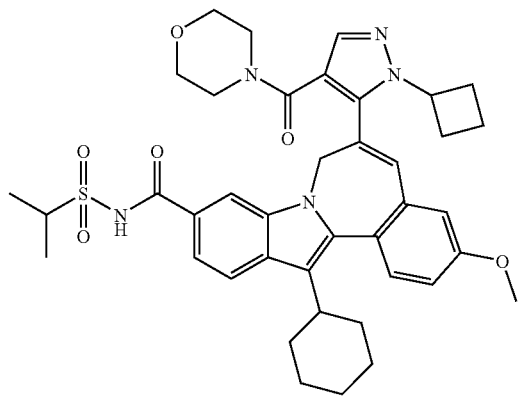

To a solution of 1H-pyrazole-4-carboxylic acid, 1-cyclobutyl-5-[13-cyclohexyl-3-methoxy-10-[[[(1-methylethyl)sulfonyl]amino]carbonyl]-7H-indolo[2,1a][2]benzazepin-6-yl]-(30 mg, 0.046 mmol) in DMSO (1 mL), TBTU (22.00 mg, 0.069 mmol) and DIPEA (0.040 mL, 0.228 mmol) were added. The reaction mixture was stirred at RT for 15 min. Then morpholine (5.97 mg, 0.069 mmol) was added. The solution was stirred at RT for 3 hr. The reaction mixture was then purified by Prep. HPLC column using CH$_3$CN—H$_2$O-TFA as solvent system. Fractions were collected and concentrated under SPEED VAC® for overnight. A yellow solid was obtained as title compound (27.4 mg, 0.038 mmol, 83% yield). MS m/z 724 (M–H$^-$), Retention time: 1.937 min. (basic). $^1$H NMR (500 MHz, MeOD) δ ppm 1.21-2.70 (m, 22H) 2.90-3.38 (m, 9H) 3.91-4.01 (m, 4H) 4.49-4.61 (m, br, 1H) 4.64 (d, J=15.26 Hz, 1H) 5.02 (d, J=14.65 Hz, 1H) 6.98 (s, 1H) 7.13 (d, J=2.44 Hz, 1H) 7.20 (dd, J=8.70, 2.59 Hz, 1H) 7.58-7.63 (m, 2H) 7.71 (s, 1H) 7.87 (d, J=1.22 Hz, 1H) 7.98 (d, J=8.55 Hz, 1H).

7H-Indolo[2,1-a][2]benzazepine-10-carboxamide, 6-[1-cyclobutyl-4-[[cis-2,6-dimethyl-4-morpholinyl]carbonyl]-1H-pyrazol-5-yl]-13-cyclohexyl-3-methoxy-N-[(1-methylethyl)sulfonyl]-

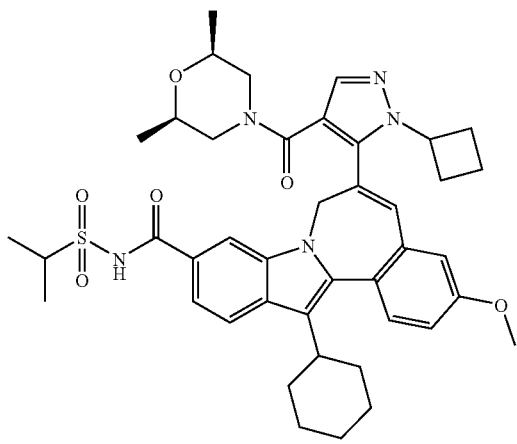

To a solution of 1H-pyrazole-4-carboxylic acid, 1-cyclobutyl-5-[13-cyclohexyl-3-methoxy-10-[[[(1-methylethyl)sulfonyl]amino]carbonyl]-7H-indolo[2,1-a][2]benzazepin-6-yl]-(30 mg, 0.046 mmol) in DMSO (1 mL), TBTU (22.00 mg, 0.069 mmol) and DIPEA (0.040 mL, 0.228 mmol) were added. The reaction mixture was stirred at RT for 15 min. Then cis-2,6-dimethylmorpholine (7.89 mg, 0.069 mmol) was added. The solution was stirred at RT for 3 hr. The reaction mixture was then purified by Prep. HPLC column using CH$_3$CN—H$_2$O-TFA as solvent system. Fractions were collected and concentrated under SPEED VAC® for overnight. A yellow solid was obtained as title compound (30.7 mg, 0.041 mmol, 89% yield). MS m/z 752 (M–H$^-$), Retention time: 2.125 min. (basic). $^1$H NMR (500 MHz, MeOD) δ ppm 0.47-2.77 (m, 29H) 2.89-3.02 (m, 1H) 3.19-3.72 (m, 5H) 3.91-4.04 (m, 5H) 4.63 (d, J=14.34 Hz, 1H) 5.00 (d, J=15.26 Hz, 1H) 7.03 (s, 1H) 7.14 (d, J=1.83 Hz, 1H) 7.21 (dd, J=8.55, 2.44 Hz, 1H) 7.58-7.64 (m, 2H) 7.69 (s, 1H) 7.88 (s, 1H) 7.97 (d, J=8.55 Hz, 1H).

7H-Indolo[2,1-a][2]benzazepine-10-carboxamide, 6-[1-cyclobutyl-4-[(8-methyl-3,8-diazabicyclo[3.2.1]oct-3-yl)carbonyl]-1H-pyrazol-5-yl]-13-cyclohexyl-3-methoxy-N-[(1-methylethyl)sulfonyl]-

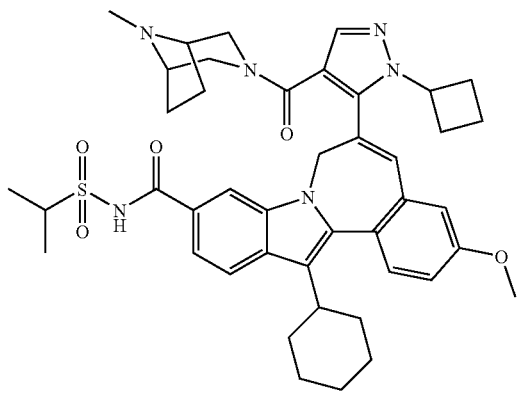

To a solution of 1H-pyrazole-4-carboxylic acid, 1-cyclobutyl-5-[13-cyclohexyl-3-methoxy-10-[[[(1-methylethyl)sulfonyl]amino]carbonyl]-7H-indolo[2,1-a][2]benzazepin-6-yl]-(30 mg, 0.046 mmol) in DMSO (1 mL), TBTU (22.00 mg, 0.069 mmol) and DIPEA (0.040 mL, 0.228 mmol) were added. The reaction mixture was stirred at RT for 15 min. Then 8-methyl-3,8-diazabicyclo[3.2.1]octane, 2HCl (13.64 mg, 0.069 mmol) was added. The solution was stirred at RT for 3 hr. The reaction mixture was then purified by Prep. HPLC column using CH$_3$CN—H$_2$O-TFA as solvent system. Fractions were collected and concentrated under SPEED VAC® for overnight. A yellow solid was obtained as title compound (31.7 mg, 0.036 mmol, 79% yield) as TFA salt. MS m/z 763 (M–H), Retention time: 2.083 min. (basic). $^1$H NMR (500 MHz, MeOD) δ ppm 1.18-2.33 (m, 25H) 2.54 (s, br, 1H) 2.71-3.58 (m, 10H) 3.84-4.05 (m, 5H) 4.63 (d, J=14.35 Hz, 1H) 4.94-5.02 (m, 1H) 6.93-7.06 (s, br, 1H) 7.12 (s, 1H) 7.21 (dd, J=8.55, 2.44 Hz, 1H) 7.53-7.64 (m, 2H) 7.81 (s, 1H) 7.90 (s, 1H) 7.97 (d, J=8.24 Hz, 1H).

7H-Indolo[2,1-a][2]benzazepine-10-carboxamide, 6-[1-cyclobutyl-4-[(3-hydroxy-3-methyl-8-azabicyclo[3.2.1]oct-8-yl)carbonyl]-1H-pyrazol-5-yl]-13-cyclohexyl-3-methoxy-N-[(1-methylethyl)sulfonyl]-

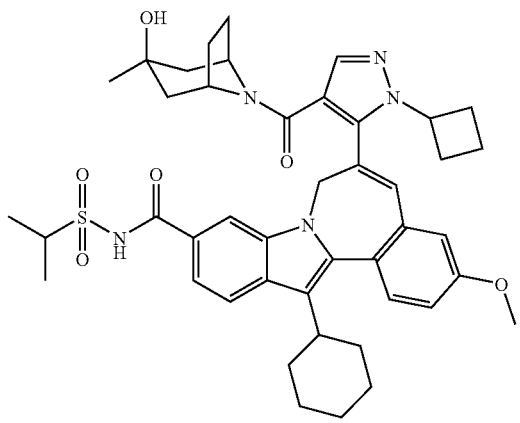

To a solution of 1H-pyrazole-4-carboxylic acid, 1-cyclobutyl-5-[13-cyclohexyl-3-methoxy-10-[[[(1-methylethyl)sulfonyl]amino]carbonyl]-7H-indolo[2,1-a][2]benzazepin-6-yl]-(30 mg, 0.046 mmol) in DMSO (1 mL), TBTU (29.3 mg, 0.091 mmol) and DIPEA (0.040 mL, 0.228 mmol) were added. The reaction mixture was stirred at RT for 15 min. Then 3-methyl-8-azabicyclo[3.2.1]octan-3-ol, HCl (12.17 mg, 0.069 mmol) was added. The solution was stirred at RT for overnight. The reaction mixture was then purified by Prep. HPLC column using $CH_3CN-H_2O$-TFA as solvent system. Fractions were collected and concentrated under SPEED VAC® for overnight. A yellow solid was obtained as title compound (22.5 mg, 0.027 mmol, 60.0% yield). MS m/z 778 (M−H), Retention time: 2.073 min. (basic). $^1$H NMR (500 MHz, MeOD) δ ppm 0.94-2.68 (m, 34H) 2.89-3.03 (m, 1H) 3.88-4.04 (m, 5H) 4.15 (s, br, 1H) 4.53-4.71 (m, 2H) 4.96-5.04 (m, 1H) 6.85-7.16 (m, 2H) 7.19 (d, J=7.63 Hz, 1H) 7.59-7.63 (m, 2H) 7.78 (s, 1H) 7.87 (s, 1H) 7.97 (d, J=8.55 Hz, 1H).

7H-Indolo[2,1-a][2]benzazepine-10-carboxylic acid, 13-cyclohexyl-6-[1-cyclopropyl-4-(ethoxycarbonyl)-1H-pyrazol-3-yl]-3-methoxy-, 1,1-dimethylethyl ester

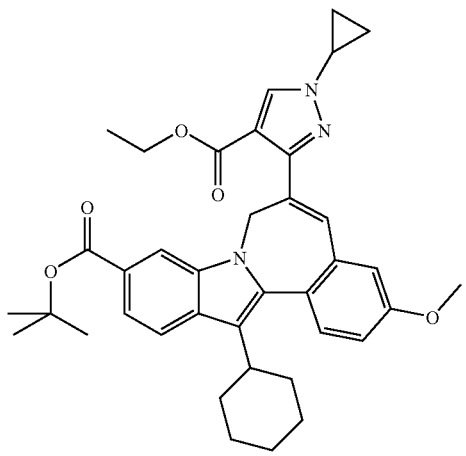

tert-Butyl 13-cyclohexyl-6-((2E,Z)-3-(dimethylamino)-2-(ethoxycarbonyl)-2-propenoyl)-3-methoxy-7H-indolo[2,1-a][2]benzazepine-10-carboxylate, (0.800 g, 1.31 mmol) was dissolved in absolute ethanol (13 mL) and triethylamine (0.264 mg, 2.61 mmol). Cyclopropylhydrazine hydrochloride (0.283 mg, 2.61 mmol) was added to the reaction and the reaction was placed under a nitrogen atmosphere. The reaction was heated to 160° C. for 2 hours in a microwave. The resulting solution was diluted with chloroform (50 mL) and extracted with 1M aqueous HCl solution (50 mL). The organic solution was concentrated in vacuo using a rotary evaporator to yield 0.810 mg of a yellow amorphous. LC-MS analysis indicated two possible isomeric products. This crude product was purified by reverse phase prep HPLC to yield 400 mg and 192 mg of the isomeric products in the following manner:

The sample was purified on a Shimadzu high pressure liquid chromatography system employing DISCOVERY VP® software interfaced with a SCL-10A controller, SIL-10A autosampler and FRC-10A fraction collector. The sample was dissolved in acetonitrile/DMF (1:1) (4 ml) purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 25% solvent A/75% solvent B to 0% solvent A/100% solvent B, a gradient time of 10 minutes with a run time of 20 minutes using % A=10% acetonitrile, 90% water, 0.1% TFA % B=90% acetonitrile, 10% water, 0.1% TFA solvent system.

First eluting product is 7H-indolo[2,1-a][2]benzazepine-10-carboxylic acid, 13-cyclohexyl-6-[1-cyclopropyl-4-(ethoxycarbonyl)-1H-pyrazol-5-yl]-3-methoxy-, 1,1-dimethylethyl ester with retention time of 12.5 minutes with the minor component product being 7H-indolo[2,1-a][2]benzazepine-10-carboxylic acid, 13-cyclohexyl-6-[1-cyclopropyl-4-(ethoxycarbonyl)-1H-pyrazol-3-yl]-3-methoxy-, 1,1-dimethylethyl ester with a retention of 15.6 minutes.

7H-Indolo[2,1-a][2]benzazepine-10-carboxylic acid, 13-cyclohexyl-6-[1-cyclopropyl-4-(ethoxycarbonyl)-1H-pyrazol-5-yl]-3-methoxy-, 1,1-dimethylethyl ester $^1$H NMR (500 MHz, CHLOROFORM-D) δ ppm 0.00 (m, 1H) 0.19 (m, 1H) 0.70 (m, 1H) 0.98 (m, 1H) 1.13-1.27 (m, 1H) 1.30 (t, J=7.02 Hz, 3H) 1.34-1.55 (m, 3H) 1.58 (s, 9H) 1.61-1.84 (m, 3H) 1.85-2.00 (m, 1H) 1.99-2.18 (m, 3H) 2.86 (t, J=11.75 Hz, 1H) 3.09 (m, 1H) 3.90 (s, 3H) 4.27 (d, J=4.27 Hz, 2H) 4.71 (s, 1H) 5.02 (s, 1H) 6.77 (s, 1H) 6.93 (d, J=2.44 Hz, 1H) 7.07 (dd, J=8.55, 2.44 Hz, 1H) 7.65 (d, J=8.55 Hz, 1H) 7.79-7.88 (m, 2H) 7.97 (s, 1H).

LC-MS retention time 3.99 min; 622 m/z (MH+). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 ml/min, a gradient of 70% solvent A/30% solvent B to 0% solvent A/100% solvent B, a gradient time of 5 min, a hold time of 1 min, and an analysis time of 6 min where solvent A was 5% acetonitrile/95% $H_2O$/10 mM ammonium acetate and solvent B was 5% $H_2O$/95% acetonitrile/10 mM ammonium acetate. MS data was determined using a MICROMASS® Platform for LC in electrospray mode.

7H-Indolo[2,1-a][2]benzazepine-10-carboxylic acid, 13-cyclohexyl-6-[1-cyclopropyl-4-(ethoxycarbonyl)-1H-pyrazol-3-yl]-3-methoxy-, 1,1-dimethylethyl ester $^1$H NMR (500 MHz, CHLOROFORM-D) δ ppm 1.13-1.26 (m, 2H) 1.30 (t, J=7.17 Hz, 3H) 1.33-1.60 (m, 4H) 1.61 (s, 9H) 1.64-1.91 (m, 5H) 1.98-2.16 (m, 3H) 2.82-2.91 (m, 1H) 3.75 (m, 1H) 3.94 (s, 3H) 4.20-4.30 (m, 2H) 4.41 (d, J=14.04 Hz, 1H) 5.76 (d, J=14.04 Hz, 1H) 6.96-7.03 (m, 2H) 7.49-7.54 (m, 1H) 7.64 (dd, J=8.39, 1.37 Hz, 1H) 7.79 (d, J=8.55 Hz, 1H) 7.84 (s, 1H) 7.90 (s, 1H) 8.26 (s, 1H).

LC-MS retention time 4.38 min; 622 m/z (MH+). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 ml/min, a gradient of 70% solvent A/30% solvent B to 0% solvent A/100% solvent B, a gradient time of 5 min, a hold time of 1 min, and an analysis time of 6 min where solvent A was 5% acetonitrile/95% $H_2O$/10 mM ammonium acetate and solvent B was 5% $H_2O$/95% acetonitrile/10 mM ammonium acetate. MS data was determined using a MICROMASS® Platform for LC in electrospray mode.

7H-Indolo[2,1-a][2]benzazepine-10-carboxylic acid, 13-cyclohexyl-6-[1-cyclopropyl-4-(ethoxycarbonyl)-1H-pyrazol-5-yl]-3-methoxy-

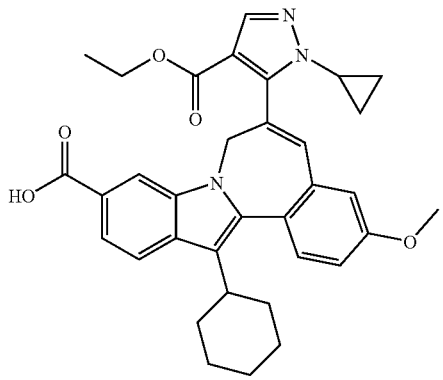

Dissolved 7H-indolo[2,1-a][2]benzazepine-10-carboxylic acid, 13-cyclohexyl-6-[1-cyclopropyl-4-(ethoxycarbonyl)-1H-pyrazol-5-yl]-3-methoxy-, 1,1-dimethylethyl ester (400 mg, 0.643 mmol) in 1,2-dichloroethane (3.2 mL), placed reaction under a nitrogen atmosphere, then added trifluoroacetic acid (3.2 ml, 26.0 mmol). The reaction was stirred at room temperature under a nitrogen atmosphere for 2 hours. Removed volatiles in vacuo using a rotary evaporator and dissolved the reaction product in benzene and remove in vacuo to aid in removal of trace TFA. Repeat dissolution in benzene and removal in vacuo. Dried sample at room temperature in vacuo to obtain 364 mg of the title compound as a yellow solid; $^1$H NMR (500 MHz, CHLOROFORM-D) δ ppm −0.09 (m, 1H) 0.19 (m, 1H) 0.69 (m, 1H) 0.99 (m, 1H) 1.12-1.26 (m, 1H) 1.31 (t, J=7.02 Hz, 3H) 1.40 (s, 2H) 1.51-1.89 (m, 3H) 1.87-2.23 (m, 4H) 2.87 (t, J=11.29 Hz, 1H) 3.10 (m, 1H) 3.91 (s, 3H) 4.27 (br.s, 2H) 4.73 (br.s, 1H) 4.97 (br.s, 1H) 6.78 (s, 1H) 6.94 (d, J=2.14 Hz, 1H) 7.08 (dd, J=8.55, 2.44 Hz, 1H) 7.54 (d, J=8.85 Hz, 1H) 7.77 (d, J=8.24 Hz, 1H) 7.86-7.95 (m, 2H) 7.98 (s, 1H). LC-MS 566 m/z (MH+).

1H-Pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-cyclopropyl-, ethyl ester

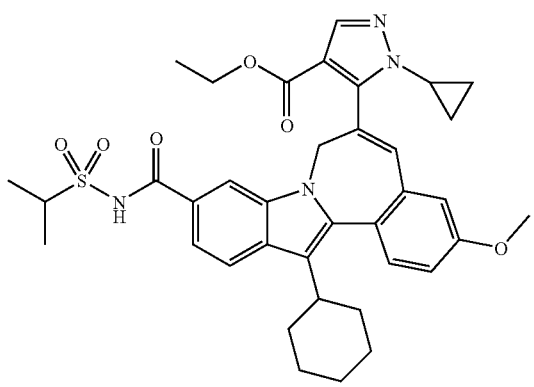

Dissolved 7H-indolo[2,1-a][2]benzazepine-10-carboxylic acid, 13-cyclohexyl-6-[1-cyclopropyl-4-(ethoxycarbonyl)-1H-pyrazol-5-yl]-3-methoxy- (120 mg, 0.212 mmol) in THF (0.700 mL). Carbonyldiimidazole (130 mg, 0.636 mmol) was added to the reaction. The reaction was placed under a nitrogen atmosphere and stirred at room temperature for 45 minutes then heated to reflux for 1 hour. The reaction was cooled under a nitrogen atmosphere and propane-2-sulfonamide (105 mg, 0.636 mmol) was added to the reaction followed by DBU (0.096 mL, 0.636 mmol). The reaction was immerse in oil bath and heated at reflux under nitrogen atmosphere overnight. The reaction was diluted with ethyl acetate (50 mL) and the organic layer washed sequentially with 1.0N aqueous hydrochloric acid (50 mL) and 0.1M aqueous $NaH_2PO_4$ (50 mL). The organic layer was dried in vacuo to yield 124 mg of the title product as a yellow foam. $^1$H NMR (500 MHz, CHLOROFORM-D) δ ppm −0.10 (m, 1H) 0.18 (m, 1H) 0.69 (m, 1H) 1.00 (m, 1H) 1.20-1.27 (m, 2H) 1.32-1.52 (m, 4H) 1.46 (d, J=7.02 Hz, 6H) 1.63-1.80 (m, 3H) 1.85-2.13 (m, 4H) 2.81-2.91 (m, 1H) 3.12 (m, 1H) 3.90 (s, 3H) 4.00-4.10 (m, 2H) 4.55 (m, 1H) 4.62 (broad d, 1H) 5.02 (broad d, 1H) 6.91 (s, 1H) 6.94 (d, J=2.44 Hz, 1H) 7.08 (dd, J=8.55, 2.75 Hz, 1H) 7.44 (d, J=8.85 Hz, 1H) 7.48 (d, J=1.22 Hz, 1H) 7.86-7.92 (m, 3H) 8.26 (br.s, 1H). LC-MS 671 m/z (MH).

1H-Pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-cyclopropyl-

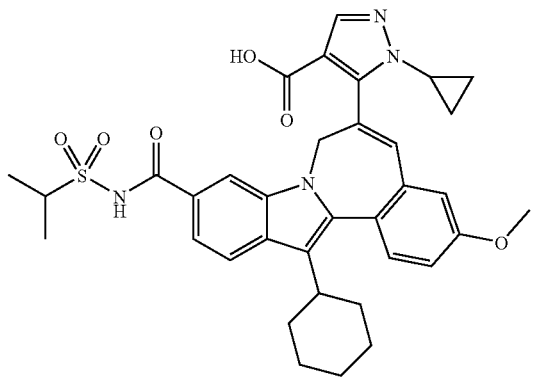

Dissolved 1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-cyclopropyl-, ethyl ester (0.120 g, 0.179 mmol) was dissolved in THF (0.500 mL) and methanol (0.500 mL) was added to the reaction followed by 1N aqueous sodium hydroxide (1.80 mL). The reaction was capped under a nitrogen atmosphere and stirred at room temperature for 18 hrs. The reaction was diluted with ethyl acetate (50.0 mL) and washed with 1.0N aqueous hydrochloric acid (2×50 ml). The organic layer was concentrated in vacuo using a rotary evaporator to yield 113 mg of title compound as a yellow solid.

LC-MS retention time 1.55 min; 643 m/z (MH). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 ml/min, a gradient of 100% solvent A 10% solvent B to 0% solvent A/100% solvent B, a gradient time of 3 min, a hold time of 1 min, and an analysis time of 4 min where solvent A was 5% acetonitrile 195% $H_2O$/10 mM ammonium acetate and solvent B was 5% H₂O 195% acetonitrile/10 mM ammonium acetate. MS data was determined using a MICROMASS® Platform for LC in electrospray mode.

7H-Indolo[2,1-a][2]benzazepine-10-carboxamide, 13-cyclohexyl-6-[1-cyclopropyl-4-(4-morpholinylcarbonyl)-1H-pyrazol-5-yl]-3-methoxy-N-[(1-methylethyl)sulfonyl]-

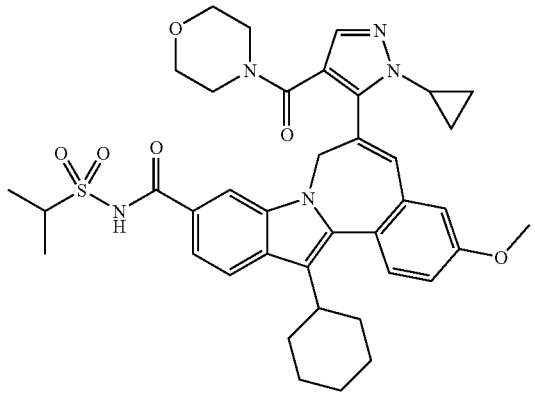

1H-Pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-cyclopropyl- (70 mg, 0.11 mmol) was dissolved in DMF (1.0 mL), TBTU (70 mg, 0.22 mmol), and DIPEA (56 mg, 0.44 mmol) were added to the reaction. The reaction was capped under a nitrogen atmosphere and stir at room temperature for 1 hour then morpholine (38 µL, 0.44 mmol) was added. The reaction was capped under a nitrogen atmosphere and stirred at room temperature overnight.

The reaction was diluted with ethyl acetate (50 mL) and washed sequentially with 1.0N aqueous hydrochloric acid (25 mL), 0.1M aqueous NaH₂PO₄ (25 mL). The organic phase was concentrated overnight in vacuo at room temperature to yield 78 mg of a yellow amorphous solid. The title compound was further purified on a Shimadzu high pressure liquid chromatography system employing DISCOVERY VP® software interfaced with a SCL-10A controller, SIL-10A autosampler and FRC-10A fraction collector. The sample was dissolved in acetonitrile/DMF (1:1) (total volume 2 ml) purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 60% solvent A/40% solvent B to 0% solvent A/100% solvent B, a gradient time of 12 minutes with a run time of 25 minutes using % A=10% acetonitrile, 90% water, 0.1% TFA % B=90% acetonitrile, 10% water, 0.1% TFA solvent system. The sample was run as two 1 ml injections. The run time of the second Prep HPLC run was truncated to 15 minutes base on data from the first run.

The product fractions (retention time=9.20 min.) were combined and solvent removed in vacuo. The compound was dried at room temperature in vacuo to yield 67 mg of the title compound as a yellow amorphous solid.

¹H NMR (500 MHz, CHLOROFORM-D) δ ppm 1.02 (m, 3H) 1.23 (q, J=12.21 Hz, 1H) 1.30-1.56 (m, 7H) 1.77 (d, J=10.38 Hz, 2H) 1.90-2.14 (m, 4H) 2.40-3.23 (m, 12H) 3.60 (m, 1H) 3.97 (s, 3H) 4.05 (m, 1H) 4.61 (d, J=14.65 Hz, 1H) 5.00 (d, J=14.65 Hz, 1H) 6.95 (d, J=2.75 Hz, 1H) 6.97 (s, 1H) 7.04 (dd, J=8.70, 2.59 Hz, 1H) 7.46 (dd, J=8.55, 1.53 Hz, 1H) 7.52 (d, J=8.55 Hz, 1H) 7.55 (s, 1H) 7.89 (d, J=8.55 Hz, 1H) 7.94 (d, J=1.22 Hz, 1H) 9.75 (br.s, 1H).

LC-MS retention time 1.94 min; 712 m/z (MH). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H₂O/10 mM ammonium acetate and solvent B was 5% H₂O/95% acetonitrile/10 mM ammonium acetate. MS data was determined using a MICROMASS® Platform for LC in electrospray mode.

The following compound was synthesized by an analogous method as described above for 7H-indolo[2,1-a][2]benzazepine-10-carboxamide, 13-cyclohexyl-6-[1-cyclopropyl-4-(4-morpholinylcarbonyl)-1H-pyrazol-5-yl]-3-methoxy-N-[(1-methylethyl)sulfonyl]-:

7H-Indolo[2,1-a][2]benzazepine-10-carboxamide, 13-cyclohexyl-6-[1-cyclopropyl-4-[[(3R,5S)-3,4,5-trimethyl-1-piperazinyl]carbonyl]-1H-pyrazol-5-yl]-3-methoxy-N-[(1-methylethyl)sulfonyl]-

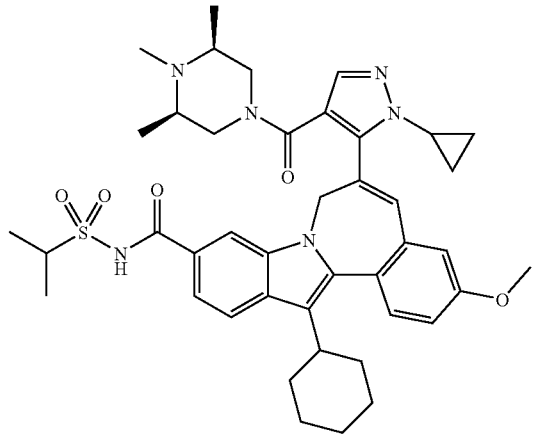

LCMS: m/e 753 (M+H), ret time 1.89 min.

7H-Indolo[2,1-a][2]benzazepine-10-carboxylic acid, 13-cyclohexyl-6-[1-cyclopropyl-4-(ethoxycarbonyl)-1H-pyrazol-3-yl]-3-methoxy-

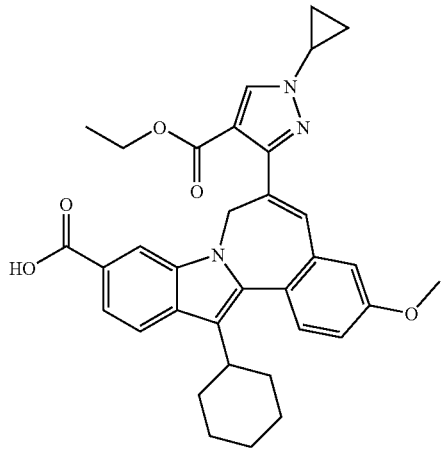

Dissolved 7H-indolo[2,1-a][2]benzazepine-10-carboxylic acid, 13-cyclohexyl-6-[1-cyclopropyl-4-(ethoxycarbonyl)-1H-pyrazol-3-yl]-3-methoxy-, 1,1-dimethylethyl ester (400 mg, 0.643 mmol) in 1,2-dichloroethane (3.2 mL), placed reaction under a nitrogen atmosphere, then added trifluoroacetic acid (3.2 ml, 26.0 mmol). The reaction was stirred at room temperature under a nitrogen atmosphere for 2 hours. Removed volatiles in vacuo using a rotary evaporator and dissolved the reaction product in benzene and remove in vacuo to aid in removal of trace TFA. Repeat dissolution in benzene and removal in vacuo. Dried sample at room temperature in vacuo to obtain 364 mg of the title compound as a yellow solid. $^1$H NMR (500 MHz, CHLOROFORM-D) δ ppm 1.12-1.26 (m, 3H) 1.31 (t, J=7.02 Hz, 3H) 1.40 (s, 2H) 1.51-1.89 (m, 5H) 1.87-2.23 (m, 4H) 2.87 (t, J=11.29 Hz, 1H) 3.58 (m, 1H) 3.91 (s, 3H) 4.27 (br.s, 2H) 4.73 (br.s, 1H) 4.97 (br.s, 1H) 6.78 (s, 1H) 6.94 (d, J=2.14 Hz, 1H) 7.08 (dd, J=8.55, 2.44 Hz, 1H) 7.54 (d, J=8.85 Hz, 1H) 7.77 (d, J=8.24 Hz, 1H) 7.86-7.95 (m, 2H) 7.98 (s, 1H). LC-MS 566 m/z (MH+).

1H-Pyrazole-4-carboxylic acid, 3-[13-cyclohexyl-3-methoxy-10-[[[(1-methylethyl)sulfonyl]amino]carbonyl]-7H-indolo[2,1-a][2]benzazepin-6-yl]-1-cyclopropyl-, ethyl ester

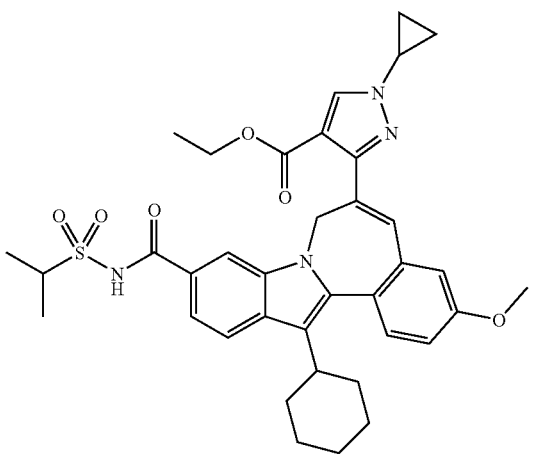

Dissolved 7H-indolo[2,1-a][2]benzazepine-10-carboxylic acid, 13-cyclohexyl-6-[1-cyclopropyl-4-(ethoxycarbonyl)-1H-pyrazol-3-yl]-3-methoxy- (32 mg, 0.06 mmol) in THF (0.30 mL). Carbonyldiimidazole (28 mg, 0.17 mmol) was added to the reaction. The reaction was placed under a nitrogen atmosphere and stirred at room temperature for 45 minutes then heated to reflux for 1 hour. The reaction was cooled under a nitrogen atmosphere and propane-2-sulfonamide (28 mg, 0.23 mmol) was added to the reaction followed by DBU (0.26 mL, 0.17 mmol). The reaction was immerse in oil bath and heated at reflux under nitrogen atmosphere overnight. The reaction was diluted with ethyl acetate (50 mL) and the organic layer washed sequentially with 1.0N aqueous hydrochloric acid (50 mL) and 0.1M aqueous NaH$_2$PO$_4$ (50 mL). The organic layer was dried in vacuo to yield 31 mg of the title product as a yellow foam. $^1$H NMR (500 MHz, CHLOROFORM-D) δ ppm 1.12-1.27 (m, 3H) 1.30 (t, J=7.02 Hz, 3H) 1.32-1.45 (m, 3H) 1.46 (d, J=9.77 Hz, 6H) 1.53-1.81 (m, 3H) 1.88-2.13 (m, 5H) 2.81-2.91 (m, 1H) 3.29 (m, 1H) 3.90 (s, 3H) 4.00-4.10 (m, 1H) 4.24 (s, 2H) 4.71 (d, J=12.21 Hz, 1H) 4.99 (d, J=16.48 Hz, 1H) 6.77 (s, 1H) 6.94 (d, J=2.44 Hz, 1H) 7.08 (dd, J=8.55, 2.75 Hz, 1H) 7.38 (dd, J=8.55, 1.22 Hz, 1H) 7.52 (d, J=8.85 Hz, 1H) 7.76 (d, J=1.22 Hz, 1H) 7.86-7.92 (m, 2H) 8.26 (br.s, 1H). LC-MS 671 m/z (MH).

1H-Pyrazole-4-carboxylic acid, 3-[13-cyclohexyl-3-methoxy-10-[[[(1-methylethyl)sulfonyl]amino]carbonyl]-7H-indolo[2,1-a][2]benzazepin-6-yl]-1-cyclopropyl-

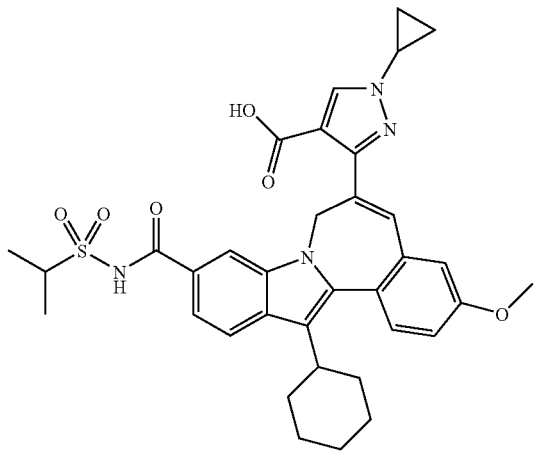

1H-Pyrazole-4-carboxylic acid, 3-[13-cyclohexyl-3-methoxy-10-[[[(1-methylethyl)sulfonyl]amino]carbonyl]-7H-indolo[2,1-a][2]benzazepin-6-yl]-1-cyclopropyl-, ethyl ester (0.31 g, 0.050 mmol) was dissolved in THF (0.20 mL) and methanol (0.20 mL) added to the reaction followed by 1N aqueous sodium hydroxide (0.50 mL). The reaction was capped under a nitrogen atmosphere and stirred at room temperature for 18 hrs. The reaction was diluted with ethyl acetate (50 mL) and washed with 1.0N aqueous hydrochloric acid (2×50 ml). The organic layer was concentrated in vacuo using a rotary evaporator to yield 30 mg of title compound as a yellow solid.

LC-MS retention time 1.78 min; 643 m/z (MH). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H$_2$O/10 mM ammonium acetate and solvent B was 5% H$_2$O/95% acetonitrile/10 mM ammonium acetate. MS data was determined using a MICROMASS® Platform for LC in electrospray mode.

7H-Indolo[2,1-a][2]benzazepine-10-carboxamide, 13-cyclohexyl-6-[1-cyclopropyl-4-(4-morpholinylcarbonyl)-1H-pyrazol-3-yl]-3-methoxy-N-[(1-methylethyl)sulfonyl]-

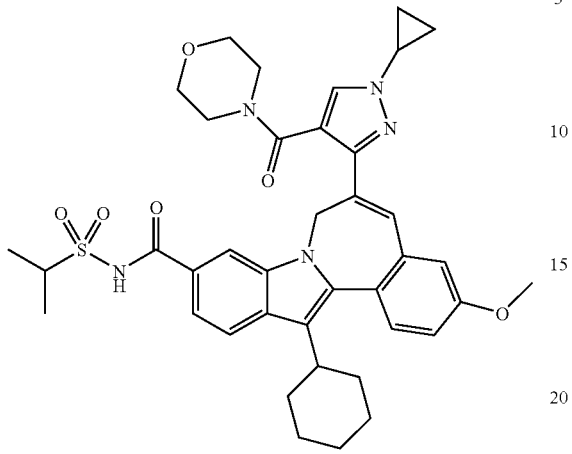

1H-Pyrazole-4-carboxylic acid, 3-[13-cyclohexyl-3-methoxy-10-[[[(1-methylethyl)sulfonyl]amino]carbonyl]-7H-indolo[2,1-a][2]benzazepin-6-yl]-1-cyclopropyl- (30 mg, 0.050 mmol) was dissolved in DMF (0.50 mL), TBTU (35 mg, 0.11 mmol), and DIPEA (19 mg, 0.22 mmol) were added to the reaction. The reaction was capped under a nitrogen atmosphere and stir at room temperature for 1 hour then morpholine (19 μL, 0.22 mmol) was added. The reaction was capped under a nitrogen atmosphere and stirred at room temperature overnight.

The reaction was diluted with ethyl acetate (50 mL) and washed sequentially with 1.0N aqueous hydrochloric acid (25 mL), 0.1M aqueous $NaH_2PO_4$ (25 mL). The organic phase was concentrated overnight in vacuo at room temperature to yield 33 mg of a yellow amorphous solid. The title compound was further purified on a Shimadzu high pressure liquid chromatography system employing DISCOVERY VP® software interfaced with a SCL-10A controller, SIL-10A autosampler and FRC-10A fraction collector. The sample was dissolved in acetonitrile/DMF (1:1) (total volume 2 ml) purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 60% solvent A/40% solvent B to 0% solvent A/100% solvent B, a gradient time of 12 minutes with a run time of 25 minutes using % A=10% acetonitrile, 90% water, 0.1% TFA % B=90% acetonitrile, 10% water, 0.1% TFA solvent system. The sample was run as two 1 ml injections. The run time of the second Prep HPLC run was truncated to 15 minutes base on data from the first run.

The product fractions (retention time=9.10 min.) were combined and solvent removed in vacuo. The compound was dried at room temperature in vacuo to yield 25 mg of the title compound as a yellow amorphous solid.

$^1$H NMR (500 MHz, CHLOROFORM-D) δ ppm 1.23 (m, 1H) 1.30-1.56 (m, 9H) 1.77 (m, 2H) 1.90-2.14 (m, 5H) 2.54-3.39 (m, 12H) 3.67 (m, 1H) 3.97 (s, 3H) 4.10 (m, 1H) 4.48 (d, J=14.65 Hz, 1H) 5.45 (d, J=14.65 Hz, 1H) 6.95 (d, J=2.75 Hz, 1H) 6.97 (s, 1H) 7.04 (dd, J=8.70, 2.59 Hz, 1H) 7.46 (dd, J=8.55, 1.53 Hz, 1H) 7.52 (d, J=8.55 Hz, 1H) 7.55 (s, 1H) 7.89 (d, J=8.55 Hz, 1H) 7.94 (d, J=1.22 Hz, 1H) 9.13 (br.s, 1H).

LC-MS retention time 1.91 min; 712 m/z (MH). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% $H_2O$/10 mM ammonium acetate and solvent B was 5% $H_2O$/95% acetonitrile/10 mM ammonium acetate. MS data was determined using a MICROMASS® Platform for LC in electrospray mode.

7H-Indolo[2,1-a][2]benzazepine-10-carboxylic acid, 13-cyclohexyl-6-[3-[(2R,6S)-2,6-dimethyl-4-morpholinyl]-1,3-dioxopropyl]-3-methoxy-, 1,1-dimethylethyl ester

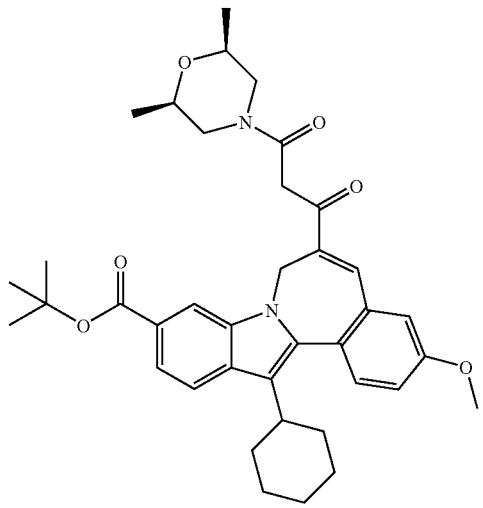

In a 250 ml round bottom flask dissolve tert-butyl 13-cyclohexyl-6-(3-ethoxy-3-oxopropanoyl)-3-methoxy-7H-indolo[2,1-a][2]benzazepine-10-carboxylate (3.13 g, 5.61 mmol) in toluene (56 mL) and add cis-2,6-dimethylmorpholine (2.6 mL, 20.99 mmol) to the reaction. Place reaction under a nitrogen atmosphere and heat to reflux for 9 hours. The reaction was partitioned between ethyl acetate and 1.0M aqueous citric acid. The organic layer was washed sequentially with 11.0M aqueous citric acid, 0.1M $NaH_2PO_4$, and brine. Dry organic phase over magnesium sulfate, filter and remove solvent in vacuo to give 3.01 g of crude product as a orange-amber foam. Dissolve the crude product in dichloromethane and adsorb onto 8.2 g of silica gel. Chromatograph crude product on 90 g of silica gel slurry packed in 5% ethyl acetate in dichloromethane, elute with gradient of 5% ethyl acetate in dichloromethane to 10% ethyl acetate in dichloromethane. Pure product fractions were combined and solvent removed in vacuo using a rotary evaporator to yield a yellow amorphous solid which was further dried in vacuo at room temperature to yield 1.28 g of the title compound. Less pure fractions yielded another 0.48 g of product. LCMS analysis gave two peaks of equivalent mass to that of the desired product. Resolution of the two peaks by Prep HPLC under the following conditions yielded peaks which interconverted when analyzed after isolation: Shimadzu high pressure liquid chromatography system employing DISCOVERY VP® software interfaced with a SCL-10A controller, S110A autosampler and FRC-10A fraction collector. The sample 76816-035-a (63 mg) was dissolved in acetonitrile/DMF mixture (2:1, 2 ml) purified using a PHENOMENEX® Luna C18 30×100 mm 10u column and monitored using a SPD-10AV UV-Vis detector at a detector wave length of 220 nM. The elution conditions employed a flow rate of 40 mL/min, a gradient of 60% solvent A/40% solvent B to 0% solvent A/100% solvent B, a gradient time of 15 minutes with a run time of 25 minutes using %A=10 mM Ammonium Acetate in 95:5 Water/Acetonitrile %B=10 mM Ammonium Acetate in 5:95 Water/Acetonitrile solvent system. Two peaks were isolated from the sample: First peak at RT=16.3 minutes. Both samples exhibited identical HPLC spectra after isolation indicating inter-conversion.

$^1$H NMR (500 MHz, CHLOROFORM-D) δ ppm 0.89 (s, 2.0H) 1.01 (s, 3.3H) 1.19 (d, J=26.25 Hz, 3.5H) 1.30-1.47 (m, 4.5H) 1.55 (s, 4.2H) 1.60 (s, 3.6H) 1.63 (s, 9.0H) 1.76 (d, J=8.24 Hz, 3.1H) 1.93 (d, J=9.46 Hz, 1.9H) 1.98-2.15 (m, 4.2H) 2.23 (s, 1.2H) 2.39 (s, 0.4H) 2.56-2.72 (m, 1.6H) 2.74-2.86 (m, 1.6H) 2.91 (s, 0.8H) 3.47-3.65 (m, 2.8H) 3.74-3.85 (m, 1.6H) 3.90 (s, 1.4H) 3.91 (s, 3.1H) 3.93-4.04 (m, 1.8H) 4.19 (d, J=12.82 Hz, 0.5H) 4.26 (d, J=14.65 Hz, 0.5H) 4.39 (s, 0.5H) 4.47 (d, J=11.29 Hz, 0.4H) 5.18 (s, 0.3H) 5.71-5.92 (m, 1.1H) 7.01 (d, J=2.75 Hz, 0.4H) 7.03-7.06 (m, 1.4H) 7.11 (dd, J=8.70, 2.59 Hz, 1.0H) 7.47-7.51 (m, 0.9H) 7.52 (s, 0.5H) 7.57 (s, 0.4H) 7.65 (d, J=1.53 Hz, 0.2H) 7.68 (dd, J=8.55, 1.22 Hz, 1.2H) 7.80 (s, 0.6H) 7.80-7.82 (m, 0.7H) 7.84 (s, 0.2H) 7.91 (s, 0.4H) 8.04 (s, 0.5H) 8.19 (s, 0.3H) 8.21 (d, J=1.22 Hz, 1.0H) 15.15 (d, J=23.80 Hz, 0.4H).

LC-MS retention time 4.21 min (88%); 625 m/z (MH−) and 5.23 min (12%); 625 m/z (MH−). LC data was recorded on a Shimadzu LC-10AS liquid chromatograph equipped with a PHENOMENEX® Luna 10u C18 4.6×50 mm column using a SPD-10AV UV-Vis detector at a detector wave length of 220 nM. The elution conditions employed a flow rate of 5 ml/min, a gradient of 70% solvent A/30% solvent B to 0% solvent A/100% solvent B, a gradient time of 5 min, a hold time of 2 min, and an analysis time of 7 min where solvent A was 5% acetonitrile/95% H$_2$O/10 mM ammonium acetate and solvent B was 5% H$_2$O/95% acetonitrile/10 mM ammonium acetate. MS data was determined using a MICROMASS® Platform for LC in electrospray.

7H-Indolo[2,1-a][2]benzazepine-10-carboxylic acid, 13-cyclohexyl-6-[(2E,Z)-3-(dimethylamino)-2-[[(2R,6S)-2,6-dimethyl-4-morpholinyl]carbonyl]-1-oxo-2-propenyl]-3-methoxy-, 1,1-dimethylethyl ester

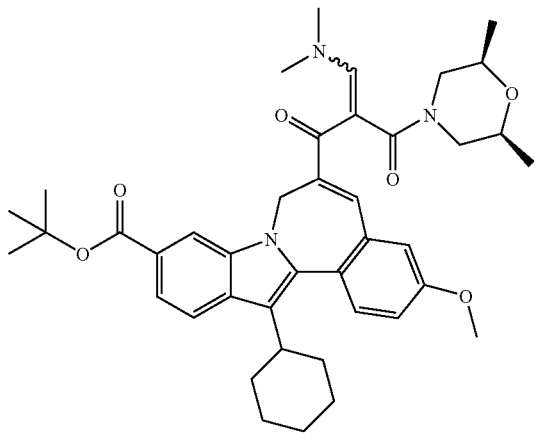

7H-Indolo[2,1-a][2]benzazepine-10-carboxylic acid, 13-cyclohexyl-6-[3-[(2R,6S)-2,6-dimethyl-4-morpholinyl]-1,3-dioxopropyl]-3-methoxy-, 1,1-dimethylethyl ester was dissolved in N,N-dimethylformamide dimethyl acetal (10 mL). The reaction was fitted with a condenser and placed under a nitrogen atmosphere. The reaction was heated to reflux for 3 hrs, cooled then the volatiles were removed in vacuo using a rotary evaporator, then dry in vacuo at room temperature to obtain the product as an amorphous orange solid (517 mg, 86%).

LC-MS retention time 4.60 min; 682 m/z (MH+). LC data was recorded on a Shimadzu LC-10AS liquid chromatograph equipped with a PHENOMENEX® Luna 10u C18 4.6×50 mm column using a SPD-10AV UV-Vis detector at a detector wave length of 220 nM. The elution conditions employed a flow rate of 4 ml/min, a gradient of 100% solvent A/0% solvent B to 0% solvent A/100% solvent B, a gradient time of 5 min, a hold time of 2 min, and an analysis time of 7 min where solvent A was 5% acetonitrile/95% H$_2$O/10 mM ammonium acetate and solvent B was 5% H$_2$O/95% acetonitrile/10 mM ammonium acetate. MS data was determined using a MICROMASS® Platform for LC in electrospray mode. The intermediate was used without further purification.

7H-Indolo[2,1-a][2]benzazepine-10-carboxylic acid, 13-cyclohexyl-6-[(2E,Z)-3-(dimethylamino)-2-[[(2R,6S)-2,6-dimethyl-4-morpholinyl]carbonyl]-1-oxo-2-propenyl]-3-methoxy-

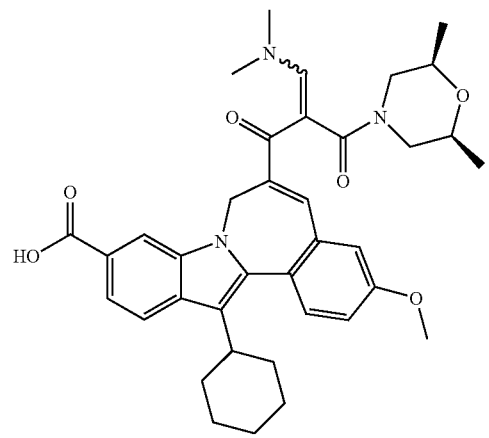

7H-Indolo[2,1-a][2]benzazepine-10-carboxylic acid, 13-cyclohexyl-6-[(2E,Z)-3-(dimethylamino)-2-[[(2R,6S)-2,6-dimethyl-4-morpholinyl]carbonyl]1-oxo-2-propenyl]-3-methoxy-, 1,1-dimethylethyl ester was dissolved in 1,2-dichloroethane (5 mL) and TFA (5 mL) was added to the reaction. The reaction was placed under a nitrogen atmosphere and stirred for 2.5 hrs. Volatiles were removed in vacuo from the reaction using a rotary evaporator to give a reddish oil. The product was dissolved in benzene/dichloromethane and the volatiles again removed in vacuo to give a red foam. The product was dissolved in ethyl acetate and washed with 1.0N aqueous hydrochloric acid. The aqueous layer was back extracted with ethyl acetate. The organic extracts were combined, washed with brine and dried over magnesium sulfate. The organic solution was filtered and the volatiles removed in vacuo using a rotary evaporator to give a amber-orange foam.

The product was dried in vacuo at room temperature to give 388 mg of amorphous amber-orange solid.

LC-MS retention time 2.83 min; 624 m/z (MH−). LC data was recorded on a Shimadzu LC-10AS liquid chromatograph equipped with a PHENOMENEX® Luna 10u C18 4.6×50 mm column using a SPD-10AV UV-Vis detector at a detector wave length of 220 nM. The elution conditions employed a flow rate of 4 ml/min, a gradient of 100% solvent A/0% solvent B to 0% solvent A/100% solvent B, a gradient time of 5 min, a hold time of 2 min, and an analysis time of 7 min where solvent A was 5% acetonitrile/95% $H_2O$/10 mM ammonium acetate and solvent B was 5% $H_2O$/95% acetonitrile/10 mM ammonium acetate. MS data was determined using a MICROMASS® Platform for LC in electrospray mode.

7H-Indolo[2,1-a][2]benzazepine-10-carboxamide, 13-cyclohexyl-6-[(2E,Z)-3-(dimethylamino)-2-[[(2R,6S)-2,6-dimethyl-4-morpholinyl]carbonyl]-1-oxo-2-propenyl]-3-methoxy-N-[(1-methylethyl)sulfonyl]-

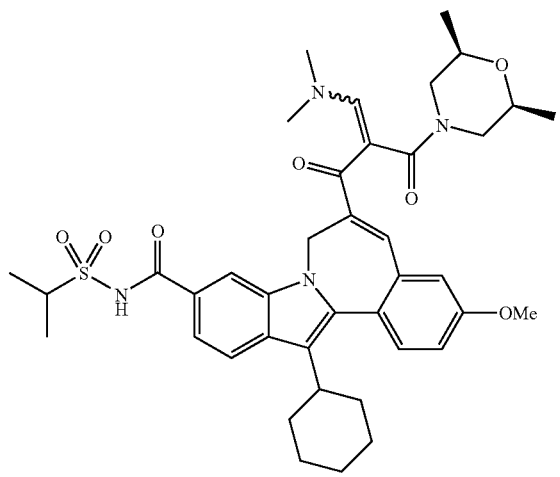

In a 25 ml rb flask, dissolve 7H-indolo[2,1-a][2]benzazepine-10-carboxylic acid, 13-cyclohexyl-6-[(2E,Z)-3-(dimethylamino)-2-[[(2R,6S)-2,6-dimethyl-4-morpholinyl]carbonyl]-1-oxo-2-propenyl]-3-methoxy- (385 mg, 0.616 mmol) in dichloromethane (6.2 mL), add propane-2-sulfonamide (233 mg, 1.892 mmol) and DMAP (230 mg, 1.880 mmol) to the reaction followed by EDC (177 mg, 0.924 mmol). The reaction was placed under a nitrogen atmosphere and stirred at room temperature for 18.5 hrs. The reaction was diluted with ethyl acetate and washed with 1.0N aqueous hydrochloric acid. The aqueous phases were combined and back extracted with ethyl acetate. The organic layers were combined and sequentially washed with 1.0N aqueous hydrochloric acid and brine. The organic solution was dried over magnesium sulfate, filtered and the solvent removed in vacuo using a rotary evaporator to give an amorphous orange solid/foam which was dried in vacuo to give 415 mg of crude product.

LC-MS retention time 3.00 min; 729 m/z (MH−). LC data was recorded on a Shimadzu LC-10AS liquid chromatograph equipped with a PHENOMENEX® Luna 10u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 5 min, a hold time of 2 min, and an analysis time of 7 min where solvent A was 5% acetonitrile/95% $H_2O$/10 mM ammonium acetate and solvent B was 5% $H_2O$/95% acetonitrile/10 mM ammonium acetate. MS data was determined using a MICROMASS® Platform for LC in electrospray mode.

The crude product was used without any further purification in subsequent pyrazole synthesis.

The following analog can be prepared using the general methodology described below.

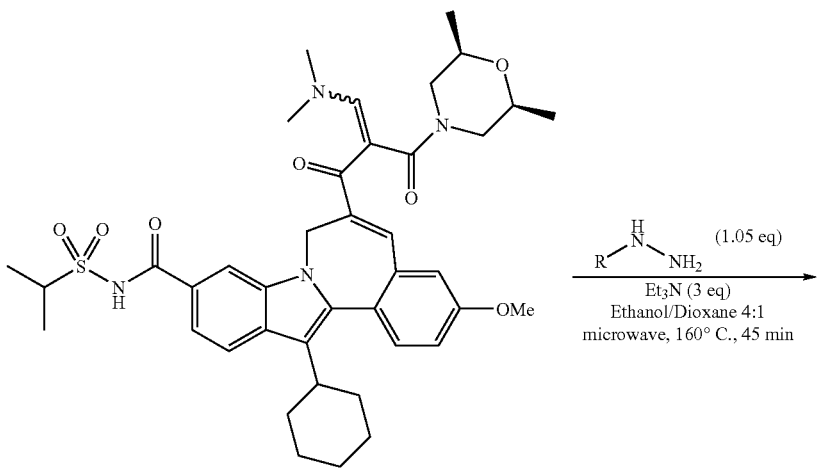

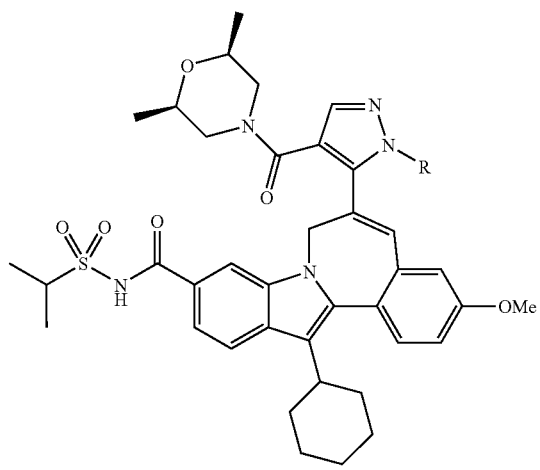

7H-Indolo[2,1-a][2]benzazepine-10-carboxamide, 13-cyclohexyl-6-[(2E,Z)-3-(dimethylamino)-2-[[(2R,6S)-2,6-dimethyl-4-morpholinyl]carbonyl]-1-oxo-2-propenyl]-3-methoxy-N-[(1-methylethyl)sulfonyl]-(100 mg, 0.137 mmol) in ethanol (547 μL) and dioxane (137 μL). Add the hydrazine reagent (0.146 mmol) followed by TEA (58.2 μL, 0.417 mmol) to the reaction in a 0.5-2 mL microwave reaction vessel. The vessel was capped under a nitrogen atmosphere and heated at 160° C. for 45 minutes. The reaction was diluted in DMF/Acetonitrile and product compound purified by reverse phase HPLC.

7H-Indolo[2,1-a][2]benzazepine-10-carboxamide, 13-cyclohexyl-6-[1-cyclopentyl-4-[[(2R,6S)-2,6-dimethyl-4-morpholinyl]carbonyl]-1H-pyrazol-5-yl]-3-methoxy-N-[(1-methylethyl)sulfonyl]-

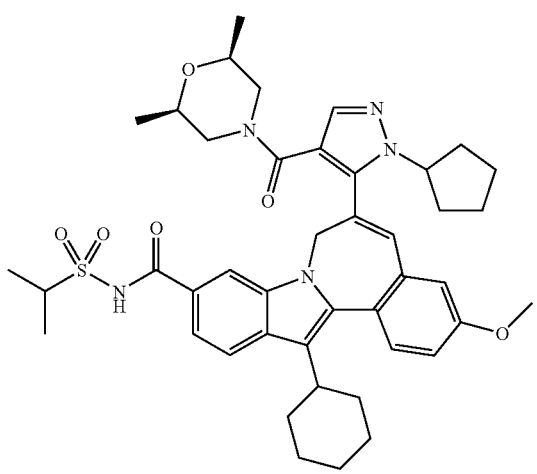

This compound was isolated using reverse phase HPLC with the instrumentation listed below using gradient method Bin#16. DIONEX® APS-3000: CHROMELEON® 6.70 sp1 LC software; Thermo-Finnigan XCALIBUR® MS software; DIONEX® P680 binary pump for analytical; DIONEX® PP150 binary pump prep; DIONEX® UVD340U UV spectrometer; Polymer Labs PL-ELS 1000 ELS detector; Thermo-Finnigan MSQ Surveyor Plus mass spectrometer. LC Conditions: Column; Waters Xbridge 19×200 mm 5 um C18; Guard Column; Waters Xbridge 19×10 mm 5 um C18; Mobile Phase; A=Water, 20 mM NH$_4$OH; B Acetonitrile. LC-MS retention time 6.05 min; 768.86 m/z (MH+). LC data was recorded using Masslynx 4.0 SP4 with a system equipped with: CTC-Leap HTS-PAL autosampler with Harney 4-port injection module, Waters 1525 binary pump, Waters 2488 UV detector at 220 nm, Polymer Lab 1000 ELS detector (evap. Temp.=90° C., Neb. Temp.=80° C.) and a Waters LCT mass spectrometer with 4 way MUX source. The sample was analyzed using an Ascentis 4.6×50 mm 5 uM C18 column. The elution conditions employed a flow rate of 2 ml/min, a gradient of 100% solvent A/0% solvent B to 0% solvent A/100% solvent B, a gradient time of 8 min, a hold time of 1 min, and an analysis time of 9 min where solvent A was 5% acetonitrile/95% H$_2$O/10 mM ammonium acetate and solvent B was 5% H$_2$O/95% acetonitrile/10 mM ammonium acetate. MS ionization using a Waters LCT mass spectrometer in ESI positive mode.

The following compounds were synthesized by the example of the general method above.

| Structure | Analytical Method | Retention time (min) | Mass ion observe (MH+) | Purification method |
|---|---|---|---|---|
| 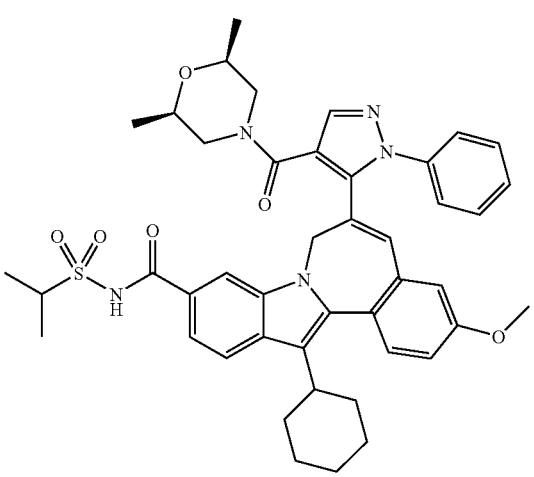 | Method A | 5.39 | 776.85 | Bin14 |
| 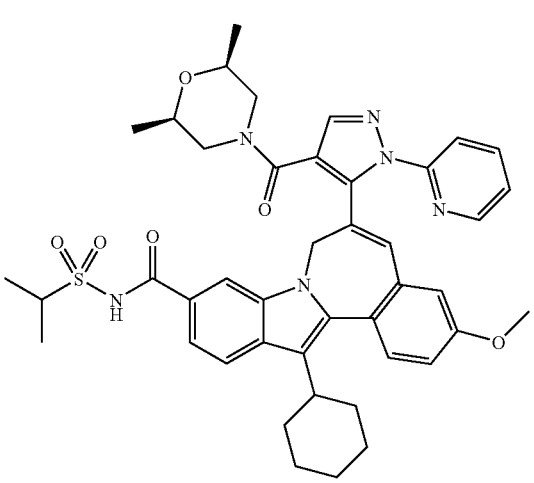 | Method A | 5.00 | 777.83 | Bin12 |
| 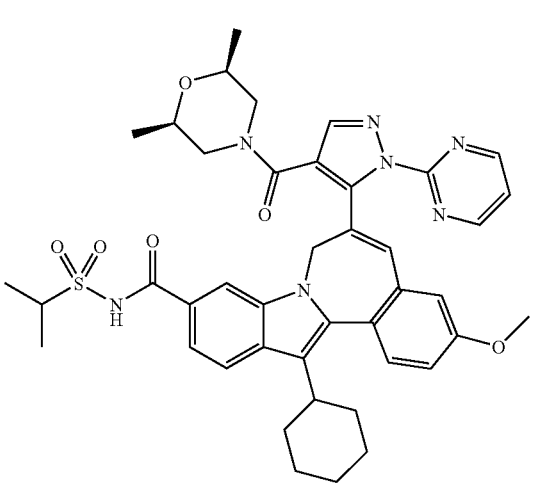 | Method A | 4.54 | 778.86 | Bin10 |

| Structure | Analytical Method | Retention time (min) | Mass ion observe (MH+) | Purification method |
|---|---|---|---|---|
| 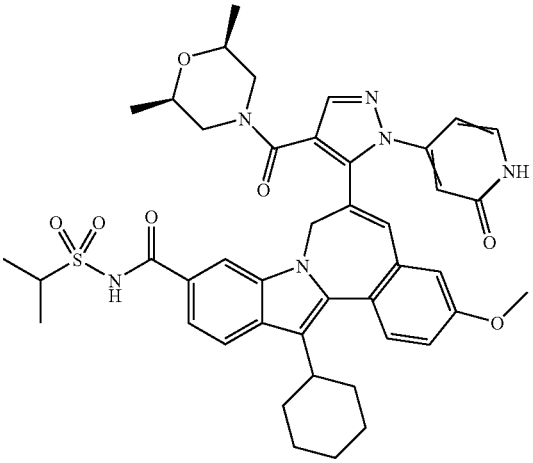 | Method A | 4.01 | 793.86 | Bin08 |
| 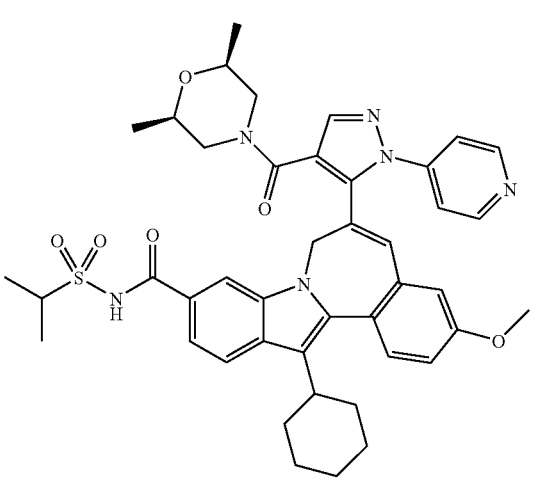 | Method A | 4.53 | 777.83 | Bin10 |
| 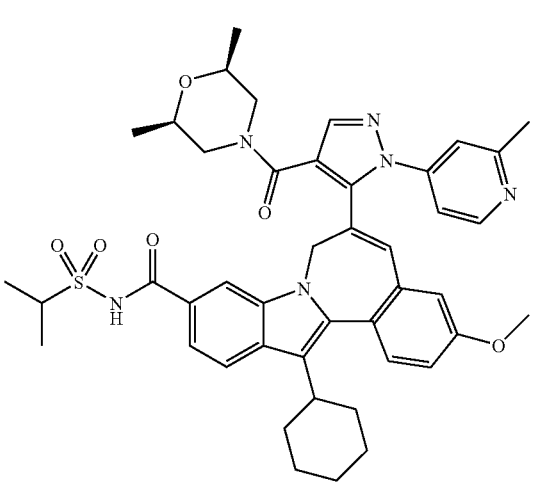 | Method A | 4.61 | 791.85 | Bin10 |

| Structure | Analytical Method | Retention time (min) | Mass ion observe (MH+) | Purification method |
|---|---|---|---|---|
| | Method A | 4.65 | 777.84 | Bin10 |
| | Method A | 4.78 | 816.88 | Bin14 |
| | Method A | 4.80 | 778.84 | Bin12 |

Analytical HPLC Method A: LC data was recorded using Masslynx 4.0 SP4 with a system equipped with: CTC-Leap HTS-PAL autosampler with Harney 4-port injection module, Waters 1525 binary pump, Waters 2488 UV detector at 220 nm, Polymer Lab 1000 ELS detector (evap. Temp.=90° C., Neb. Temp.=80° C.) and a Waters LCT mass spectrometer with 4 way MUX source. The sample was analyzed using an Ascentis 4.6×50 mm 5 uM C18 column. The elution conditions employed a flow rate of 2 ml/min, a gradient of 100% solvent A/0% solvent B to 0% solvent A/100% solvent B, a gradient time of 8 min, a hold time of 1 min, and an analysis time of 9 min where solvent A was 5% acetonitrile/95%

H₂O/10 mM ammonium acetate and solvent B was 5% H₂O/ 95% acetonitrile/10 mM ammonium acetate. MS ionization using a Waters LCT mass spectrometer in ESI positive mode.

7H-Indolo[2,1-a][2]benzazepine-10-carboxamide, 13-cyclohexyl-N-(cyclopropylsulfonyl)-6-[4-[[(2R, 6S)-2,6-dimethyl-4-morpholinyl]carbonyl]-1-(3-methyl-4-pyridinyl)-1H-pyrazol-5-yl]-3-methoxy-

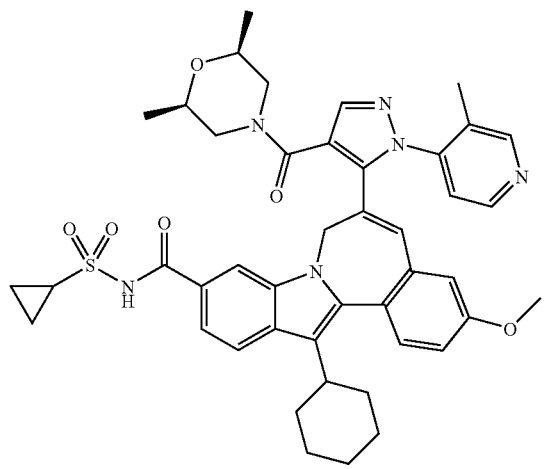

In a 0.5-2.0 mL microwave reaction vessel, 7H-indolo[2,1-a][2]benzazepine-10-carboxylic acid, 13-cyclohexyl-6-[(2E,Z)-3-(dimethylamino)-2-[[(2R,6S)-2,6-dimethyl-4-morpholinyl]carbonyl]-1-oxo-2-propenyl]-3-methoxy-, 1,1-dimethylethyl ester (106 mg, 0.155 mmol) was suspended in ethanol (504 μL) and dioxane (126 μL). Triethyl amine (65.9 μL, 0.473 mmol) was added to the reaction followed by 4-hydrazinyl-3-methylpyridine hydrochloride, 0.4H₂O (26.7 mg, 0.160 mmol). The reaction was capped under a nitrogen atmosphere and heated in a microwave to 140° C. for 40 minutes.

HPLC analysis indicates reaction incomplete with starting material present. Recap reaction under a nitrogen atmosphere and heat reaction at 140° C. for an additional 40 minutes. The reaction was diluted with ethyl acetate and washed sequentially with 1.0N aqueous hydrochloric acid. The aqueous layer was back extracted with ethyl acetate and the organic phases combined. The organic phase washed sequentially with 1.0N aqueous hydrochloric acid, 0.1M aqueous NaH₂PO₄ and brine. The organic phase was dried over Na₂SO₄, filtered and solvent removed in vacuo to obtain yellow film. The crude product was dried in vacuo at room temperature to yield 83 mg of product as a yellow amorphous foam-film.

Intermediate as t-butyl ester: LC-MS retention time 4.71 min; 742 m/z (MH+). LC data was recorded on a Shimadiu LC-10AS liquid chromatograph equipped with a PHENOMENEX® Luna 10u C18 4.6×50 mm column using a SPD-10AV UV-Vis detector at a detector wave length of 220 nM. The elution conditions employed a flow rate of 4 ml/min, a gradient of 100% solvent A/0% solvent B to 0% solvent A/100% solvent B, a gradient time of 5 min, a hold time of 2 min, and an analysis time of 7 min where solvent A was 5% acetonitrile/95% H₂O/10 mM ammonium acetate and solvent B was 5% H₂O/95% acetonitrile/10 mM ammonium acetate. MS data was determined using a MICROMASS® Platform for LC in electrospray mode The crude product was used without further purification. The tert-butyl ester intermediate (81 mg) was dissolved in 1,2-dichloroethane (1 mL) and TFA (1 mL) added. The reaction was stirred at room temperature under a nitrogen atmosphere for 2.5 hrs. Reaction volatiles were removed in vacuo using a rotary evaporator. The residue was then dissolved in benzene-dichloromethane mixture and volatiles removed in vacuo. The resulting crude acid product was dried in vacuo at room temperature overnight to yield 88 mg of a orange solid. LCMS of intermediate carboxylic acid: LC-MS retention time 2.61 min; 684 m/z (MH−). LC data was recorded on a Shimadzu LC-10AS liquid chromatograph equipped with a PHENOMENEX® Luna 10u C18 4.6×50 mm column using a SPD-10AV UV-Vis detector at a detector wave length of 220 nM. The elution conditions employed a flow rate of 4 ml/min, a gradient of 100% solvent A/0% solvent B to 0% solvent A/100% solvent B, a gradient time of 5 min, a hold time of 2 min, and an analysis time of 7 min where solvent A was 5% acetonitrile/95% H₂O/10 mM ammonium acetate and solvent B was 5% H₂O/95% acetonitrile/10 mM ammonium acetate. MS data was determined using a MICROMASS® Platform for LC in electrospray mode. The carboxylic acid intermediate was used without further purification:

In a 2 dram vial, the above carboxylate acid as the TFA salt (85.4 mg, 0.107 mmol) was dissolved in THF (1 mL). Carbonyldiimidazole (43.5 mg, 0.268 mmol) was added to the reaction then the reaction was caped under a nitrogen atmosphere and stir at room temperature for 1 hour then heated to 70° C. for 2 hours followed by cooling to room temperature. Cyclopropanesulfonamide (64.3 mg, 0.531 mmol) was added to the reaction followed by 2,3,4,6,7,8,9,10-octahydropyrimido[1,2-a]azepine (DBU) (40 μL, 0.268 mmol). The reaction was capped under a nitrogen atmosphere and immerse in an oil bath at 70° C. for 18 hrs.

The product was purified on a Shimadzu high pressure liquid chromatography system employing DISCOVERY VP® software interfaced with a SCL-10A controller, SIL-10A autosampler and FRC-10A fraction collector. The reaction was diluted to 2 ml with acetonitrile with the addition of a few drops of TFA and purified using a Waters Sunfire Prep C18 OBD, 5 uM 19 mm×150 mm column and monitored using a SPD-10AV UV-V is detector at a detector wave length of 220 nM. The elution conditions employed a flow rate of 25 mL/min, a gradient of 70 solvent A/30% solvent B to 0% solvent A/100% solvent B, a gradient time of 30 minutes with a run time of 40 minutes using % A=10% acetonitrile, 90% water, 0.1% TFA % B=90% acetonitrile, 10% water, 0.1% TFA solvent system. Retention time of product was 23.24 minutes. Volatiles were removed from the product fraction in vacuo to yield 39.0 mg of the title compound.

¹H NMR (500 MHz, CHLOROFORM-D) δ ppm 0.87 (s, 2H) 1.05 (s, 3H) 1.10-1.31 (m, 4H) 1.31-1.60 (m, 5H) 1.80 (s, 2H) 1.88-2.12 (m, 4H) 2.13-2.37 (m, 1H) 2.45 (s, 3H) 2.71 (s, 0.5H) 2.78-2.88 (m, 1H) 3.17-3.25 (m, 1H) 3.37 (s, 1H) 3.54 (s, 1H) 3.87 (s, 3H) 3.97-4.64 (m, 6H) 4.79 (s, 1H) 6.57-6.84

(m, 1H) 6.94 (s, 1H) 7.02-7.15 (m, 1H) 7.35-7.51 (m, 2H) 7.51-7.72 (m, 1H) 7.78-7.95 (m, 2H) 8.03 (s, 0.5H) 8.53 (d, J=45.17 Hz, 1H) 10.18 (s, 0.6H).

LC-MS retention time 1.54 min; 787 m/z (MH−). LC data was recorded on a Shimadzu LC-10AS liquid chromatograph equipped with a PHENOMENEX® Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% $H_2O$/10 mM ammonium acetate and solvent B was 5% $H_2O$/95% acetonitrile/10 mM ammonium acetate. MS data was determined using a MICROMASS® Platform for LC in electrospray mode.

The procedures that followed were analyzed using the following conditions until noted:

HPLC data was recorded on a LC-10AS liquid chromatograph equipped with a PHENOMENEX® 10u C18 3.0×160 mm column using a SPD-10AV UV-Vis detector at a wave length of 220 nM. The elution conditions employed a flow rate of 1 ml/min, a gradient of 100% solvent A/0% solvent B to 0% solvent A/100% solvent B, a gradient time of 30 min, where solvent A was 10% acetonitrile/90% $H_2O$/10 mM TFA and solvent B was 10% $H_2O$/90% acetonitrile/10 mM TFA.

LC data was recorded on a Shimadzu LC-10AS liquid chromatograph equipped with a PHENOMENEX® Luna 10u C18 3.0×50 mm column using an SPD-10AV UV-Vis detector at a wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% $H_2O$/10 mM ammonium acetate and solvent B was 5% $H_2O$/95% acetonitrile/10 mM ammonium acetate. MS data was determined using a MICROMASS® Platform for LC in electrospray mode.

7H-Indolo[2,1-a][2]benzazepine-10-carboxamide, 6-[1-cyclobutyl-4-[[(2R,6S)-2,6-dimethyl-4-morpholinyl]carbonyl]-1H-pyrazol-5-yl]-13-cyclohexyl-3-methoxy-N-[(1-methylethyl)sulfonyl]-

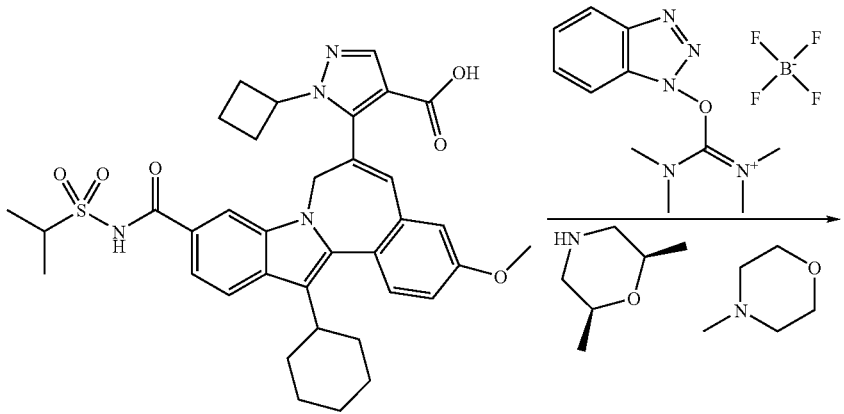

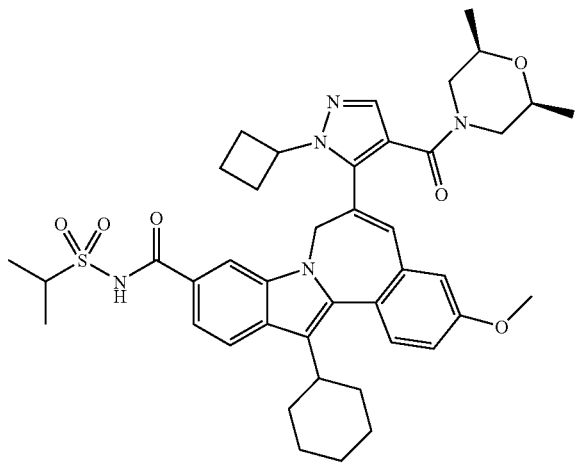

A 2 dram vial was charged with 1H-pyrazole-4-carboxylic acid, 1-cyclobutyl-5-[13-cyclohexyl-3-methoxy-10-[[[(1-methylethyl)sulfonyl]amino]carbonyl]-7H-indolo[2,1-a][2]benzazepin-6-yl]-(400 mg, 0.609 mmol), DMF (4 mL), 4-Methylmorpholine (0.134 mL, 1.218 mmol), cis-2,6-Dimethylmorpholine (0.090 mL, 0.731 mmol) and o-Benzotriazol-1-yl-N,N,N',N'-tetramethyluronium tetrafluoroborate (TBTU) (215 mg, 0.670 mmol). The rxn was stirred for 1 hour. LCMS indicates the rxn was done, 754.19 at 4.05 minutes. It was diluted with ether, washed with saturated ammonium chloride then brine, dried (MgSO$_4$) and evaporated giving a yellow foam. The foam was dissolved in DCM, the solution was added to a Thompson silica gel cartridge and it was eluted with ethyl acetate/methanol (0% to 5%). The appropriate fractions (TLC) were combined and evaporated giving a light yellow foam. The foam was dissolved in ether and crystals formed upon setting. The mixture was filtered giving the product (341 mg, 0.452 mmol, 74.2% yield) as slightly yellow powder. HPLC: 99.9% pure, 23.32 minutes.

LCMS: 754.19 at 4.05 minutes, mp: 217-219° C. HRMS: calculate—754.3633, found—754.3633. $^1$H NMR: (400 Mz, CD$_3$OD) δ 1.23-1.29 (m, 3H), 1.37-1.43 (m, 3H), 1.46-1.47 (d, J=7 Hz, 3H), 1.53-1.54 (d, J=7 Hz, 3H), 1.63 (s, 1H), 1.77-1.80 (d, J=11 Hz, 3H), 1.84 (bs, 1H), 1.96 (bs, 4H), 2.03 (s, 1H), 2.09-2.13 (m, 3 h), 2.21 (bs, 1H), 2.29 (bs, 2H), 2.45 (s, 1H), 2.71-2.75 (t, J=12 Hz, 1H), 2.81 (bs, 1H), 2.85-2.90 (t, J=12 Hz, 1H), 3.20 (bs, 2H), 3.96 (s, 3H), 4.04-4.13 (spt, J=7 Hz, 1H), 4.55-4.58 (d, J=16 Hz, 1H), 4.79 (bs, 1H), 4.84-4.87 (d, J=16 Hz, 1H), 6.71 (s, 1H), 6.94 (s, 1H), 7.11-7.13 (d, J=7 Hz, 1H), 7.58-7.63 (dd, J=8 Hz & 13.5 Hz, 2H), 7.68-7.71 (d, J=13.5 Hz, 2H), 7.90-7.92 (d, J=8 Hz, 1H) & 10.6 (bs, 1H).

7H-Indolo[2,1-a][2]benzazepine-10-carboxamide, 6-[1-cyclobutyl 4-[[(2S)-2-(methoxymethyl)-4-morpholinyl]carbonyl]-1H-pyrazol-5-yl]-13-cyclohexyl-3-methoxy-N-[(1-methylethyl)sulfonyl]-

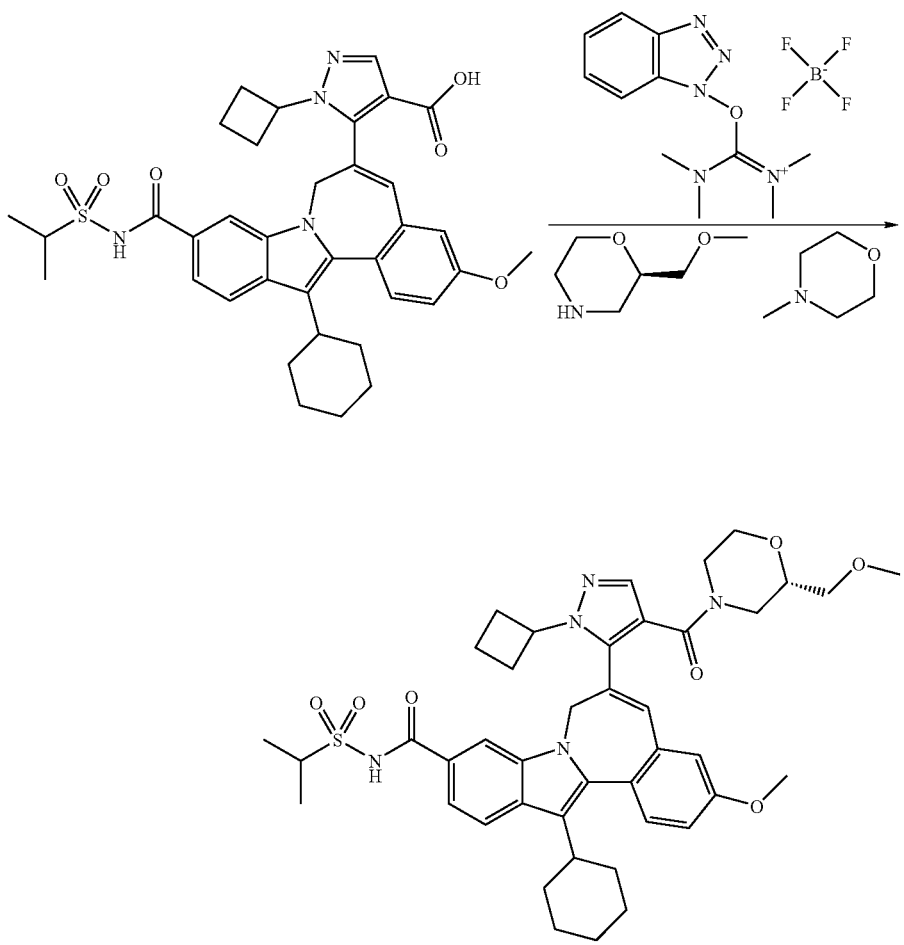

A 2 dram vial was charged with 1H-pyrazole-4-carboxylic acid, 1-cyclobutyl-5-[13-cyclohexyl-3-methoxy-10-[[[(1-methylethyl)sulfonyl]amino]carbonyl]-7H-indolo[2,1-a][2]benzazepin-6-yl]-(70 mg, 0.107 mmol), DMF (1 mL), (R)-2-(methoxymethyl)morpholine, HCl (35.7 mg, 0.213 mmol), 4-methylmorpholine (0.035 mL, 0.320 mmol) and o-Benzotriazol-1-yl-N,N,N',N'-tetramethyluronium tetrafluoroborate (TBTU) (37.6 mg, 0.117 mmol). The rxn was stirred for 1 hour. It was diluted with ether, washed with saturated ammonium chloride then brine, dried (MgSO₄) and evaporated giving a yellow foam. The foam was dissolved in DCM, the solution was added to a Thompson silica gel cartridge and it was eluted with ethyl acetate/methanol (0% to 10%). The appropriate fractions (TLC) were combined and evaporated giving a light yellow film. The film was dissolved in DCM, re-evaporated, the residue triturated in hexane/ether (5%) and filtered giving the product (66 mg, 0.084 mmol, 79% yield) as light a yellow powder. HPLC: 98.0% pure, 22.52 minutes.

LCMS: 770.32 at 3.96 minutes, mp: 176-178° C. HRMS: calculated—770.3582, found 770.3583. ¹H NMR: (400 Mz, CD₃OD) δ 1.23-1.26 (td, J=7 Hz & 3.5 Hz, 2H), 1.35-1.44 (m, 4H), 1.46-1.48 (d, J=6 Hz, 2H), 1.52-1.53 (d, J=6 Hz, 3H), 1.68 (bs, 1H), 1.77-1.80 (d, J=10 Hz, 3H), 1.84 (bs, 1H), 1.92-2.01 (m, 3H), 2.03 (s, 1H), 2.08-2.16 (bm, 3 h), 2.28 (bs, 1H), 2.28 (bs, 2H), 2.44 (bs, 1H), 2.70-2.74 (t, J=10 Hz, 2H), 2.79 (s, 1H), 2.84-2.89 (m, 2H), 2.97 (bs, 2H), 3.04 (bs, 1H), 3.19 (bs, 2H), 3.24 (s, 2H), 3.38 (bs, 1H), 3.95 (s, 3H), 4.06-4.13 (m, 1H), 4.55-4.59 (dd, J=15 Hz & 5 Hz, 1H), 4.77 (bs, 1H), 4.83-4.90 (t, J=15 Hz, 1H), 6.73-6.75 (d, J=8 Hz, 1H), 6.94 (s, 1H), 7.11-7.12 (d, J=8 Hz, 1H), 7.56-7.66 (m, 3H), 7.71 (s, 1H), 7.88-7.92 (t, J=8 Hz, 1H) & 10.5 (bs, 1H).

7H-Indolo[2,1-a][2]benzazepine-10-carboxamide, 6-[1-cyclobutyl-4-(8-oxa-3-azabicyclo[3.2.1]octan-3-yl)carbonyl-1H-pyrazol-5-yl]-13-cyclohexyl-3-methoxy-N-[(1-methylethyl)sulfonyl]-

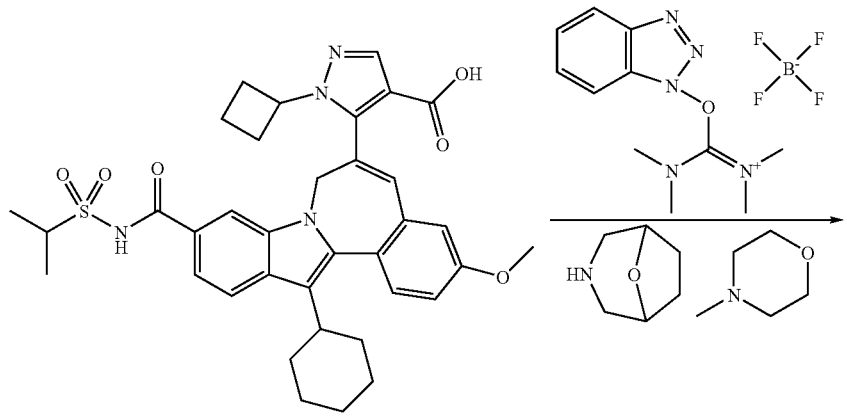

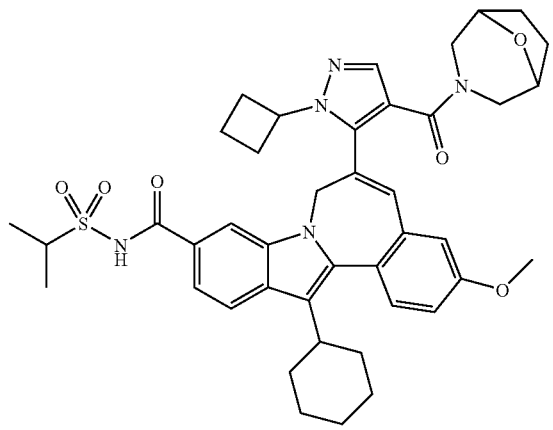

A 2 dram vial was charged with 1H-pyrazole-4-carboxylic acid, 1-cyclobutyl-5-[13-cyclohexyl-3-methoxy-10-[[[(1-methylethyl)sulfonyl]amino]carbonyl]-7H-indolo[2,1-a][2]benzazepin-6-yl]-(70 mg, 0.107 mmol), DMF (1 mL), 4-methylmorpholine (0.035 mL, 0.320 mmol), 8-oxa-3-azabicyclo[3.2.1]octane, HCl (31.9 mg, 0.213 mmol) and o-Benzotriazol-1-yl-N,N,N',N'-tetramethyluronium tetrafluoroborate (TBTU) (37.6 mg, 0.117 mmol). The rxn was stirred for 1 hour. It was diluted with ether, washed with saturated ammonium chloride then brine, dried (MgSO$_4$) and evaporated giving a yellow foam. The foam was dissolved in DCM, the solution was added to a Thompson silica gel cartridge and it was eluted with ethyl acetate/methanol (0% to 10%). The appropriate fractions (TLC) were combined and evaporated giving a light yellow film. The film was dissolved in DCM, re-evaporated, the residue triturated in hexane/ether (5%) and filtered giving the product (59 mg, 0.075 mmol, 70.7% yield) as light a yellow powder. HPLC: 96.1% pure, 22.80 minutes. LCMS: 752.29 at 3.98 minutes, mp: 188-190° C. HRMS: calculate—752.3476, found—752.3478. $^1$H NMR: (400 Mz, CD$_3$OD) δ 1.23-1.29 (m, 3H), 1.37-1.43 (m, 3H), 1.46-1.47 (d, J=7 Hz, 3H), 1.53-1.54 (d, J=7 Hz, 3H), 1.63 (s, 1H), 1.77-1.80 (d, J=11 Hz, 3H), 1.84 (bs, 1H), 1.96 (bs, 4H), 2.03 (s, 1H), 2.09-2.13 (bm, 3 h), 2.21 (bs, 1H), 2.29 (bs, 2H), 2.45 (s, 1H), 2.71-2.75 (t, J=12 Hz, 1H), 2.81 (bs, 1H), 2.85-2.90 (t, J=12 Hz, 1H), 3.20 (bs, 2H), 3.96 (s, 3H), 4.04-4.13 (spt, J=7 Hz, 1H), 4.55-4.58 (d, J=16 Hz, 1H), 4.79 (bs, 1H), 4.84-4.87 (d, J=16 Hz, 1H), 6.71 (s, 1H), 6.94 (s, 1H), 7.11-7.13 (d, J=7 Hz, 1H), 7.58-7.63 (dd, J=8 Hz & 13.5 Hz, 2H), 7.68-7.71 (d, J=13.5 Hz, 2H), 7.90-7.92 (d, J=8 Hz, 1H) & 10.6 (bs, 1H).

7H-Indolo[2,1-a][2]benzazepine-10-carboxamide, 6-[1-cyclobutyl-4-(1-methylpiperazin-4-yl)carbonyl-1H-pyrazol-5-yl]-13-cyclohexyl-3-methoxy-N-[(1-methylethyl)sulfonyl]-

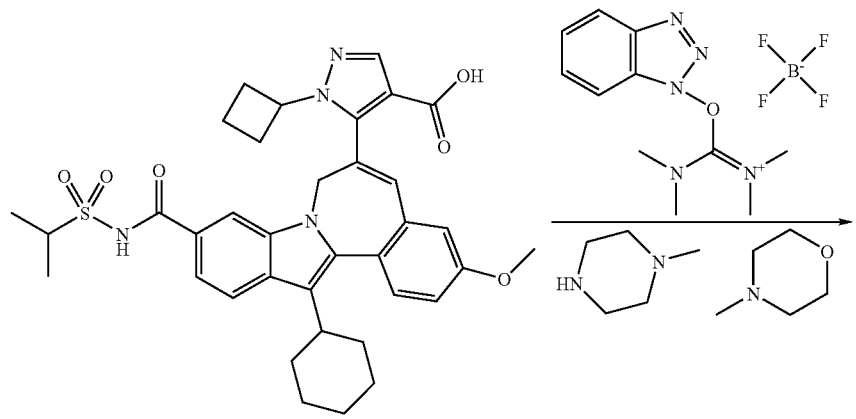

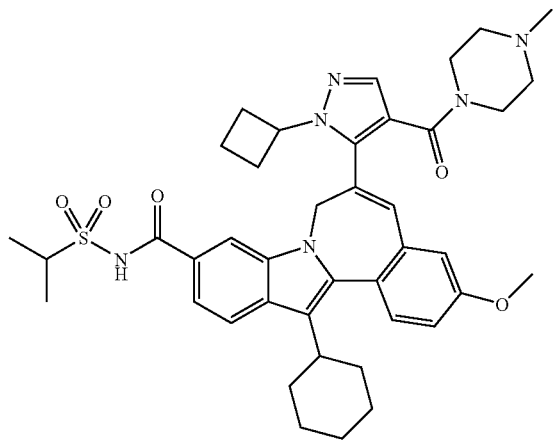

A 2 dram vial was charged with 1H-pyrazole-4-carboxylic acid, 1-cyclobutyl-5-[13-cyclohexyl-3-methoxy-10-[[[(1-methylethyl)sulfonyl]amino]carbonyl]-7H-indolo[2,1-a][2]benzazepin-6-yl]-(70 mg, 0.107 mmol), DMF (1 mL), 1-methylpiperazine, HCl (0.032 mL, 0.213 mmol), 4-methylmorpholine (0.035 mL, 0.320 mmol) and o-Benzotriazol-1-yl-N,N,N',N'-tetramethyluronium tetrafluoroborate (TBTU) (37.6 mg, 0.117 mmol). The rxn was stirred for 1 hour. It was diluted with ether, washed with water then brine, dried (MgSO₄) and evaporated giving a yellow foam. The foam was dissolved in DCM, the solution was added to a Thompson silica gel cartridge and it was eluted with ethyl acetate/methanol (5% to 30%). The appropriate fractions (TLC) were combined and evaporated giving a light yellow film. The film was dissolved in DCM, re-evaporated, the residue triturated in hexane/ether (5%) and filtered giving the product (44 mg, 0.059 mmol, 55.3% yield) as light a yellow powder. HPLC: 99.1% pure, 24.07 minutes. LCMS: 739.31 at 3.70 minutes, mp: 224-226° C. HRMS: calculate—739.3636, found—739.3630.

7H-Indolo[2,1-a][2]benzazepine-10-carboxamide, 6-[1-cyclobutyl-4-((1S,4S)-2-oxa-5-azabicyclo[2.2.1]heptan-5-yl)carbonyl-1H-pyrazol-5-yl]-13-cyclohexyl-3-methoxy-N-[(1-methylethyl)sulfonyl]-

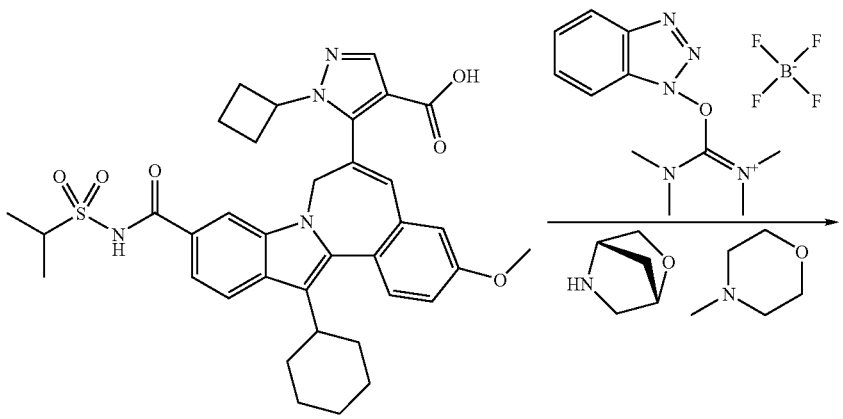

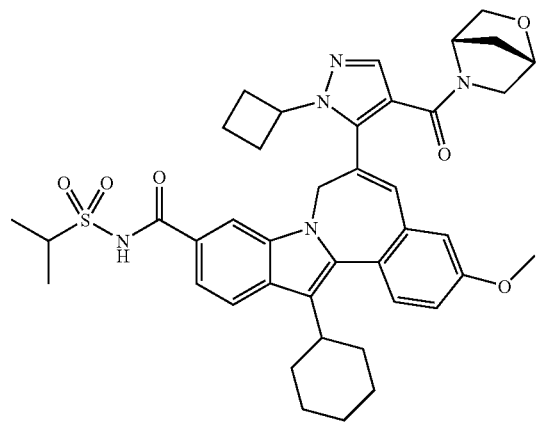

A 2 dram vial was charged with 1H-pyrazole-4-carboxylic acid, 1-cyclobutyl-5-[13-cyclohexyl-3-methoxy-10-[[[(1-methylethyl)sulfonyl]amino]carbonyl]-7H-indolo[2,1-a][2]benzazepin-6-yl]-(70 mg, 0.107 mmol), DMF (1 mL), (1S,4S)-2-oxa-5-azabicyclo[2.2.1]heptane, HCl (28.9 mg, 0.213 mmol), 4-methylmorpholine (0.035 mL, 0.320 mmol) and o-Benzotriazol-1-yl-N,N,N',N'-tetramethyluronium tetrafluoroborate (TBTU) (37.6 mg, 0.117 mmol). The rxn was stirred for 1 hour. It was diluted with ether, washed with saturated ammonium chloride then brine, dried (MgSO$_4$) and evaporated giving a yellow foam. The foam was dissolved in DCM, the solution was added to a Thompson silica gel cartridge and it was eluted with ethyl acetate/methanol (0% to 10%). The appropriate fractions (TLC) were combined and evaporated giving a light yellow film. The film was dissolved in DCM, re-evaporated, the residue triturated in hexane/ether (5%) and filtered giving the product (58 mg, 0.078 mmol, 73.0% yield) as light a yellow powder. HPLC: 99.9% pure, 22.39 minutes. LCMS: 738.26 at 3.96 minutes, mp: 164-166° C. HRMS: calculate—738.3820, found—738.382.

7H-Indolo[2,1-a][2]benzazepine-10-carboxamide, 6-[1-cyclobutyl-4-[[(1S,4S)-5-cyclopropylmethyl-2,5-diazabicyclo[2.2.1]hept-2-yl]carbonyl]-1H-pyrazol-5-yl]-13-cyclohexyl-3-methoxy-N-[(1-methylethyl)sulfonyl]-

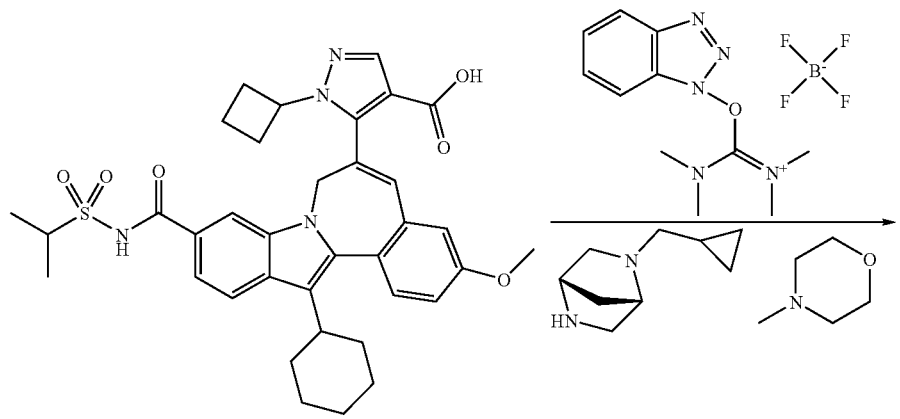

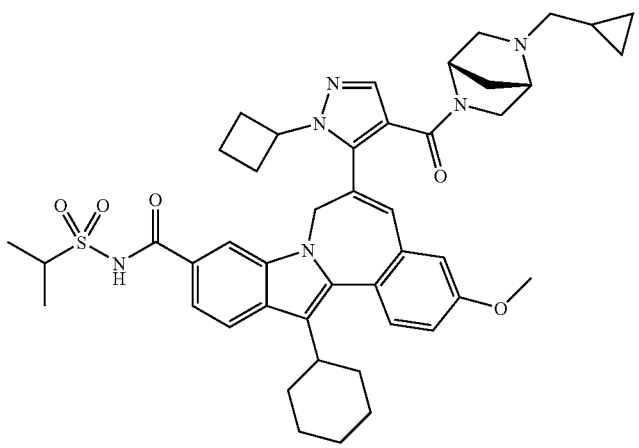

A 2 dram vial was charged with 1H-pyrazole-4-carboxylic acid, 1-cyclobutyl-5-[13-cyclohexyl-3-methoxy-10-[[[(1-methylethyl)sulfonyl]amino]carbonyl]-7H-indolo[2,1-a][2]benzazepin-6-yl]-(70 mg, 0.107 mmol), DMF (1 mL), (1S,4S)-2-(cyclopropylmethyl)-2,5-diazabicyclo[2.2.1]heptane, HCl (40.2 mg, 0.213 mmol), 4-methylmorpholine (0.035 mL, 0.320 mmol) and o-Benzotriazol-1-yl-N,N,N',N'-tetramethyluronium tetrafluoroborate (TBTU) (37.6 mg, 0.117 mmol). The rxn was stirred for one hour. It was diluted with ether, washed with water then brine, dried (MgSO$_4$) and evaporated giving a yellow foam. The foam was dissolved in DCM, the solution was added to a Thompson silica gel cartridge and it was eluted with ethyl acetate/methanol (5% to 30%). The appropriate fractions (TLC) were combined and evaporated giving a light yellow film. The film was dissolved in DCM, re-evaporated, the residue triturated in hexane/ether (5%) and filtered giving the product (57 mg, 0.071 mmol, 66.9% yield) as light a yellow powder. HPLC: 99.9% pure, 23.89 minutes. LCMS: 791.36 at 3.74 minutes, mp: 216-218° C. HRMS: calculate 791.3949, found 791.3945. $^1$H NMR: (400 Mz, CD$_3$OD) δ 0.02-0.05 (m, 2H), 0.83 (bs, 2H), 1.23-1.26 (m, 3H), 1.38-1.45 (m, 9H), 1.76 (bs, 3H), 1.94 (bs, 2H), 2.03-2.04 (m, 5H), 2.16-2.28 (m, 2H), 2.53 (bs, 1H), 2.70 (bs, 2H), 2.83-2.86 (m, 2 h), 3.06 (bs, 1H), 3.19 (bs, 1H), 3.78 (bs, 1H), 3.93-3.95 (m, 4H), 4.08-4.13 (m, 1H), 4.56 (bs, 1H), 4.86-4.88 (m, 2H), 6.69-6.80 (m, 1H), 6.92-6.95 (d, J=13 Hz, 1H), 7.08 (bs, 1H), 7.52 (bs, 1H), 7.64-7.84 (m, 4H).

7H-Indolo[2,1-a][2]benzazepine-10-carboxamide, 6-[1-cyclobutyl-4-(((S)-octahydropyrrolo[1,2-a]pyrazin-4-yl)carbonyl)-1H-pyrazol-5-yl]-13-cyclohexyl-3-methoxy-N-[(1-methylethyl)sulfonyl]-

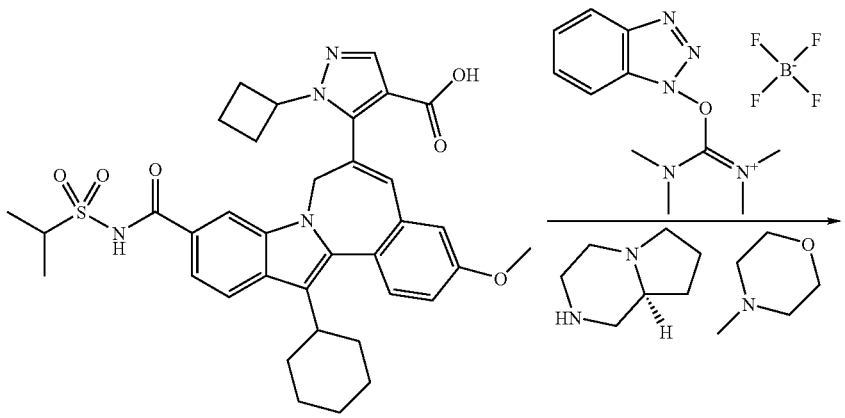

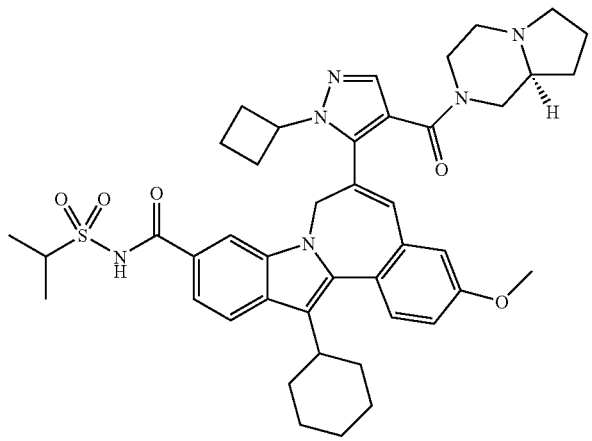

A 2 dram vial was charged with 1H-pyrazole-4-carboxylic acid, 1-cyclobutyl-5-[13-cyclohexyl-3-methoxy-10-[[[(1-methylethyl)sulfonyl]amino]carbonyl]-7H-indolo[2,1-a][2]benzazepin-6-yl]-(70 mg, 0.107 mmol), DMF (1 mL), 4-methylmorpholine (0.035 mL, 0.320 mmol), (S)-octahydropyrrolo[1,2-a]pyrazine (13.45 mg, 0.107 mmol) and o-Benzotriazol-1-yl-N,N,N',N'-tetramethyluronium tetrafluoroborate (TBTU) (37.6 mg, 0.117 mmol). The rxn was stirred for one hour. It was diluted with ether, washed with water then brine, dried (MgSO4) and evaporated giving a yellow foam. The foam was dissolved in DCM, the solution was added to a Thompson silica gel cartridge and it was eluted with ethyl acetate/methanol (5% to 30%). The appropriate fractions (TLC) were combined and evaporated giving a light yellow film. The film was dissolved in DCM, re-evaporated, the residue triturated in hexane/ether (5%) and filtered giving the product (58 mg, 0.075 mmol, 70.4% yield) as light a yellow powder. HPLC: 99.9% pure, 24.23 minutes. LCMS: 765.34 at 3.72 minutes, mp: 199-201° C. HRMS: calculate 765.3793, found 765.3788.

7H-Indolo[2,1-a][2]benzazepine-10-carboxamide, 6-[1-cyclobutyl-4-((1R,5S)-1,3,5-trimethyl-3,7-diazabicyclo[3.3.1]nonan-7-ylcarbonyl)-1H-pyrazol-5-yl]-13-cyclohexyl-3-methoxy-N-[(1-methylethyl)sulfonyl]-

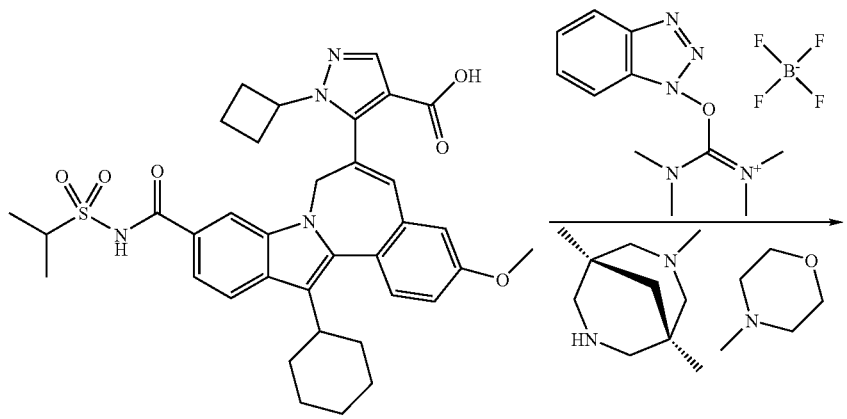

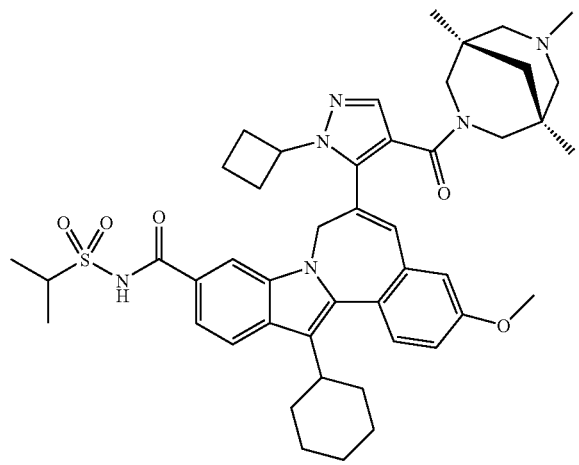

A 2 dram vial was charged with 1H-pyrazole-4-carboxylic acid, 1-cyclobutyl-5-[13-cyclohexyl-3-methoxy-10-[[[(1-methylethyl)sulfonyl]amino]carbonyl]-7H-indolo[2,1-a][2]benzazepin-6-yl]-(70 mg, 0.107 mmol), DMF (1 mL), 4-methylmorpholine (0.035 mL, 0.320 mmol), (1R,5S)-1,3,5-trimethyl-3,7-diazabicyclo[3.3.1]nonane (17.9 mg, 0.107 mmol) and o-benzotriazol-1-yl-N,N,N',N'-tetramethyluronium tetrafluoroborate (TBTU) (37.6 mg, 0.117 mmol). The rxn was stirred for 1 hour. It was diluted with ether, washed with saturated ammonium chloride then brine, dried (MgSO$_4$) and evaporated giving a yellow foam. The foam was dissolved in DCM, the solution was added to a Thompson silica gel cartridge and it was eluted with ethyl acetate/methanol (5% to 30%). The appropriate fractions (TLC) were combined and evaporated giving a light yellow film. The film was dissolved in DCM, re-evaporated, the residue triturated in hexane/ether (5%) and filtered giving the product (64 mg, 0.079 mmol, 73.7% yield) as light a yellow powder. HPLC: 99.9% pure, 26.31 minutes. LCMS: 807.43 at 3.76 minutes, mp: 210-212° C. HRMS: calculate 807.4262, found 807.4260.

7H-Indolo[2,1-a][2]benzazepine-10-carboxamide, 6-[1-cyclobutyl 4-(1,4-oxazepan-4-yl carbonyl)-1H-pyrazol-5-yl]-13-cyclohexyl-3-methoxy-N-[(1-methylethyl)sulfonyl]

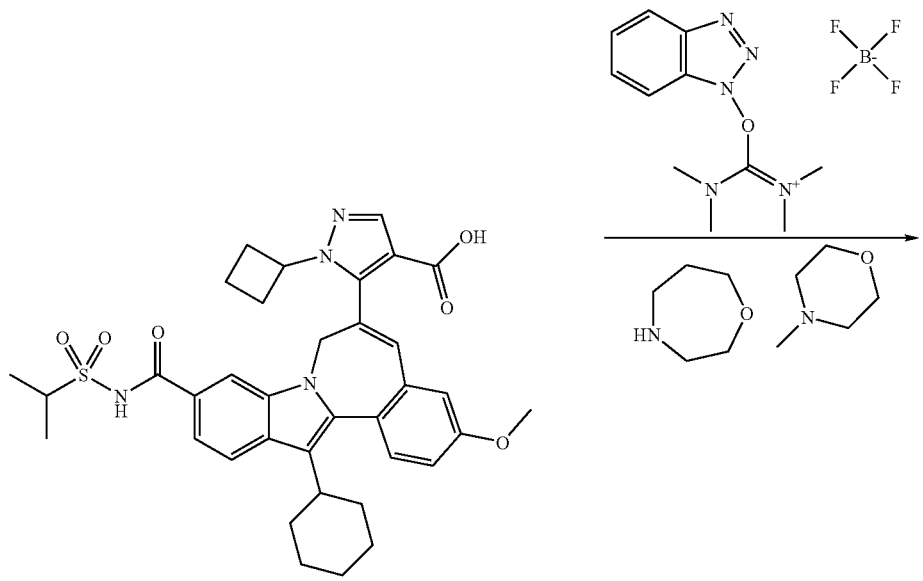

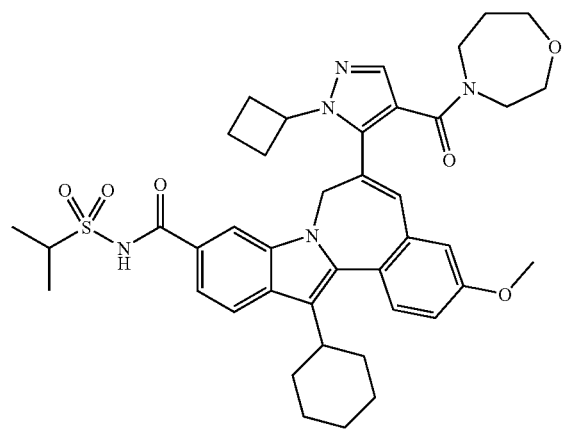

A 2 dram vial was charged with 1H-pyrazole-4-carboxylic acid, 1-cyclobutyl-5-[13-cyclohexyl-3-methoxy-10-[[[(1-methylethyl)sulfonyl]amino]carbonyl]-7H-indolo[2,1-a][2]benzazepin-6-yl]-(70 mg, 0.107 mmol), DMF (1 mL), 4-methylmorpholine (0.035 mL, 0.320 mmol), 1,4-oxazepane (14.67 mg, 0.107 mmol) and o-benzotriazol-1-yl-N,N,N',N'-tetramethyluronium tetrafluoroborate (TBTU) (37.6 mg, 0.117 mmol). The rxn was stirred for 1 hour. LCMS indicates the rxn was complete after 10 minutes, 740.30 at 3.96 minutes. It was diluted with ether, washed with saturated ammonium chloride then brine, dried (MgSO₄) and evaporated giving a yellow foam. The foam was dissolved in DCM, the solution was added to a Thompson silica gel cartridge and it was eluted with ethyl acetate/methanol (0% to 10%). The appropriate fractions (TLC) were combined and evaporated giving a light yellow film. The film was dissolved in DCM, re-evaporated, the residue triturated in hexane/ether (5%) and filtered giving the product (51 mg, 0.068 mmol, 64.0% yield)] as light a yellow powder. HPLC: 99.9% pure, 22.69 minutes. LCMS: 740.30 at 3.98 minutes, mp: 153-155° C. HRMS: calculate 740.3476, found 740.3480.

7H-Indolo[2,1-a][2]benzazepine-10-carboxamide, 6-[1-cyclobutyl-4-[(3-methyl-3,8-diazabicyclo[3.2.1]oct-8-yl)carbonyl]-1H-pyrazol-5-yl]-13-cyclohexyl-3-methoxy-N-[(1-methylethyl)sulfonyl]-

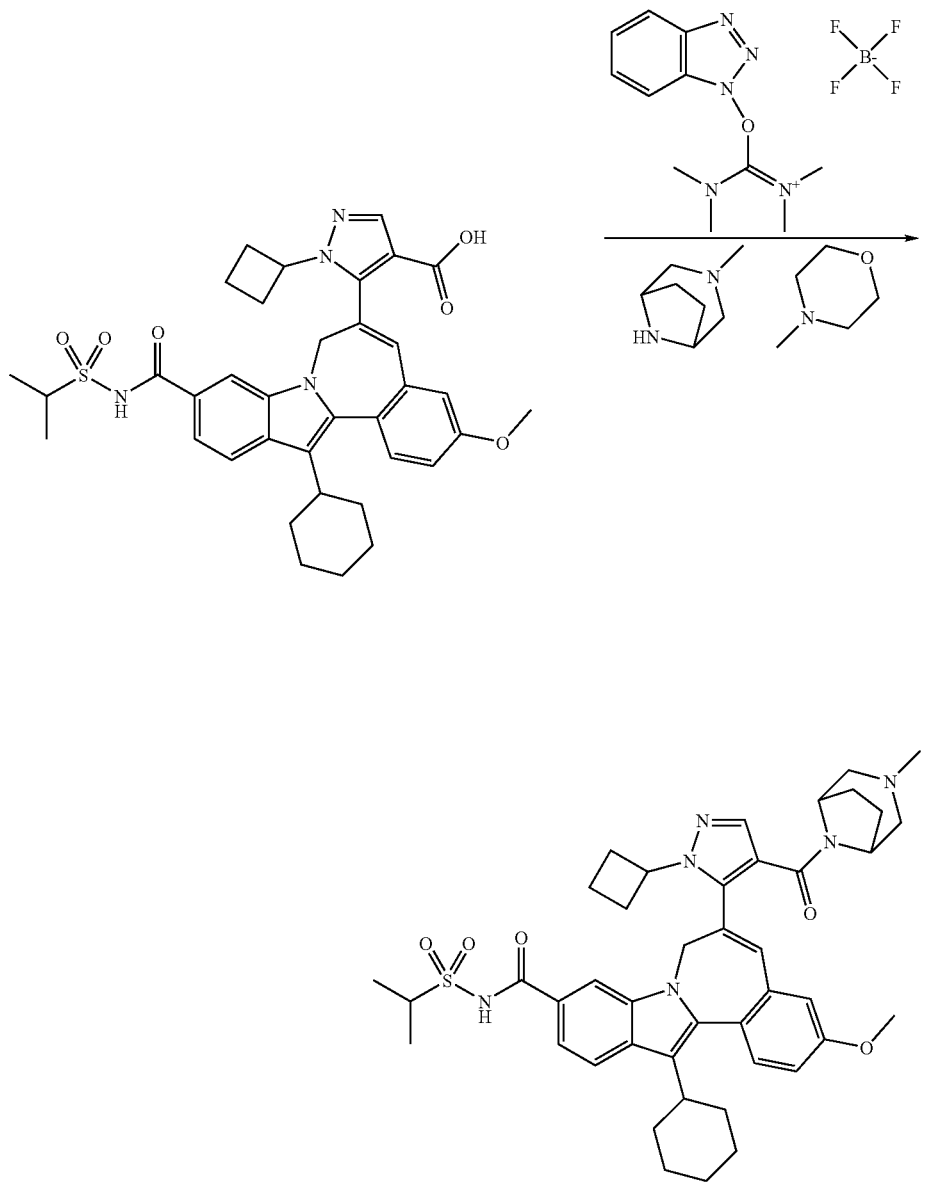

A 2 dram vial was charged with 1H-pyrazole-4-carboxylic acid, 1-cyclobutyl-5-[13-cyclohexyl-3-methoxy-10-[[[(1-methylethyl)sulfonyl]amino]carbonyl]-7H-indolo[2,1-a][2]benzazepin-6-yl]-(70 mg, 0.107 mmol), DMF (1 mL), 4-methylmorpholine (0.035 mL, 0.320 mmol), 3-methyl-3,8-diazabicyclo[3.2.1]octane (14 mg, 0.107 mmol) and o-benzotriazol-1-yl-N,N,N',N'-tetramethyluronium tetrafluoroborate (TBTU) (37.6 mg, 0.117 mmol). The rxn was stirred for 1 hour. LCMS indicates the rxn was complete, 765.37 at 3.76 minutes. It was diluted with ether, washed with saturated ammonium chloride then brine, dried (MgSO$_4$) and evaporated giving a yellow film. The solid was dissolved in DCM, the solution was added to a Thomson silica gel column and the column was eluted with ethyl acetate/methanol (10% to 60%). The appropriate fractions (TLC) were combined and evaporated giving a light yellow solid. The solid was triturated in ether/hexane giving the product (60 mg, 0.078 mmol, 73.5% yield) as a yellow powder. HPLC: 99.99%. LCMS: 765.41 at 3.77 minutes. $^1$H NMR: (400 Mz, CD$_3$OD) δ 1.16-1.26 (m, 5H), 1.34 (bs, 7H), 1.60 (bs, 4H), 1.74-1.77 (m, 3H), 1.90 (bs, 3H), 2.03 (bs, 4H), 2.20 (bs, 2H), 2.64 (bs, 2H), 2.79 (bs, 1H), 3.92 (s, 3H), 6.67 (s, 1H), 6.87 (s, 1H), 7.04-7.05 (m, 1H), 7.45 (bs, 1H), 7.71 (m, 3H).

7H-Indolo[2,1-a][2]benzazepine-10-carboxamide, 6-[1-cyclobutyl-4-(3-oxa-9-azabicyclo[3.3.1]non-9-ylcarbonyl)-1H-pyrazol-5-yl]-13-cyclohexyl-3-methoxy-N-[(1-methylethyl)sulfonyl]-

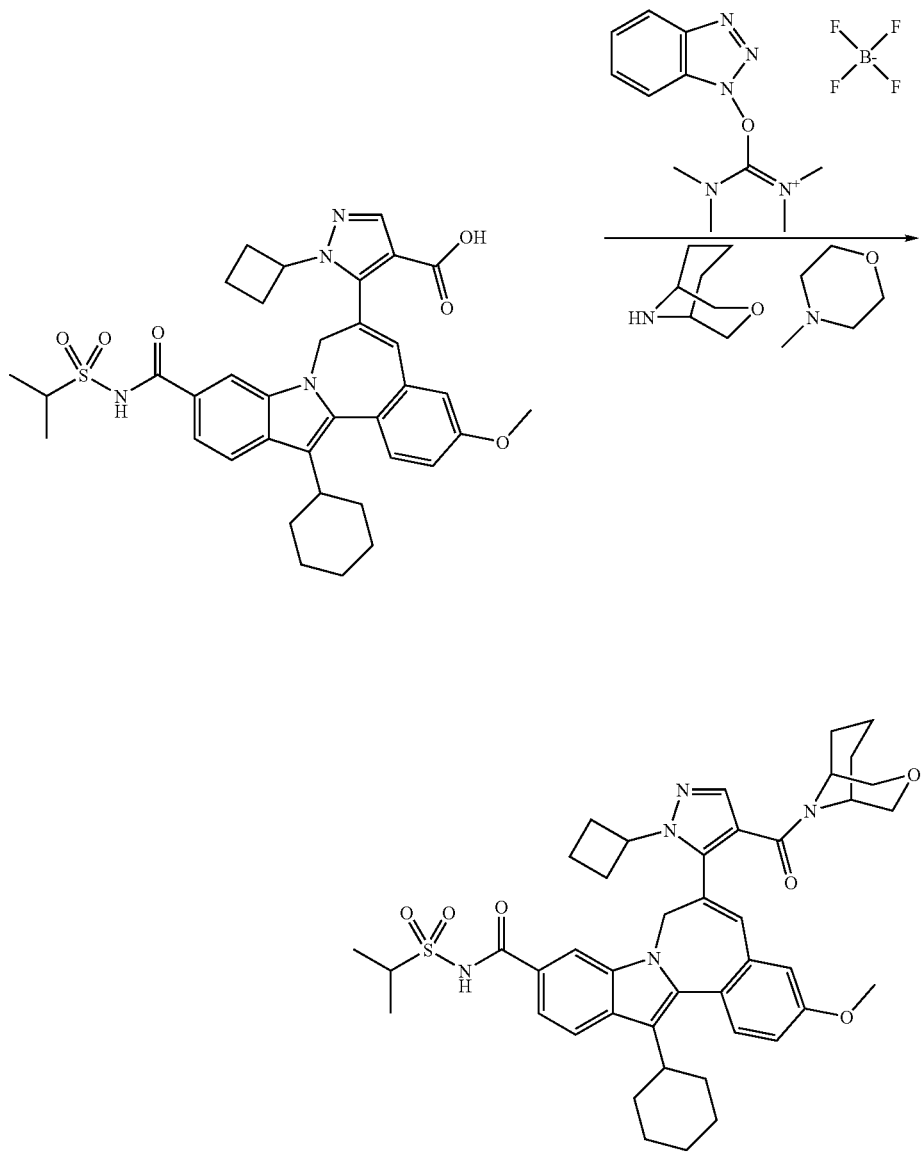

A 2 dram vial was charged with 1H-pyrazole-4-carboxylic acid, 1-cyclobutyl-5-[13-cyclohexyl-3-methoxy-10-[[[(1-methylethyl)sulfonyl]amino]carbonyl]-7H-indolo[2,1-a][2]benzazepin-6-yl]-(70 mg, 0.107 mmol), DMF (1 mL), 4-methylmorpholine (0.035 mL, 0.320 mmol), 3-oxa-9-azabicyclo[3.3.1]nonane (13.56 mg, 0.107 mmol) and o-benzotriazol-1-yl-N,N,N',N'-tetramethyluronium tetrafluoroborate (TBTU) (37.6 mg, 0.117 mmol). The rxn was stirred for 1 hour. LCMS indicates the rxn was complete, 766.36 at 4.11 minutes. It was diluted with ether, washed with saturated ammonium chloride then brine, dried (MgSO$_4$) and evaporated giving a yellow solid. The solid was dissolved in DCM, the solution was added to a Thomson silica gel column and the column was eluted with hexane/ethyl acetate (30% to 100%). The appropriate fractions (TLC) were combined and evaporated giving a light yellow solid. The solid was triturated in ether/hexane giving the product (54 mg, 0.070 mmol, 66.1% yield)] as a light yellow powder. HPLC: 99.99%. LCMS: 766.36 at 4.11 minutes. $^1$H NMR: (400 Mz, CD$_3$OD) δ 1.18-1.26 (m, 3H), 1.37-1.42 (m, 3H), 1.44-1.45 (d, J=6 Hz, 6H), 1.53-1.54 (d, J=7 Hz, 3H), 1.57 (s, 3H), 1.76-1.78 (m, 3H), 1.96-1.99 (m, 2H), 2.03 (s, 1H), 2.10-2.11 (m, 2 h), 2.27 (bs, 1H), 2.68-2.76 (m, 1H), 2.85-2.88 (m, 1H), 3.21 (bs, 1H), 3.32-3.34 (m, 1H), 3.95 (s, 3H), 4.03-4.13 (spt, J=13 Hz, 1H), 4.56-4.59 (d, J=16 Hz, 1H), 4.82 (bs, 1H), 4.87-4.95 (d, J=16 Hz, 1H), 6.72-6.75 (m, 1H), 6.93 (s, 1H), 7.12-7.13 (m, 1H), 7.58-7.64 (dd, J=8 Hz & 19 Hz, 2H), 7.71 (s, 1H), 7.76 (s, 1H), 7.90-7.91 (d, J=8 Hz, 1H) & 10.78 (bs, 1H).

7H-Indolo[2,1-a][2]benzazepine-10-carboxamide, 6-[1-cyclobutyl-4-(1-methyl-1,4-diazepan-4-ylcarbonyl)-1H-pyrazol-5-yl]-13-cyclohexyl-3-methoxy-N-[(1-methylethyl)sulfonyl]-

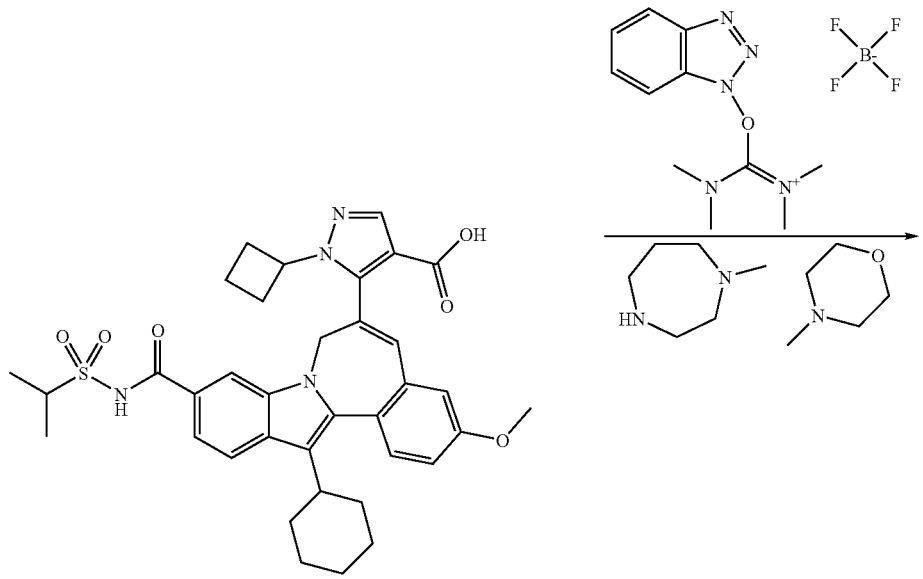

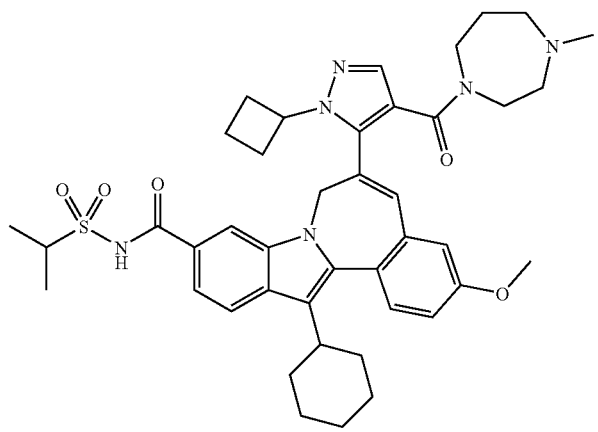

A 2 dram vial was charged with 1H-pyrazole-4-carboxylic acid, 1-cyclobutyl-5-[13-cyclohexyl-3-methoxy-10-[[[(1-methylethyl)sulfonyl]amino]carbonyl]-7H-indolo[2,1-a][2]benzazepin-6-yl]-(70 mg, 0.107 mmol), DMF (1 mL), 4-methylmorpholine (0.035 mL, 0.320 mmol), 1-methyl-1,4-diazepane (0.013 mL, 0.107 mmol) and o-benzotriazol-1-yl-N,N,N',N'-tetramethyluronium tetrafluoroborate (TBTU) (37.6 mg, 0.117 mmol). The rxn was stirred for 1 hour. LCMS indicates the rxn was complete, 766.36 at 4.11 minutes. It was diluted with ether, washed with saturated ammonium chloride then brine, dried (MgSO$_4$) and evaporated giving a yellow solid. The solid was dissolved in DCM, the solution was added to a Thomson silica gel column and the column was eluted with hexane/ethyl acetate (30% to 100%). The appropriate fractions (TLC) were combined and evaporated giving a light yellow solid. The solid was triturated in ether/hexane giving the product (34 mg, 0.042 mmol, 39.8% yield) as a light yellow powder. HPLC: 93% with a 7% impurity. LCMS: 753.44 at 3.72 minutes.

7H-Indolo[2,1-a][2]benzazepine-10-carboxamide, 6-[1-cyclobutyl-4-(1-cyclopentylpiperazin-4-ylcarbonyl)-1H-pyrazol-5-yl]-13-cyclohexyl-3-methoxy-N-[(1-methylethyl)sulfonyl]-

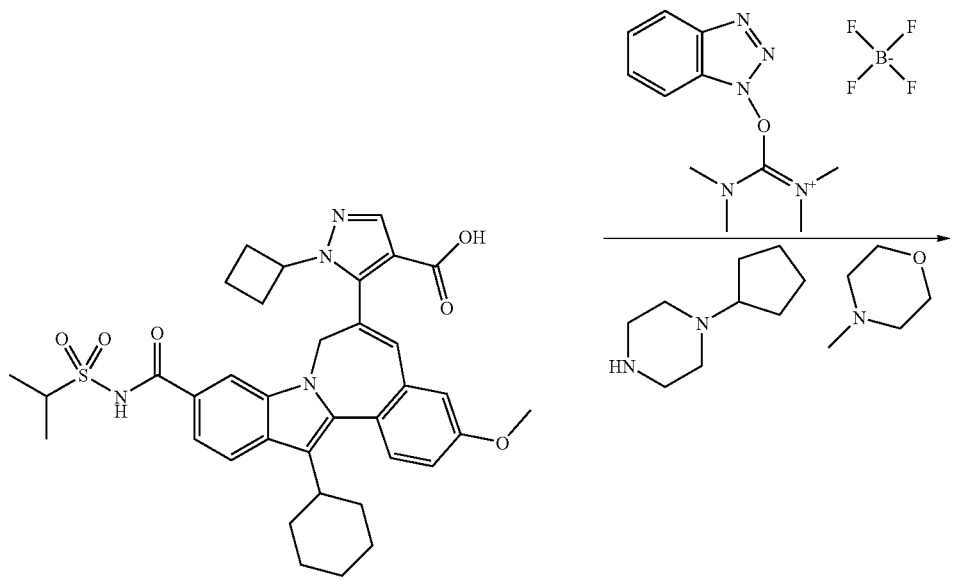

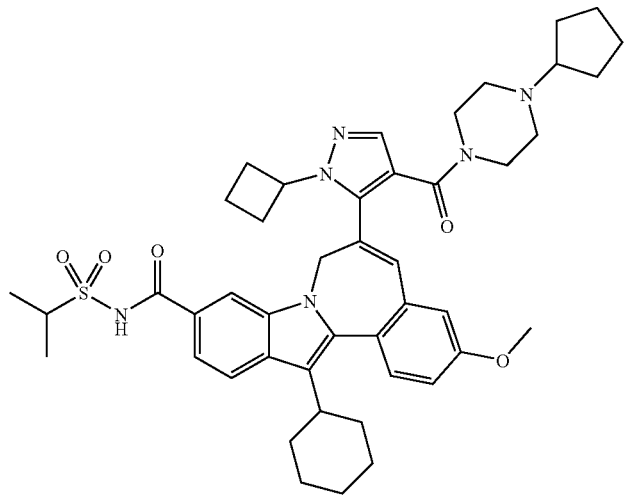

A 2 dram vial was charged with 1H-pyrazole-4-carboxylic acid, 1-cyclobutyl-5-[13-cyclohexyl-3-methoxy-10-[[[(1-methylethyl)sulfonyl]amino]carbonyl]-7H-indolo[2,1-a][2]benzazepin-6-yl]-(60 mg, 0.091 mmol), DMF (1 mL), 4-methylmorpholine (0.030 mL, 0.274 mmol), 1-cyclopentylpiperazine (15.50 mg, 0.100 mmol) and o-benzotriazol-1-yl-N,N,N',N'-tetramethyluronium tetrafluoroborate (TBTU) (32.3 mg, 0.100 mmol). The rxn was stirred for 1 hour. LCMS indicates the rxn was complete, 766.36 at 4.11 minutes. It was diluted with ether, washed with saturated ammonium chloride then brine, dried (MgSO$_4$) and evaporated giving a yellow solid. The solid was dissolved in DCM, the solution was added to a Thomson silica gel column and the column was eluted with DCM/methanol (0% to 5%). The appropriate fractions (TLC) were combined and evaporated giving a light yellow solid. The solid was triturated in ether/hexane giving the product (52 mg, 0.065 mmol, 71.5% yield) as a light yellow powder. HPLC: 99.6%. LCMS: 793.43 at 3.77 minutes.

7H-Indolo[2,1-a][2]benzazepine-10-carboxamide, 6-[1-cyclobutyl-4-[[(2R,6S)-2,6-dimethyl-4-morpholinyl]carbonyl])-1H-pyrazol-5-yl]-13-cyclohexyl-3-methoxy-N-[(1-methylethyl)sulfonyl]-

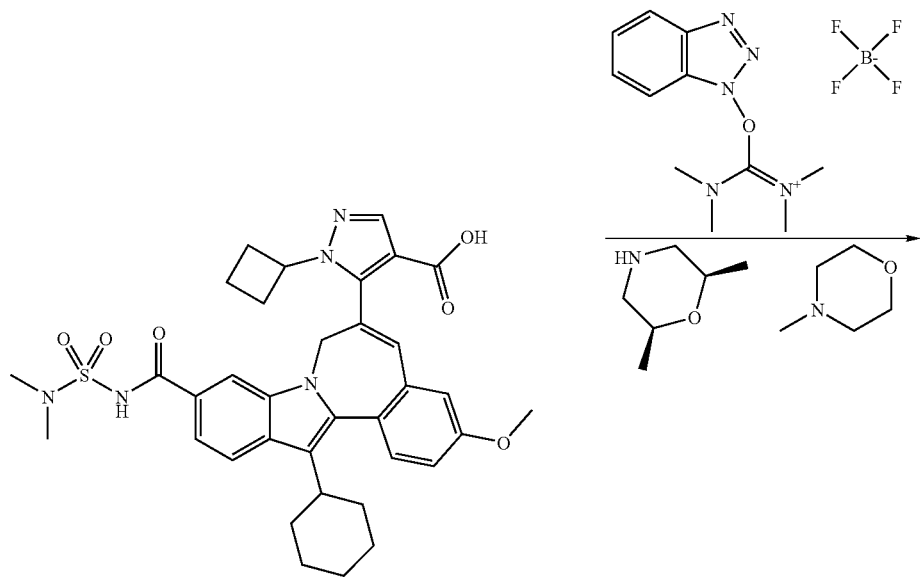

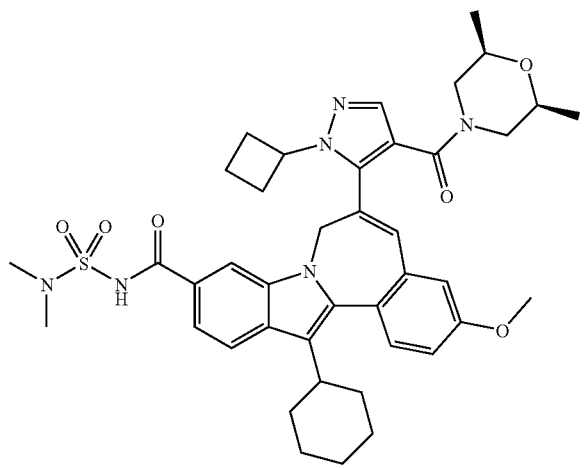

A 2 dram vial was charged with 1H-pyrazole-4-carboxylic acid, 1-cyclobutyl-5-[13-cyclohexyl-3-methoxy-10-[[[(N,N-dimethylamino)sulfonyl]amino]carbonyl]-7H-indolo[2,1-a][2]benzazepin-6-yl]-(70 mg, 0.106 mmol), DMF (1 mL), 4-methylmorpholine (0.023 mL, 0.213 mmol), cis-2,6-dimethylmorpholine (0.016 mL, 0.128 mmol) and o-benzotriazol-1-yl-N,N,N',N'-tetramethyluronium tetrafluoroborate (TBTU) (37.6 mg, 0.117 mmol). The rxn was stirred over night. LCMS indicates the rxn was done, 753.2/755.2 at 3.08 minutes. The rxn was diluted with DCM, washed with 0.1 N HCl (aqueous) then brine, dried (MgSO4) and evaporated giving a yellow syrup. The syrup was dissolved in DCM, the solution was added to a Thompson silica gel cartridge and it was eluted with hexane/ethyl acetate (30% to 100%). The appropriate fractions (TLC) were combined and evaporated giving a creamy white solid. The solid was triturated in ether/hexane and filtered giving the product (39 mg, 0.051 mmol, 48% yield) as a white powder. HPLC: 99.9% pure at 22.94 minutes. LCMS pos/neg: 753.2/755.1 at 2.98 minutes. $^1$H NMR: (400 Mz, CD$_3$OD) δ 1.20-1.29 (m, 5H), 1.37-1.43 (m, 4H), 1.58-1.60 (d, J=13 Hz, 2H), 1.67 (s, 3H), 1.77-1.79 (d, J=11 Hz, 3H), 1.91-1.97 (m, 4H), 2.03-2.14 (m, 3H), 2.28-2.30 (d, J=7 Hz, 6H), 2.50-2.52 (m, 1H), 2.72-2.76 (m, 1H), 2.80 (s, 3H), 2.87 (s, 3H), 2.94 (s, 3H), 3.95 (s, 2H), 4.08 (s, 2H), 4.38-4.41 & 4.52-4.55 (m, 1H), 4.76 (bs, 1H), 6.47 & 6.68 (s, 1H), 6.93 (s, 1H), 7.11-7.12 (m, 1H), 7.31-7.33 (m, 1H), 7.57 (s, 1H), 7.65 (s, 1H), 7.73-7.75 (d, J=7 Hz, 2H), 8.01 (s, 1H), 8.27-8.29 (d, J=7 Hz, 1H), 9.26 & 10.85 (m, 1H).

7H-Indolo[2,1-a][2]benzazepine-10-carboxamide, 6-[1-cyclobutyl-4-[[(2R,6S)-2,6-dimethyl-4-morpholinyl]carbonyl]-3-methyl-1H-pyrazol-5-yl]-13-cyclohexyl-3-methoxy-N-[(1-methylethyl)sulfonyl]-

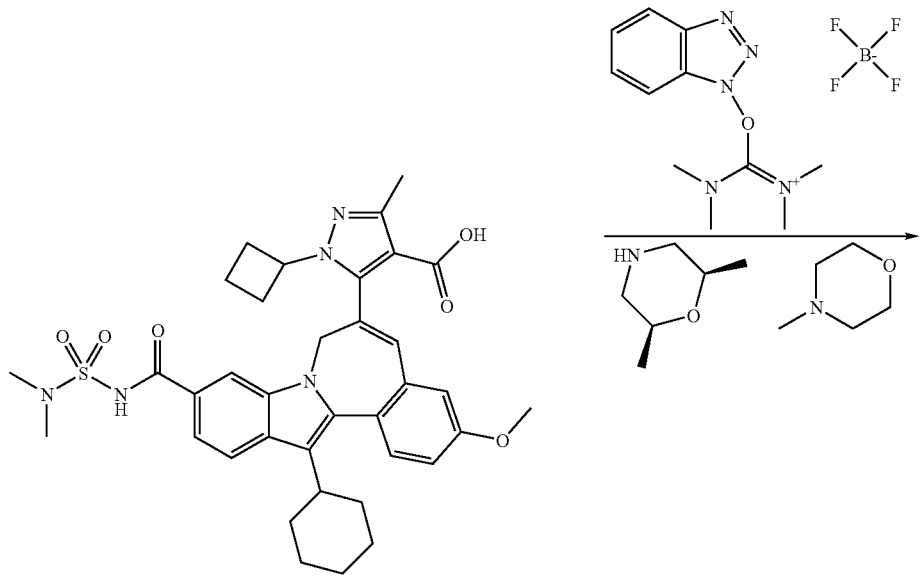

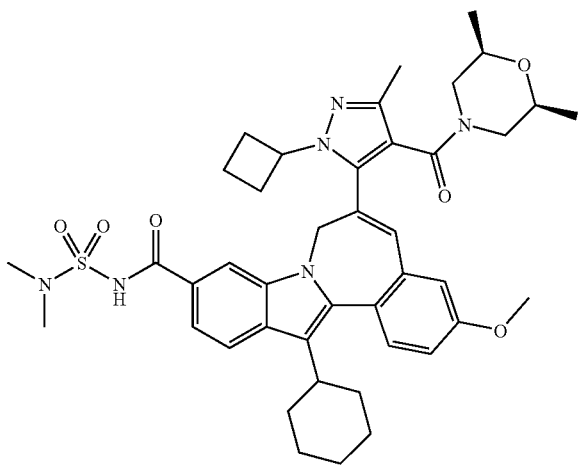

A 2 dram vial was charged with 1H-pyrazole-4-carboxylic acid-5-methyl, 1-cyclobutyl-5-[13-cyclohexyl-3-methoxy-10-[[[(N,N-dimethylamino)sulfonyl]amino]carbonyl]-7H-indolo[2,1-a][2]benzazepin-6-yl]-(70 mg, 0.104 mmol), DMF (1 mL), 4-methylmorpholine (0.023 mL, 0.208 mmol), cis-2,6-dimethylmorpholine (0.015 mL, 0.125 mmol) and o-benzotriazol-1-yl-N,N,N',N'-tetramethyluronium tetrafluoroborate (TBTU) (36.8 mg, 0.115 mmol). The rxn was stirred over night. LCMS indicates the rxn was done, 767.3/767.2 at 3.10 minutes. The rxn was diluted with DCM, washed with 0.1 N HCl (aqueous) then brine, dried (MgSO$_4$) and evaporated giving a yellow syrup. The syrup was dissolved in DCM, the solution was added to a Thompson silica gel cartridge and it was eluted with hexane/ethyl acetate (30% to 100%). The appropriate fractions (TLC) were combined and evaporated giving a creamy white solid. The solid was triturated in ether/hexane and filtered giving the product (59 mg, 0.076 mmol, 72.9% yield) as a creamy white powder.

HPLC: 99.9% pure, 23.13 minutes. LCMS: 769.18 at 4.05 minutes. $^1$H NMR: (400 Mz, CD$_3$OD) δ 1.20-1.26 (m, 3H), 1.37-1.43 (m, 3H), 1.45-1.48 (m, 4H), 1.53-1.54 (d, J=7 Hz, 2H), 1.67 (s, 4H), 1.77-1.80 (d, J=11 Hz, 2H), 1.82-1.86 (m, 1H), 1.90-1.99 (m, 3H), 2.03 (s, 3H), 2.06-2.12 (m, 2H), 2.28-2.31 (d, J=14 Hz, 4H), 2.50-2.52 (m, 1H), 2.72-2.76 (m, 1H), 2.85-2.90 (m, 2H), 3.07 (bs, 1H), 3.20-3.22 (m, 1H), 3.96 (s, 2H), 4.08 (s, 2H), 4.40-4.43 & 4.52-4.55 (m, 1H), 4.75-4.83 (bm, 1H), 6.37 & 6.67 (s, 1H), 6.93 (s, 1H), 7.11-7.13 (m, 1H), 7.28-7.33 (m, 2H), 7.58-7.68 & 7.74-7.75 (m, 3H), 7.88-7.90 (d, J=8 Hz, 1H), 8.27-8.28 & 8.95-8.97 (d, J=8 Hz, 1H), 9.27 & 10.84 (m, 1H).

7H-Indolo[2,1-a][2]benzazepine-10-carboxamide, 6-[1-cyclobutyl-4-[[(2R,6S)-2,6-dimethyl-4-morpholinyl]carbonyl]-3-methyl-1H-pyrazol-5-yl]-13-cyclohexyl-3-methoxy-N-[(1-methylethyl)sulfonyl]-

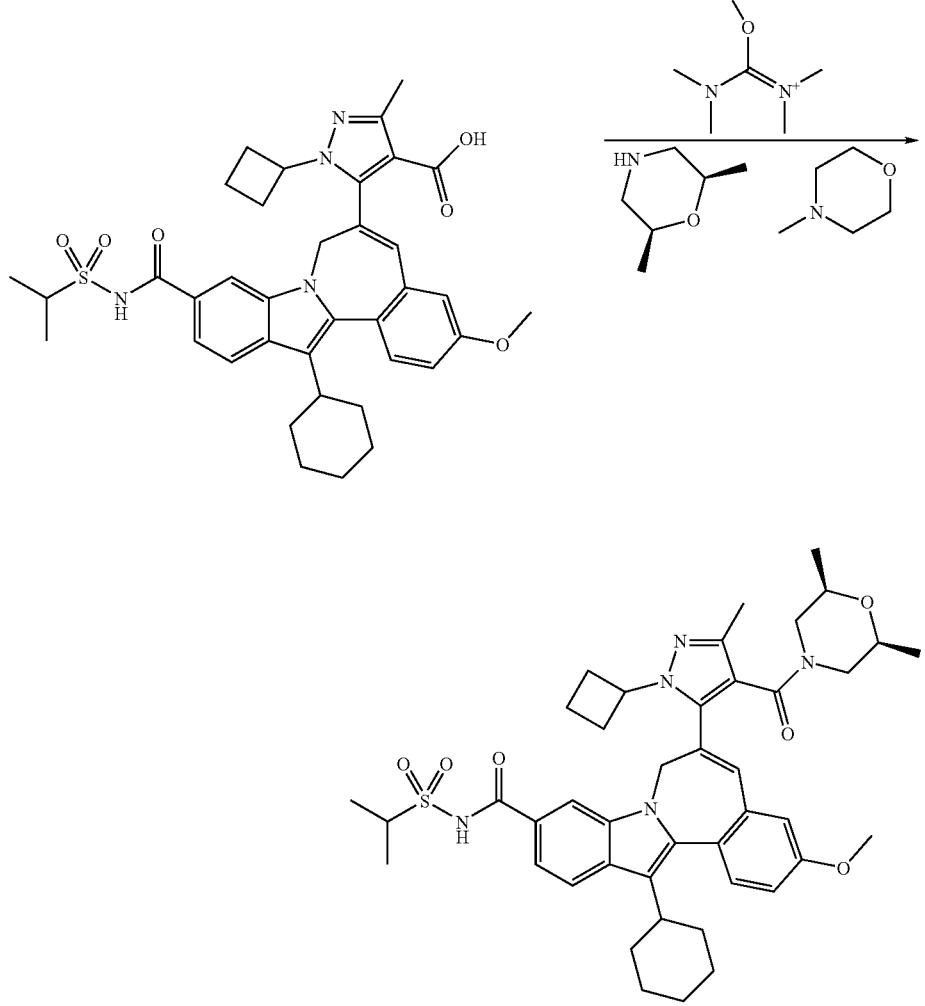

A 2 dram vial was charged with 1H-pyrazole-4-carboxylic acid-5-methyl, 1-cyclobutyl-5-[13-cyclohexyl-3-methoxy-10-[[[(1-methylethyl)sulfonyl]amino]carbonyl]-7H-indolo[2,1-a][2]benzazepin-6-yl]-(70 mg, 0.104 mmol), DMF (1 mL), 4-methylmorpholine (0.023 mL, 0.209 mmol), cis-2,6-dimethylmorpholine (0.015 mL, 0.125 mmol) and o-benzotriazol-1-yl-N,N,N',N'-tetramethyluronium tetrafluoroborate (TBTU) (36.9 mg, 0.115 mmol). The rxn was stirred over night. LCMS indicates the rxn was done, 766.21768.2 at 2.83 minutes. The rxn was diluted with DCM, washed with 0.1 N HCl (aqueous) then brine, dried (MgSO$_4$) and evaporated giving a yellow syrup. The syrup was dissolved in DCM, the solution was added to a Thompson silica gel cartridge and it was eluted with hexane/ethyl acetate (30% to 100%). The appropriate fractions (TLC) were combined and evaporated giving a creamy white solid. The solid was triturated in ether/hexane and filtered giving the product (50 mg, 0.064 mmol, 61.8% yield) as a white powder. HPLC: 99.99% pure, 26.43 minutes. LCMS: 768.19 at 4.09 minutes. $^1$H NMR: (400 Mz, CD$_3$OD) δ 1.26-1.30 (m, 5H), 1.41-1.45 (m, 2H), 1.58 (s, 6H), 1.78-1.80 (d, J=10 Hz, 1H), 1.87-1.98 (m, 3H), 2.03-2.14 (m, 2H), 2.28 (bs, 1H), 2.49-2.51 (m, 1H), 2.62-2.66 (t, J=10 Hz, 1H), 2.73 (bs, 1H), 2.85-2.90 (m, 2H), 3.07 & 3.08 (2 s, 6H), 3.95 (s, 2H), 4.07 (s, 2H), 4.43-4.46 & 4.56-4.59 (m, 1H), 4.80-4.88 (bm, 1H), 6.44-6.47 & 6.70-6.73 (m, 1H), 6.94 (m, 1H), 7.11-7.13 (m, 1H), 7.21-7.22 (m, 1H), 7.31-7.33 (m, 1H), 7.56-7.66 (m, 2H), 7.71-7.73 (m, 1H), 7.90-7.92 & 8.27-8.28 (d, J=8 Hz, 1H), 8.97-8.99 (d, J=8 Hz, 1H), 9.37 & 12.56 (bs, 1H).

7H-Indolo[2,1-a][2]benzazepine-10-carboxamide, 6-[1-cyclobutyl 4-[[(1S,4S)-5-ethyl-2,5-diazabicyclo[2.2.1]hept-2-yl]carbonyl]-1H-pyrazol-5-yl]-13-cyclohexyl-3-methoxy-N-[(1-methylethyl)sulfonyl]-

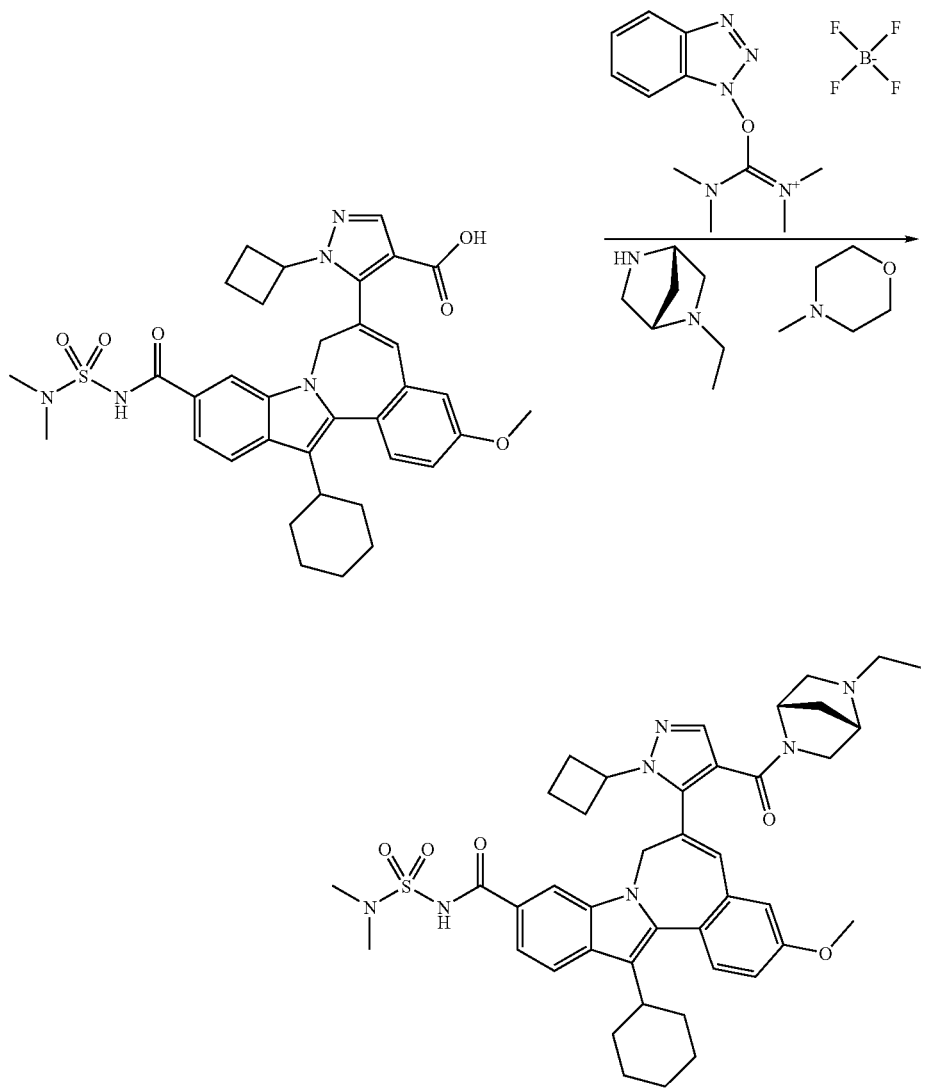

A 2 dram vial was charged with 1H-pyrazole-4-carboxylic acid, 1-cyclobutyl-5-[13-cyclohexyl-3-methoxy-10-[[[(N,N-dimethylamino)sulfonyl]amino]carbonyl]-7H-indolo[2,1-a][2]benzazepin-6-yl]-(70 mg, 0.106 mmol), DMF (1 mL), (1S, 4S)-2-ethyl-2,5-diazabicyclo[2.2.1]heptane, 2 TFA (49.0 mg, 0.138 mmol), [Reactants] and o-benzotriazol-1-yl-N,N,N',N'-tetramethyluronium tetrafluoroborate (TBTU) (37.6 mg, 0.117 mmol). The rxn was stirred over night. LCMS indicates the rxn was done, 764.2/766.2 at 2.67 minutes. The rxn was diluted with DCM, washed with 0.1 N HCl (aqueous) then brine, dried (MgSO$_4$) and evaporated giving a yellow syrup. The syrup was dissolved in DCM, the solution was added to a Thompson silica gel cartridge and it was eluted with DCM/methanol (0% to 5%). The appropriate fractions (TLC) were combined and evaporated giving a creamy white solid. The solid was triturated in ether/hexane and filtered giving the product (52 mg, 0.067 mmol, 63.2% yield) as a yellow powder. HPLC: 99.99% pure, 23.71 minutes. LCMS: 766.16 at 3.92 minutes. $^1$H NMR: (400 Mz, CD$_3$OD) δ 1.18-1.30 (m, 6H), 1.36-1.46 (m, 5H), 1.52 (m, 4H), 1.59 (bs, 5H), 1.76-1.78 (d, J=10 Hz, 3H), 1.92-1.94 (d, J=10 Hz, 2H), 2.01-2.09 (m, 4H), 2.15-2.17 (d, J=12 Hz, 1H), 2.29-2.32 (11, 1H), 2.43-2.49 (t, J=11 Hz, 1H), 2.79 (s, 1H), 2.82-2.85 (m, 1H), 2.87 (s, 1H), 2.91 (s, 1H), 2.99 (s, 4H), 3.05 (s, 1H), 3.08 (bs, 1H), 3.25 (bs, 1H), 3.89 (s, 3H), 3.96-3.98 (d, J=9 Hz, 1H), 4.06-4.12 (m, 1H), 4.35 (bs, 1H), 4.56-4.60 (m, 1H), 4.69-4.71 (d, J=9 Hz, 1H), 4.77 (bs, 1H), 6.66 (s, 1H), 6.99 (s, 1H), 7.04-7.05 (m, 1H), 7.52-7.53 (d, J=8 Hz, 1H), 7.60 (s, 1H), 7.64-7.66 (d, J=8 Hz, 1H), 7.78-7.79 (d, J=8 Hz, 1H) & 11.27 (bs, 1H).

7H-Indolo[2,1-a][2]benzazepine-10-carboxamide, 6-[1-cyclobutyl-3-methyl-4-[[(1S,4S)-5-ethyl-2,5-diazabicyclo[2.2.1]hept-2-yl]carbonyl]-1H-pyrazol-5-yl]-13-cyclohexyl-3-methoxy-N-[(1-methylethyl)sulfonyl]-

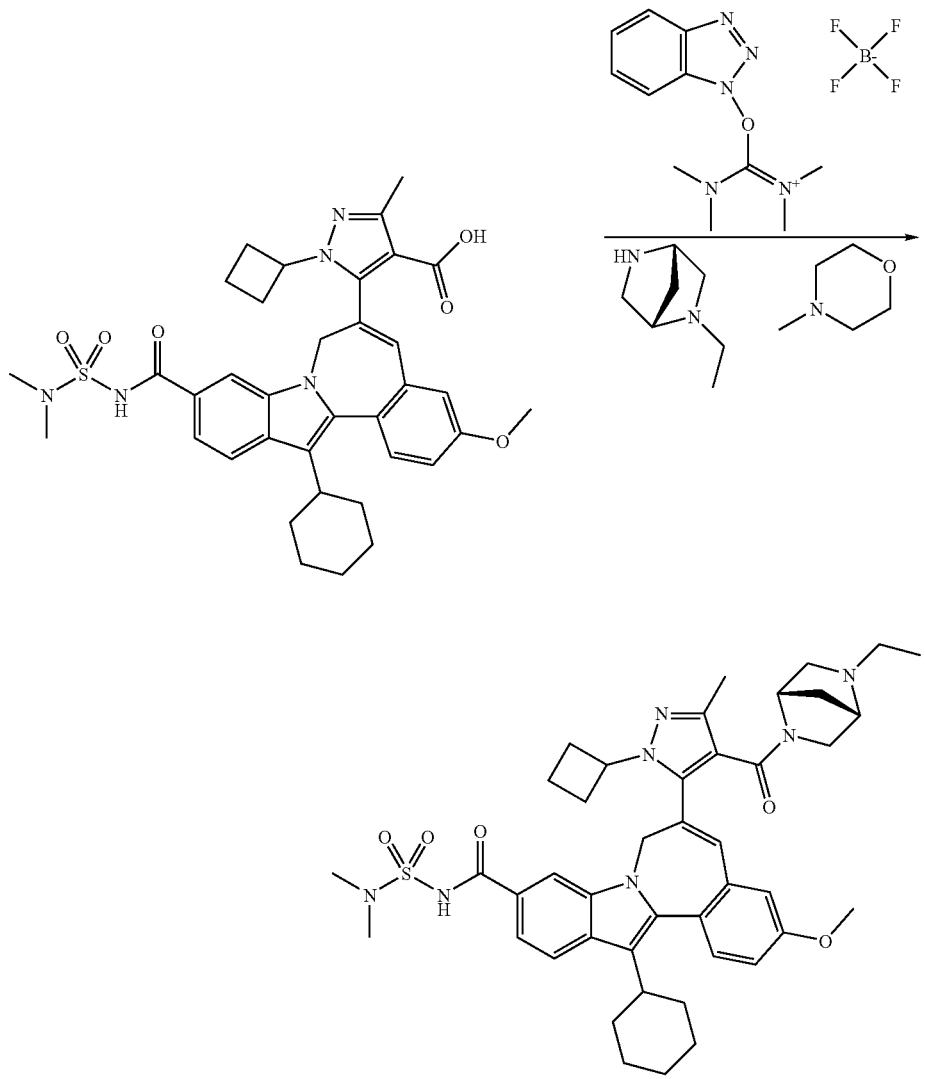

A 2 dram vial was charged with 1H-pyrazole-4-carboxylic acid-5-methyl, 1-cyclobutyl-5-[13-cyclohexyl-3-methoxy-10-[[[(N,N-dimethylamino)sulfonyl]amino]carbonyl]-7H-indolo[2,1-a][2]benzazepin-6-yl]-(70 mg, 0.104 mmol), DMF (1 mL), 4-methylmorpholine (0.037 mL, 0.333 mmol), (1S,4S)-2-ethyl-2,5-diazabicyclo[2.2.1]heptane, 2 TFA (48.0 mg, 0.135 mmol) and o-benzotriazol-1-yl-N,N,N',N'-tetramethyluronium tetrafluoroborate (TBTU) (36.8 mg, 0.115 mmol). The rxn was stirred over night. LCMS indicates the rxn was done, 778.3/780.2 at 2.67 minutes. The rxn was diluted with DCM, washed with 0.1 N HCl (aqueous) then brine, dried (MgSO$_4$) and evaporated giving a yellow syrup. The syrup was dissolved in DCM, the solution was added to a Thompson silica gel cartridge and it was eluted with DCM/methanol (0% to 5%). The appropriate fractions (TLC) were combined and evaporated giving a creamy white solid. The solid was triturated in hexane/ether and filtered giving the product (53 mg, 0.067 mmol, 64.6% yield) as a yellow powder. HPLC: 99.99% pure, 22.85 minutes. LCMS: 780.19 at 3.63 minutes. $^1$H NMR: (400 Mz, CD$_3$OD) δ 1.25-1.29 (m, 7H), 1.36-1.45 (m, 3H), 1.49-1.50 (m, 2H), 1.58 (bs, 5H), 1.79-1.81 (d, J=9 Hz, 4H), 1.95-1.97 (m, 3H), 2.03-2.07 (m, 4H), 2.16 (bs, 1H), 2.29 (bs, 2H), 2.32 (bs, 3H), 2.35 (bs, 1H), 2.76 (bs, 1H), 2.87 (bs, 1H), 2.96 (s, 1H), 3.00 (bs, 2H), 3.05 (s, 1H), 3.08 (bs, 6H), 3.89 (bs, 2H), 3.96 (bs, 3H), 4.06-4.12 (m, 1H), 4.54-5.58 (m, 1H), 4.77-4.79 (m, 1H), 6.79-6.85 (m, 1H), 6.97 (s, 1H), 7.12-7.13 (m, 1H), 7.50-7.59 (m, 3H), 7.90-7.91 (d, J=8 Hz, 1H) & 11.28 (bs, 1H).

7H-Indolo[2,1-a][2]benzazepine-10-carboxamide, 6-[1-cyclobutyl-3-methyl-4-[[(1S,4S)-5-ethyl-2,5-diazabicyclo[2.2.1]hept-2-yl]carbonyl]-1H-pyrazol-5-yl]-13-cyclohexyl-3-methoxy-N-[(1-methylethyl)sulfonyl]-

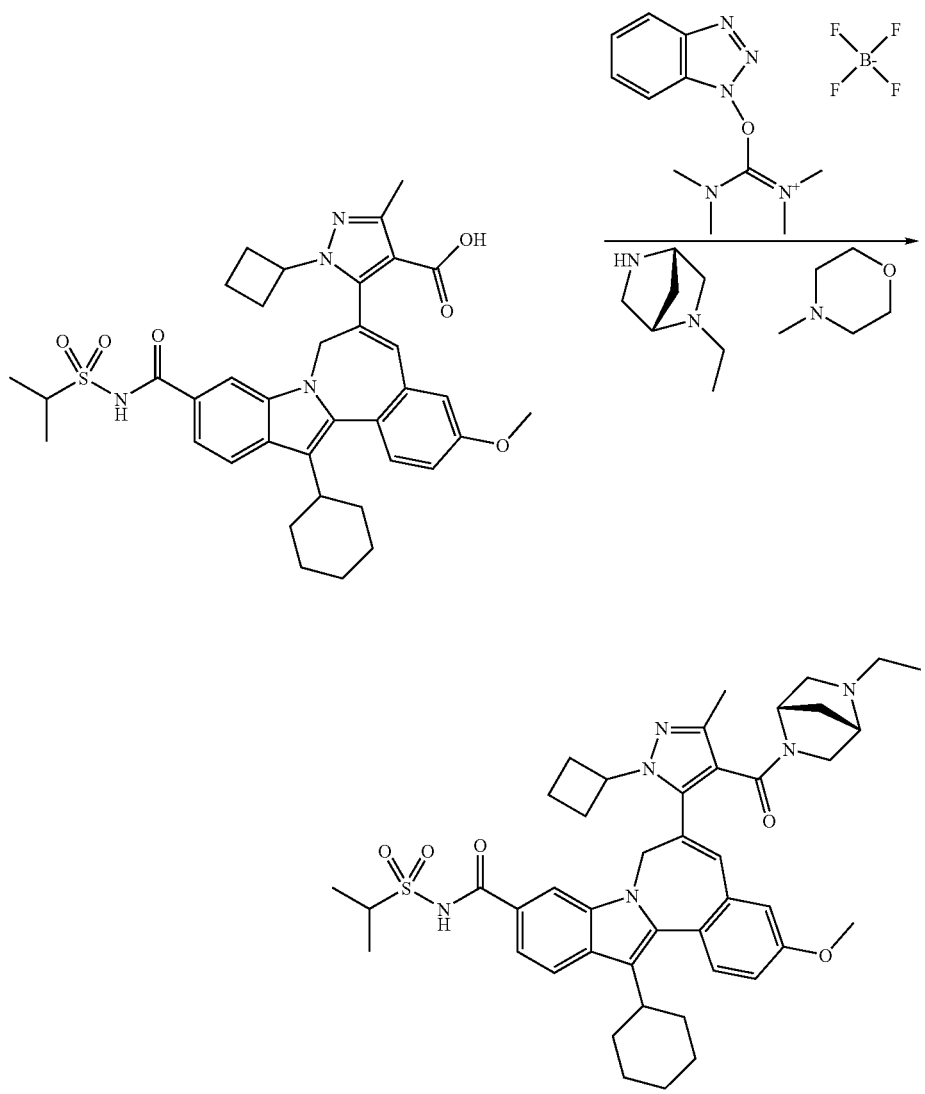

A 2 dram vial was charged with 1H-pyrazole-4-carboxylic acid-5-methyl, 1-cyclobutyl-5-[13-cyclohexyl-3-methoxy-10-[[[(1-methylethyl)sulfonyl]amino]carbonyl]-7H-indolo[2,1-a][2]benzazepin-6-yl]-(70 mg, 0.104 mmol), DMF (1 mL), 4-methylmorpholine (0.037 mL, 0.334 mmol), (1S,4S)-2-ethyl-2,5-diazabicyclo[2.2.1]heptane, 2 TFA (48.1 mg, 0.136 mmol) and o-benzotriazol-1-yl-N,N,N',N'-tetramethyluronium tetrafluoroborate (TBTU) (36.9 mg, 0.115 mmol). The rxn was stirred over night. LCMS indicates the rxn was done, 777.2/779.2 at 2.42 minutes. The rxn was diluted with DCM, washed with 0.1 N HCl (aqueous) then brine, dried (MgSO$_4$) and evaporated giving a yellow syrup. The syrup was dissolved in DCM, the solution was added to a Thompson silica gel cartridge and it was eluted with DCM/methanol (0% to 5%). The appropriate fractions (TLC) were combined and evaporated giving a creamy white solid. The solid was triturated in hexane/ether and filtered giving the product (44 mg, 0.056 mmol, 53.6% yield) as a yellow powder. HPLC: 99.99% pure, 23.10 minutes. LCMS: 779.21 at 3.64 minutes. $^1$H NMR: (400 Mz, CD$_3$OD) 1.25-1.29 (m, 8H), 1.42-1.43 (d, J=7 Hz, 6H), 1.46-1.48 (d, J=7 Hz, 6H), 1.52-1.53 (d, J=6 Hz, 8H), 1.58 (bs, 9H), 1.75-1.82 (m, 4H), 1.94-1.97 (bs, 4H), 2.01-2.08 (m, 6H), 2.15-2.16 (m, 1 h), 2.29 (s, 3H), 2.32 (bs, 4H), 2.35 (bs, 1H), 2.46 (m, 1H), 2.50-2.54 (m, 2H), 2.76-2.87 (m, 3H), 2.95-2.97 (m, 1H), 3.89 (s, 3H), 3.96 (s, 4H), 4.00-4.12 (m, 4H), 4.44-4.46 (m, 1H), 4.53-4.58 (m, 3H), 4.78 (bs, 1H), 4.92 (m, 1H), 6.67 & 6.86 (m, 1H), 6.97 (s, 1H), 7.13-7.14 (d, J=9 Hz, 1H), 7.50-7.52 (d, J=9 Hz, 1H), 7.54-7.55 (d, J=8 Hz, 1H), 7.58-7.60 (d, J=9 Hz, 1H), 7.79-7.79 (d, J=8 Hz, 1H), 7.90-7.92 (d, J=8 Hz, 1H) & 11.39 (bs, 1H).

7H-Indolo[2,1-a][2]benzazepine-10-carboxamide, 6-[1-cyclobutyl-4-[(3-methyl-3,8-diazabicyclo[3.2.1]oct-8-yl)carbonyl]-1H-pyrazol-5-yl]-13-cyclohexyl-3-methoxy-N-[(1-methylethyl)sulfonyl]-

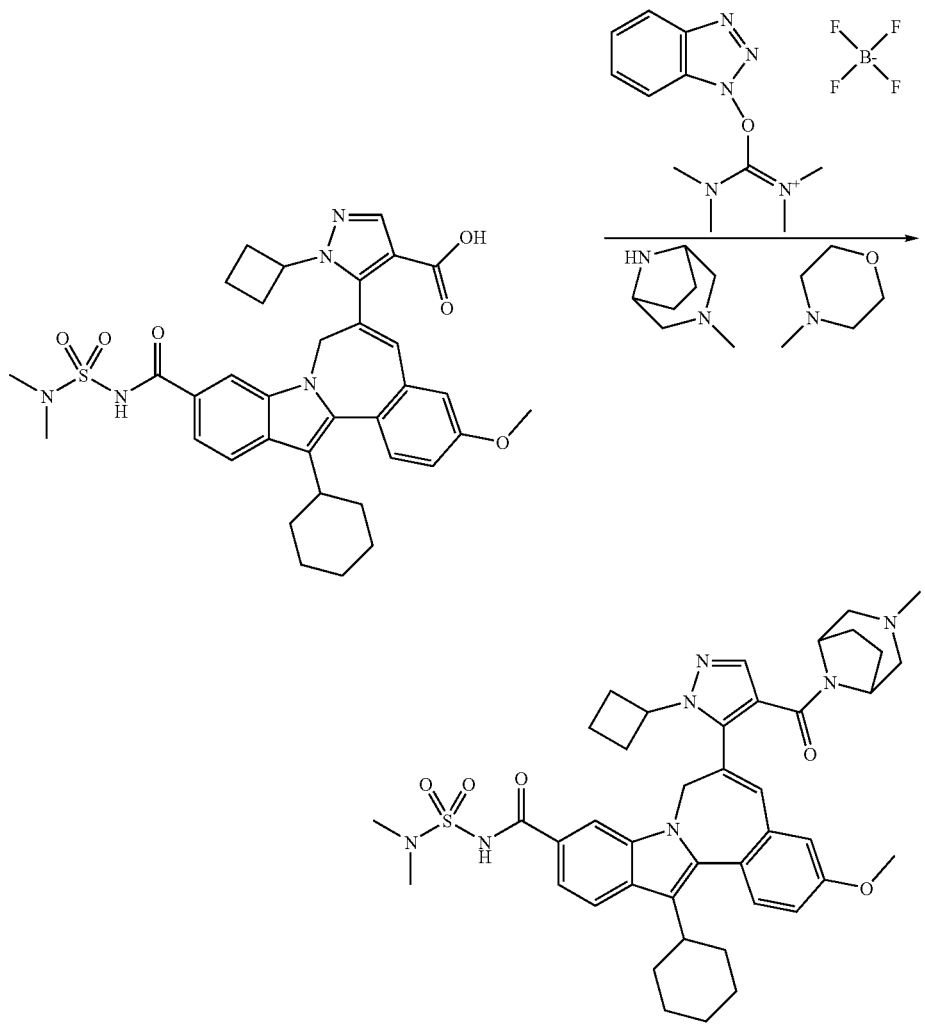

A 2 dram vial was charged with 1H-pyrazole-4-carboxylic acid, 1-cyclobutyl-5-[13-cyclohexyl-3-methoxy-10-[[[(N,N-dimethylamino)sulfonyl]amino]carbonyl]-7H-indolo[2,1-a][2]benzazepin-6-yl]-(70 mg, 0.106 mmol), DMF (1 mL), 3-methyl-3,8-diazabicyclo[3.2.1]octane, HCl (22.50 mg, 0.138 mmol), 3-methyl-3,8-diazabicyclo[3.2.1]octane, HCl (22.50 mg, 0.138 mmol) and o-benzotriazol-1-yl-N,N,N',N'-tetramethyluronium tetrafluoroborate (TBTU) (37.6 mg, 0.117 mmol). The rxn was stirred over night. LCMS indicates the rxn was done, 764.2/766.2 at 3.03 minutes. The rxn was diluted with DCM, washed with 0.1 N HCl (aqueous) then brine, dried (MgSO₄) and evaporated giving a yellow syrup. The syrup was dissolved in DCM, the solution was added to a Thompson silica gel cartridge and it was eluted with DCM/methanol (0% to 5%). The appropriate fractions (TLC) were combined and evaporated giving a creamy white solid. The solid was triturated in ether/hexane and filtered giving the product (51 mg, 0.066 mmol, 61.9% yield) as a light yellow powder. HPLC: 99.9% pure, 23.67 minutes. LCMS: 766.16 at 3.68 minutes. ¹H NMR: (400 Mz, CD₃OD) 1.25-1.29 (m, 4H), 1.37-1.46 (m, 4H), 1.59 (bs, 3H), 1.75-1.83 (m, 4H), 1.95-1.98 (m, 2H), 2.00-2.08 (m, 6H), 2.26 (s, 3H), 2.51-2.54 (m, 1H), 2.79 (s, 1H), 2.87 (m, 2H), 2.94-2.96 (m, 1H), 3.07 (s, 6H), 3.14 (s, 1H), 3.95 (s, 3H), 4.07 (s, 1H), 4.55-4.58 (m, 1H), 4.55-4.58 (m, 1H), 4.77-4.87 (m, 2H), 6.79 (bs, 1H), 6.94-6.95 (m, 1H), 7.10-7.11 (d, J=8 Hz, 1H), 7.56-7.57 (d, J=9 Hz, 1H), 7.64 (bs, 1H), 7.82 (bs, 1H), 7.89-7.90 (d, J=8 Hz, 1H) & 9.28 (bs, 1H).

7H-Indolo[2,1-a][2]benzazepine-10-carboxamide, 6-[1-cyclobutyl-3-methyl-4-[(3-methyl-3,8-diazabicyclo[3.2.1]oct-8-yl)carbonyl]-1H-pyrazol-5-yl]-13-cyclohexyl-3-methoxy-N-[(1-methylethyl)sulfonyl]-

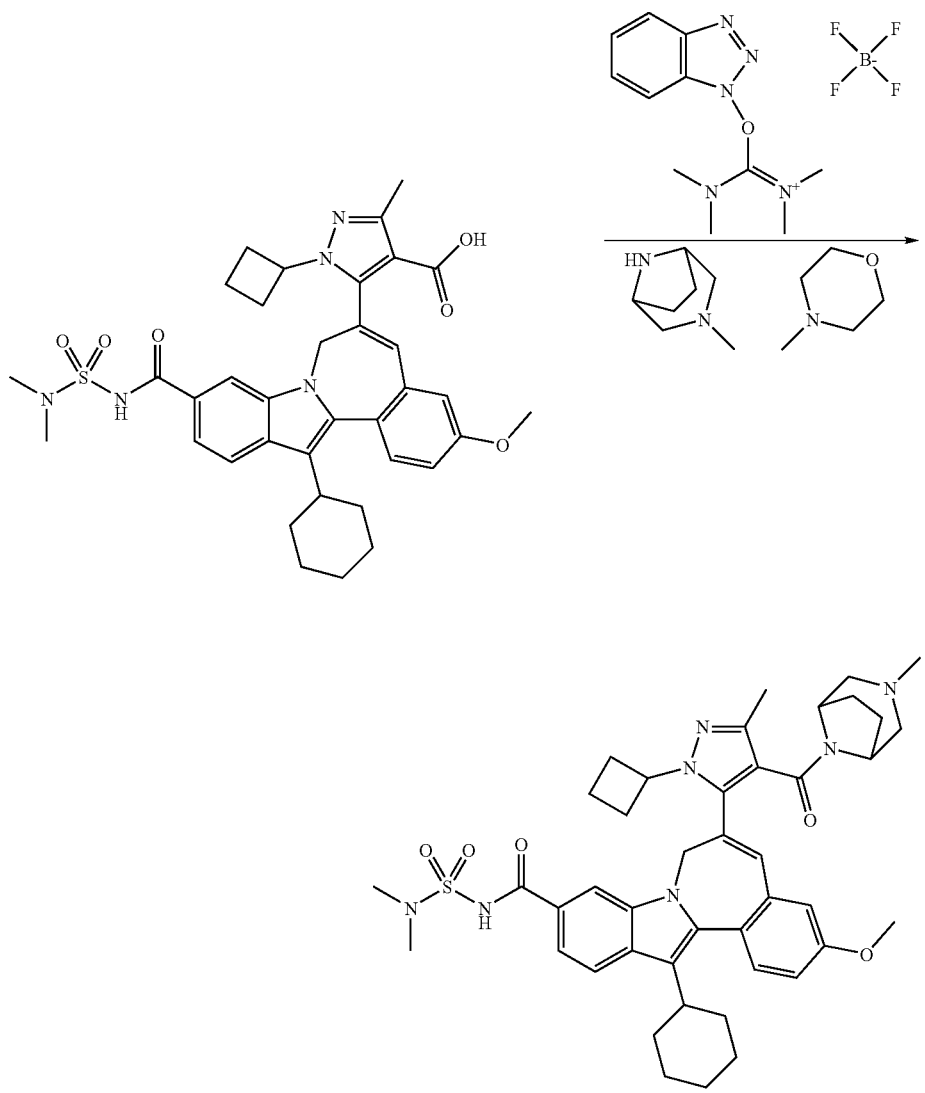

A 2 dram vial was charged with 1H-pyrazole-4-carboxylic acid-5-methyl, 1-cyclobutyl-5-[13-cyclohexyl-3-methoxy-10-[[[(N,N-dimethylamino)sulfonyl]amino]carbonyl]-7H-indolo[2,1-a][2]benzazepin-6-yl]-(70 mg, 0.104 mmol), DMF (1 mL), 4-methylmorpholine (0.037 mL, 0.333 mmol), 3-methyl-3,8-diazabicyclo[3.2.1]octane, 2HCl (27.0 mg, 0.135 mmol) and o-benzotriazol-1-yl-N,N,N',N'-tetramethyluronium tetrafluoroborate (TBTU) (36.8 mg, 0.115 mmol). The rxn was stirred over night. LCMS indicates the rxn was done, 778.2/780.2 at 3.15 minutes. The rxn was diluted with DCM, washed with 0.1 N HCl (aqueous) then brine, dried (MgSO$_4$) and evaporated giving a yellow syrup. The syrup was dissolved in DCM, the solution was added to a Thompson silica gel cartridge and it was eluted with DCM/methanol (0% to 5%). The appropriate fractions (TLC) were combined and evaporated giving a creamy white solid. The solid was triturated in ether/hexane and filtered giving the product (50 mg, 0.063 mmol, 60.9% yield) as a creamy white powder. HPLC: 99.8% pure, 23.11 minutes. LCMS of a byproduct that eluted before the product: 686.17 at 4.18 minutes. LCMS: 780.19 at 3.64 minutes. $^1$H NMR: (400 Mz, CD$_3$OD) 1.25-1.30 (m, 4H), 1.36-1.45 (m, 3H), 1.60 (bs, 3H), 1.77-1.79 (d, J=11 Hz, 3H), 1.94-1.97 (d, J=14 Hz, 3H), 2.00-2.06 (m, 3H), 2.24 (bs, 2H), 2.34-2.35 (m, 3H), 2.49 (m, 1H), 2.69-2.73 (m, 1H), 2.79 (s, 1H), 2.85-2.91 (m, 2H), 3.95 (s, 3H), 4.03-4.06 (m, 1H), 4.53-4.56 (d, J=15 Hz, 1H), 4.80 (bs, 1H), 6.77 (s, 1H), 6.94 (s, 1H), 7.10-7.12 (d, J=8 Hz, 1H), 7.55-7.57 (d, J=9 Hz, 1H), 7.64-7.66 (d, J=8 Hz, 1H), 7.89-7.90 (d, J=8 Hz, 1H) & 9.42 (bs, 1H).

7H-Indolo[2,1-a][2]benzazepine-10-carboxamide, 6-[1-cyclobutyl-3-methyl-4-[(3-methyl-3,8-diazabicyclo[3.2.1]oct-8-yl)carbonyl]-1H-pyrazol-5-yl]-13-cyclohexyl-3-methoxy-N-[(1-methylethyl)sulfonyl]-

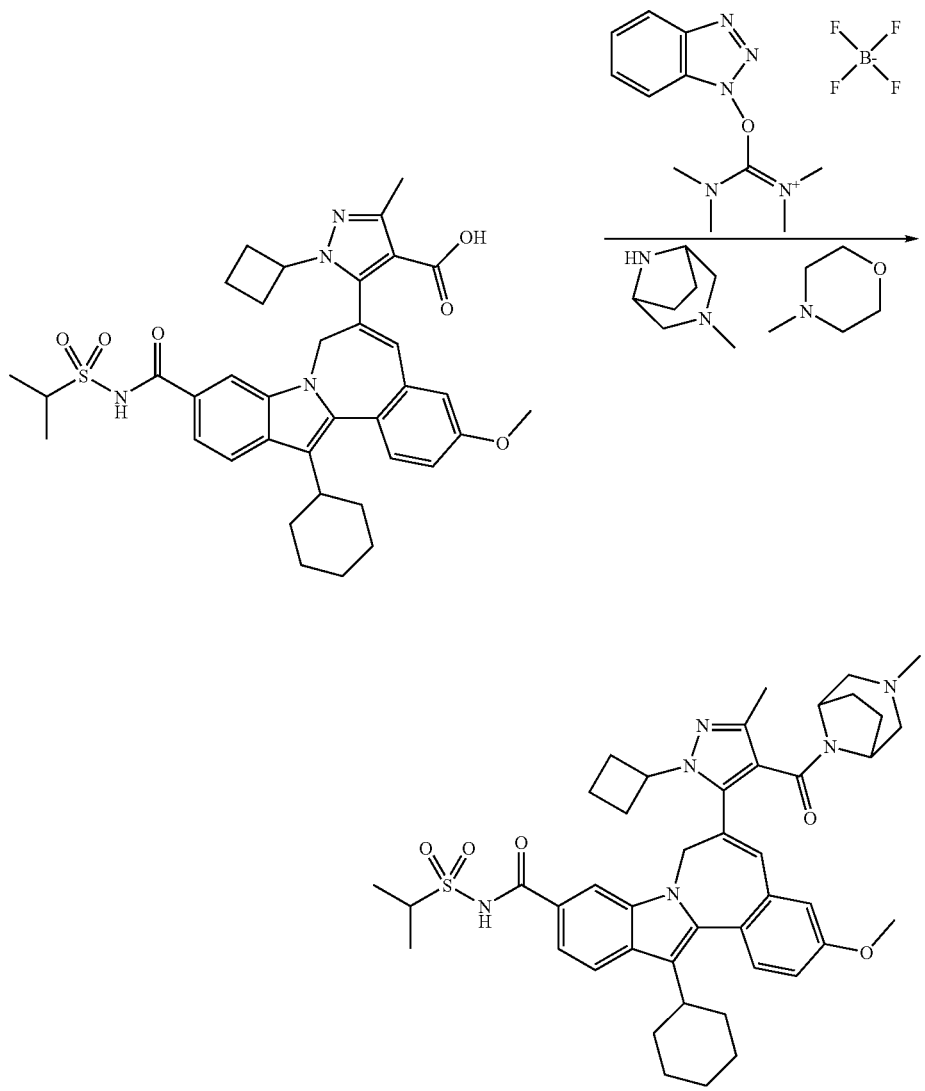

A 2 dram vial was charged with 1H-pyrazole-4-carboxylic acid-5-methyl, 1-cyclobutyl-5-[13-cyclohexyl-3-methoxy-10-[[[(1-methylethyl)sulfonyl]amino]carbonyl]-7H-indolo[2,1-a][2]benzazepin-6-yl]-(70 mg, 0.104 mmol), DMF (1 mL), 4-methylmorpholine (0.037 mL, 0.334 mmol), 3-methyl-3,8-diazabicyclo[3.2.1]octane, 2HCl (27.0 mg, 0.136 mmol) and o-benzotriazol-1-yl-N,N,N',N'-tetramethyluronium tetrafluoroborate (TBTU) (36.9 mg, 0.115 mmol). The rxn was stirred over night. LCMS indicates the rxn was done, 777.2/779.2 at 2.88 minutes. The rxn was diluted with DCM, washed with 0.1 N HCl (aqueous) then brine, dried (MgSO$_4$) and evaporated giving a yellow syrup. The syrup was dissolved in DCM, the solution was added to a Thompson silica gel cartridge and it was eluted with DCM/methanol (0% to 5%). The appropriate fractions (TLC) were combined and evaporated giving a creamy white solid. The solid was triturated in ether/hexane and filtered giving the product (28 mg, 0.036 mmol, 34.1% yield) as a creamy white powder. HPLC: 99.99% pure, 23.29 minutes. LCMS: 779.21 at 3.68 minutes. $^1$H NMR: (400 Mz, CD$_3$OD) 1.22-1.30 (m, 3H), 1.34-1.41 (m, 4H), 1.46-1.47 (d, J=7 Hz, 4H), 1.52-1.54 (d, J=7 Hz, 4H), 1.77-1.79 (m, 4H), 1.94-1.97 (d, J=13 Hz, 3H), 2.00 (s, 1H), 2.02-2.05 (d, J=13 Hz, 3H), 2.25 (bs, 2H), 2.35 (s, 4H), 2.49 (bs, 1H), 2.69-2.75 (m, 2H), 2.79 (s, 1H), 2.87 (m, 3H), 3.96 (s, 3H), 4.03-4.09 (m, 2H), 4.52-4.56 (d, J=16 Hz, 1H), 4.80 (bs, 1H), 6.78 (bs, 1H), 6.94 (s, 1H), 7.10-7.12 (dd, J=2 Hz & J=9 Hz, 1H), 7.56-7.57 (d, J=8 Hz, 1H), 7.66-7.67 (d, J=8 Hz, 1H), 7.89-7.91 (d, J=8 Hz, 1H) & 9.39 (bs, 1H).

7H-Indolo[2,1-a][2]benzazepine-10-carboxamide, 6-[1-cyclobutyl-3-methyl-4-(4-morpholinylcarbonyl)-1H-pyrazol-5-yl]-13-cyclohexyl-3-methoxy-N-[(1-methylethyl)sulfonyl]-

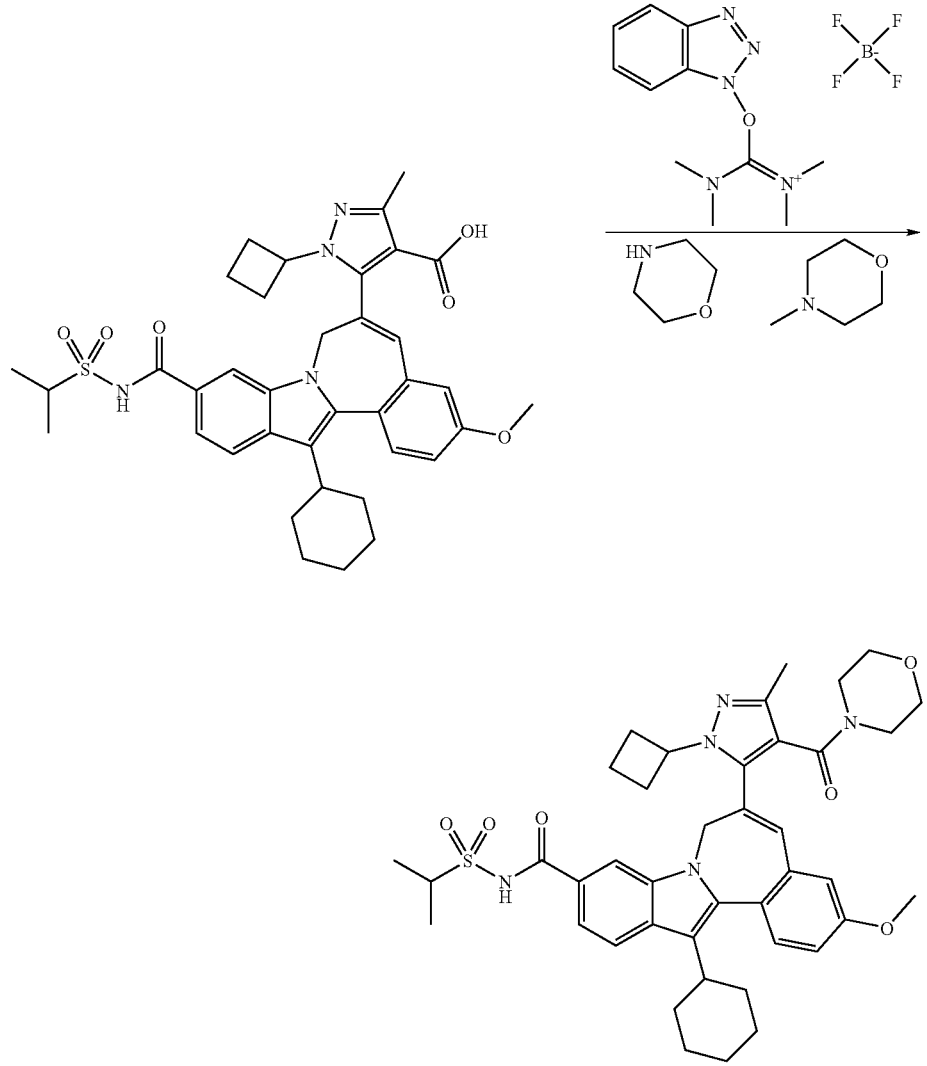

A 2 dram vial was charged with 1H-pyrazole-4-carboxylic acid-5-methyl, 1-cyclobutyl-5-[13-cyclohexyl-3-methoxy-10-[[[(1-methylethyl)sulfonyl]amino]carbonyl]-7H-indolo[2,1-a][2]benzazepin-6-yl]-(70 mg, 0.104 mmol), DMF (1 mL), 4-methylmorpholine (0.023 mL, 0.209 mmol), morpholine (10.91 mg, 0.125 mmol) and o-benzotriazol-1-yl-N,N,N',N'-tetramethyluronium tetrafluoroborate (TBTU) (36.9 mg, 0.115 mmol). The rxn was stirred over night. LCMS pos/neg: 738.2 & 740.1 at 2.48 minutes, no trace of SM. The rxn was diluted with DCM, washed with 0.1 N HCl (aqueous) then brine, dried (MgSO$_4$) and evaporated giving a yellow syrup. The syrup was dissolved in DCM, the solution was added to a Thompson silica gel cartridge and it was eluted with DCM/methanol (0% to 4%). The appropriate fractions (TLC) were combined and evaporated giving a light yellow solid. The solid was triturated in ether/hexane and filtered giving the product (46 mg, 0.061 mmol, 58.1% yield) as a creamy white powder. HPLC: 97.6% pure, 23.26 minutes. LCMS pos/neg: 738.2/740.1 at 2.44 minutes. $^1$H NMR: (400 Mz, CD$_3$OD) δ 1.19-1.25 (m, 2H), 1.41 (m, 2H), 1.48-1.52 (m, 9H), 1.63 (s, 7 h), 1.78-1.79 (m, 3H), 1.92-1.98 (m, 3H), 2.03-2.09 (m, 4H), 2.29 (s, 3H), 2.35 (s, 1 h), 2.48-2.55 (m, 2H), 2.66 (m, 1H), 2.73-2.87 (m, 6h), 3.05-3.09 (m, 2H), 3.66 (bs, 1H), 3.84 (bs, 1H), 3.95 (s, 3H), 4.04-4.08 (m, 3H), 4.40-4.43 & 4.53-4.56 (d, J=16 Hz, 1H), 4.79-4.82 (d, J=16 Hz, 2H), 6.72 (s, 1H), 6.94 (s, 1H), 7.11-7.12 (d, J=8 Hz, 1H), 7.56-7.58 (d, J=8 Hz, 1H), 7.64 (s, 1H), 7.90-7.92 (d, J=8 Hz, 1H), & 10.72 (bs, 1H).

7H-Indolo[2,1-a][2]benzazepine-10-carboxamide, 6-[1-cyclobutyl-4-[[(2S)-2-(methoxymethyl)-4-morpholinyl]carbonyl-3-methyl]-1H-pyrazol-5-yl]-13-cyclohexyl-3-methoxy-N-[(1-methylethyl)sulfonyl]-

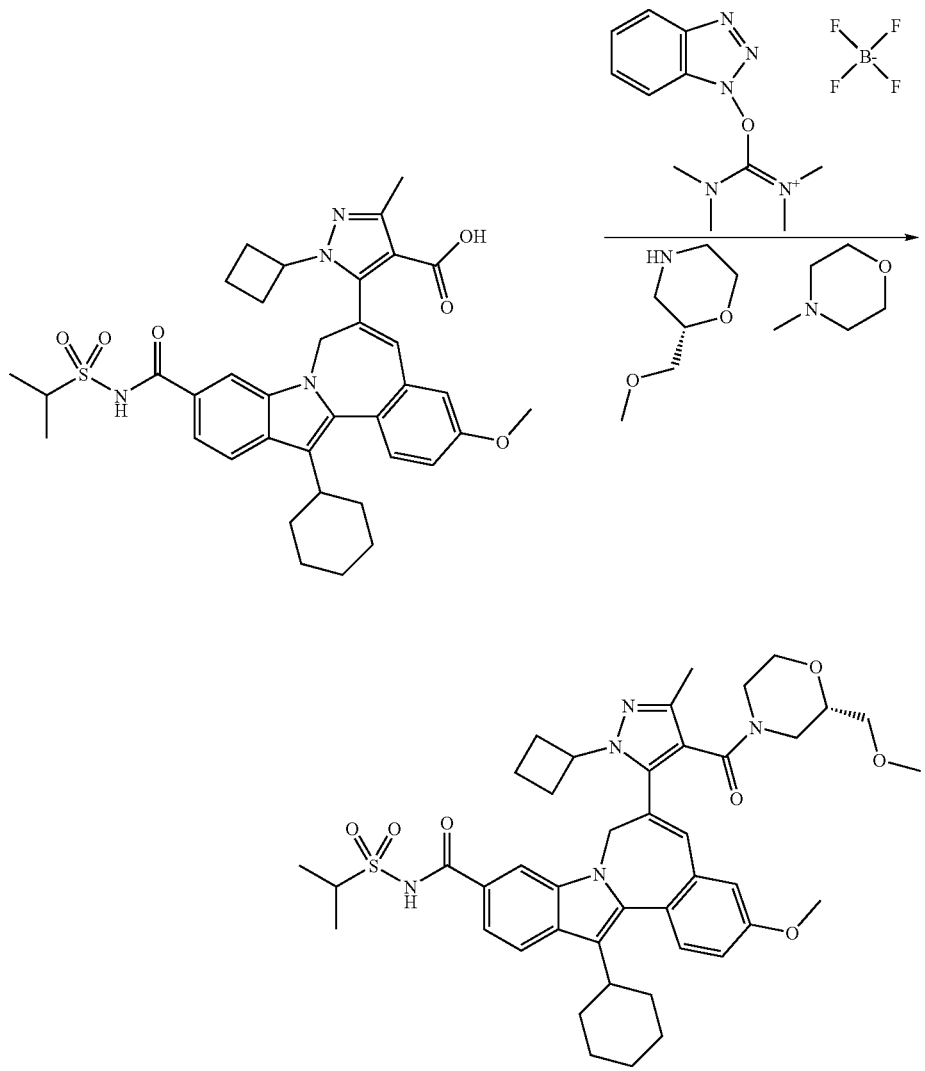

A 2 dram vial was charged with 1H-pyrazole-4-carboxylic acid-5-methyl, 1-cyclobutyl-5-[13-cyclohexyl-3-methoxy-10-[[[(1-methylethyl)sulfonyl]amino]carbonyl]-7H-indolo[2,1-a][2]benzazepin-6-yl]-(70 mg, 0.104 μmmol), DMF (1 mL), 4-methylmorpholine (0.023 mL, 0.209 mmol), (S)-2-(methoxymethyl)morpholine (16.43 mg, 0.125 mmol) and o-benzotriazol-1-yl-N,N,N',N'-tetramethyluronium tetrafluoroborate (TBTU) (36.9 mg, 0.115 mmol). The rxn was stirred over night. The rxn was diluted with DCM, washed with 0.1 N HCl (aqueous) then brine, dried (MgSO$_4$) and evaporated giving a yellow syrup. The syrup was dissolved in DCM, the solution was added to a Thompson silica gel cartridge and it was eluted with DCM/methanol (0% to 4%). The appropriate fractions (TLC) were combined and evaporated giving a light yellow solid. The solid was triturated in ether/hexane and filtered giving the product (37 mg, 0.046 mmol, 44.3% yield) as a creamy white powder. HPLC: 97.9% pure, 22.34 minutes. LCMS: 784.19 at 3.98 minutes. $^1$H NMR: (400 Mz, CD$_3$OD) δ 1.20-1.24 (m, 3H), 1.34-1.42 (m, 2H), 1.47-1.48 (m, 6H), 1.53-1.54 (m, 3 h), 1.77-1.79 (m, 6H), 1.93-1.98 (m, 3H), 2.08 (s, 3H), 2.29 (s, 3H), 2.33-2.35 (m, 2 h), 2.48 (bs, 1H), 2.74 (bs, 1H), 2.80 (s, 3 h), 2.87 (s, 3H), 2.94 (s, 2H), 3.03 (s, 1H), 3.17 (bs, 1H), 3.23 (s, 2H), 3.34-3.38 (m, 2H), 3.46-3.47 (d, J=7 Hz, 1H), 3.84 (bs, 1H), 3.95 (s, 3H), 4.08-4.09 (m, 2H), 4.52-4.55 (m, 1H), 4.76-4.86 (m, 2H), 6.71-6.74 (m, 1H), 6.93 (s, 1H), 7.11-7.12 (d, J=7 Hz, 1H), 7.58-7.66 (m, 2H), 7.71-7.73 (m, 1H), 7.89-7.90 (m, 1H), & 10.78 (bs, 1H).

7H-Indolo[2,1-a][2]benzazepine-10-carboxamide, 6-[1-cyclobutyl-3-methyl-4-(8-oxa-3-azabicyclo[3.2.1]octan-3-ylcarbonyl)-1H-pyrazol-5-yl]-13-cyclohexyl-3-methoxy-N-[(1-methylethyl)sulfonyl]-

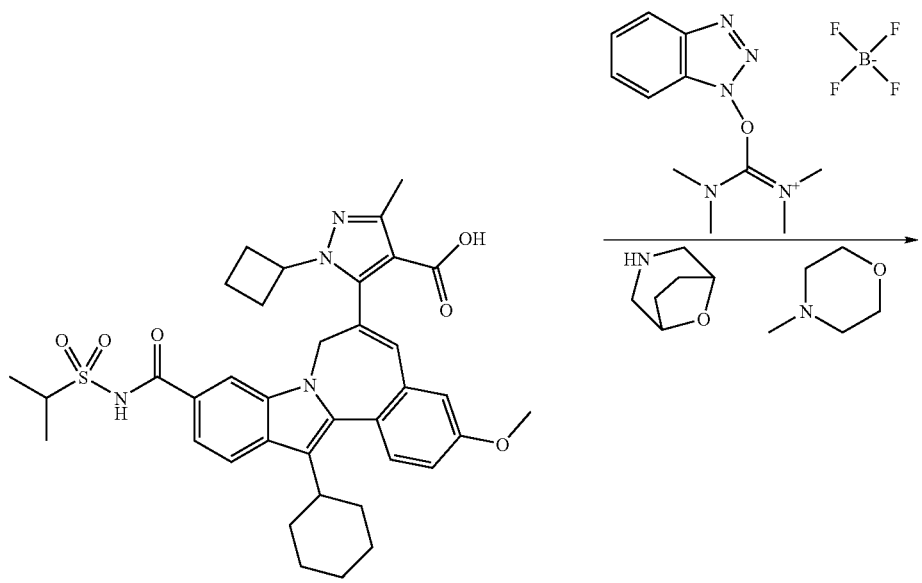

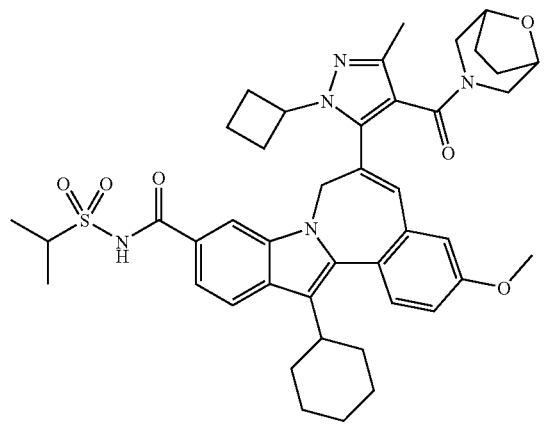

A 2 dram vial was charged with 1H-pyrazole-4-carboxylic acid-5-methyl, 1-cyclobutyl-5-[13-cyclohexyl-3-methoxy-10-[[[(1-methylethyl)sulfonyl]amino]carbonyl]-7H-indolo[2,1-a][2]benzazepin-6-yl]-(70 mg, 0.104 mmol), DMF (1 mL), 4-methylmorpholine (0.023 mL, 0.209 mmol), 8-oxa-3-azabicyclo[3.2.1]octane, HCl (18.74 mg, 0.125 mmol) and o-benzotriazol-1-yl-N,N,N',N'-tetramethyluronium tetrafluoroborate (TBTU) (36.9 mg, 0.115 mmol). The rxn was stirred over night. The rxn was diluted with DCM, washed with 0.1 N HCl (aqueous) then brine, dried (MgSO₄) and evaporated giving a yellow syrup. The syrup was dissolved in DCM, the solution was added to a Thompson silica gel cartridge and it was eluted with DCM/methanol (0% to 4%). The appropriate fractions (TLC) were combined and evaporated giving a light yellow solid. The solid was triturated in ether/hexane and filtered giving the product (54 mg, 0.069 mmol, 66.3% yield) as a creamy white powder. HPLC: 98.2% pure, 22.41 minutes. LCMS neg/pos: 764.2/66.1 at 2.53 minutes. ¹H NMR: (400 Mz, CD₃OD) δ 1.19-1.24 (m, 4H), 1.46-1.53 (m, 9H), 1.58-1.64 (m, 3 h), 1.79 (m, 4H), 1.90-1.95 (m, 5H), 2.08-2.10 (m, 3H), 2.31 (s, 6H), 2.47 (bs, 1 h), 2.74-2.76 (m, 1 h), 2.80-2.87 (m, 6H), 2.94 (s, 2H), 3.07 (bs, 1H), 3.35-3.47 (m, 1H), 3.79-3.84 (m, 2H), 3.95 (s, 3H), 4.03-4.10 (m, 2H), 4.50-4.54 (d, J=16 Hz, 1H), 4.72-4.80 (m, 2H), 6.72 (s, 1H), 6.94 (s, 1H), 7.09-7.11 (d, J=8 Hz, 1H), 7.53-7.60 (m, 3H), 7.92-7.93 (d, J=8 Hz, 1H), & 10.74 (bs, 1H).

7H-Indolo[2,1-a][2]benzazepine-10-carboxamide, 6-[1-cyclobutyl-3-methyl-4-((1S,4S)-2-oxa-5-azabicyclo[2.2.1]heptan-5-ylcarbonyl)-1H-pyrazol-5-yl]-13-cyclohexyl-3-methoxy-N-[(1-methylethyl)sulfonyl]-

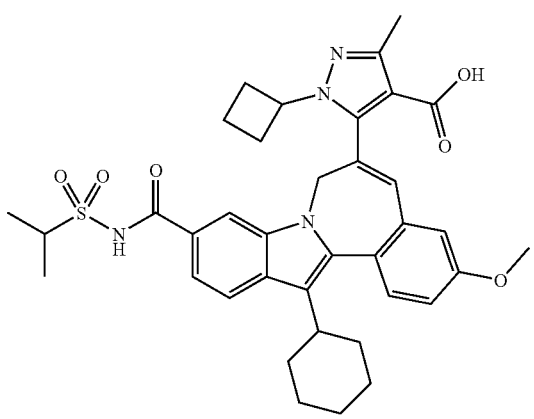
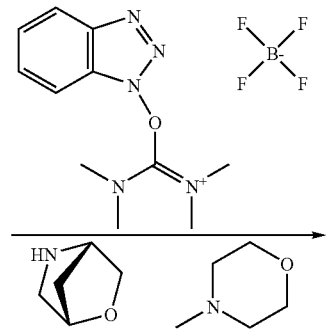
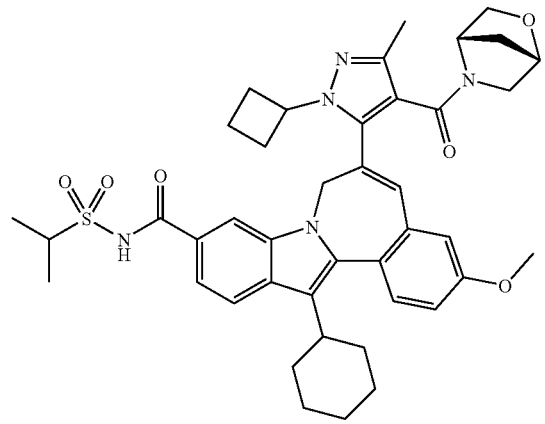

A 2 dram vial was charged with 1H-pyrazole-4-carboxylic acid-5-methyl, 1-cyclobutyl-5-[13-cyclohexyl-3-methoxy-10-[[[(1-methylethyl)sulfonyl]amino]carbonyl]-7H-indolo[2,1-a][2]benzazepin-6-yl]-(70 mg, 0.104 mmol), DMF (1 mL), 4-methylmorpholine (0.023 mL, 0.209 mmol), (1S,4S)-2-oxa-5-azabicyclo[2.2.1]heptane, HCl (16.98 mg, 0.125 mmol) and o-benzotriazol-1-yl-N,N,N',N'-tetramethyluronium tetrafluoroborate (TBTU) (36.9 mg, 0.115 mmol). The rxn was stirred over night. The rxn was diluted with DCM, washed with 0.1 N HCl (aqueous) then brine, dried (MgSO₄) and evaporated giving a yellow syrup. The syrup was dissolved in DCM, the solution was added to a Thompson silica gel cartridge and it was eluted with DCM/methanol (0% to 4%). The appropriate fractions (TLC) were combined and evaporated giving a light yellow solid. The solid was triturated in ether/hexane and filtered giving the product (53 mg, 0.068 mmol, 64.8% yield) as a creamy white powder. HPLC: 96.0% pure, 24.07 minutes. LCMS: 752.20 at 3.83 minutes. LCMS neg/pos: 750.2/752.1 at 2.51 minutes. ¹H NMR: (400 Mz, CD₃OD) δ 1.18-1.24 (m, 2H), 1.41 (m, 5H), 1.53 (s, 2H), 1.78-1.80 (m, 3H), 1.95 (bs, 3H), 2.05 (m, 3H), 2.31 (s, 3H), 2.47-2.50 (m, 1H), 2.67-2.76 (m, 1H), 2.81 (s, 3 h), 2.87 (s, 3H), 2.94 (s, 2H), 3.31-3.38 (m, 1H), 3.84-3.89 (m, 1H), 3.95 (m, 3H), 4.03-4.12 (m, 2H), 4.55-4.58 (d, J=14 Hz, 1H), 4.82-4.85 (d, J=14 Hz, 2H), 6.71-6.83 (m, 1H), 6.93-6.96 (m, 1H), 7.11-7.12 (d, J=8 Hz, 1H), 7.54-7.72 (m, 3H), 7.86-7.95 (m, 1H) & 10.99 (bs, 1H).

7H-Indolo[2,1-a][2]benzazepine-10-carboxamide, 6-[1-cyclobutyl-3-methyl-4-[[(1R,4R)-5-methyl-2,5-diazabicyclo[2.2.1]hept-2-yl]carbonyl]-1H-pyrazol-5-yl]-13-cyclohexyl-3-methoxy-N-[(1-methylethyl)sulfonyl]-

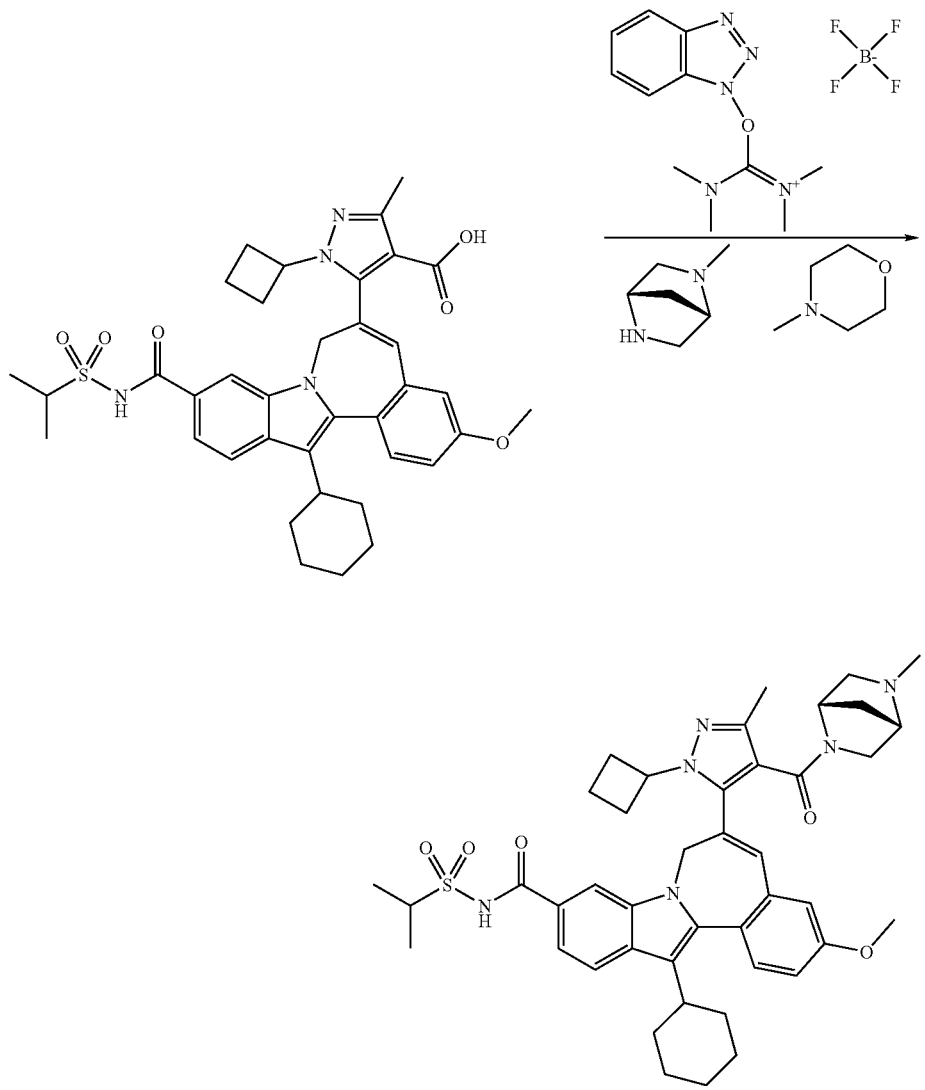

A 2 dram vial was charged with 1H-pyrazole-4-carboxylic acid-5-methyl, 1-cyclobutyl-5-[13-cyclohexyl-3-methoxy-10-[[[(1-methylethyl)sulfonyl]amino]carbonyl]-7H-indolo[2,1-a][2]benzazepin-6-yl]-(70 mg, 0.104 mmol), DMF (1 mL), 4-methylmorpholine (0.023 mL, 0.209 mmol), (1S,4S)-2-methyl-2,5-diazabicyclo[2.2.1]heptane, 2hydrobromide (34.3 mg, 0.125 mmol) and o-benzotriazol-1-yl-N,N,N',N'-tetramethyluronium tetrafluoroborate (TBTU) (36.9 mg, 0.115 mmol). The rxn was stirred over night. The rxn was diluted with DCM, washed with NaHCO₃ (aqueous) then brine, dried (MgSO₄) and evaporated giving a yellow syrup. The syrup was dissolved in DCM, the solution was added to a Thompson silica gel cartridge and it was eluted with DCM/methanol (0% to 4%). The appropriate fractions (TLC) were combined and evaporated giving a creamy white solid. The solid was triturated in ether/hexane and filtered giving the product (52 mg, 0.067 mmol, 64.5% yield) as a yellow powder. HPLC: 99.9% pure, 23.06 minutes. LCMS: 765.24 at 3.64 minutes. ¹H NMR: (400 Mz, CD₃OD) δ 1.18-1.25 (m, 3H), 1.36-1.41 (m, 2H), 1.46-1.47 (d, J=5 Hz, 5H), 1.52-1.54 (d, J=5 Hz, 4H), 1.77-1.79 (m, 4H), 1.94-2.06 (m, 6H), 2.25 (bs, 2H), 2.35 (S. 4H), 2.49 (bs, 1H), 2.69-2.73 (m, 2H), 2.79 (S, 1 h), 2.83-2.89 (m, 2H), 3.11 (bs, 1H), 3.45-3.49 (m, 1H), 3.96 (s, 3H), 4.03-4.08 (m, 2H), 4.53-4.56 (d, J=15 Hz, 1H), 4.80 (bs, 2H), 6.78 (s, 1H), 6.94 (s, 1H), 7.10-7.12 (m, 1H), 7.55-7.57 (d, J=8 Hz, 1H), 7.66-7.67 (m, 1H), 7.89-7.90 (d, J=8 Hz, 1H) & 11.14 (bs, 1H).

7H-Indolo[2,1-a][2]benzazepine-10-carboxamide, 6-[1-cyclobutyl-4-[[(2R)-2-(methoxymethyl)-4-morpholinyl]carbonyl]-1H-pyrazol-5-yl]-13-cyclohexyl-3-methoxy-N-[(1-methylethyl)sulfonyl]-

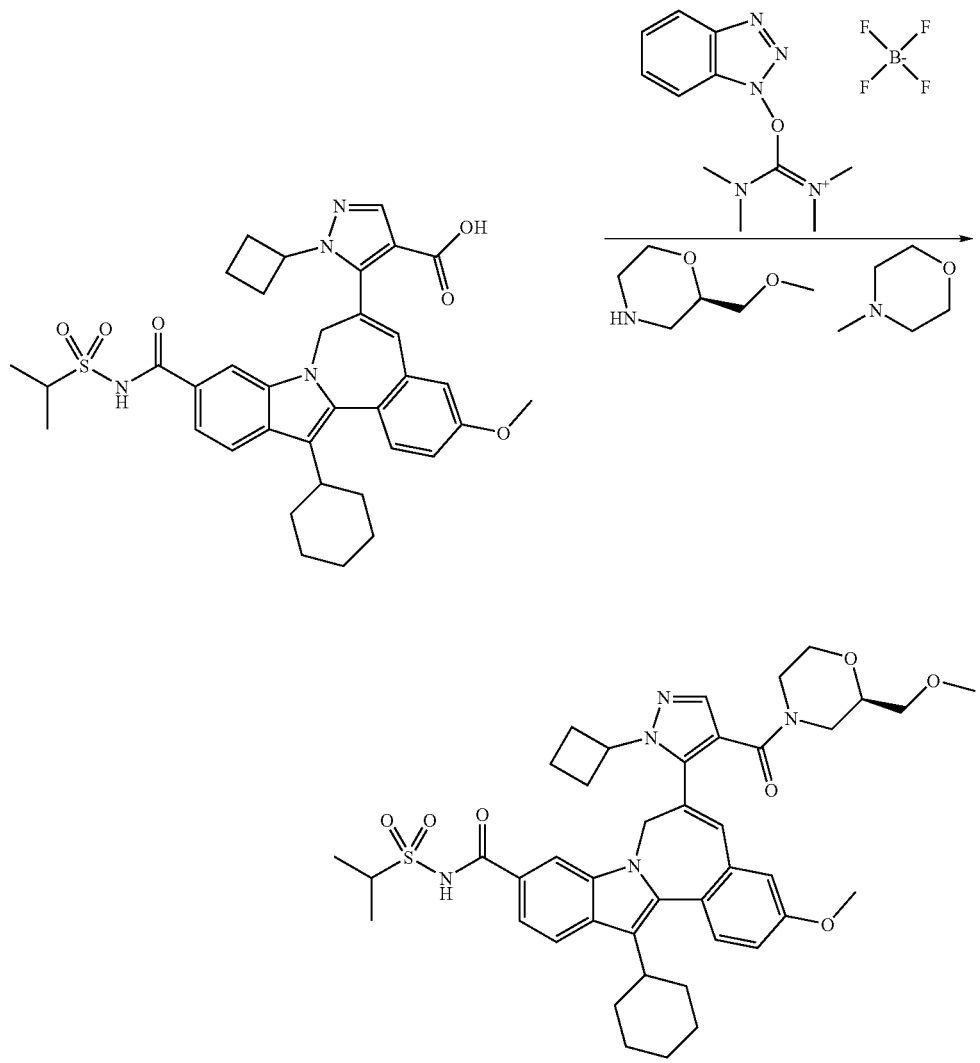

A 2 dram vial was charged with 1H-pyrazole-4-carboxylic acid, 1-cyclobutyl-5-[13-cyclohexyl-3-methoxy-10-[[[(1-methylethyl)sulfonyl]amino]carbonyl]-7H-indolo[2,1-a][2]benzazepin-6-yl]-(70 mg, 0.107 mmol), DMF (1 mL), (R)-2-(methoxymethyl)morpholine, HCl (21.44 mg, 0.128 mmol), 4-methylmorpholine (0.023 mL, 0.213 mmol) and o-benzotriazol-1-yl-N,N,N',N'-tetramethyluronium tetrafluoroborate (TBTU) (37.6 mg, 0.117 mmol). The rxn was stirred over night. LCMS: 679.29 at 4.00 minutes. LCMS pos/neg: 768.2/770.2 at 2.48 minutes. The rxn was diluted with DCM, washed with saturated NaHCO₃ (aqueous) then brine, dried (MgSO₄) and evaporated giving a yellow film. The film was dissolved in DCM, the solution was added to a Thompson silica gel cartridge and it was eluted with DCM/methanol (0% to 10%). The appropriate fractions (TLC) were combined and evaporated giving a light yellow solid. The solid was triturated in ether/hexane and filtered giving the product (57 mg, 0.073 mmol, 68.8% yield) as a creamy white powder. HPLC: 99.5% pure, 22.26 minutes. LCMS neg/pos: 768.2/769.9 at 2.48 minutes. $^1$H NMR: (400 Mz, CD₃OD) 1.24-1.32 (m, 2H), 1.36-1.46 (m, 2H), 1.49-1.48 (d, J=6 Hz, 6H), 1.54-1.56 (d, J=7 Hz, 5H), 1.60 (s, 4H), 1.80-1.83 (d, J=9 Hz, 4H), 1.92-2.04 (m, 4H), 2.07-2.15 (m, 4H), 2.30-2.32 (m, 3H), 2.73-2.80 (m, 3H), 2.82 (s, 5H), 2.89-2.91 (m, 3H), 2.97 (s, 2H), 2.99-3.02 (m, 2H), 3.05-3.09 (m, 1H), 3.26 (s, 6H), 3.98 (s, 3H), 4.06-4.13 (m, 1H), 4.58-4.61 (m, 1H), 4.78 (bs, 1H), 4.84-4.92 (m, 1H), 6.77 (s, 1H), 6.96 (d, J=3 Hz, 1H), 7.13-7.15 (dd, J=9 Hz & J=3 Hz, 1H), 7.59-7.68 (m, 3H), 7.74 (s, 1H), 7.91-7.94 (t, J=7 Hz, 1H) & 10.47 (bs, 1H).

7H-Indolo[2,1-a][2]benzazepine-10-carboxamide, 6-[1-cyclobutyl-3-methyl-4-(3-oxa-9-azabicyclo[3.3.1]non-9-ylcarbonyl)-1H-pyrazol-5-yl]-13-cyclohexyl-3-methoxy-N-[(1-methylethyl)sulfonyl]-

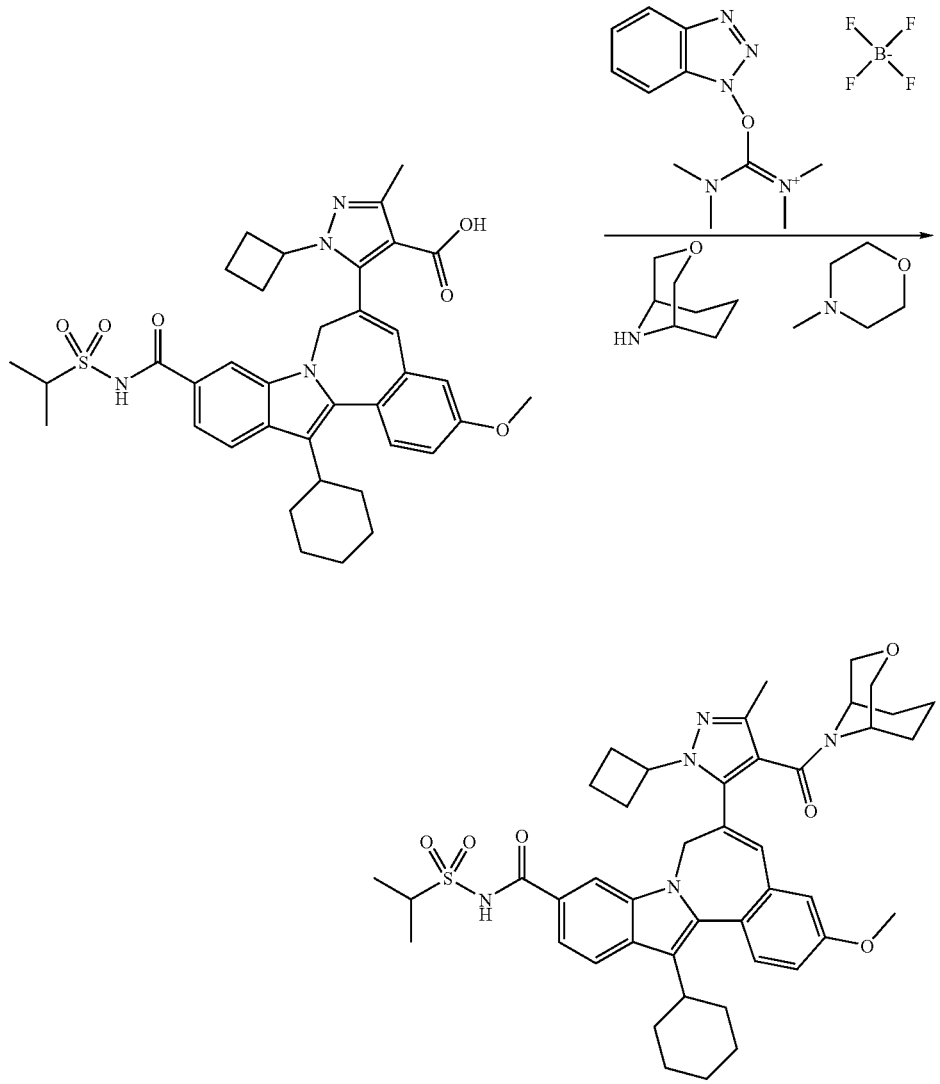

A 2 dram vial was charged with 1H-pyrazole-4-carboxylic acid-5-methyl, 1-cyclobutyl-5-[13-cyclohexyl-3-methoxy-10-[[[(1-methylethyl)sulfonyl]amino]carbonyl]-7H-indolo[2,1-a][2]benzazepin-6-yl]-(70 mg, 0.104 mmol), DMF (1 mL), 4-methylmorpholine (0.023 mL, 0.209 mmol), 3-oxa-9-azabicyclo[3.3.1]nonane, HCl (20.49 mg, 0.125 mmol) and o-benzotriazol-1-yl-N,N,N',N'-tetramethyluronium tetrafluoroborate (TBTU) (36.9 mg, 0.115 mmol). The rxn was stirred over night. The rxn was diluted with DCM, washed with 0.1 N HCl (aqueous) then brine, dried (MgSO₄) and evaporated giving a yellow syrup. The syrup was dissolved in DCM, the solution was added to a Thompson silica gel cartridge and it was eluted with DCM/methanol (0% to 4%). The appropriate fractions (TLC) were combined and evaporated giving a light yellow solid. The solid was triturated in ether/hexane and filtered giving the product (53 mg, 0.068 mmol, 64.7% yield) as a creamy white powder. HPLC: 99.4% pure, 24.20 minutes. LCMS: 780.26 at 4.14 minutes.

7H-Indolo[2,1-a][2]benzazepine-10-carboxamide, 6-[1-cyclobutyl-3-methyl-4-(1-methylpiperazin-4-ylcarbonyl)-1H-pyrazol-5-yl]-13-cyclohexyl-3-methoxy-N-[(1-methylethyl)sulfonyl]-

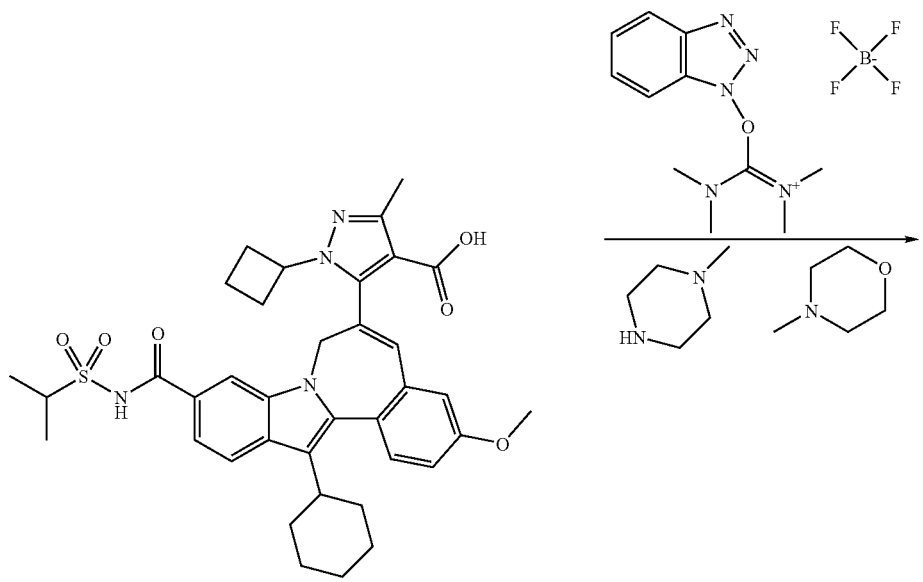

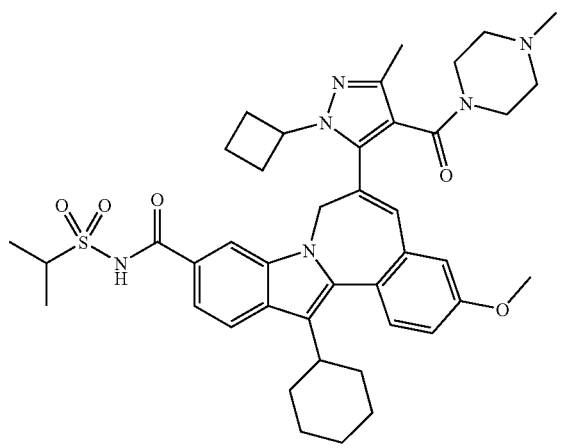

A 2 dram vial was charged with 1H-pyrazole-4-carboxylic acid-5-methyl, 1-cyclobutyl-5-[13-cyclohexyl-3-methoxy-10-[[[(1-methylethyl)sulfonyl]amino]carbonyl]-7H-indolo[2,1-a][2]benzazepin-6-yl]-(70 mg, 0.104 mmol), DMF (1 mL), 4-methylmorpholine (0.023 mL, 0.209 mmol), 1-methylpiperazine (12.5 mg, 0.104 mmol) and o-benzotriazol-1-yl-N,N,N',N'-tetramethyluronium tetrafluoroborate (TBTU) (36.9 mg, 0.115 mmol). The rxn was stirred over night. The rxn was diluted with DCM, washed with saturated NaHCO₃ (aqueous) then brine, dried (MgSO₄) and evaporated giving a yellow syrup. The syrup was dissolved in DCM, the solution was added to a Thompson silica gel cartridge and it was eluted with DCM/methanol (0% to 4%). The appropriate fractions (TLC) were combined and evaporated giving a light yellow solid. The solid was triturated in ether/hexane and filtered giving the product (54 mg, 0.071 mmol, 68.0% yield) as a yellow powder. HPLC: 99.9% pure, 23.28 minutes. LCMS: 753.24 at 3.68 minutes.

7H-Indolo[2,1-a][2]benzazepine-10-carboxamide, 6-[1-cyclobutyl-3-methyl-4-((2S,6R)-1,2,6-trimethylpiperazin-4-ylcarbonyl)-1H-pyrazol-5-yl]-13-cyclohexyl-3-methoxy-N-[(1-methylethyl)sulfonyl]-

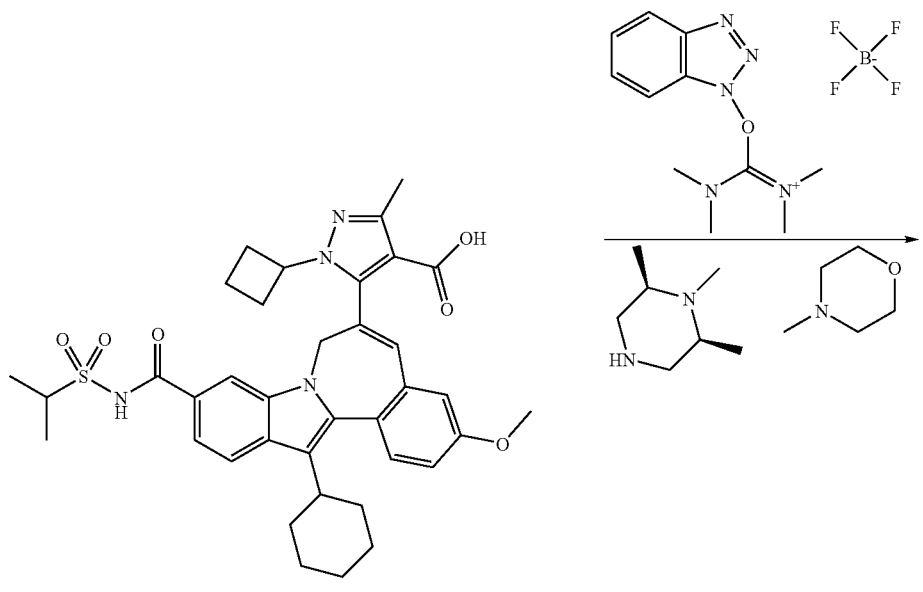

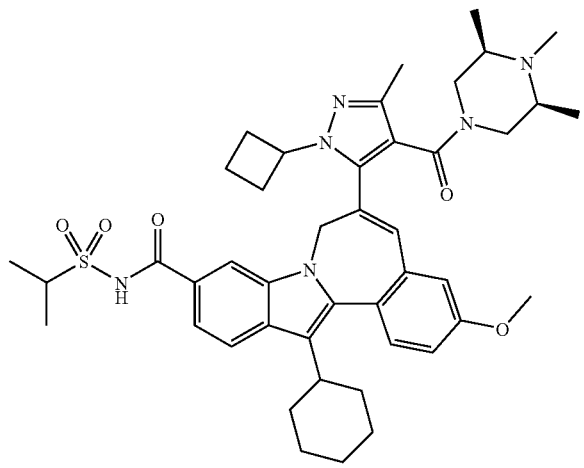

A 2 dram vial was charged with 1H-pyrazole-4-carboxylic acid-5-methyl, 1-cyclobutyl-5-[13-cyclohexyl-3-methoxy-10-[[[(1-methylethyl)sulfonyl]amino]carbonyl]-7H-indolo[2,1-a][2]benzazepin-6-yl]-(70 mg, 0.104 mmol), DMF (1 mL), 4-methylmorpholine (0.023 mL, 0.209 mmol), (2S,6R)-1,2,6-trimethylpiperazine, HCl (20.62 mg, 0.125 mmol) and o-benzotriazol-1-yl-N,N,N',N'-tetramethyluronium tetrafluoroborate (TBTU) (36.9 mg, 0.115 mmol). The rxn was stirred over night. The rxn was diluted with DCM, washed with NaHCO₃ (aqueous) then brine, dried (MgSO₄) and evaporated giving a yellow syrup. The syrup was dissolved in DCM, the solution was added to a Thompson silica gel cartridge and it was eluted with DCM/methanol (0% to 4%). The appropriate fractions (TLC) were combined and evaporated giving a light yellow solid. The solid was triturated in ether/hexane and filtered giving the product (40 mg, 0.051 mmol, 48.6% yield) as a light yellow powder. HPLC: 99.9% pure, 22.78 minutes. LCMS: 781.24 at 3.55 minutes. LCMS pos/neg: 779.2/781.2 at 2.44 minutes.

7H-Indolo[2,1-a][2]benzazepine-10-carboxamide, 6-[1-cyclobutyl 4-[[(1S,4S)-5-cyclopropylmethyl-2, 5-diazabicyclo[2.2.1]hept-2-yl]carbonyl]-3-methyl-1H-pyrazol-5-yl]-13-cyclohexyl-3-methoxy-N-[(1-methylethyl)sulfonyl]-

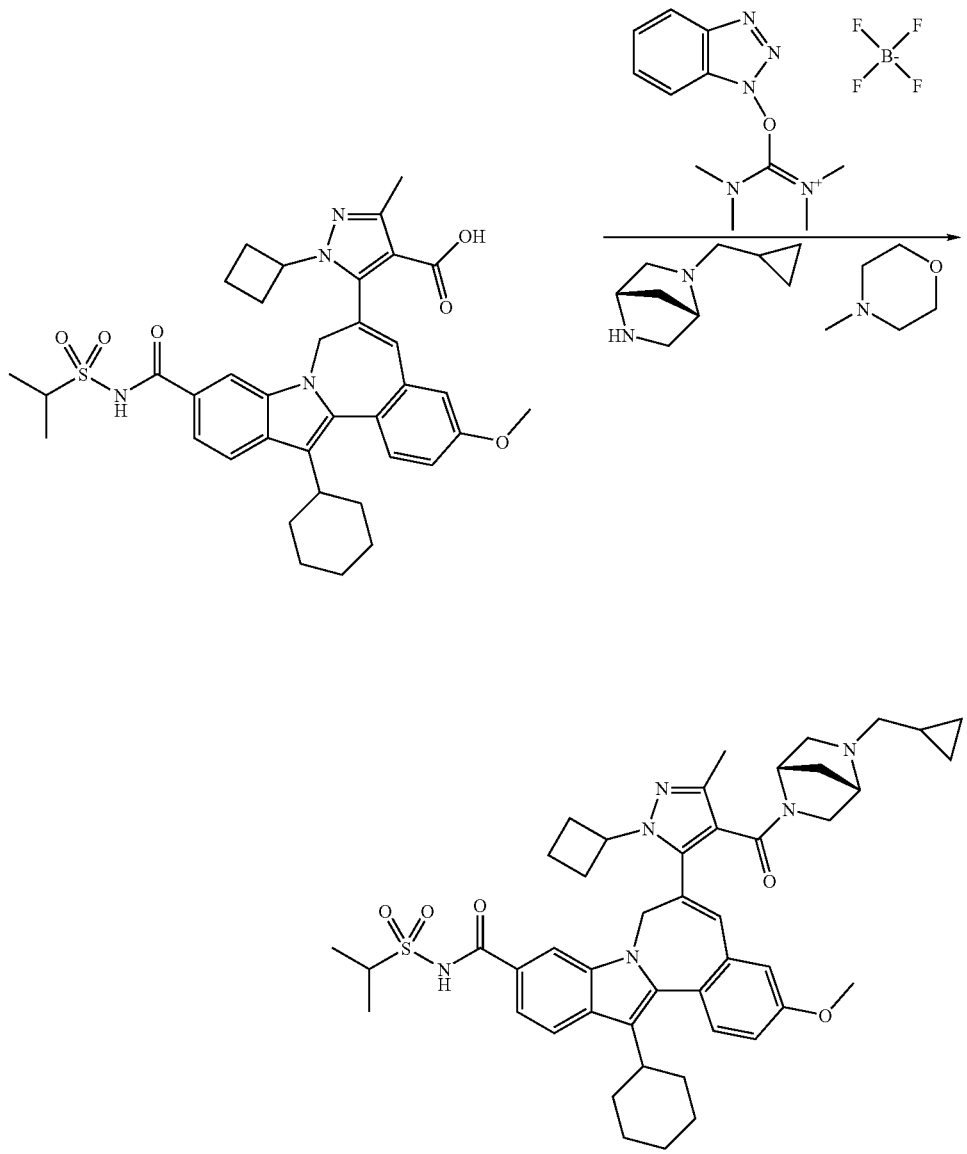

A 2 dram vial was charged with 1H-pyrazole-4-carboxylic acid-5-methyl, 1-cyclobutyl-5-[13-cyclohexyl-3-methoxy-10-[[[(1-methylethyl)sulfonyl]amino]carbonyl]-7H-indolo[2,1-a][2]benzazepin-6-yl]- (70 mg, 0.104 mmol), DMF (1 mL), (1S,4S)-2-(cyclopropylmethyl)-2,5-diazabicyclo[2.2.1]heptane, 2 TFA (47.6 mg, 0.125 mmol), 4-methylmorpholine (0.011 mL, 0.104 mmol) and o-benzotriazol-1-yl-N,N,N',N'-tetramethyluronium tetrafluoroborate (TBTU) (36.9 mg, 0.115 mmol). The rxn was stirred over night. LCMS at 15 minutes: 805 at 3.66 minutes, no trace of SM. The rxn was diluted with DCM, washed with NaHCO₃ (aqueous) then brine, dried (MgSO₄) and evaporated giving a yellow syrup. The syrup was dissolved in DCM, the solution was added to a Thompson silica gel cartridge and it was eluted with DCM/methanol (0% to 4%). The appropriate fractions (TLC) were combined and evaporated giving a creamy white solid. The solid was triturated in ether/hexane and filtered giving the product (56 mg, 0.069 mmol, 66.0% yield) as a yellow powder. HPLC: 99.9% pure, 23.00 minutes. LCMS: 805.23 at 3.66 minutes.

7H-Indolo[2,1-a][2]benzazepine-10-carboxamide, 6-[1-ethyl-4-[[(1R,4R)-5-cyclopropylmethyl-2,5-diazabicyclo[2.2.1]hept-2-yl]carbonyl]-1H-pyrazol-5-yl]-13-cyclohexyl-3-methoxy-N-[(1-methylethyl)sulfonyl]-

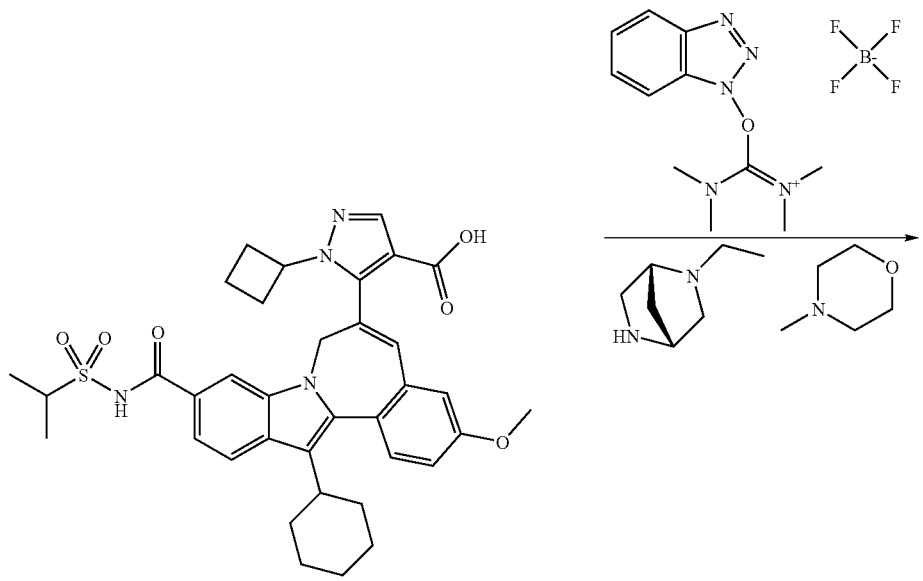

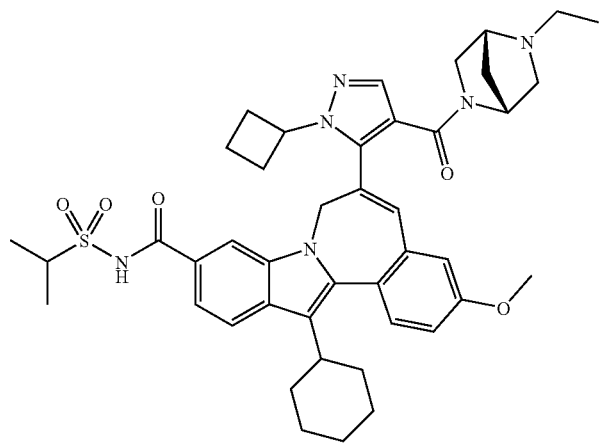

A 2 dram vial was charged with 1H-pyrazole-4-carboxylic acid, 1-cyclobutyl-5-[13-cyclohexyl-3-methoxy-10-[[[(1-methylethyl)sulfonyl]amino]carbonyl]-7H-indolo[2,1-a][2]benzazepin-6-yl]-(70 mg, 0.107 mmol), DMF (1 mL), (1R,4R)-2-ethyl-2,5-diazabicyclo[2.2.1]heptane, 2HCl (23.34 mg, 0.117 mmol), 4-methylmorpholine (0.012 mL, 0.107 mmol) and o-benzotriazol-1-yl-N,N,N',N'-tetramethyluronium tetrafluoroborate (TBTU) (37.6 mg, 0.117 mmol). The rxn was stirred over night. LCMS at 30 minutes: 765.24 at 3.78 minutes, trace of SM. The rxn was diluted with DCM, washed with NaHCO₃ (aqueous) then brine, dried (MgSO₄) and evaporated giving a yellow film. The film was dissolved in DCM, the solution was added to a Thompson silica gel cartridge and it was eluted with DCM/methanol (0% to 10%). The appropriate fractions (TLC) were combined and evaporated giving a light yellow solid. The solid was triturated in ether/hexane and filtered giving 15-A [42 mg] as a yellow powder. HPLC: 93.3% pure, 23.99 minutes, one major impurity—SM. The product was re-chromatographed as above giving the product (24 mg, 0.031 mmol, 28.8% yield) as a yellow powder. HPLC: 97.9% pure. LCMS: 765.24 at 3.77 minutes.

7H-Indolo[2,1-a][2]benzazepine-10-carboxamide, 6-[1-methyl-4-[[(1S,4S)-5-cyclopropylmethyl-2,5-diazabicyclo[2.2.1]hept-2-yl]carbonyl]-1H-pyrazol-5-yl]-13-cyclohexyl-3-methoxy-N-[(1-methylethyl)sulfonyl]-

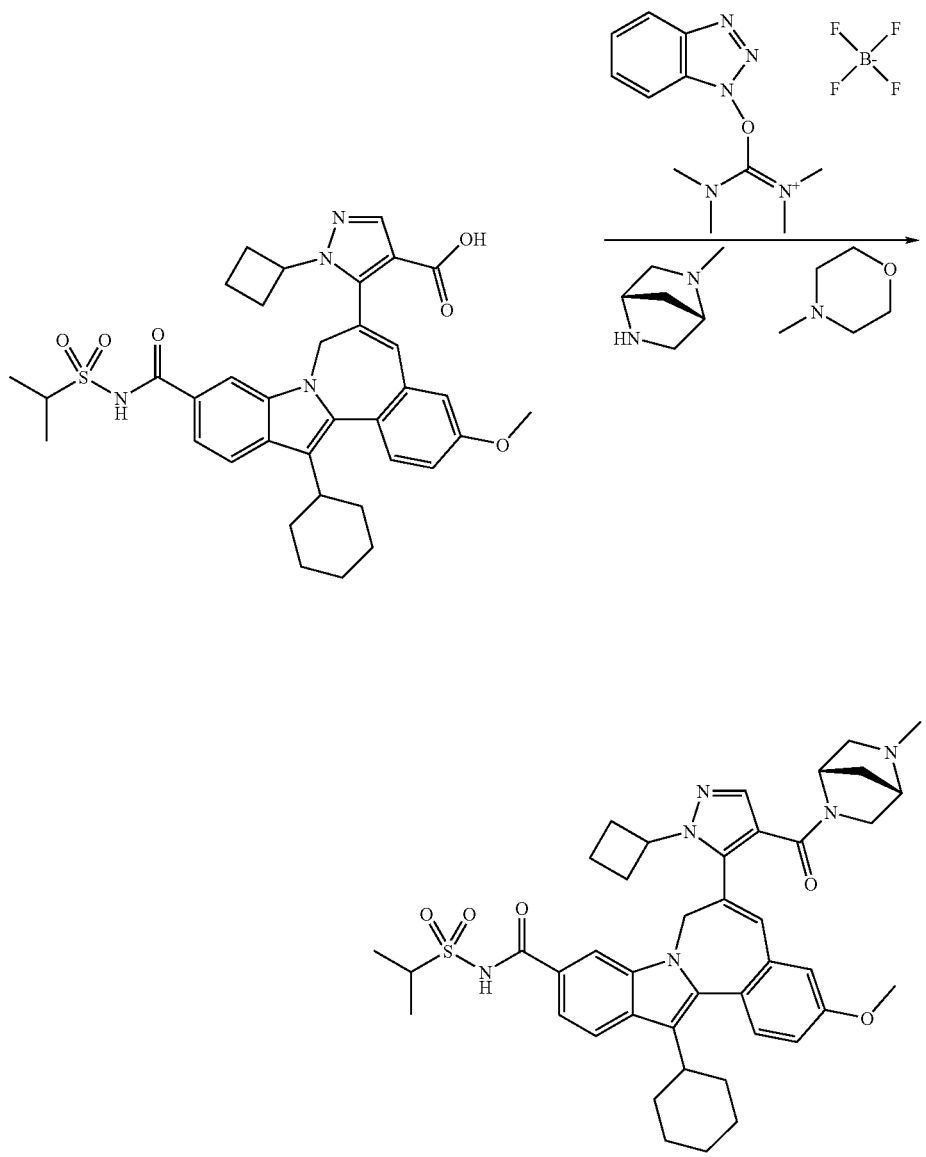

A 2 dram vial was charged with 1H-pyrazole-4-carboxylic acid, 1-cyclobutyl-5-[13-cyclohexyl-3-methoxy-10-[[[(1-methylethyl)sulfonyl]amino]carbonyl]-7H-indolo[2,1-a][2]benzazepin-6-yl]-(70 mg, 0.107 mmol), DMF (1 mL), (1S,4S)-2-methyl-2,5-diazabicyclo[2.2.1]heptane, 2bromide salt (34.8 mg, 0.128 mmol), 4-methylmorpholine (0.023 mL, 0.213 mmol) and o-benzotriazol-1-yl-N,N,N',N'-tetramethyluronium tetrafluoroborate (TBTU) (37.6 mg, 0.117 mmol). The rxn was stirred over night. LCMS: 751.28 at 4.00 minutes. The rxn was diluted with DCM, washed with saturated NaHCO₃ (aqueous)1 then brine, dried (MgSO₄) and evaporated giving a yellow film. The film was dissolved in DCM, the solution was added to a Thompson silica gel cartridge and it was eluted with DCM/methanol (0% to 10%). The appropriate fractions (TLC) were combined and evaporated giving a light yellow solid. The solid was triturated in ether/hexane and filtered giving the product (46 mg, 0.061 mmol, 56.9% yield) as a yellow powder. HPLC: 99.9% pure, 22.07 minutes. LCMS: 751.21 at 3.74 minutes.

7H-Indolo[2,1-a][2]benzazepine-10-carboxamide, 6-[1-H-4-[[(1S,4S)-5-cyclopropylmethyl-2,5-diazabicyclo[2.2.1]hept-2-yl]carbonyl]-3-methyl-1H-pyrazol-5-yl]-13-cyclohexyl-3-methoxy-N-[(1-methylethyl)sulfonyl]-

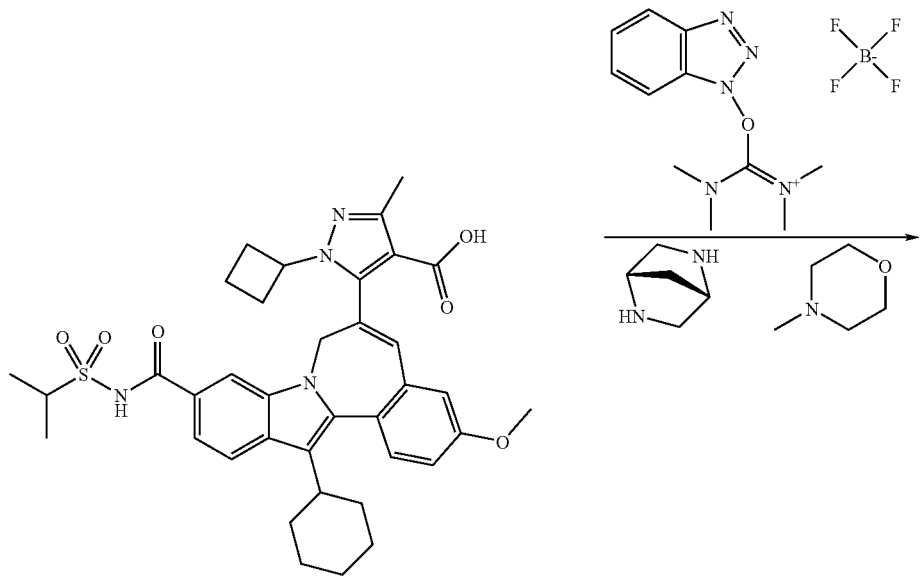

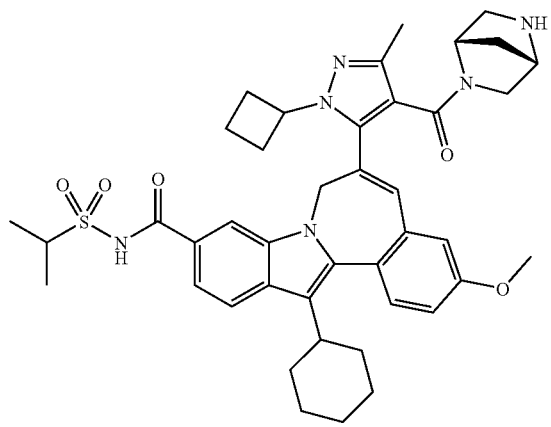

A 2 dram vial was charged with 1H-pyrazole-4-carboxylic acid-5-methyl, 1-cyclobutyl-5-[13-cyclohexyl-3-methoxy-10-[[[(1-methylethyl)sulfonyl]amino]carbonyl]-7H-indolo[2,1-a][2]benzazepin-6-yl]-(140 mg, 0.209 mmol), DMF (4 mL), (1S,4S)-2,5-diazabicyclo[2.2.1]heptane, 2HCl (35.7 mg, 0.209 mmol), 4-methylmorpholine (0.046 mL, 0.417 mmol) and o-benzotriazol-1-yl-N,N,N',N'-tetramethyluronium tetrafluoroborate (TBTU) (73.7 mg, 0.230 mmol). LCMS at 1 hour: 751.21 at 3.68 minutes. The rxn was diluted with DCM, washed with saturated NaHCO₃ (aqueous) then brine, dried (MgSO₄) and evaporated giving a yellow film. The film was dissolved in DCM, the solution was added to a Thompson silica gel cartridge and it was eluted with DCM/methanol (0% to 10%). The appropriate fractions (TLC) were combined and evaporated giving a light yellow solid. The solid was triturated in ether/hexane and filtered giving the product (66 mg, 0.087 mmol, 41.7% yield) as a yellow powder. HPLC: 99.1% pure at 20.77 minutes. LCMS: 751.21 at 3.55 minutes.

Intermediate KP1: Preparation of tert-butyl 13-cyclohexyl-6-((2Z)-2-(ethoxycarbonyl)-4-methyl-2-pentenoyl)-3-methoxy-7H-indolo[2,1-a][2]benzazepine-10-carboxylate

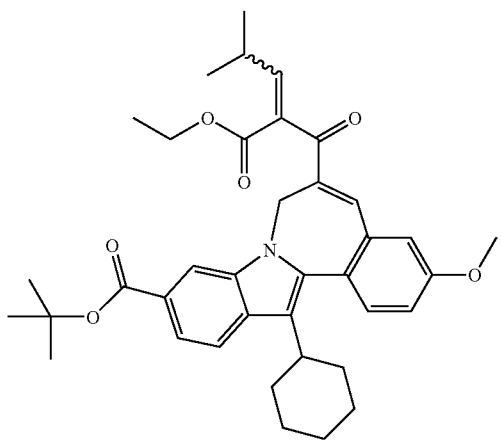

Piperidine (17 µL, 0.18 mmol) was added to a stirring solution of tert-butyl 13-cyclohexyl-6-(3-ethoxy-3-oxopropanoyl)-3-methoxy-7H-indolo[2,1-a][2]benzazepine-10-carboxylate (1.0 g, 1.79 mmol) and isobutyraldehyde (16.4 mL, 179 mmol) in EtOH (9 mL) at room temperature. After 3 hrs of stirring an additional amount of piperidine (38 µL, 0.40 mmol) was added and the reaction was allowed to stir overnight at room temperature. The mixture was concentrated and was purified on silica gel (BIOTAGE®, EtOAc/hexanes gradient, fraction collection at λ=254 nm) to give the titled compound (950 mg, 1.55 mmol, 87% yield) consistent by LCMS and NMR as a yellow foamy sticky solid.

¹H NMR (500 MHz, CHLOROFORM-d) δ ppm 8.21 (1H, s), 7.83 (1H, d, J=8.55 Hz), 7.71 (1H, dd, J=8.55, 1.53 Hz), 7.55 (1H, d, J=8.55 Hz), 7.45 (1H, s), 7.12 (1H, dd, J=8.55, 2.75 Hz), 6.85-6.94 (2H, m), 5.77-5.89 (1H, m), 4.08-4.17 (1H, m), 3.88-3.96 (6H, m), 2.77-2.86 (1H, m), 2.20-2.29 (1H, m), 2.01-2.14 (3H, m), 1.73-1.81 (2H, m), 1.65 (9H, s), 1.34-1.43 (2H, m), 1.16-1.31 (3H, m), 0.86-1.03 (5H, m), 0.69-0.81 (3H, m).

LC-MS retention time: 2.74 min; m/z (MH+): 612. LC data was recorded on a Shimadzu LC-10AS liquid chromatograph equipped with a Waters SunFire 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 2 min, and an analysis time of 4 min where solvent A was 10% MeOH/90% H₂O/0.1% trifluoroacetic acid and solvent B was 10% H₂O/90% MeOH/0.1% trifluoroacetic acid. MS data was determined using a MICROMASS® Platform for LC in electrospray mode.

Intermediate KP2: Preparation of tert-butyl 13-cyclohexyl-6-(1-cyclopropyl-4-(ethoxycarbonyl)-3-isopropyl-1H-pyrazol-5-yl)-3-methoxy-7H-indolo[2,1-a][2]benzazepine-10-carboxylate

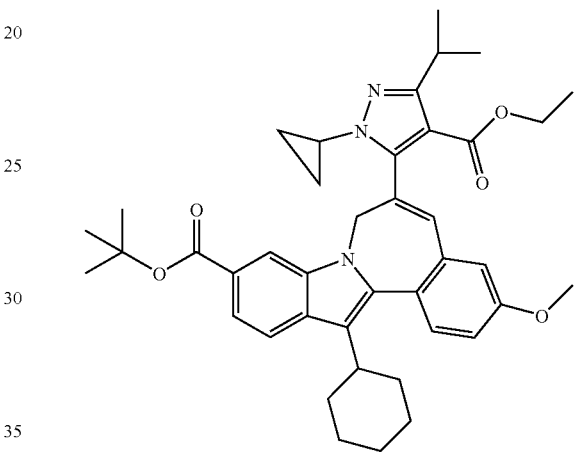

DIEA (204 µL, 1.17 mmol) was added to a stirring slurry of tert-butyl 13-cyclohexyl-6-((2Z)-2-(ethoxycarbonyl)-4-methyl-2-pentenoyl)-3-methoxy-7H-indolo[2,1-a][2]benzazepine-10-carboxylate (550 mg, 0.899 mmol) and cyclopropylhydrazine hydrochloride (117 mg, 1.08 mmol) (prepared according to WO 2005/040169, PCT/US2004/030190) in ethanol (9 mL) at room temperature. The slurry was allowed to stir overnight at room temperature. An additional amount of cyclopropylhydrazine hydrochloride (117 mg, 1.08 mmol) and DIEA (204 µL, 1.17 mmol) was added. After 1 hr the slurry became a solution. The reaction was heated to 75° C. and allowed to stir for 3 days. The mixture then was subjected to MW irradiation 160° C. for 7 min. The reaction was concentrated and purified on silica gel (BIOTAGE®, EtOAc/hexanes gradient, fraction collection at λ=254 nm) to give the titled compound (350 mg, 0.475 mmol, 53% yield) consistent by LCMS and NMR.

¹H NMR (500 MHz, CHLOROFORM-d) δ ppm 7.90 (1H, s), 7.84 (1H, d, J=8.24 Hz), 7.67 (1H, dd, J=8.39, 1.37 Hz), 7.53 (1H, d, J=8.55 Hz), 7.06 (1H, dd, J=9.55, 2.75 Hz), 6.95 (1H, d, J=2.75 Hz), 6.86 (1H, s), 4.97-5.06 (1H, m), 4.63-4.72 (1H, m), 4.21-4.34 (1H, m), 3.91 (4H, s), 3.48-3.58 (1H, m), 2.95-3.04 (1H, m), 2.84-2.93 (1H, m), 2.04-2.15 (3H, m), 1.92-2.00 (1H, m), 1.74-1.84 (2H, m), 1.60 (9H, s), 1.43-1.49 (1H, m), 1.21-1.38 (10H, m), 0.89 (4H, s), 0.51-0.64 (1H, m), −0.04-0.09 (1H, m).

LC-MS retention time: 3.14 min; m/z (MH+): 664. LC data was recorded on a Shimadzu LC-10AS liquid chromatograph equipped with a Waters SunFire 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 2 min, and an analysis time of 4 min where solvent A was 10% MeOH/90% $H_2O$/0.1% trifluoroacetic acid and solvent B was 10% $H_2O$/90% MeOH/0.1% trifluoroacetic acid. MS data was determined using a MICROMASS® Platform for LC in electrospray mode.

Intermediate KP3: Preparation of 5-(13-cyclohexyl-10-((isopropylsulfonyl)carbamoyl)-3-methoxy-7H-indolo[2,1-a][2]benzazepin-6-yl)-1-cyclopropyl-3-isopropyl-1H-pyrazole-4-carboxylic acid

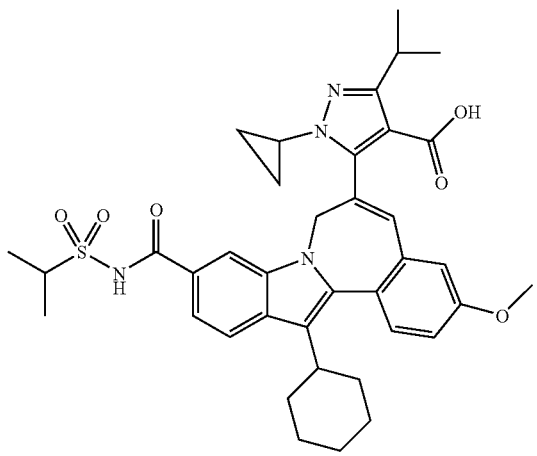

Step 1: Preparation of 13-cyclohexyl-6-(1-cyclopropyl-4-(ethoxycarbonyl)-3-isopropyl-1H-pyrazol-5-yl)-3-methoxy-7H-indolo[2,1-a][2]benzazepine-10-carboxylic acid

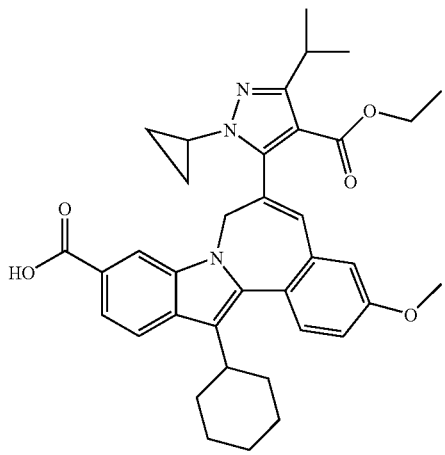

TFA (2.8 mL, 37 mmol) was added to a stirring solution of tert-butyl 13-cyclohexyl-6-(1-cyclopropyl-4-(ethoxycarbonyl)-3-isopropyl-1H-pyrazol-5-yl)-3-methoxy-7H-indolo[2,1-a][2]benzazepine-10-carboxylate (350 mg, 0.527 mmol) in dichloroethane (5 mL) at room temperature. The reaction was allowed to stir for 2.5 hrs and then was concentrated to dryness to give expected product (320 mg, 0.526 mmol, quant) consistent by LCMS.

LC-MS retention time: 2.44 min; m/z (MH+): 608. LC data was recorded on a Shimadzu LC-10AS liquid chromatograph equipped with a Waters SunFire 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 2 min, and an analysis time of 4 min where solvent A was 10% MeOH/90% $H_2O$/0.1% trifluoroacetic acid and solvent B was 10% $H_2O$/90% MeOH/0.1% trifluoroacetic acid. MS data was determined using a MICROMASS® Platform for LC in electrospray mode.

Step 2: Preparation of Ethyl 5-(13-cyclohexyl-10-((isopropylsulfonyl)carbamoyl)-3-methoxy-7H-indolo[2,1-a][2]benzazepin-6-yl)-1-cyclopropyl-3-isopropyl-1H-pyrazole-4-carboxylate

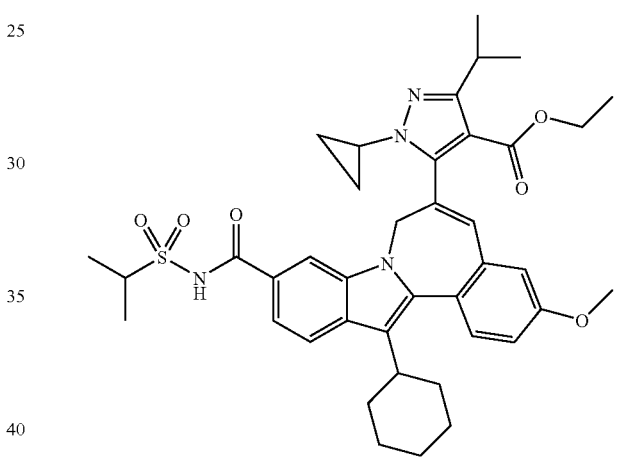

EDC (151 mg, 0.790 mmol) was added to a stirring solution of 13-cyclohexyl-6-(1-cyclopropyl-4-(ethoxycarbonyl)-3-isopropyl-1H-pyrazol-5-yl)-3-methoxy-7H-indolo[2,1-a][2]benzazepine-10-carboxylic acid (320 mg, 0.527 mmol), propane-2-sulfonamide (227 mg, 1.843 mmol), DMAP (193 mg, 1.58 mmol) in dichloroethane (5 mL) at room temperature. The reaction was allowed to stir overnight. The mixture was diluted with EtOAc and washed with 1M HCl, sat $NaHCO_3$ and Brine. The organic phase was dried over $Na_2SO_4$, filtered and concentrated to give the expected product (375 mg, 0.526 mmol, quant) as a light brown residue consistent by LCMS.

LC-MS retention time: 2.19 min; m/z (MH+): 713. LC data was recorded on a Shimadzu LC-10AS liquid chromatograph equipped with a Waters Xbridge 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 2 min, and an analysis time of 4 min where solvent A was 5% MeOH/95% $H_2O$/10 mM ammonium acetate and solvent B was 5% $H_2O$/95% MeOH/10 mM ammonium acetate. MS data was determined using a MICROMASS® Platform for LC in electrospray mode.

Step 3: Preparation of the Titled Compound

LiOH (4 mL, 16.0 mmol, 4M aq) was added to a stirring solution of ethyl 5-(13-cyclohexyl-10-((isopropylsulfonyl)carbamoyl)-3-methoxy-7H-indolo[2,1-a][2]benzazepin-6-yl)-1-cyclopropyl-3-isopropyl-1H-pyrazole-4-carboxylate (375 mg, 0.526 mmol) in THF (12 mL) at rt. The reaction was allowed to stir overnight. The biphasic mixture was diluted ethanol (6 mL) and H$_2$O (3 mL). The reaction was allowed to stir for 6 hrs and then was concentrated and diluted with THF (6 mL), EtOH (6 mL), and NaOH (6 mL, 6.00 mmol, 1M aq.). The reaction was allowed to stir overnight. An additional amount of NaOH (6 mL, 6.00 mmol, 1M aq.) was added and the reaction was allowed to stir for 3 days at rt. An additional amount of NaOH (6 mL, 6.00 mmol, 1M aq) was added and the reaction was allowed to stir overnight. The reaction was then heated to 60° C. for 7 hrs then allowed to cool and stir at room temperature overnight. The reaction was treated with NaOH (6 mL, 6.00 mmol, 1M aq) and the reaction was allowed to stir overnight at room temperature. The reaction was heated to 50° C. and allowed to stir for 7 hrs. The reaction was then diluted with EtOAc and washed with 1M HCl, and sat NaCl. The organic phase was dried over Na$_2$SO$_4$, filtered and concentrated to give the titled compound (370 mg, 0.330 mmol, 63% yield) consistent by LCMS.

LC-MS retention time: 2.18 min; m/z (MH+): 685. LC data was recorded on a Shimadzu LC-10AS liquid chromatograph equipped with a PHENOMENEX® Luna 3u C18 2.0×30 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 2 min, and an analysis time of 4 min where solvent A was 10% acetonitrile/90% H$_2$O/0.1% trifluoroacetic acid and solvent B was 10% H$_2$O/90% acetonitrile/0.1% trifluoroacetic acid. MS data was determined using a MICROMASS® Platform for LC in electrospray mode.

Example KP1

Preparation of 13-cyclohexyl-6-(1-cyclopropyl-4-(((2R,6S)-2,6-dimethyl-4-morpholinyl)carbonyl)-3-isopropyl-1H-pyrazol-5-yl)-N-(isopropylsulfonyl)-3-methoxy-7H-indolo[2,1-a][2]benzazepine-10-carboxamide HATU (65.0 mg, 0.171 mmol) was added to a stirring solution of 5-(13-cyclohexyl-10-((isopropylsulfonyl)carbamoyl)-3-methoxy-7H-indolo[2,1-a][2]benzazepin-6-yl)-1-cyclopropyl-3-isopropyl-1H-pyrazole-4-carboxylic acid (78 mg, 0.114 mmol), cis-2,6-dimethylmorpholine (28 µL, 0.23 mmol), DIEA (80 µL, 0.456 mmol) in DMF (1 mL) at room temperature. The reaction was allowed to stir for 2 hours. The reaction was purified by preparative reverse phase HPLC on a C18 column using a TFA buffered H$_2$O/CH$_3$CN gradient, and concentrated to give the titled compound (28 mg, 0.035 mmol, 31% yield) consistent by LCMS and NMR, with sufficient purity by HPLC.

$^1$H NMR (500 MHz, CHLOROFORM-d) δ ppm 10.47 (0.75H, br. s.), 10.15 (0.25H, br. s.), 7.98 (0.25H, d), 7.93 (0.75H, d, J=8.55 Hz), 7.84 (0.75H, s), 7.77 (0.25H, s), 7.64-7.71 (1H, m), 7.54-7.63 (1H, m), 7.10-7.18 (1H, m), 6.94-7.00 (1H, m), 6.90-6.94 (2H, m), 4.98 (0.75H, d, J=15.87 Hz), 4.90 (0.25H, d), 4.56-4.65 (1H, m), 4.02-4.13 (1H, m), 3.89-3.98 (4H, m), 3.54-3.65 (1H, m), 2.98-3.33 (9H, m), 2.85-2.96 (2H, m), 2.07-2.17 (2H, m), 1.93-2.04 (2H, m), 1.76-1.85 (2H, m), 1.46-1.57 (5H, m), 1.38-1.46 (2H, m), 1.22-1.33 (3H, m), 1.12-1.21 (2H, m), 0.98-1.09 (2H, m), 0.80-0.87 (2H, m), 0.75 (2H, d, J=6.10 Hz), 0.68 (2H, d, J=6.10 Hz), 0.04-0.21 (1H, m).

LC-MS retention time: 2.36 min; m/z (MH+): 782. LC data was recorded on a Shimadzu LC-10AS liquid chromatograph equipped with a PHENOMENEX® Luna 3u C18 2.0×30 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 10% acetonitrile/90% H$_2$O/0.1% trifluoroacetic acid and solvent B was 10% H$_2$O/90% acetonitrile/0.1% trifluoroacetic acid. MS data was determined using a MICROMASS® Platform for LC in electrospray mode.

Additional HPLC method: Solvent A=5% CH$_3$CN/95% H$_2$O/0.1% TFA, Solvent B=95% CH$_3$CN/5% H$_2$O/0.1% TFA, Start % B=10, Final % B=100, Gradient time=15 min, Stop time=18 min, Flow Rate=1 ml/min. Column: Waters Sunfire C-18, 4.6×150 mm, 3.5 mm, Rt=17.45 min, purity=99%; Column: Waters Xbridge Phenyl column 4.6×150 mm, 3.5 mm, Rt=14.56 min, purity=98%.

Example KP2

Preparation of 13-cyclohexyl-6-(1-cyclopropyl-3-isopropyl-4-(((3R,5S)-3,4,5-trimethyl-1-piperazinyl)carbonyl)-1H-pyrazol-5-yl)-N-(isopropylsulfonyl)-3-methoxy-7H-indolo[2,1-a][2]benzazepine-10-carboxamide

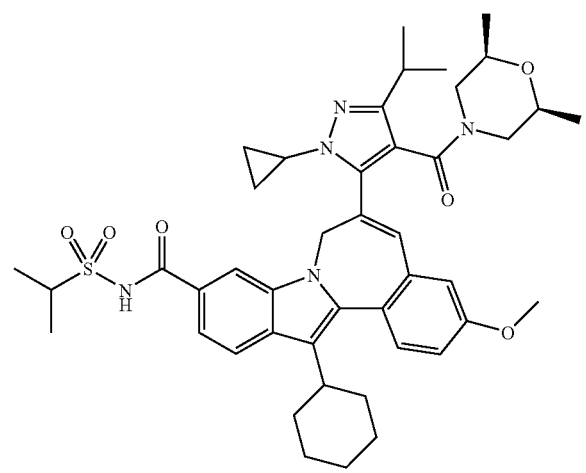

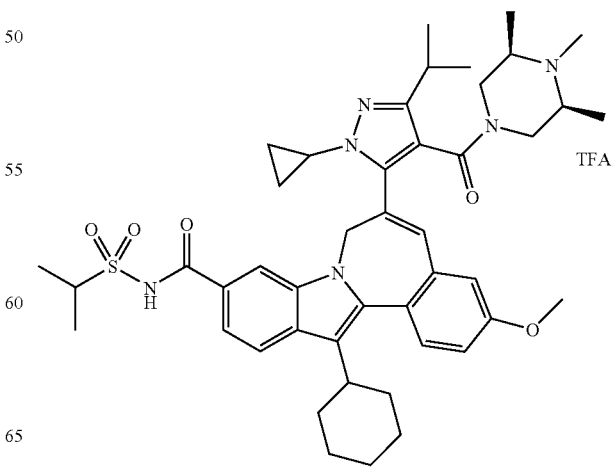

HATU (65.0 mg, 0.171 mmol) was added to a stirring solution of 5-(13-cyclohexyl-10-((isopropylsulfonyl)carbamoyl)-3-methoxy-7H-indolo[2,1-a][2]benzazepin-6-yl)-1-cyclopropyl-3-isopropyl-1H-pyrazole-4-carboxylic acid (78 mg, 0.114 mmol), (2S,6R)-1,2,6-trimethylpiperazine dihydrochloride (46 mg, 0.23 mmol), DIEA (80 µL, 0.456 mmol) in DMF (1 mL) at room temperature. The reaction was allowed to stir for 2 hours. The reaction was purified by preparative reverse phase HPLC on a C18 column using a TFA buffered H₂O/CH₃CN gradient, and concentrated to give the titled compound (31 mg, 0.033 mmol, 29% yield) consistent by LCMS and NMR, with sufficient purity by HPLC.

¹H NMR (500 MHz, CHLOROFORM-d) δ ppm 10.37 (1H, br. s.), 7.93-7.90 (2H, m), 7.76-7.83 (1H, m), 7.53-7.64 (1H, m), 7.10-7.19 (1H, m), 6.93-7.02 (2H, m), 4.99 (1H, d), 4.63 (1H, d), 4.03-4.12 (1H, m), 3.92-3.99 (3H, m), 3.81-3.91 (1H, m), 3.54-3.61 (1H, m), 3.37-3.47 (1H, m), 3.19-3.32 (1H, m), 2.87-3.05 (2H, m), 2.24-2.33 (2H, m), 1.76-2.11 (19H, m), 1.47-1.59 (5H, m), 1.23-1.31 (4H, m), 1.16-1.23 (3H, m), 1.03-1.09 (2H, m), 0.95-1.01 (2H, m), 0.21-0.33 (1H, m).

LC-MS retention time: 1.75 min; m/z (MH+): 795. LC data was recorded on a Shimadzu LC-10AS liquid chromatograph equipped with a PHENOMENEX® Luna 3u C18 2.0×30 mm column using a SPD-10AV UV-Vis detector at a detector wave length of 220 nM. The elution conditions employed a flow rate of 5 mL/min, a gradient of 100% solvent A/0% solvent B to 0% solvent A/100% solvent B, a gradient time of 2 min, a hold time of 1 min, and an analysis time of 3 min where solvent A was 10% acetonitrile/90% H₂O/0.1% trifluoroacetic acid and solvent B was 10% H₂O/90% acetonitrile/0.1% trifluoroacetic acid. MS data was determined using a MICROMASS® Platform for LC in electrospray mode.

Additional HPLC method: Solvent A=5% CH₃CN/95% H₂O/0.1% TFA, Solvent B=95% CH₃CN/5% H₂O/0.1% TFA, Start % B 10, Final % B=100, Gradient time=15 min, Stop time=18 min, Flow Rate=1 ml/min. Column: Waters Sunfire C-18, 4.6×150 mm, 3.5 mm, Rt=10.61 min, purity=96%; Column: Waters Xbridge Phenyl column 4.6× 150 mm, 3.5 mm, Rt=11.47 min, purity=96%.

Example KP3

Preparation of 13-cyclohexyl-6-(1-cyclopropyl-3-isopropyl-4-((3-methyl-3,8-diazabicyclo[3.2.1]oct-8-yl)carbonyl)-1H-pyrazol-5-yl)-N-(isopropylsulfonyl)-3-methoxy-7H-indolo[2,1-a][2]benzazepine-10-carboxamide

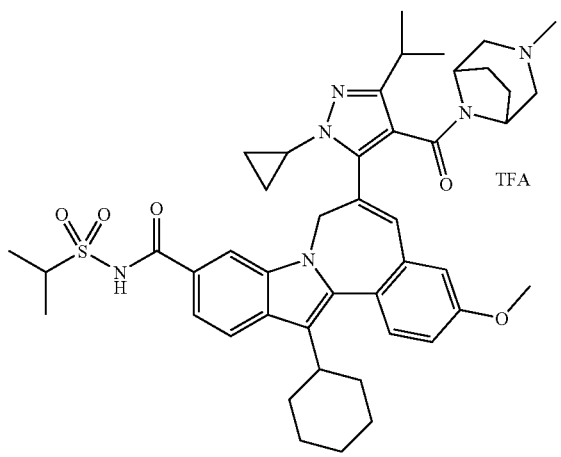

HATU (65.0 mg, 0.171 mmol) was added to a stirring solution of 5-(13-cyclohexyl-10-((isopropylsulfonyl)carbamoyl)-3-methoxy-7H-indolo[2,1-a][2]benzazepin-6-yl)-1-cyclopropyl-3-isopropyl-1H-pyrazole-4-carboxylic acid (78 mg, 0.114 mmol), 3-methyl-3,8-diazabicyclo[3.2.1]octane dihydrochloride (45 mg, 0.23 mmol), DIEA (80 µL, 0.456 mmol) in DMF (1 mL) at room temperature. The reaction was allowed to stir for 2 hours. The reaction was purified by preparative reverse phase HPLC on a C18 column using a suitably buffered H₂O/CH₃CN gradient, and concentrated to give the titled compound (37 mg, 0.041 mmol, 36% yield) consistent by LCMS and NMR, with sufficient purity by HPLC.

¹H NMR (500 MHz, CHLOROFORM-d) δ ppm 10.54 (0.25H, br. s.), 10.39 (0.75H, br. s.), 7.86-8.01 (1H, m), 7.65-7.76 (1H, m), 7.55-7.65 (2H, m), 7.11-7.18 (1H, m), 7.01-7.08 (1H, m), 6.90-7.00 (1H, m), 4.75-4.92 (1H, m), 4.52-4.72 (1H, m), 3.99-4.17 (1H, m), 3.90-4.00 (3H, m), 3.81-3.90 (1H, m), 3.51-3.64 (1H, m), 3.37-3.49 (1H, m), 3.10-3.28 (2H, m), 2.80-2.99 (2H, m), 2.53-2.67 (2H, m), 2.37-2.50 (1H, m), 1.94 (19H, m), 1.38-1.46 (2H, m), 1.35-1.38 (2H, m), 1.32 (3H, m), 1.16-1.24 (2H, m), 0.99-1.10 (2H, m), 0.72-0.93 (1H, m), 0.09-0.28 (1H, m).

LC-MS retention time: 1.78 min; m/z (MH+): 793. LC data was recorded on a Shimadzu LC-10AS liquid chromatograph equipped with a PHENOMENEX® Luna 3u C18 2.0×30 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 10% acetonitrile/90% H₂O/0.1% trifluoroacetic acid and solvent B was 10% H₂O/90% acetonitrile/0.1% trifluoroacetic acid. MS data was determined using a MICROMASS® Platform for LC in electrospray mode.

Additional HPLC method: Solvent A=5% CH₃CN/95% H₂O/0.1% TFA, Solvent B=95% CH₃CN/5% H₂O/0.1% TFA, Start % B=10, Final % B=100, Gradient time=15 min, Stop time=18 min, Flow Rate=1 ml/min. Column: Waters Sunfire C-18, 4.6×150 mm, 3.5 mm, Rt=10.97 min, purity=98%; Column: Waters Xbridge Phenyl column 4.6× 150 mm, 3.5 mm, Rt=11.80 min, purity=98%.

Example KP4

Preparation of 13-cyclohexyl-6-(1-cyclopropyl-3-isopropyl-4-(3-oxa-8-azabicyclo[3.2.1]oct-8-ylcarbonyl)-1H-pyrazol-5-yl)-N-(isopropylsulfonyl)-3-methoxy-7H-indolo[2,1-a][2]benzazepine-10-carboxamide

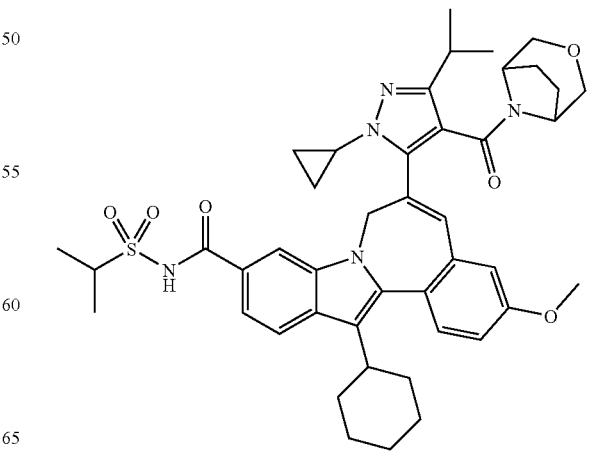

HATU (65.0 mg, 0.171 mmol) was added to a stirring solution of 5-(13-cyclohexyl-10-((isopropylsulfonyl)carbamoyl)-3-methoxy-7H-indolo[2,1-a][2]benzazepin-6-yl)-1-cyclopropyl-3-isopropyl-1H-pyrazole-4-carboxylic acid (78 mg, 0.114 mmol), 3-oxa-8-azabicyclo[3.2.1]octane hydrochloride (34 mg, 0.23 mmol), DIEA (80 µL, 0.456 mmol) in DMF (1 mL) at room temperature. The reaction was allowed to stir for 2 hours. The reaction was purified by preparative reverse phase HPLC on a C18 column using a TFA buffered H₂O/MeOH gradient, and concentrated to give the titled compound (30 mg, 0.038 mmol, 34% yield) consistent by LCMS and NMR, with sufficient purity by HPLC.

¹H NMR (500 MHz, CHLOROFORM-d) d ppm 10.98 (1H, br. s.), 7.89-7.97 (1H, m), 7.81-7.86 (1H, m), 7.64-7.77 (1H, m), 7.55-7.63 (1H, m), 7.10-7.16 (1H, m), 6.92-7.02 (2H, m), 4.84-4.99 (1H, m), 4.57-4.68 (1H, m), 4.00-4.11 (1H, m), 3.95 (3H, s), 3.49-3.57 (2H, m), 3.32-3.39 (1H, m), 3.21-3.29 (1H, m), 3.12-3.19 (1H, m), 2.96-3.07 (1H, m), 2.81-2.96 (1H, m), 2.66-2.79 (1H, m), 2.05-2.16 (2H, m), 1.95-2.04 (1H, m), 1.74-1.86 (2H, m), 1.53-1.57 (4H, m), 1.43-1.51 (5H, m), 1.36-1.42 (4H, m), 1.31-1.36 (2H, m), 1.24-1.29 (3H, m), 1.17-1.24 (3H, m), 1.05-1.15 (1H, m), 0.93-1.02 (2H, m), 0.82-0.91 (1 H, m), 0.51-0.68 (1H, m).

LC-MS retention time: 2.36 min; m/z (MH+): 780. LC data was recorded on a Shimadzu LC-10AS liquid chromatograph equipped with a PHENOMENEX® Luna 3u C18 2.0×30 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 10% acetonitrile/90% H₂O/0.1% trifluoroacetic acid and solvent B was 10% H₂O/90% acetonitrile/0.1% trifluoroacetic acid. MS data was determined using a MICROMASS® Platform for LC in electrospray mode.

Additional HPLC method: Solvent A=5% MeOH/95% H₂O/10 mM ammonium bicarbonate, Solvent B=95% MeOH/5% H₂O/10 mM ammonium bicarbonate, Start % B=10, Final % B=100, Gradient time=15 min, Stop time=18 min, Flow Rate=1 ml/min. Column: PHENOMENEX® Gemini C1 C-18, 4.6×150 mm, 3 mm, Rt=15.84 min, purity=100%; Column: Waters Xbridge Phenyl column 4.6× 150 mm, 3.5 mm, Rt=15.96 min, purity=100%.

For all compounds described below Prep HPLC purifications were run at following conditions except for the other conditions that mentioned in individual procedures.
Solvent A: 10% MeOH-90% H₂O-0.1% TFA;
Solvent B: 90% MeOH-10% H₂O-0.1% TFA;
Column: PHENOMENEX® Luna AXIA 5 u 21×100 mm S5.
LCMS methods: All LCMS analysis conditions used method 1 except mentioned in individual procedure.
Method 1:
Start % B: 0
Final % B: 100
Gradient time: 4 min
Stop time: 5 min
Flow rate: 4 ml/min
Wavelength: 220
Solvent A: 10% MeOH/90% H₂O/0.1% Trifluoroacetic Acid
Solvent B: 10% H₂O/90% MeOH/0.1% Trifluoroacetic Acid
Column: PHENOMENEX® Luna 3.0×50 mm S10

13-Cyclohexyl-6-(1-cyclopropyl-5-(4-morpholinylcarbonyl)-1H-imidazol-4-yl)-N-(isopropylsulfonyl)-3-methoxy-7H-indolo[2,1-a][2]benzazepine-10-carboxamide

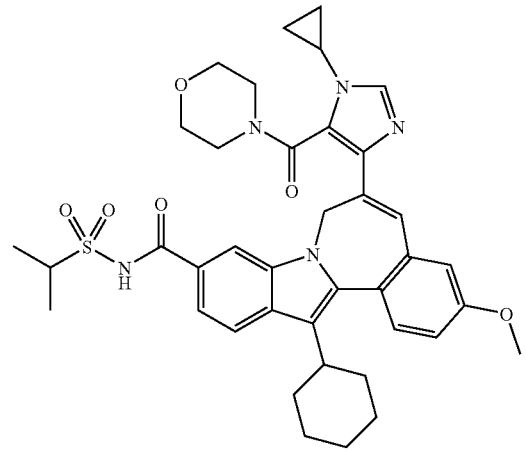

Scheme Depicting Synthesis of Compound 9:

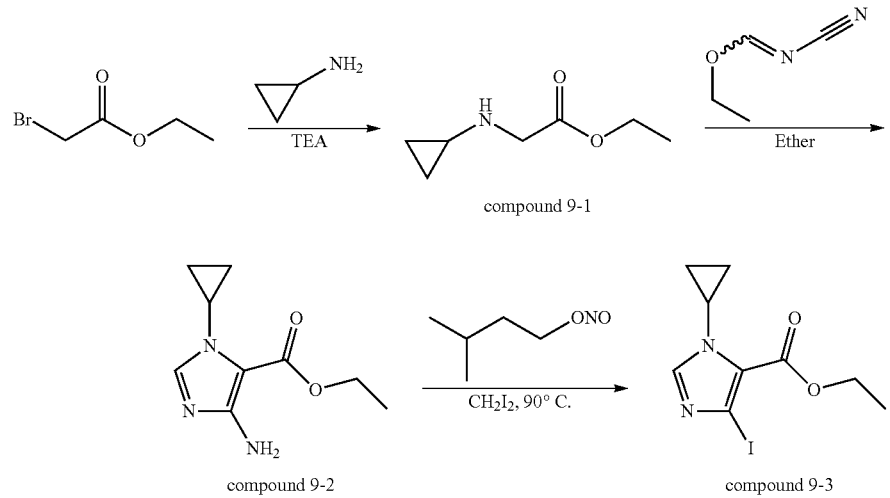

-continued
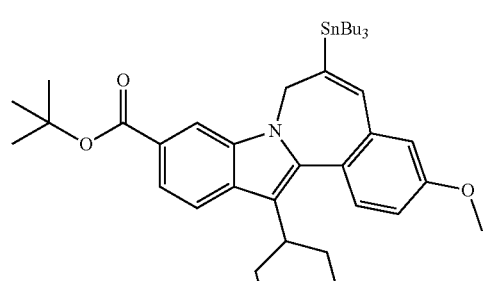
compound 1-3
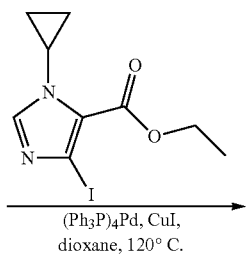
(Ph₃P)₄Pd, CuI, dioxane, 120° C.
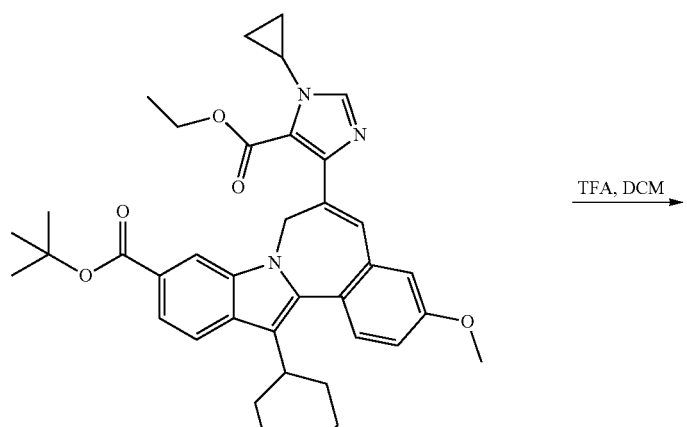
compound 9-4
TFA, DCM
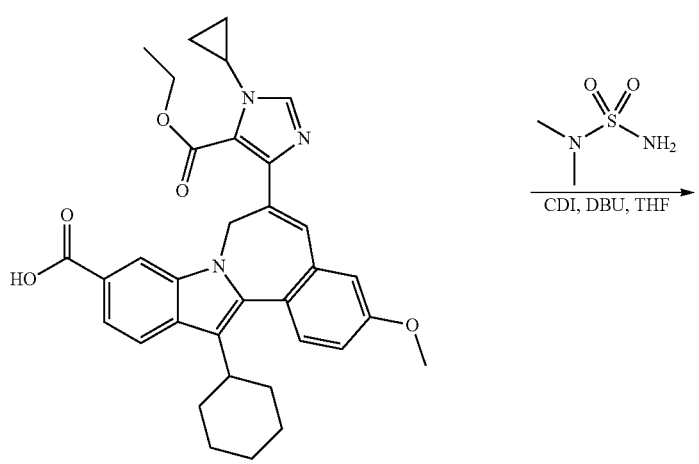
compound 9-5
CDI, DBU, THF

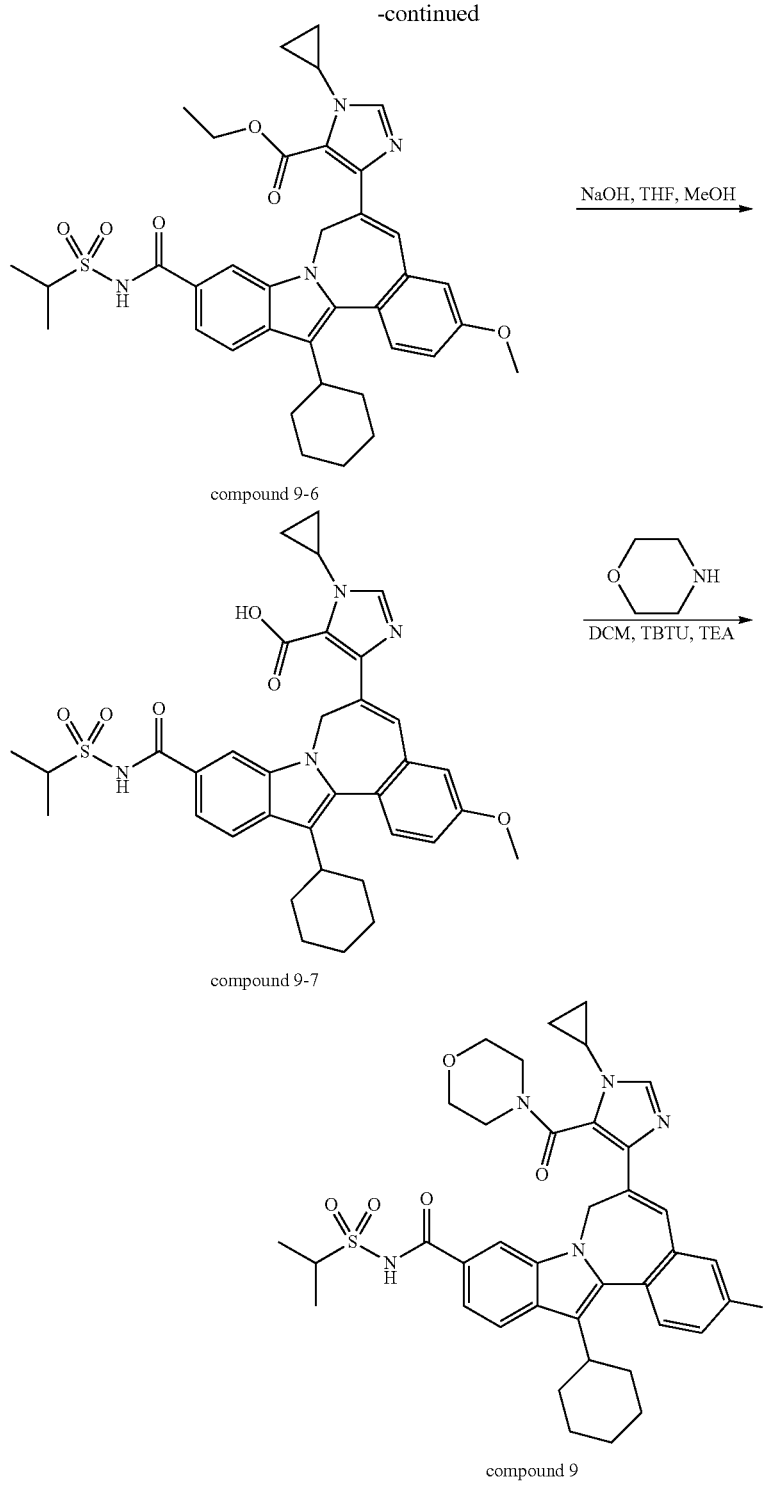

compound 9-6 compound 9-7 compound 9

Step 1: Preparation of Compound 9-1

To a solution of cyclopropanamine (0.8 g, 14.01 mmol) and TEA (1.673 mL, 12.00 mmol) in ether (20 mL) was added ethyl 2-bromoacetate (1.109 mL, 10 mmol). The reaction mixture was stirred at rt overnight. The solvent was concentrated and the residue was diluted with hexane. The solid was filtered off and the filtrate was concentrated to afford an oil as compound 9-1 (1.432 g, 100%). The crude product was used in next step.

Step 2: Preparation of Compound 9-2

To compound 9-1 (1.3 g, 9.08 mmol) in ether (5 mL) was added ethyl N-cyanoformimidate (0.891 g, 9.08 mmol) in ether (5 mL) dropwise. The reaction mixture was stirred at rt for 1 h. Removed the solvent. To the grease residue was added EtOH (5 mL) and potassium tert-butoxide (1.223 g, 10.90 mmol). The reaction mixture was stirred at rt overnight. The reaction mixture was concentrated, then diluted with EtOAc, washed with sat. NaHCO₃, sat. NaCl, dried over anhydrous Na₂SO₄, filtered and concentrated to yield a yellow solid as compound 9-2 (0.79 g, 4.05 mmol, 44.6% yield). The crude product was used in next step. LC/MS m/1195 (M+H)⁺ 196, RT=1.027 min; ¹H NMR (400 MHz, MeOD) δ ppm 7.35-7.45 (1H, m), 4.25-4.35 (2H, m), 3.48 (1H, ddd, J=7.30, 3.53, 3.27 Hz), 1.32-1.38 (3H, m), 0.96-1.02 (2H, m), 0.92-0.96 (2H, m).

Step 3: Preparation of Compound 9-3

To a solution of compound 9-2 (0.820 g, 4.20 mmol) and 12 (4.58 g, 18.06 mmol) in acetonitrile (8 mL) at 45° C. was added isopentyl nitrite (0.677 mL, 5.04 mmol) dropwise. The reaction mixture was stirred at 45° C. for 3 h, then cooled to rt. The reaction mixture was diluted with EtOAc, washed with sat. Na₂SO₃, sat. NaCl, dried over anhydrous Na₂SO₄, filtered and concentrated to yield a yellow oil. The crude product was dissolved in a small amount of methylene chloride and charged to a 80 g silica gel cartridge which was eluted with a 20 min gradient of 0-100% EtOAc in hexane. The fractions containing the desired product were concentrated to yield a yellow oil as compound 9-3 (0.31 g, 1.013 mmol, 24.11% yield). LC/MS m/z 306 (M+H)⁺ 307, RT=1.92 min; ¹H NMR (400 MHz, CHLOROFORM-d) δ ppm 7.51 (1H, s), 4.31-4.43 (2H, m), 3.61 (1H, ddd, J=7.49, 3.59, 3.27 Hz), 1.37-1.47 (3H, m), 1.04-1.13 (2H, m), 0.87-0.97 (2H, m).

Step 4: Preparation of Compound 9-4

In a 5 mL microwave vessel was added compound 1-3 (0.694 g, 0.947 mmol), compound 9-3 (0.290 g, 0.947 mmol) and copper(I) iodide (0.018 g, 0.095 mmol). The mixture was degassed with N2, then Tetrakis (0.109 g, 0.095 mmol) was added. The reaction mixture was heated in oil bath at 120° C. for 5 h. The reaction mixture was cooled to rt, concentrated to remove most solvent. The residue was dissolved in a small amount of methylene chloride and charged to a 40 g silica gel cartridge which was eluted with a 25 min gradient of 0-80% EtOAc in hexane. The fractions containing the desired product were concentrated to yield a yellow solid as compound 9-4 (0.22 g, 0.351 mmol, 37.0% yield). LC/MS m/z 621 (M+H)⁺ 622.5, RT=4.31 min.

Step 5: Preparation of Compound 9-5

To a solution of compound 9-4 (0.22 g, 0.354 mmol) in DCM (2 mL) was added TFA (1 mL, 12.98 mmol). The reaction mixture was stirred at rt. The reaction mixture was concentrated to remove most solvent. The residue was diluted with EtOAc, washed with 1N HCl, sat. NaCl, dried over anhydrous Na₂SO₄, filtered and concentrated to yield a yellow solid as compound 9-5 (0.20 g, 0.354 mmol, 100% yield). LC/MS m/z 565 (M+H)⁺ 566, RT=3.91 min.

Step 6: Preparation of Compound 9-6

To a mixture of compound 9-5 (0.20 g, 0.354 mmol) in THF (3 mL) was added CDI (0.126 g, 0.778 mmol). The mixture was heated at 50° C. for 0.5 h, then cooled down. Propane-2-sulfonamide (0.13 g, 1.055 mmol) and DBU (0.176 mL, 1.167 mmol) were added. The reaction mixture was stirred at rt overnight. The reaction mixture was concentrated and the crude product was dissolved in a small amount of methylene chloride and charged to a 80 g silica gel cartridge which was eluted with a 20 min gradient of 0-15% MeOH in CH₂Cl₂. The fractions containing the product were combined and concentrated to yield a yellow solid as compound 9-6 (0.156 g, 0.233 mmol, 59.8% yield). LC/MS m/z 670 (M+H)⁺ 671, RT=3.713 min.

Step 7: Preparation of Compound 9-7

To a solution of compound 9-6 (0.12 g, 0.179 mmol) in THF (2 mL) and MeOH (0.500 mL) was added 1 N NaOH (1 mL, 1.000 mmol). The reaction mixture was stirred at rt for 5 h. The reaction mixture was concentrated to dryness. Then the residue was diluted with EtOAc, washed with 1 N HCl, sat. NaCl, dried over anhydrous Na₂SO₄, filtered and concentrated to yield a yellow solid as compound 9-7 (0.11 g, 0.171 mmol, 96% yield). LC/MS m/z 642 (M+H)⁺ 643, RT=3.48 min.

Step 8: Preparation of Compound 9

To a solution of compound 9-7 (0.025 g, 0.039 mmol) in DCM (1 mL) was added TEA (0.1 mL, 0.717 mmol), morpholine (0.03 mL, 0.039 mmol), followed by O-(Benzotriazol-1-yl)-N,N,N',N'-tetramethyluronium tetrafluoroborate (0.025 g, 0.078 mmol). The reaction mixture was stirred at rt overnight. The reaction mixture was concentrated to dryness and the residue was redissolved in MeOH, filtered and purified by reverse phase prep-HPLC. Fractions from main peak were evaporated overnight in the SPEEDVAC® tp yield compound 9 mono TFA salt (0.020 g, 0.023 mmol, 59.1% yield) as a yellow solid. LC/MS m/z 711 (M+H)⁺ 712.48, RT=3.65 min. ¹H NMR (400 MHz, CHLOROFORM-d) δ ppm 8.59 (1H, s), 8.19 (1H, br. s.), 7.89 (1H, d, J=8.81 Hz), 7.65 (1H, d, J=8.06 Hz), 7.51 (1H, d, J=8.31 Hz), 7.04-7.14 (2H, m), 6.94 (1H, br. s.), 5.40 (1H, br. s.), 4.52 (1H, d, J=14.60 Hz), 4.01 (1H, d, J=6.80 Hz), 3.96 (3H, s), 3.89 (6H, br. s.), 2.86 (2H, br. s.), 2.68 (2H, br. s.), 2.36 (1H, br. s.), 2.22 (1H, br. s.), 2.01 (6H, br. s.), 1.77 (3H, d, J=9.82 Hz), 1.36-1.54 (6H, m), 1.19-1.28 (3H, m), 0.89 (1H, br. s.).

Preparation of Compound 10: 6-(1-cyclobutyl-5-(4-morpholinylcarbonyl)-1H-imidazol-4-yl)-13-cyclohexyl-N-(isopropylsulfonyl)-3-methoxy-7H-indolo[2,1-a][2]benzazepine-10-carboxamide

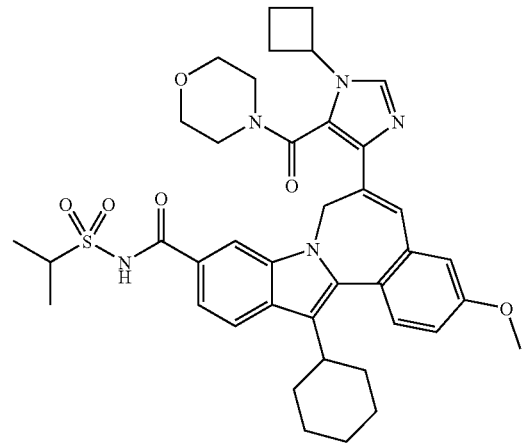

Prepared as described in preparation of compound 9. LC/MS m/z 725 (M+H)⁺ 726.4, RT=3.64 min. ¹H NMR (400 MHz, CHLOROFORM-d) δ ppm 8.61 (1H, br. s.), 8.25 (1H, br. s.), 7.89 (1H, d, J=8.56 Hz), 7.67 (1H, d, J=8.06 Hz), 7.52 (1H, d, J=8.81 Hz), 7.10 (1H, dd, J=8.81, 2.52 Hz), 7.03 (1H, br. s.), 6.93 (1H, br. s.), 5.47 (1H, d, J=15.11 Hz), 4.80 (1H, t, J=8.18 Hz), 4.53 (1H, d, J=14.35 Hz), 3.96 (3H, s), 3.89 (1H, s), 3.82 (1H, br. s.), 3.51 (2H, s), 3.21 (1H, br. s.), 2.86 (2H, br. s.), 2.62 (3H, br. s.), 2.57 (2H, br. s.), 2.34 (4H, br. s.), 2.00 (6H, d, J=11.58 Hz), 1.76 (3H, br. s.), 1.18-1.57 (7H, m), 1.18-1.26 (1H, m).

187

6-(1-Cyclobutyl-5-((5-ethyl-2,5-diazabicyclo[2.2.1]hept-2-yl)carbonyl)-1H-imidazol-4-yl)-13-cyclohexyl-N-(isopropylsulfonyl)-3-methoxy-7H-indolo[2,1-a][2]benzazepine-10-carboxamide

188

Prepared as described in preparation of compound 9. LC/MS m/z 753 (M+H)+ 754.5, RT=3.798 min.

13-Cyclohexyl-6-(1-cyclopropyl-5-((5-ethyl-2,5-diazabicyclo[2.2.1]hept-2-yl)carbonyl)-1H-imidazol-4-yl)-N-(isopropylsulfonyl)-3-methoxy-7H-indolo[2,1-a][2]benzazepine-10-carboxamide

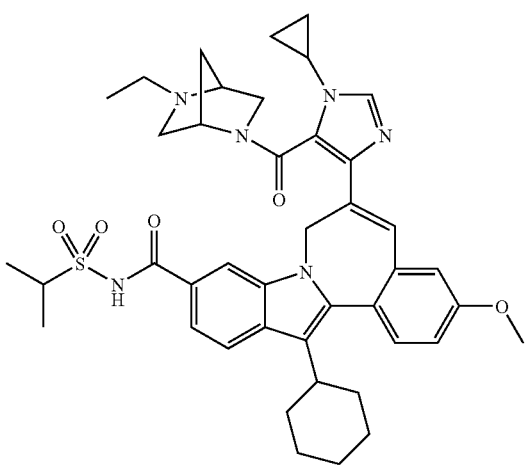

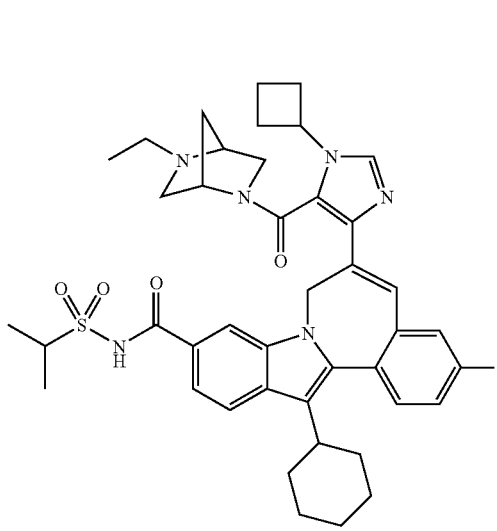

Prepared as described in preparation of compound 9. LC/MS m/z 764 (M+H)+ 765.49, RT=3.33 min.

6-(1-Cyclobutyl-5-(((2R,6S)-2,6-dimethyl-4-morpholinyl)carbonyl)-1H-imidazol-4-yl)-13-cyclohexyl-N-(isopropylsulfonyl)-3-methoxy-7H-indolo[2,1-a][2]benzazepine-10-carboxamide Prepared as described in preparation of compound 9. LC/MS m/z 750 (M+H)+ 751.39, RT=3.303 min.

13-Cyclohexyl-6-(1-cyclopropyl-5-(((2R,6S)-2,6-dimethyl-4-morpholinyl)carbonyl)-1H-imidazol-4-yl)-N-(isopropylsulfonyl)-3-methoxy-7H-indolo[2,1-a][2]benzazepine-10-carboxamide

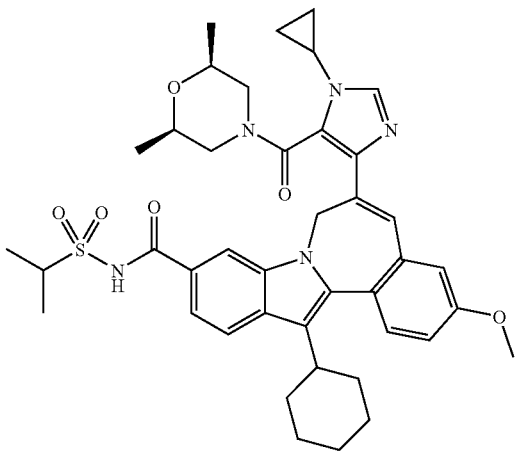

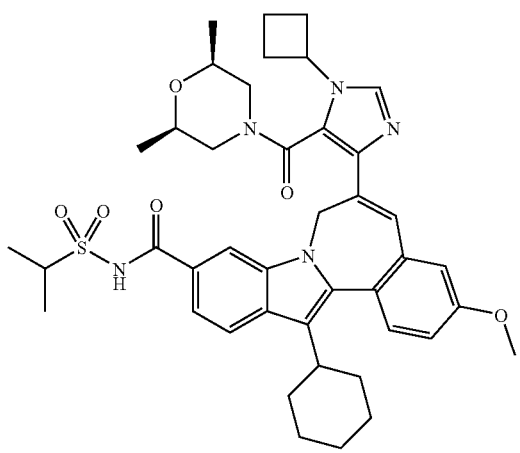

Prepared as described in preparation of compound 9. LC/MS m/z 739 (M+H)+ 740.47, RT=3.81 min. $^1$H NMR (500 MHz, CHLOROFORM-d) δ ppm 8.56 (1H, d, J=9.16 Hz), 7.89 (2H, t, J=8.09 Hz), 7.67 (1H, dd, J=13.58, 8.39 Hz), 7.49-7.54 (2H, m), 7.10 (1H, dd, J=8.55, 2.14 Hz), 6.93 (1H, d, J=2.44 Hz), 5.43 (1H, d, J=14.95 Hz), 4.50 (1H, d, J=14.34 Hz), 4.02-4.09 (1H, m), 3.97 (3H, s), 3.89 (4H, d, J=3.36 Hz), 3.51 (1H, s) 3.40 (1H, s), 2.83-2.93 (2H, m), 1.99-2.11 (5H, m), 1.79 (3H, br. s.), 1.46 (4H, br. s.), 1.44 (7H, dd, J=7.02, 3.36 Hz), 1.20-1.28 (3H, m), 1.09 (2H, d, J=5.80 Hz), 1.06 (1H, d, J=5.80 Hz), 0.89 (1H, br. s.), 0.72 (1H, br. s.).

Biological Methods

The compounds demonstrated activity against HCV NS5B as determined in the following HCV RdRp assays.

HCV NS5B RdRp Cloning, Expression, and Purification

The cDNA encoding the NS5B protein of HCV, genotype 1b, was cloned into the pET21a expression vector. The protein was expressed with an 18 amino acid C-terminal truncation to enhance the solubility. The *E. coli* competent cell line BL21(DE3) was used for expression of the protein. Cultures were grown at 37° C. for ~4 hours until the cultures reached an optical density of 2.0 at 600 nm. The cultures were cooled to 20° C. and induced with 1 mM IPTG. Fresh ampicillin was added to a final concentration of 50 µg/ml and the cells were grown overnight at 20° C.

Cell pellets (3 L) were lysed for purification to yield 15-24 mgs of purified NS5B. The lysis buffer consisted of 20 mM Tris-HCl, pH 7.4, 500 mM NaCl, 0.5% triton X-100, 1 mM DTT, 1 mM EDTA, 20% glycerol, 0.5 mg/ml lysozyme, 10 mM $MgCl_2$, 15 ug/ml deoxyribonuclease I, and Complete TM protease inhibitor tablets (Roche). After addition of the lysis buffer, frozen cell pellets were resuspended using a tissue homogenizer. To reduce the viscosity of the sample, aliquots of the lysate were sonicated on ice using a microtip attached to a Branson sonicator. The sonicated lysate was centrifuged at 100,000×g for 1 hr at 4° C. and filtered through a 0.2 µm filter unit (Corning).

The protein was purified using three sequential chromatography steps: Heparin sepharose CL-6B, polyU sepharose 4B, and Dual-Glo SP sepharose (Pharmacia). The chromatography buffers were identical to the lysis buffer but contained no lysozyme, deoxyribonuclease I, $MgCl_2$ or protease inhibitor and the NaCl concentration of the buffer was adjusted according to the requirements for charging the protein onto the column. Each column was eluted with a NaCl gradient which varied in length from 5-50 column volumes depending on the column type. After the final chromatography step, the resulting purity of the enzyme is >90% based on SDS-PAGE analysis. The enzyme was aliquoted and stored at −80° C.

Standard HCV NS5B RdRp Enzyme Assay

HCV RdRp genotype 1b assays were run in a final volume of 60 µl in 96 well plates (Costar 3912). The assay buffer is composed of 20 mM Hepes, pH 7.5, 2.5 mM KCl, 2.5 mM $MgCl_2$, 1 mM DTT, 1.6 U RNAse inhibitor (Promega N2515), 0.1 mg/ml BSA (Promega R3961), and 2% glycerol. All compounds were serially diluted (3-fold) in DMSO and diluted further in water such that the final concentration of DMSO in the assay was 2%. HCV RdRp genotype 1b enzyme was used at a final concentration of 28 nM. A polyA template was used at 6 nM, and a biotinylated oligo-dT12 primer was used at 180 nM final concentration. Template was obtained commercially (Amersham 27-4110). Biotinylated primer was prepared by Sigma Genosys. 3H-UTP was used at 0.6 µCi (0.29 µM total UTP). Reactions were initiated by the addition of enzyme, incubated at 30° C. for 60 min, and stopped by adding 25 µl of 50 mM EDTA containing SPA beads (4 µg/µl, Amersham RPNQ 0007). Plates were read on a Packard TOPCOUNT® NXT after >1 hr incubation at room temperature.

Modified HCV NS5B RdRp Enzyme Assay

A modified enzyme assay was performed essentially as described for the standard enzyme assay except for the following: The biotinylated oligo dT12 primer was precaptured on streptavidin-coated SPA beads by mixing primer and beads in assay buffer and incubating at room temperature for one hour. Unbound primer was removed after centrifugation. The primer-bound beads were resuspended in 20 mM Hepes buffer, pH 7.5 and used in the assay at final concentrations of 20 nM primer and 0.67 µg/µl beads. Order of addition in the assay: enzyme (14 nM) was added to diluted compound followed by the addition of a mixture of template (0.2 nM), 3H-UTP (0.6 µCi, 0.29 µM), and primer-bound beads, to initiate the reaction; concentrations given are final. Reactions were allowed to proceed for 4 hours at 30° C.

$IC_{50}$ values for compounds were determined using seven different [I]. $IC_{50}$ values were calculated from the inhibition using the formula $y=A+((B-A)/(1+((C/x)^D)))$.

FRET Assay Preparation

To perform the HCV FRET screening assay, 96-well cell culture plates were used, The FRET peptide (Anaspec, Inc.) (Taliani et al., *Anal. Biochem.*, 240:60-67 (1996)) contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent. The assay reagent was made as follows: 5× cell Luciferase cell culture lysis reagent from Promega (#E153A) diluted to 1× with $dH_2O$, NaCl added to 150 mM final, the FRET peptide diluted to 20 µM final from a 2 mM stock.

To prepare plates, HCV replicon cells, with or without a *Renilla* luciferase reporter gene, were trypsinized and placed into each well of a 96-well plate with titrated test compounds added in columns 3 through 12; columns 1 and 2 contained a control compound (HCV protease inhibitor), and the bottom row contained cells without compound. The plates were then placed in a $CO_2$ incubator at 37° C.

Assays

Subsequent to addition of the test compounds described above (FRET Assay Preparation), at various times the plate was removed and Alamar blue solution (Trek Diagnostics, #00-100) was added per well as a measure of cellular toxicity. After reading in a CYTOFLUOR® 4000 instrument (PE Biosystems), plates were rinsed with PBS and then used for FRET assay by the addition of 30 ul of the FRET peptide assay reagent described above (FRET Assay Preparation) per well. The plate was then placed into the CYTOFLUOR® 4000 instrument which had been set to 340 excite/490 emission, automatic mode for 20 cycles and the plate read in a kinetic mode. Typically, the signal to noise using an endpoint analysis after the reads was at least three-fold. Alternatively, after Alamar blue reading, plates were rinsed with PBS, 50 ul of DMEM (high glucose) without phenol red was added and plates were then used for luciferase assay using the Promega DUAL-GLO® Luciferase Assay System.

Compound analysis was determined by quantification of the relative HCV replicon inhibition and the relative cytotoxicity values. To calculate cytoxicity values, the average Alamar Blue fluorescence signals from the control wells were set as 100% non-toxic. The individual signals in each of the compound test wells were then divided by the average control signal and multiplied by 100% to determine percent cytotoxicity. To calculate the HCV replicon inhibition values, an average background value was obtained from the two wells containing the highest amount of HCV protease inhibitor at the end of the assay period. These numbers were similar to those obtained from naïve Huh-7 cells.

The background numbers were then subtracted from the average signal obtained from the control wells and this number was used as 100% activity. The individual signals in each of the compound test wells were then divided by the averaged control values after background subtraction and multiplied by 100% to determine percent activity. $EC_{50}$ values for a protease inhibitor titration were calculated as the concentration which caused a 50% reduction in FRET or luciferase activity. The two numbers generated for the compound plate, percent cytoxicity and percent activity were used to determine compounds of interest for further analysis.

HCV Replicon Luciferase Reporter Assay

The HCV replicon luciferase assay was developed to monitor the inhibitory effects of compounds described in the disclosure on HCV viral replication. Utilization of a replicon luciferase reporter assay was first described by Krieger et al (Krieger, N. et al., *J. Virology*, 75(10):4614-4624 (2001)). HUH-7 cells, constitutively expressing the HCV replicon, were grown in Dulbecco's Modified Eagle Media (DMEM) (Gibco-BRL) containing 10% Fetal calf serum (FCS) (Sigma) and 1 mg/ml G418 (Gibco-BRL). Compounds were serially diluted 3 folds in DMSO for a twenty-point titration and subsequently transferred to sterile 384-well tissue-culture treated plates (Corning cat #3571). The plates were then seeded with 50 µl of cells at a density of $3.0 \times 10^3$ cells/well in DMEM containing 4% FCS (final DMSO concentration at 0.5%). After 3 days incubation at 37° C., cells were analyzed for *Renilla* Luciferase activity using the EnduRen as substrate (Promega cat #E6485). The EnduRen substrate was diluted in DMEM and then added to the plates to a final concentration of 7.5 µM. The plates were incubated for 2 hrs at 37° C. and then read immediately for 30 seconds with VIEWLUX® Imager (PerkinElmer) using a luminescence program. To assess cytotoxicity of compounds, $CC_{50}$ values were generated by multiplexing the EnduRen-containing plates with CELLTITER-BLUE® (Promega cat #G8082). 3 µl of CELLTITER-BLUE® was added to each well and incubated for 8 hrs at 37° C. The fluorescence signal from each well was read, with an excitation wavelength at 525/10 nm and an emission wavelength of 598/10 nm, using the VIEWLUX® Imager.

Representative data for compounds are reported in Table 1.

TABLE 1

| Structure | $IC_{50}$ (µM) | $EC_{50}$ (µM) |
|---|---|---|
| | B | B |
| | B | B |

TABLE 1-continued
| Structure | IC$_{50}$ (μM) | EC$_{50}$ (μM) |
|---|---|---|
| 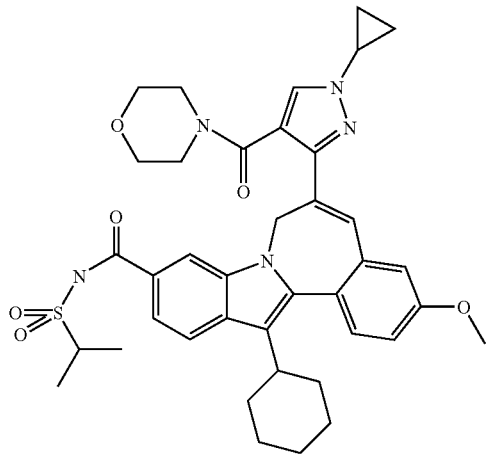 | B | B |
| 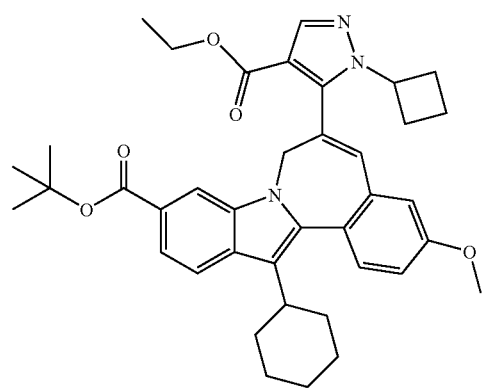 | A | |
| 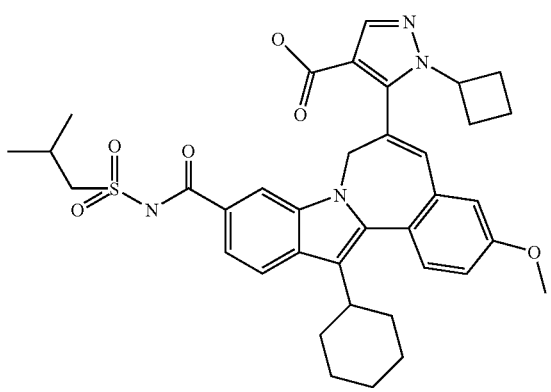 | B | |

TABLE 1-continued
| Structure | IC$_{50}$ (µM) | EC$_{50}$ (µM) |
|---|---|---|
| 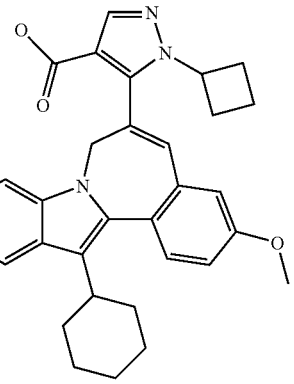 | B | |
| 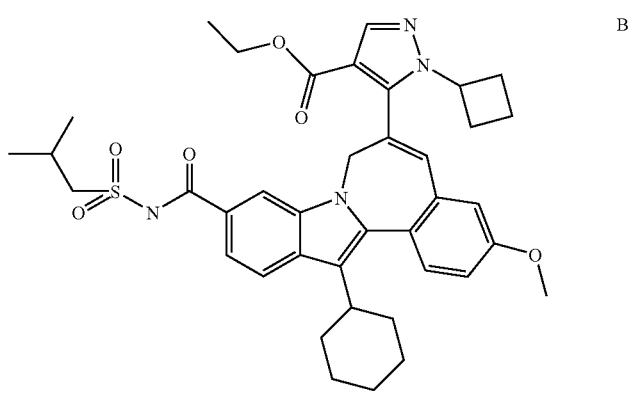 | B | |
| 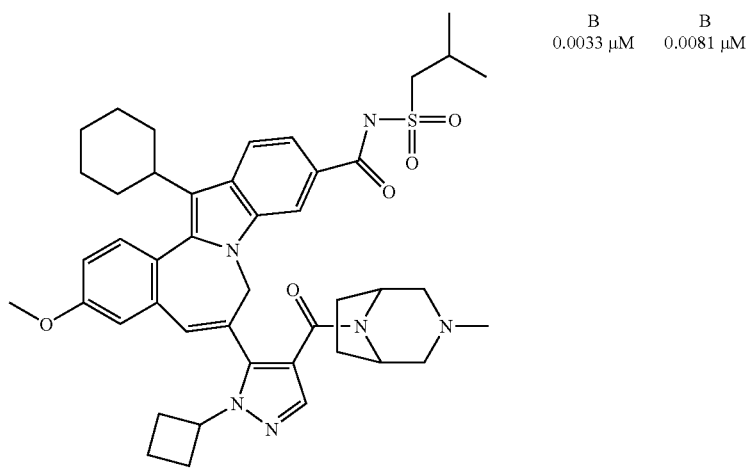 | B<br>0.0033 µM | B<br>0.0081 µM |

TABLE 1-continued
| Structure | IC$_{50}$ (µM) | EC$_{50}$ (µM) |
|---|---|---|
| 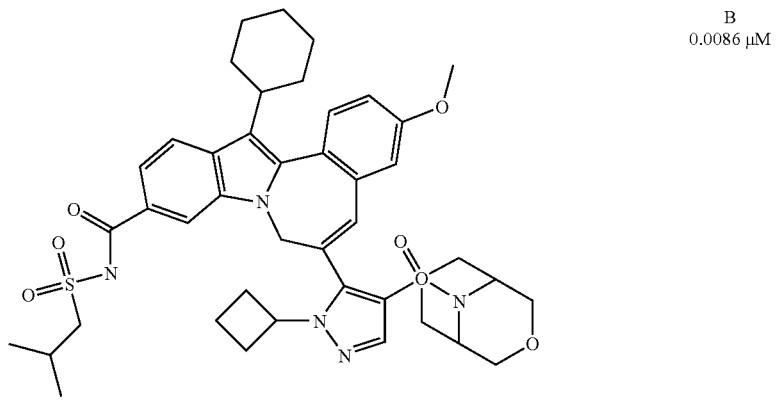 | B | 0.0086 µM |
| 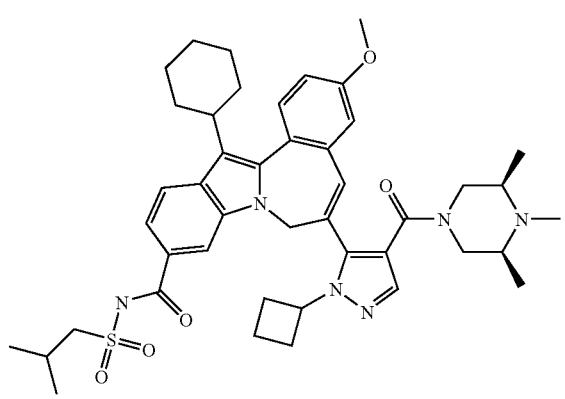 | B | B |
| 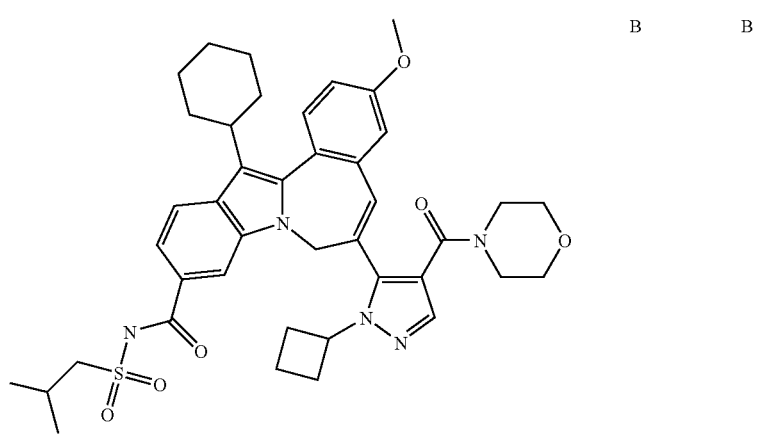 | B | B |

TABLE 1-continued
| Structure | IC$_{50}$ (μM) | EC$_{50}$ (μM) |
|---|---|---|
| 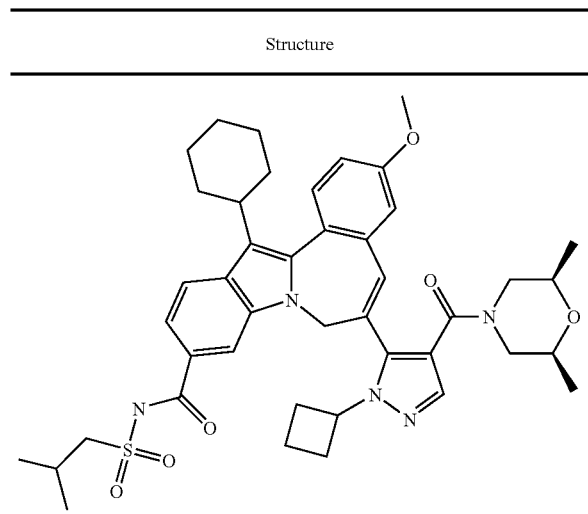 | B | B |
| 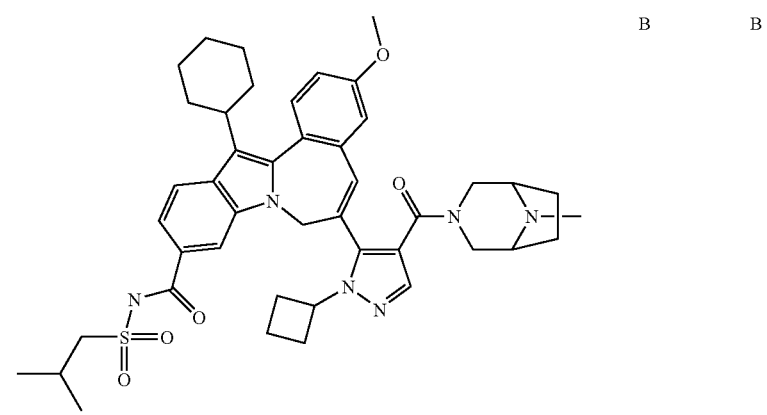 | B | B |
| 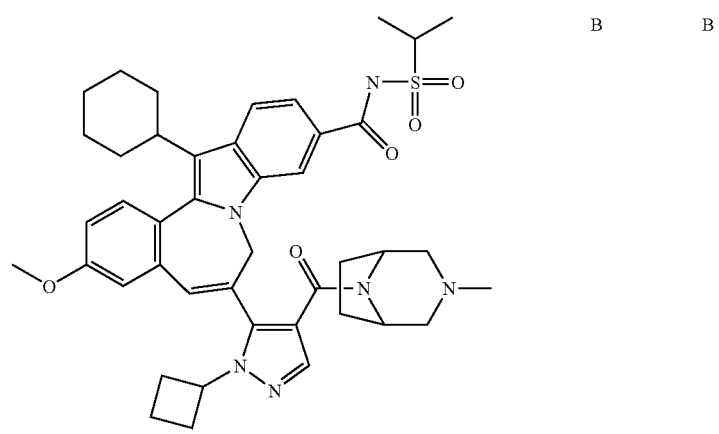 | B | B |

TABLE 1-continued
| Structure | IC$_{50}$ (μM) | EC$_{50}$ (μM) |
|---|---|---|
| 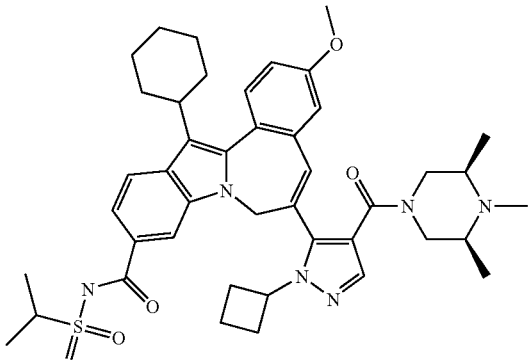 | B | B |
| 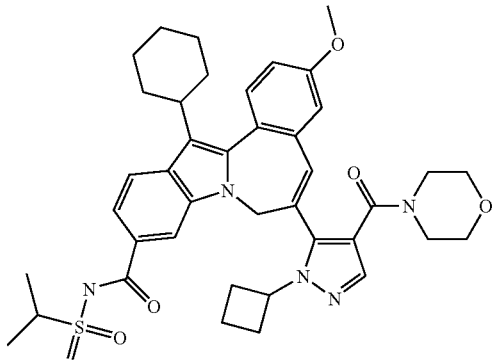 | B | B |
| 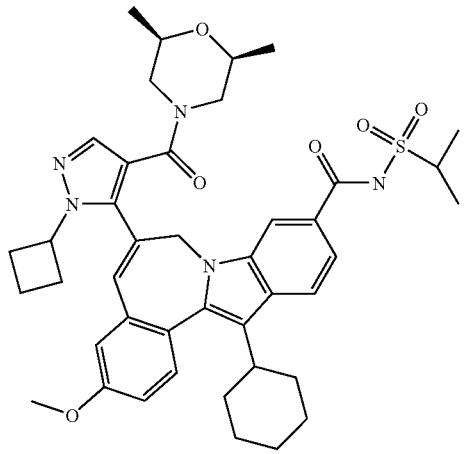 | B | B |
| 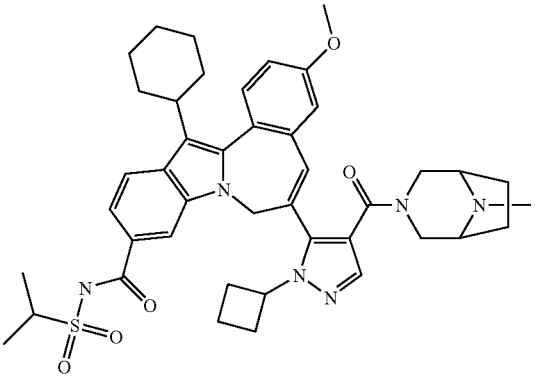 | B | B |

TABLE 1-continued
| Structure | IC$_{50}$ (μM) | EC$_{50}$ (μM) |
|---|---|---|
| 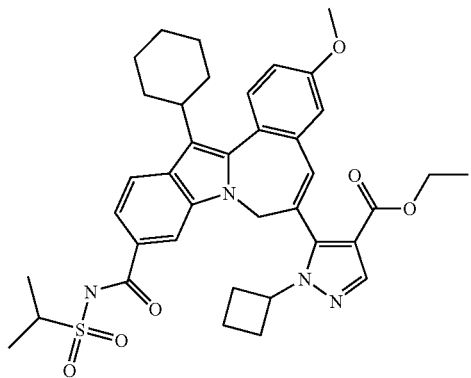 | B | |
| 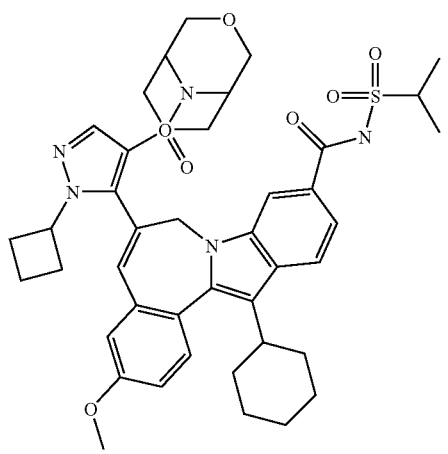 | B | B |
| 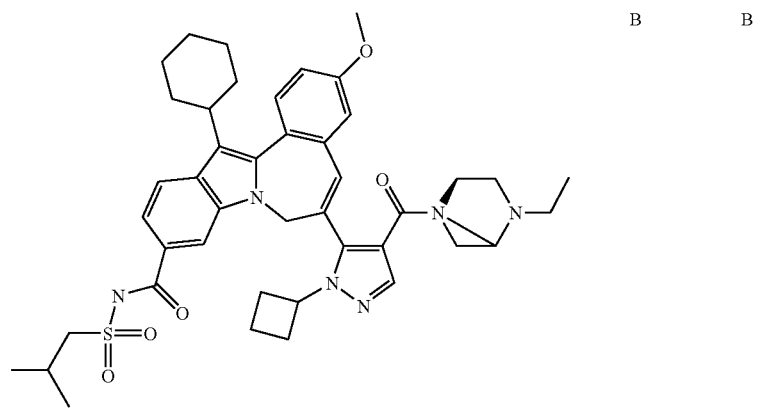 | B | B |

TABLE 1-continued

| Structure | IC$_{50}$ (μM) | EC$_{50}$ (μM) |
|---|---|---|
| | B | B |
| | B | B |
| | B | B |
| | | |

TABLE 1-continued
| Structure | IC$_{50}$ (μM) | EC$_{50}$ (μM) |
| --- | --- | --- |
| 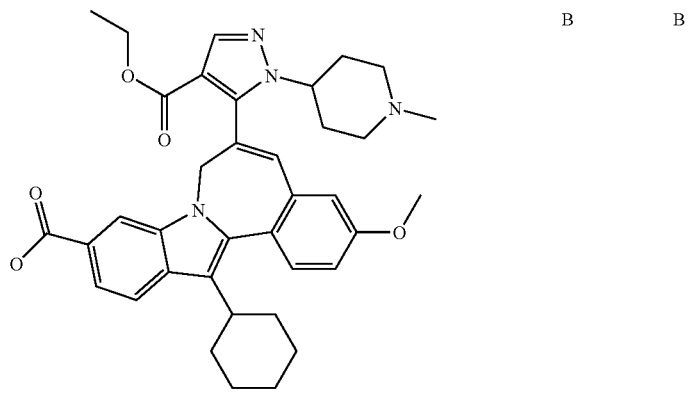 | B | B |
| 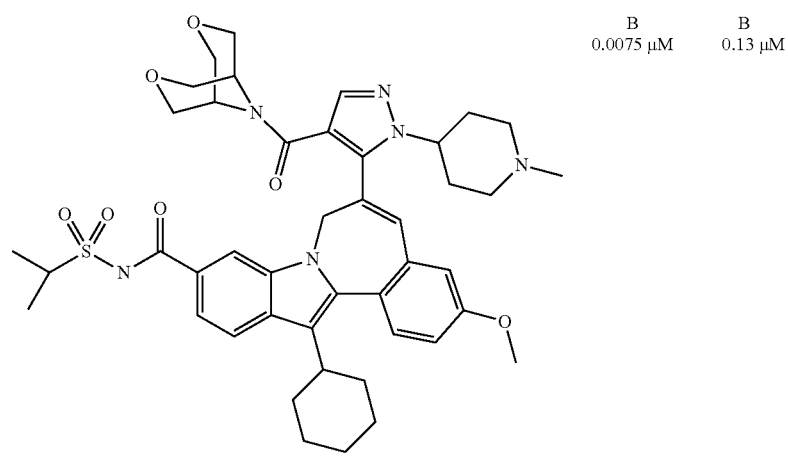 | B<br>0.0075 μM | B<br>0.13 μM |
| 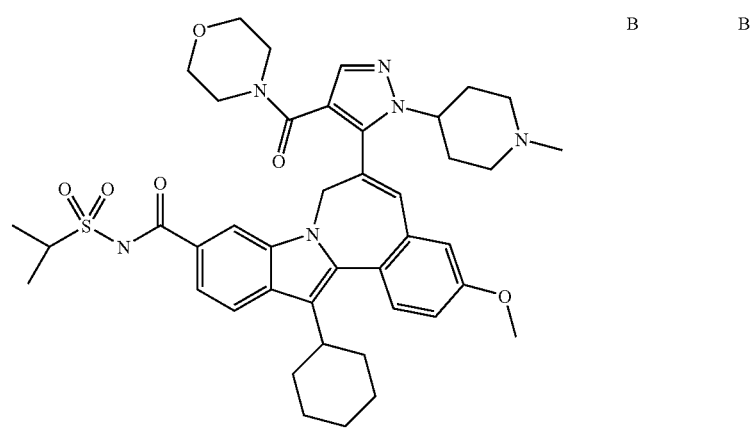 | B | B |

TABLE 1-continued
| Structure | IC$_{50}$ (μM) | EC$_{50}$ (μM) |
|---|---|---|
| 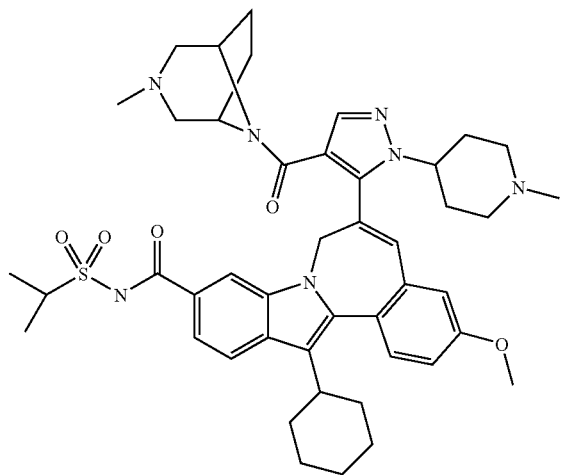 | B | B |
| 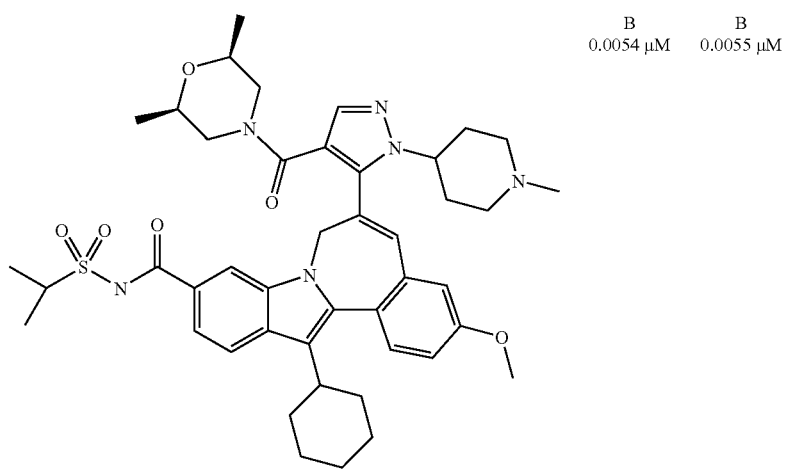 | B 0.0054 μM | B 0.0055 μM |
| 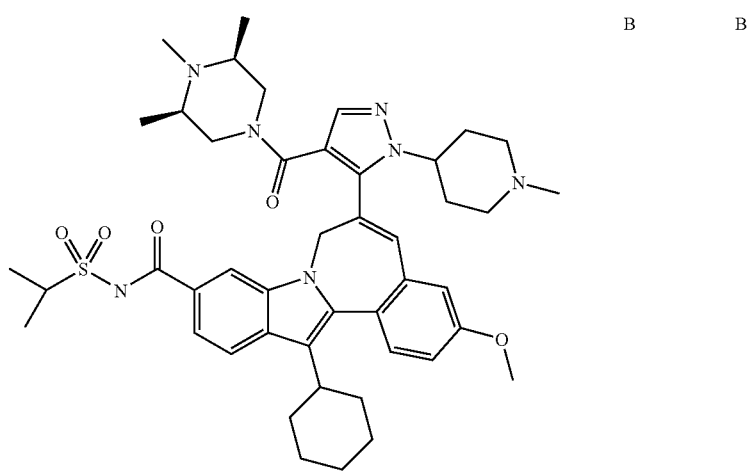 | B | B |

TABLE 1-continued

| Structure | IC$_{50}$ (μM) | EC$_{50}$ (μM) |
|---|---|---|
| | B | B |
| 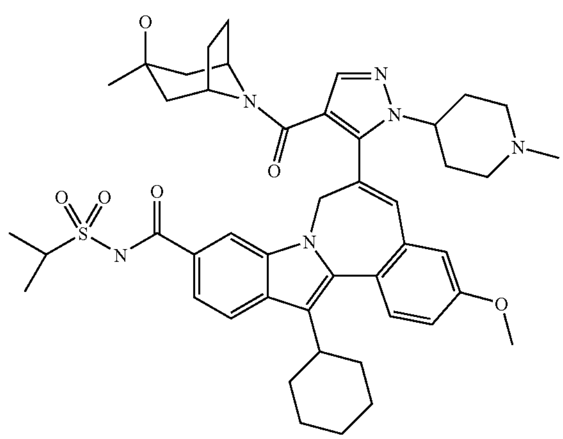 | B<br>0.096 μM | B<br>0.01 μM |
| | B | B |

TABLE 1-continued
| Structure | IC$_{50}$ (μM) | EC$_{50}$ (μM) |
|---|---|---|
| 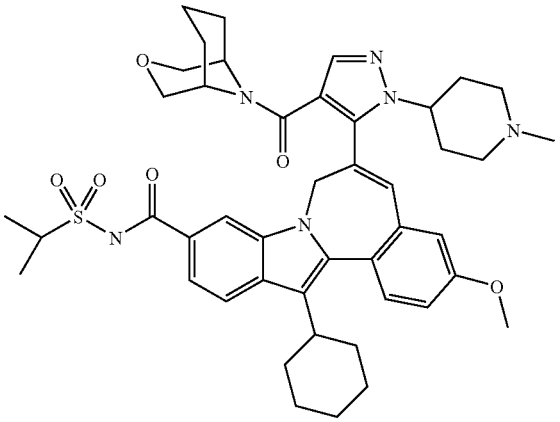 | B | B |
| 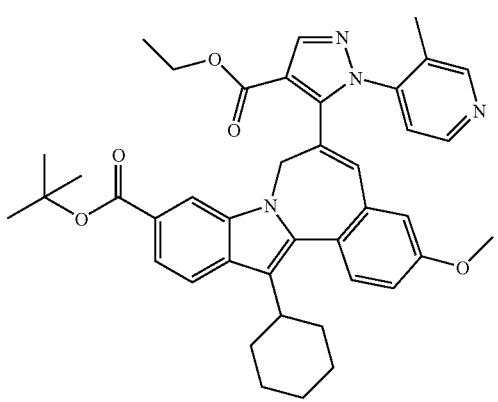 | | |
| 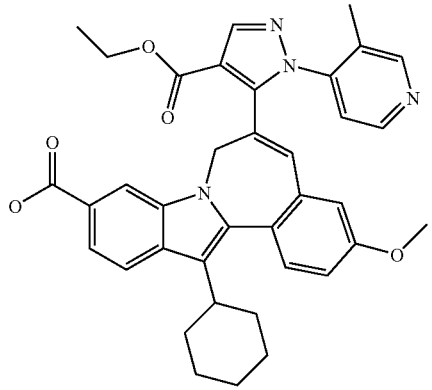 | B | B |
| 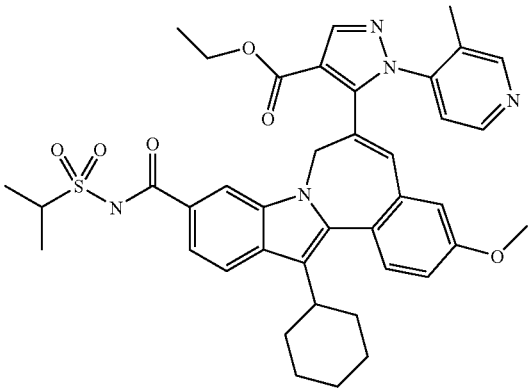 | B | B |

TABLE 1-continued
| Structure | IC$_{50}$ (μM) | EC$_{50}$ (μM) |
| --- | --- | --- |
| 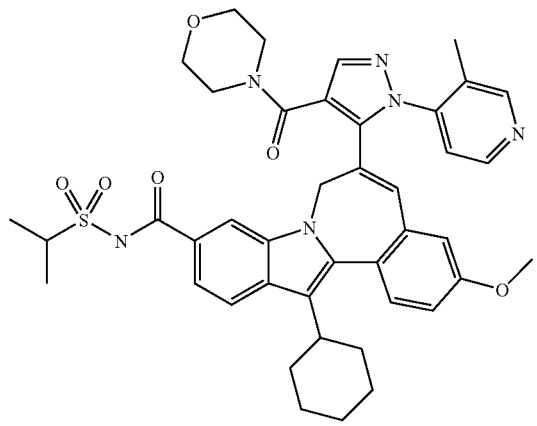 | B | B |
| 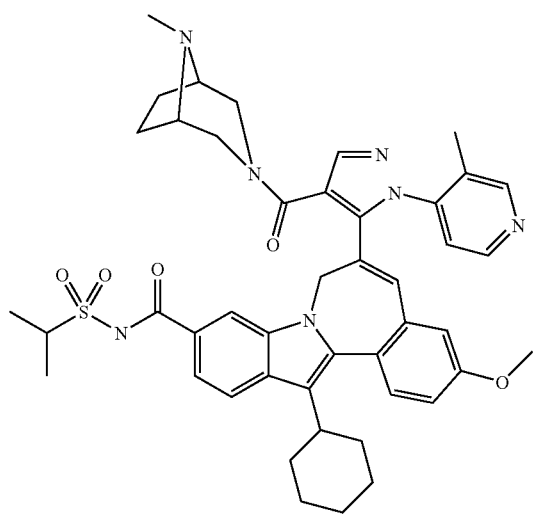 | B | B |
| 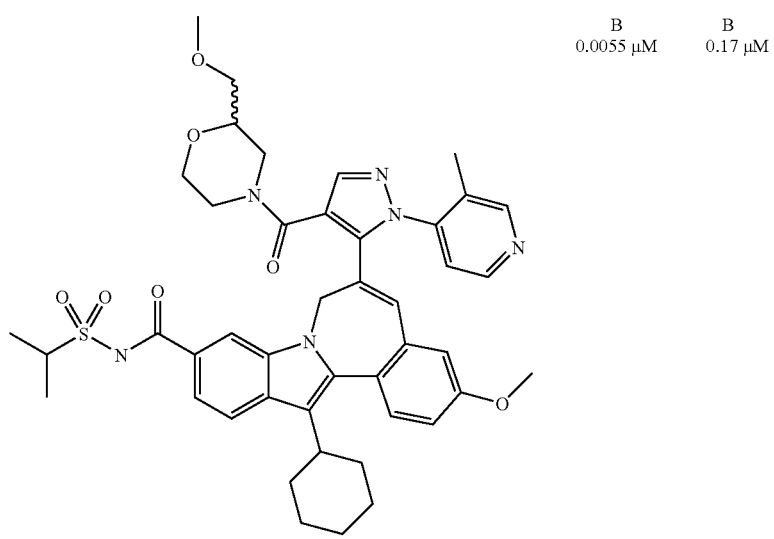 | B<br>0.0055 μM | B<br>0.17 μM |

TABLE 1-continued
| Structure | IC$_{50}$ (μM) | EC$_{50}$ (μM) |
|---|---|---|
| 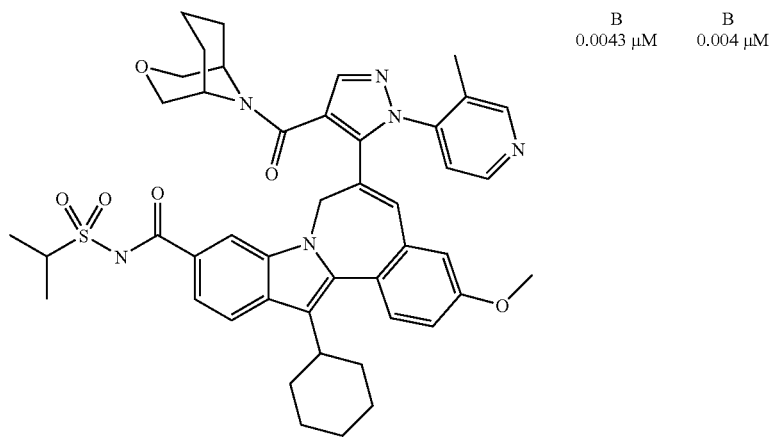 | B<br>0.0043 μM | B<br>0.004 μM |
| 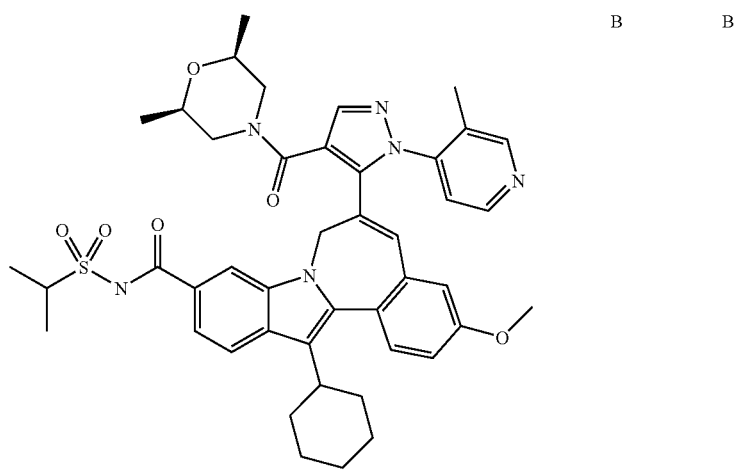 | B | B |
| 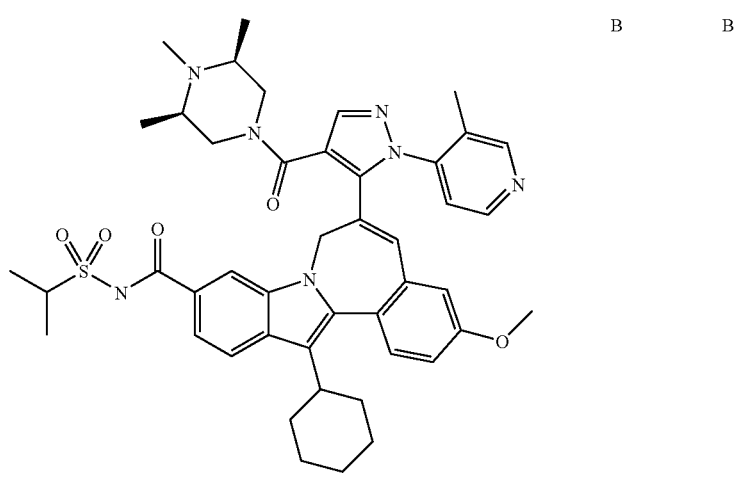 | B | B |

TABLE 1-continued
| Structure | IC$_{50}$ (μM) | EC$_{50}$ (μM) |
|---|---|---|
| 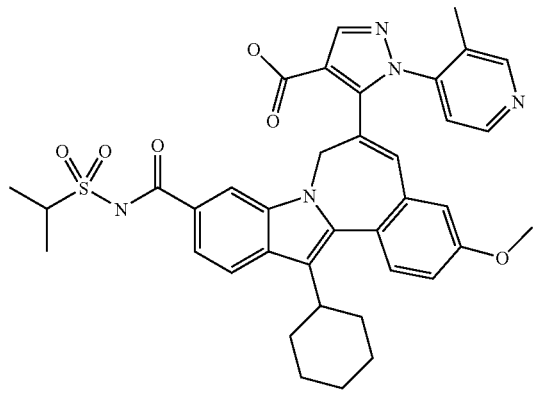 | | |
| 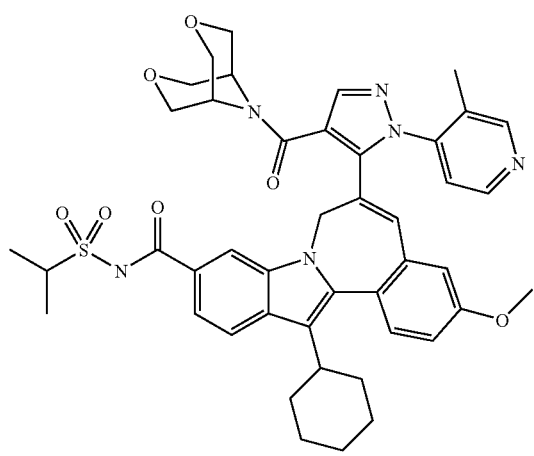 | B | B |
| 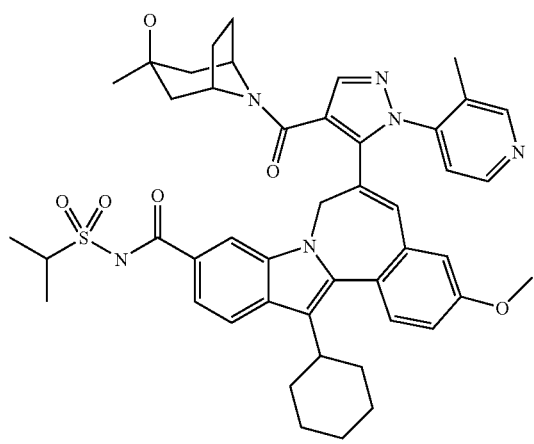 | B | B |

TABLE 1-continued

| Structure | IC$_{50}$ (μM) | EC$_{50}$ (μM) |
|---|---|---|
| | B 0.0051 μM | B 0.22 μM |
| | B | |
| | B | |

TABLE 1-continued
| Structure | IC$_{50}$ (μM) | EC$_{50}$ (μM) |
|---|---|---|
| 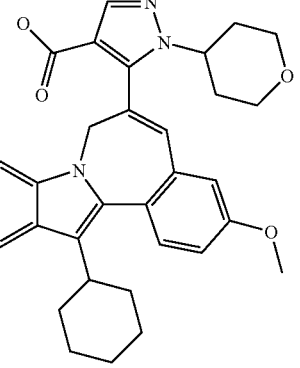 | B | |
| 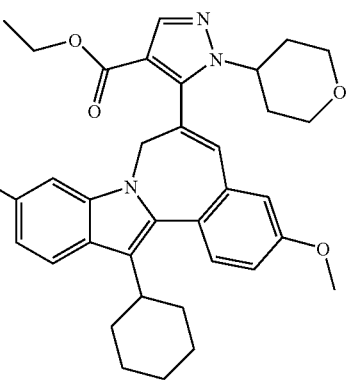 | B | |
| 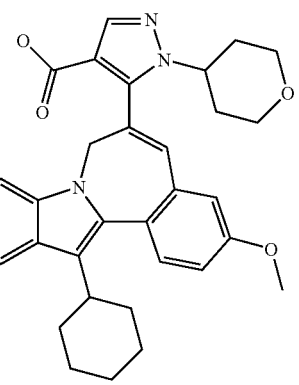 | B | |
| 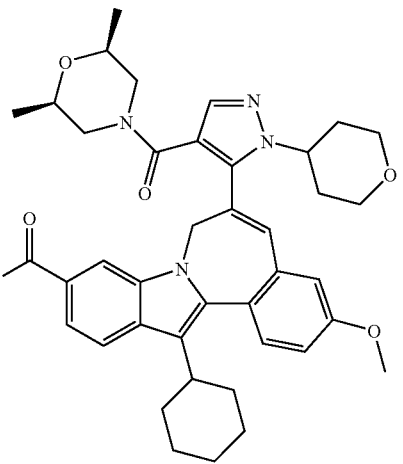 | B<br>0.0026 μM | B<br>0.0089 μM |

TABLE 1-continued
| Structure | IC$_{50}$ (μM) | EC$_{50}$ (μM) |
|---|---|---|
| 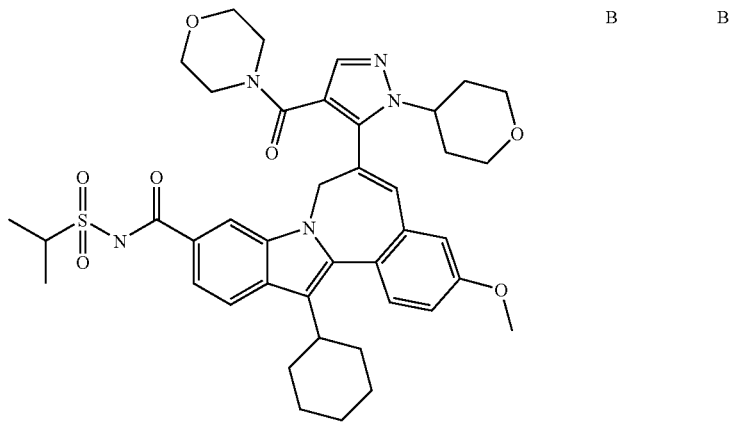 | B | B |
| 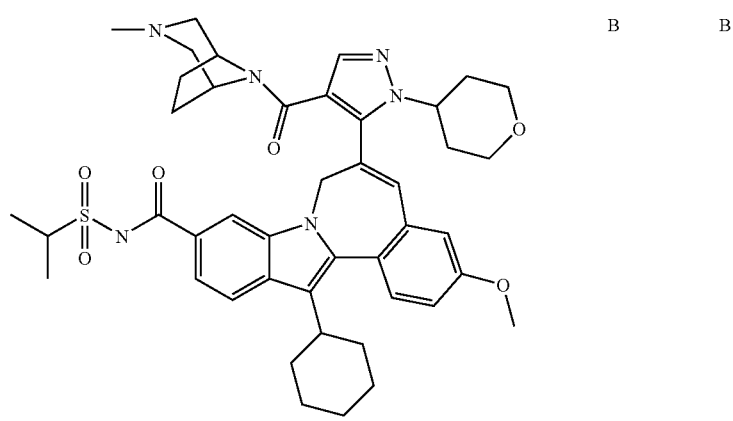 | B | B |
| 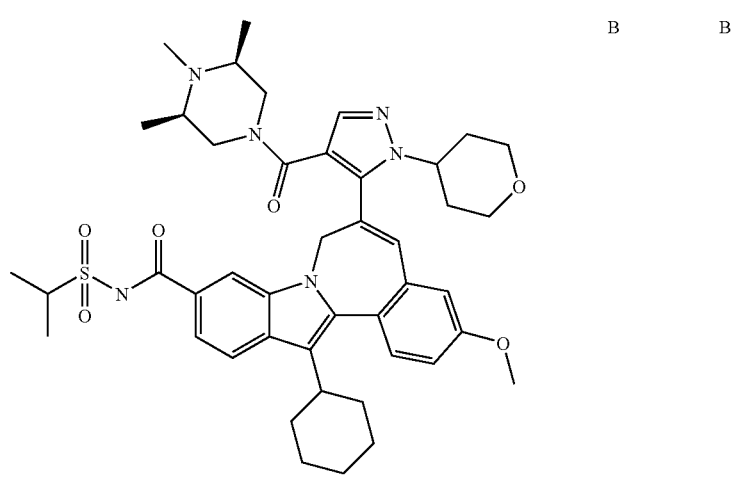 | B | B |

TABLE 1-continued
| Structure | IC$_{50}$ (μM) | EC$_{50}$ (μM) |
|---|---|---|
| Chiral | B | B |
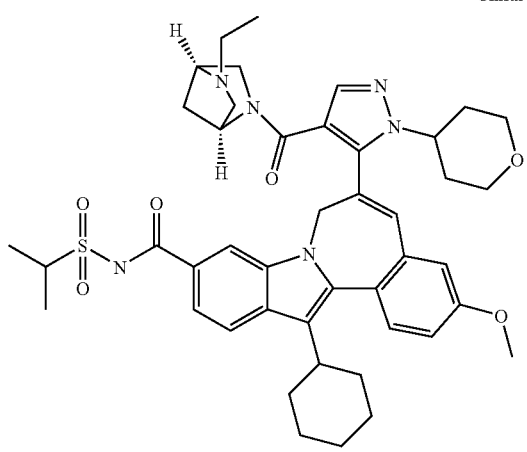
| | B | B |
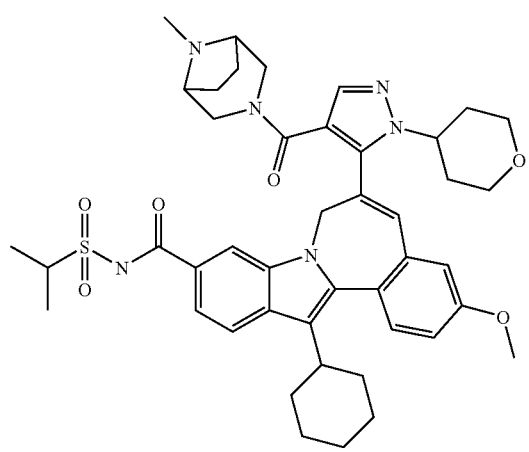
| | B | B |
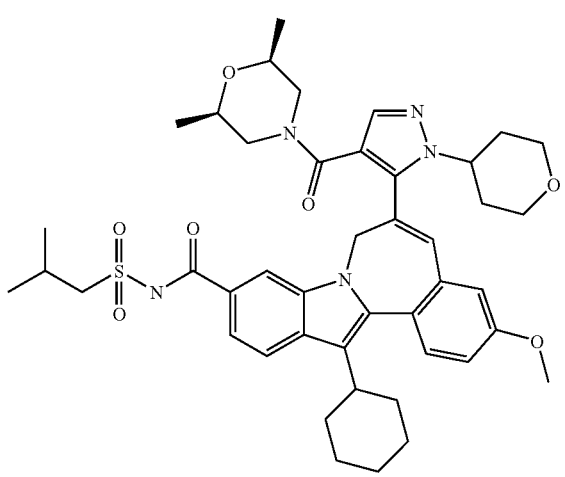

TABLE 1-continued
| Structure | IC$_{50}$ (μM) | EC$_{50}$ (μM) |
| --- | --- | --- |
| 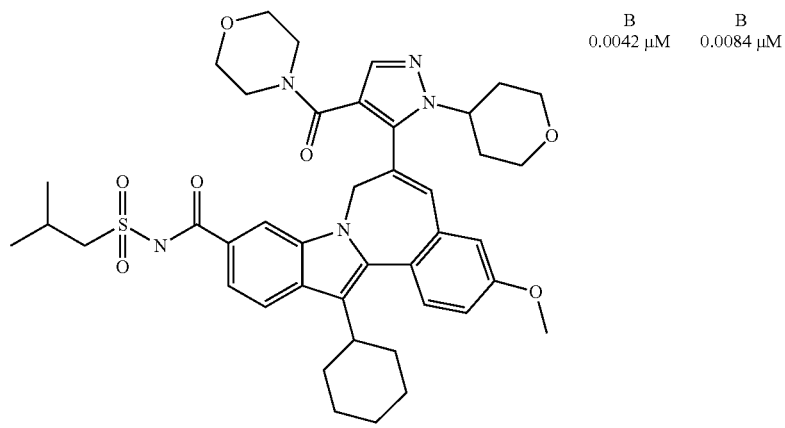 | B<br>0.0042 μM | B<br>0.0084 μM |
| 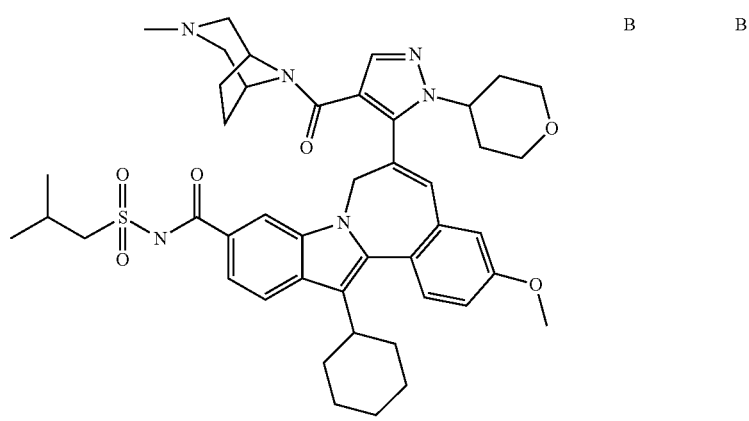 | B | B |
| 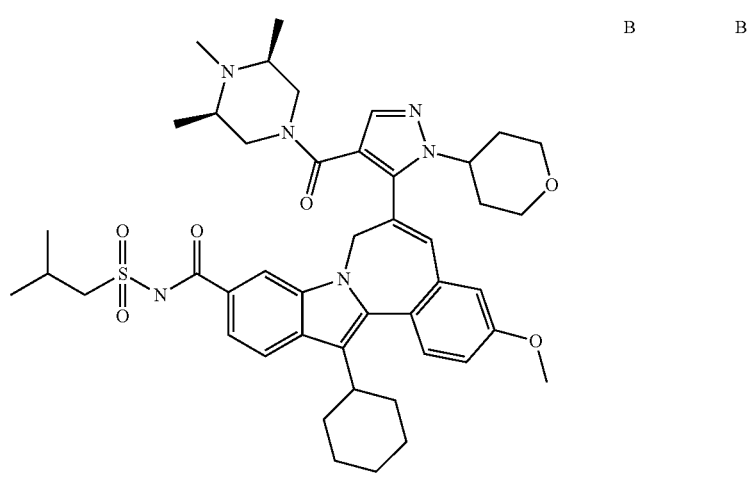 | B | B |

TABLE 1-continued
| Structure | IC$_{50}$ (µM) | EC$_{50}$ (µM) |
|---|---|---|
| 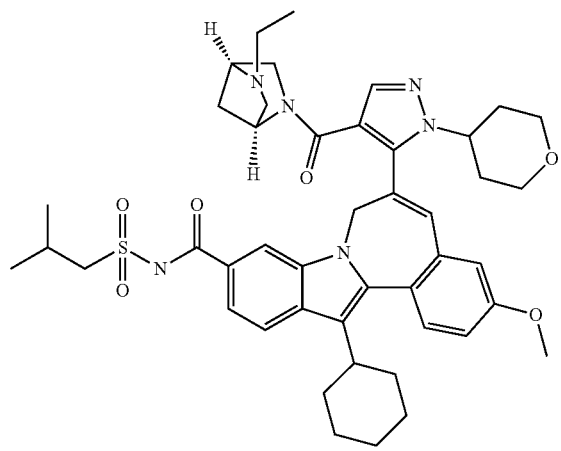 | B | B |
| 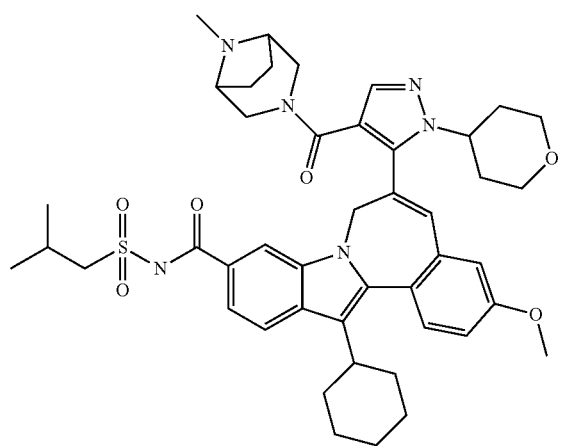 | B | B |
| 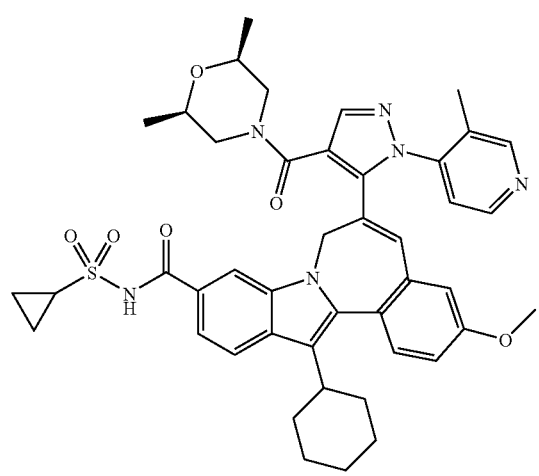 | B | B |

TABLE 1-continued
| Structure | IC$_{50}$ (µM) | EC$_{50}$ (µM) |
|---|---|---|
| 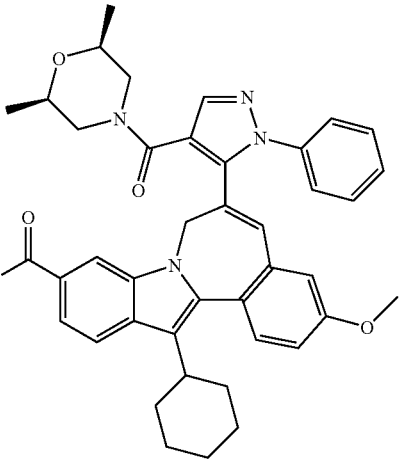 | B | B |
| 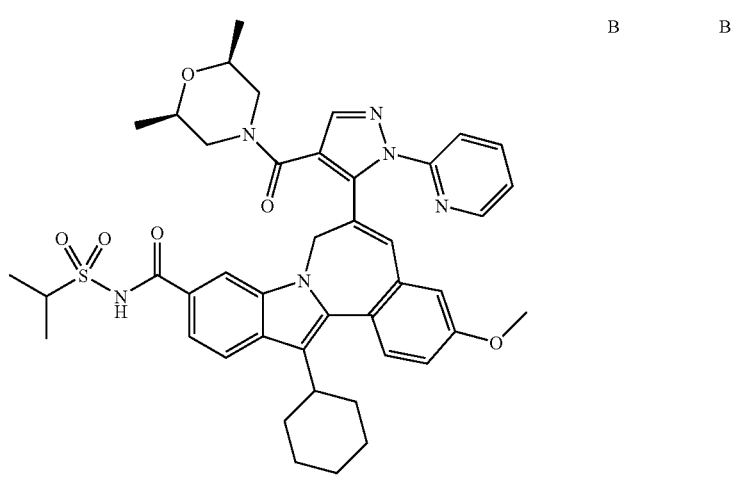 | B | B |
| 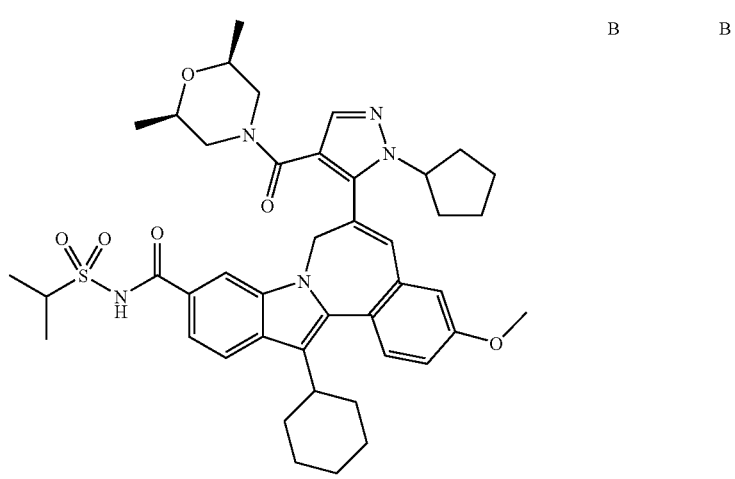 | B | B |

TABLE 1-continued
| Structure | IC$_{50}$ (µM) | EC$_{50}$ (µM) |
|---|---|---|
| 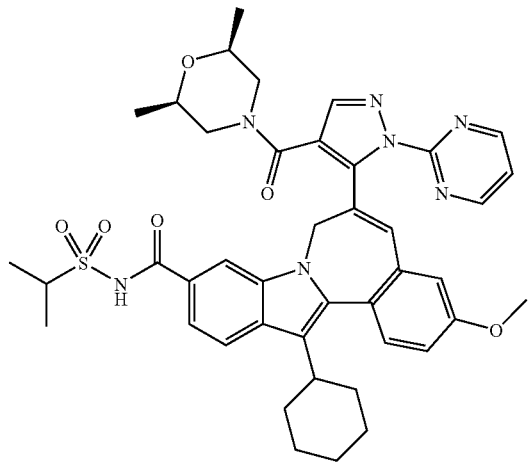 | B | B |
| 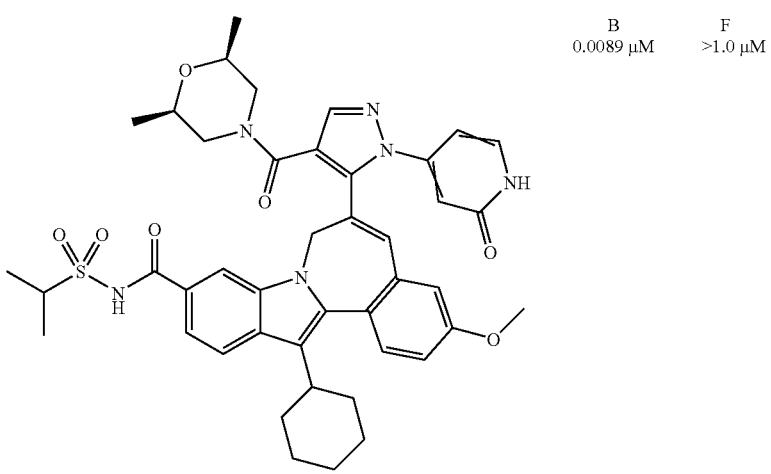 | B<br>0.0089 µM | F<br>>1.0 µM |
| 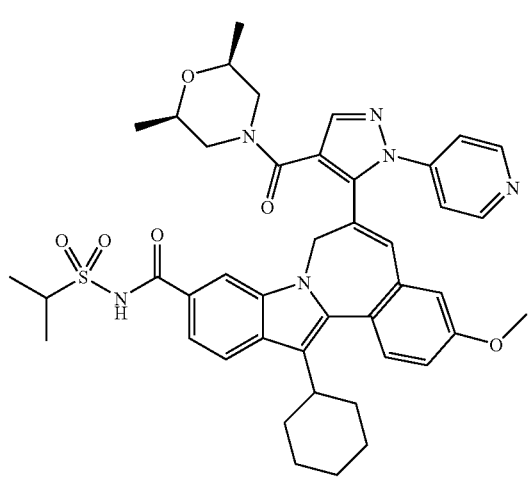 | B | B |

TABLE 1-continued
| Structure | IC$_{50}$ (μM) | EC$_{50}$ (μM) |
|---|---|---|
| 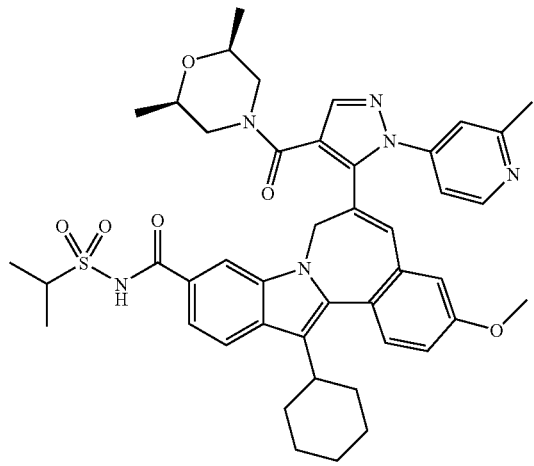 | B | B |
| 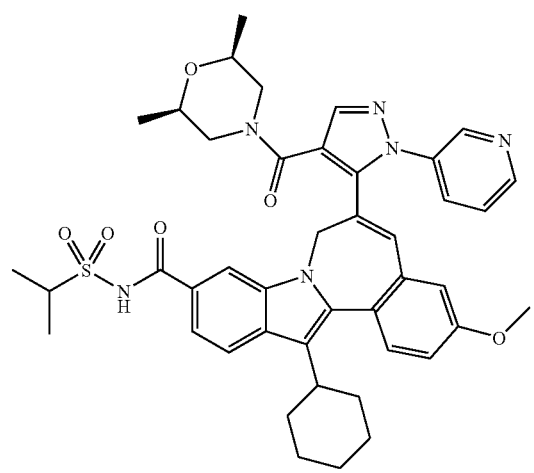 | B | B |
| 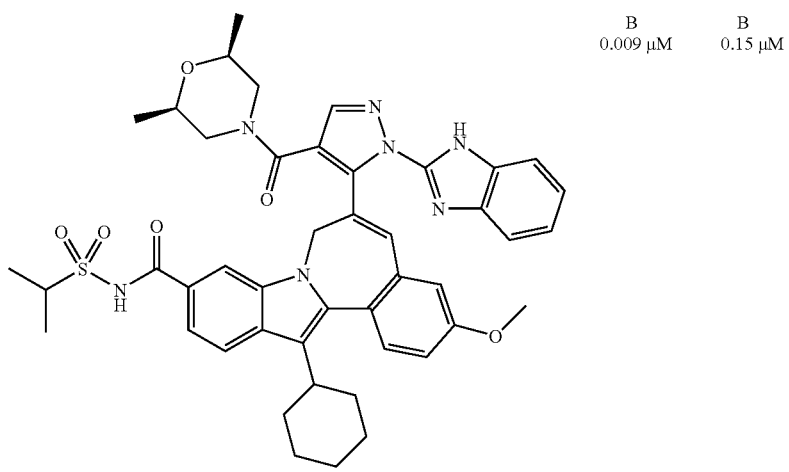 | B<br>0.009 μM | B<br>0.15 μM |

TABLE 1-continued
| Structure | IC$_{50}$ (μM) | EC$_{50}$ (μM) |
|---|---|---|
| 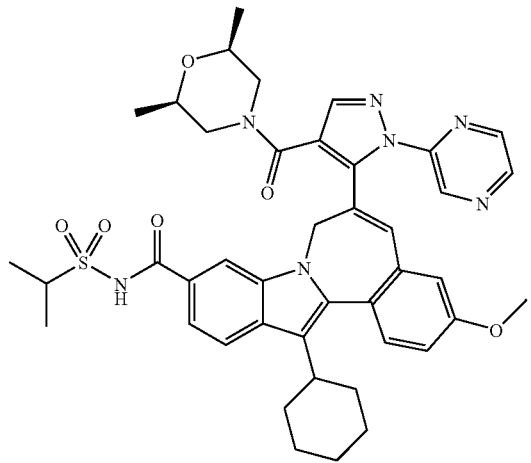 | B | B |
| 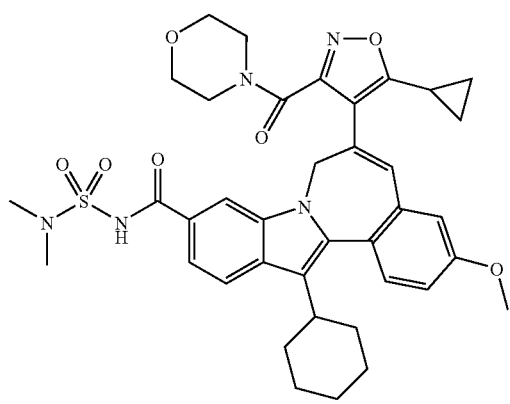 | B | B |
| 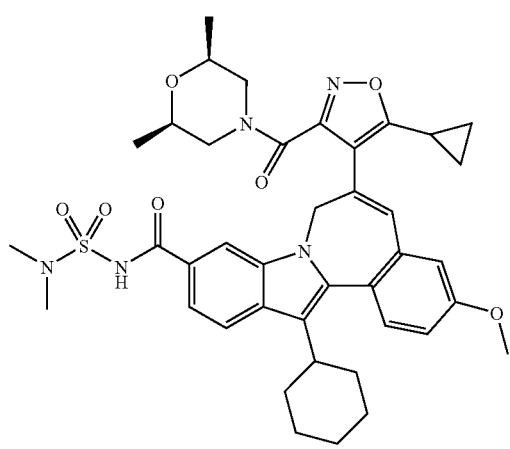 | B | B |

TABLE 1-continued
| Structure | IC$_{50}$ (μM) | EC$_{50}$ (μM) |
|---|---|---|
| Chiral | B | B |
| 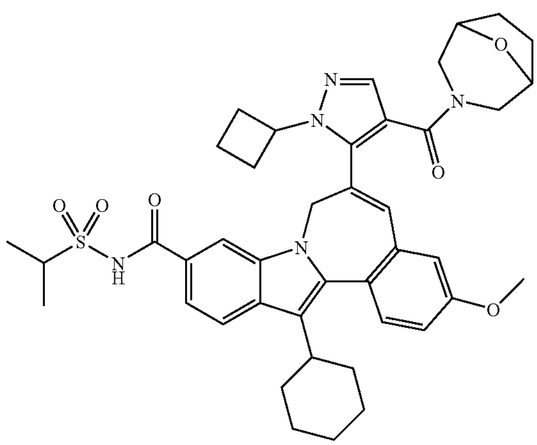 | B 0.0039 μM | B 0.01 μM |
| | B | B |
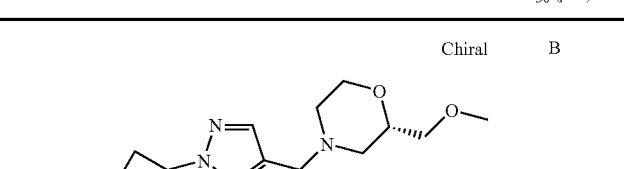

TABLE 1-continued
| Structure | IC$_{50}$ (μM) | EC$_{50}$ (μM) |
|---|---|---|
| 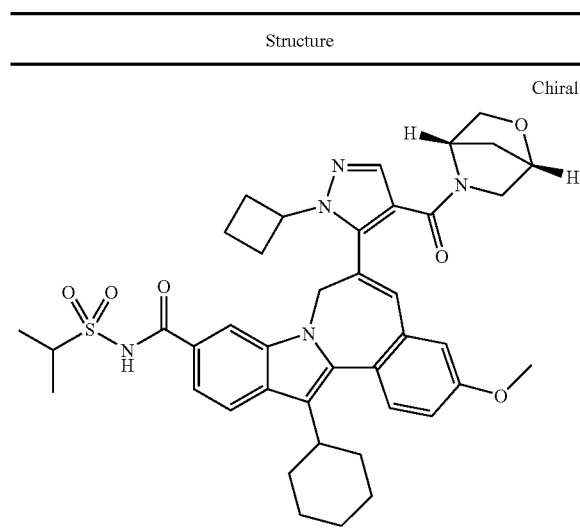 Chiral | B 0.0054 μM | B 0.03 μM |
| 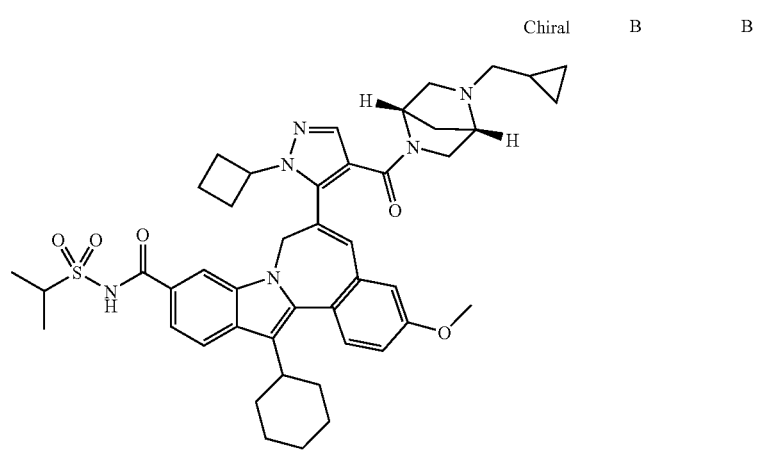 Chiral | B | B |
| 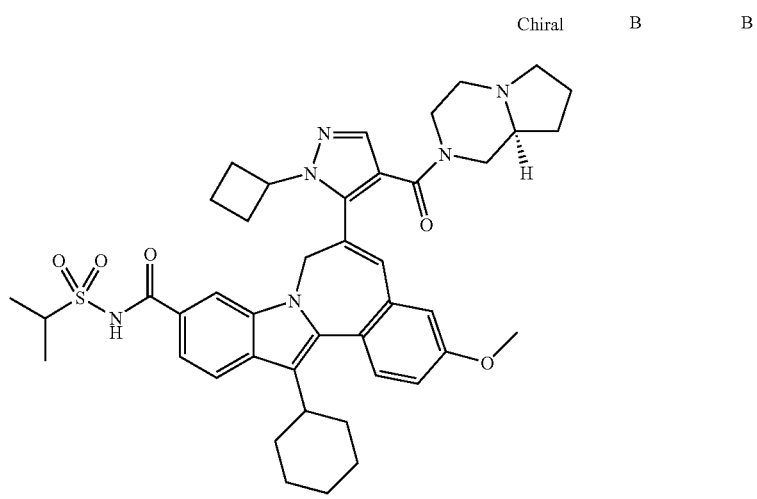 Chiral | B | B |

TABLE 1-continued
| Structure | IC$_{50}$ (μM) | EC$_{50}$ (μM) |
|---|---|---|
| 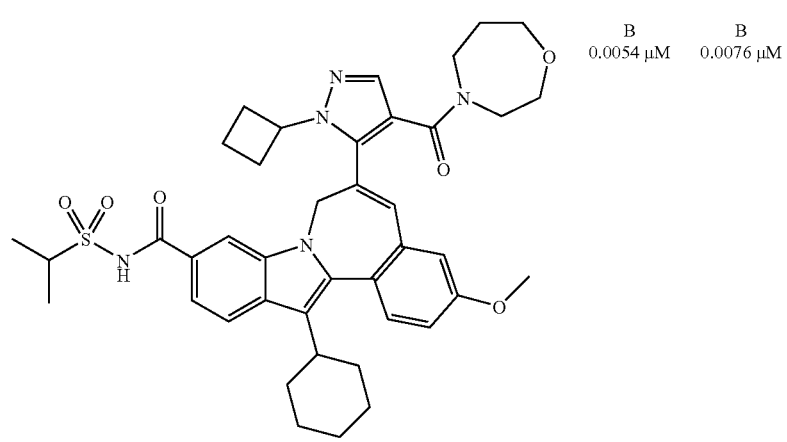 | B | B |
| | B 0.0054 μM | B 0.0076 μM |
| 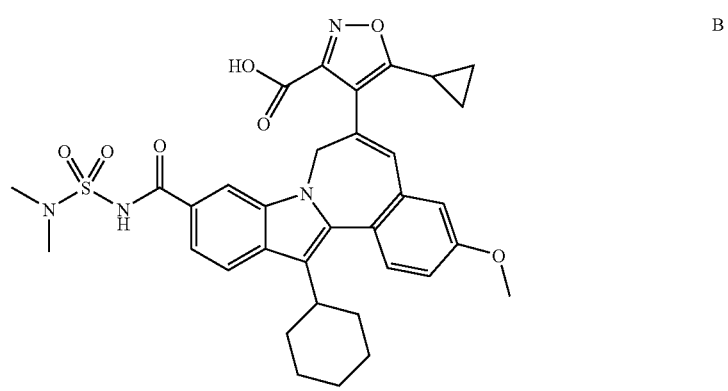 | B | |

TABLE 1-continued
| Structure | IC$_{50}$ (μM) | EC$_{50}$ (μM) |
|---|---|---|
| 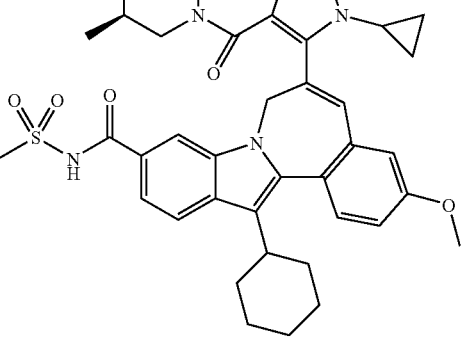 | B | B |
| 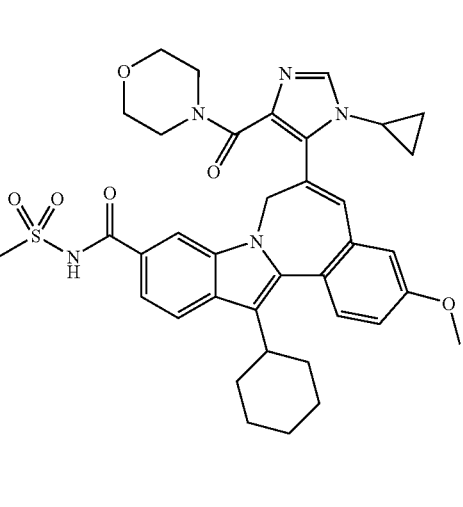 | B | B |
| 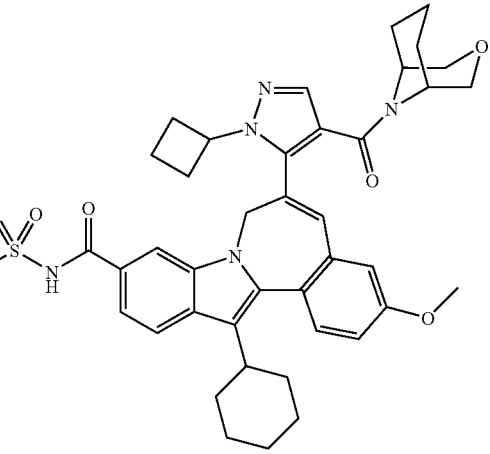 | B | B |

TABLE 1-continued
| Structure | IC$_{50}$ (μM) | EC$_{50}$ (μM) |
|---|---|---|
| 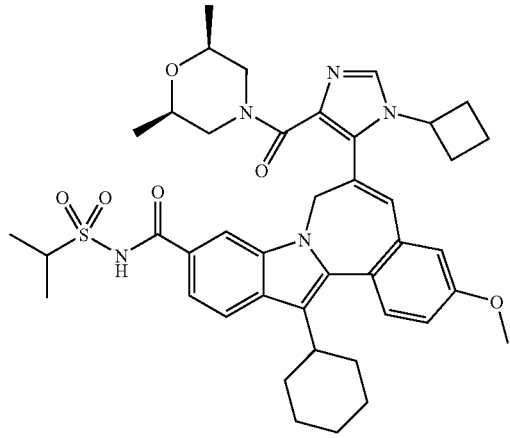 | B | B |
| 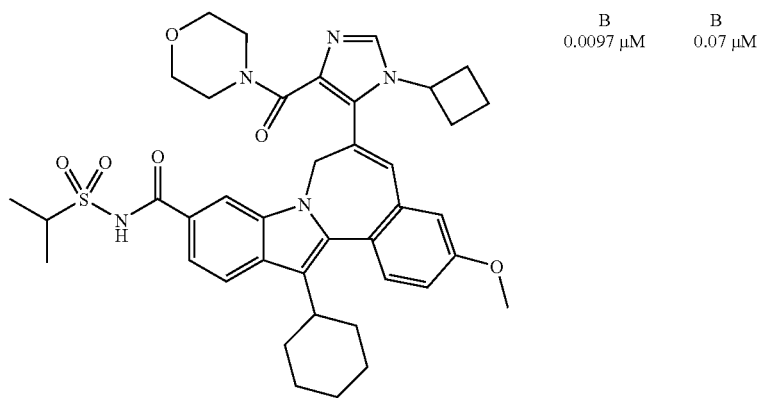 | B<br>0.0097 μM | B<br>0.07 μM |
| 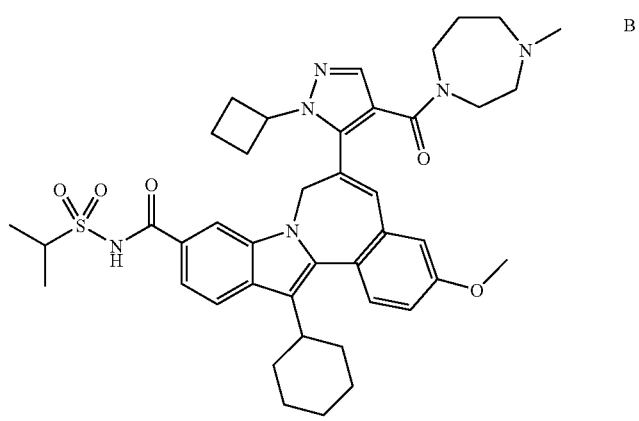 | B | |

TABLE 1-continued
| Structure | IC$_{50}$ (μM) | EC$_{50}$ (μM) |
|---|---|---|
| 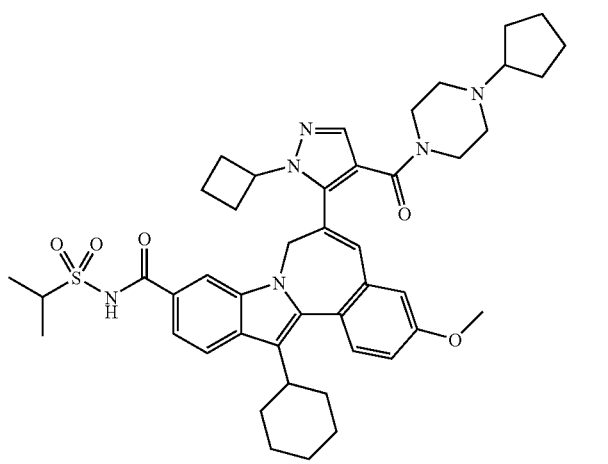 | B | B |
| 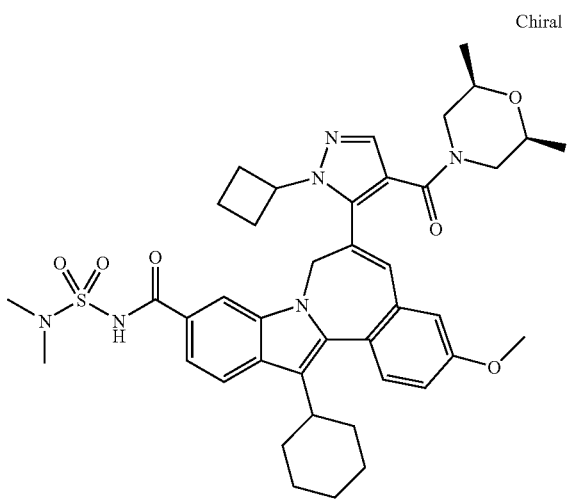 Chiral | B | B |
| 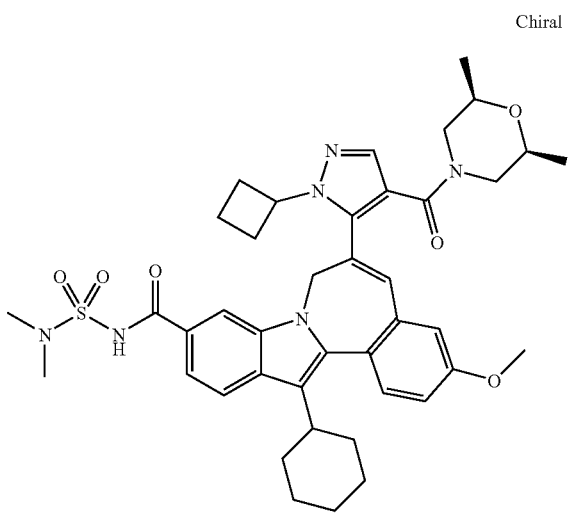 Chiral | B | B |

TABLE 1-continued
| Structure | IC$_{50}$ (µM) | EC$_{50}$ (µM) |
|---|---|---|
| Chiral 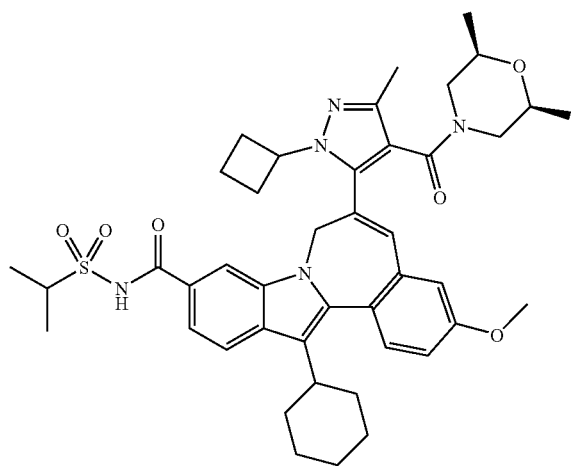 | B<br>0.0064 µM | B<br>0.01 µM |
| Chiral 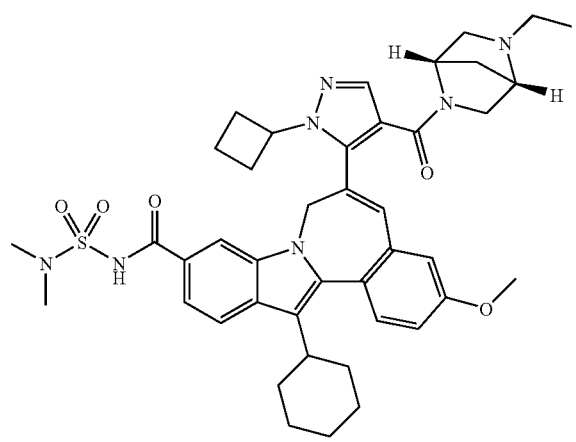 | B | B |
| Chiral 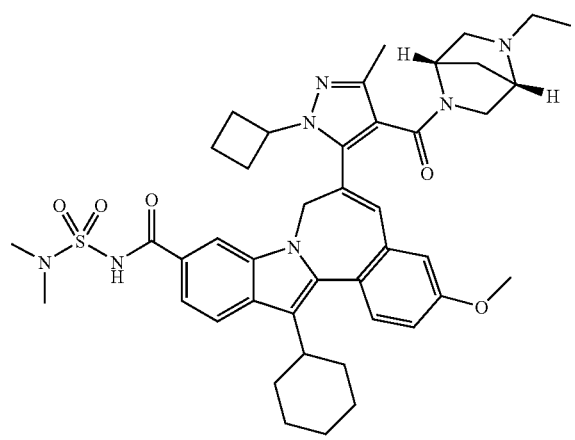 | B<br>0.0034 µM | B<br>0.01 µM |

TABLE 1-continued
| Structure | IC$_{50}$ (μM) | EC$_{50}$ (μM) |
|---|---|---|
| Chiral 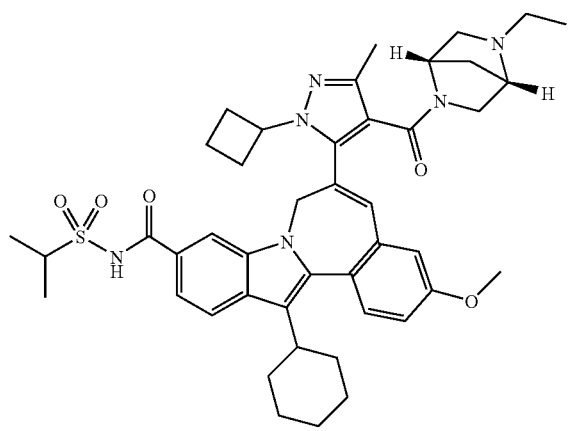 | B | B |
| 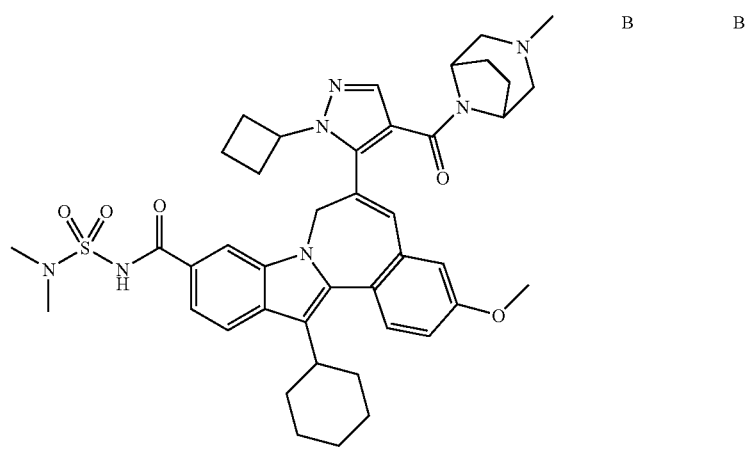 | B | B |
| 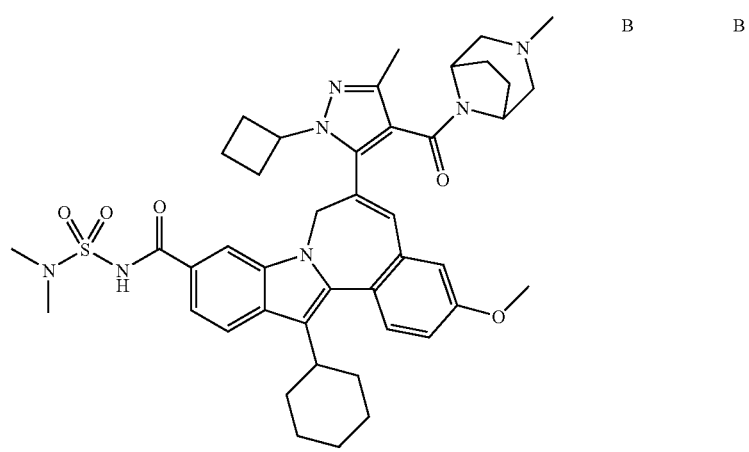 | B | B |

TABLE 1-continued
| Structure | IC$_{50}$ (μM) | EC$_{50}$ (μM) |
|---|---|---|
| 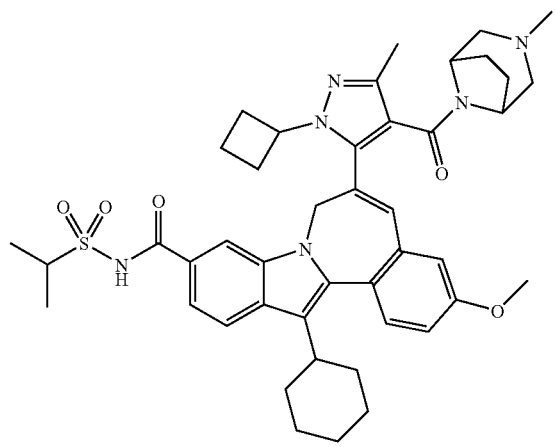 | B | B |
| 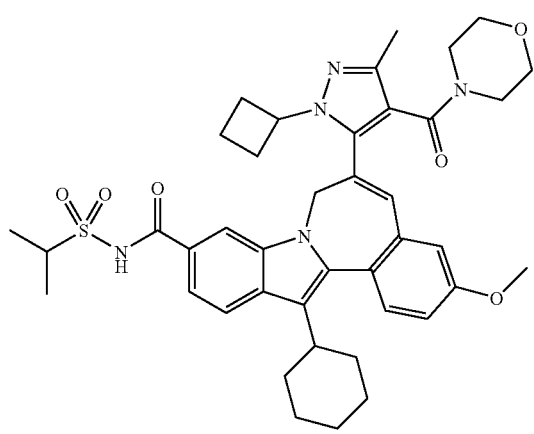 | B | B |
| 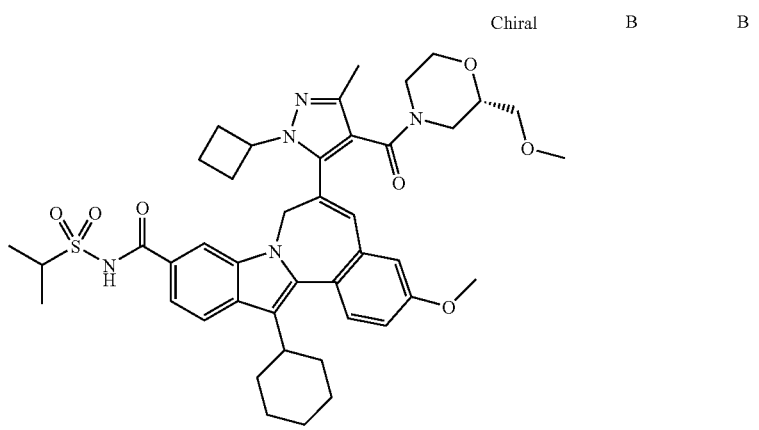 Chiral | B | B |

TABLE 1-continued
| Structure | IC$_{50}$ (µM) | EC$_{50}$ (µM) |
|---|---|---|
| 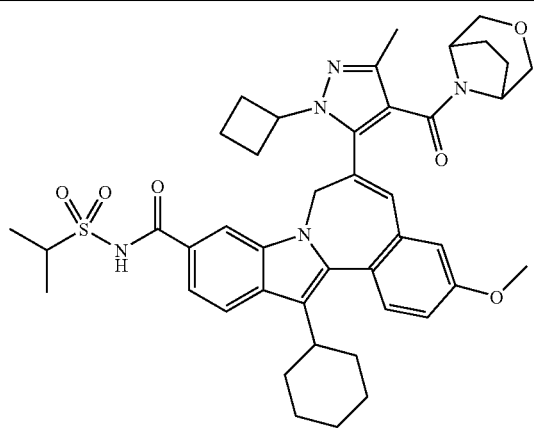 | B | B |
| 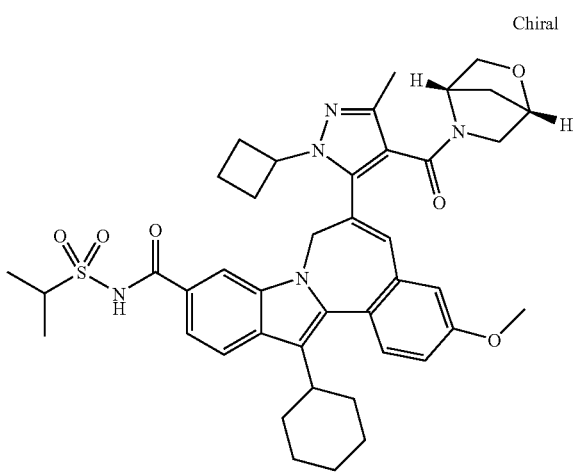 Chiral | B | B |
| 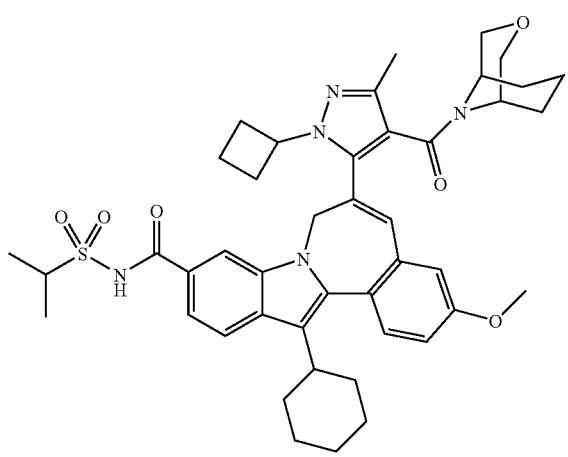 | B | B |

TABLE 1-continued
| Structure | IC$_{50}$ (μM) | EC$_{50}$ (μM) |
|---|---|---|
| 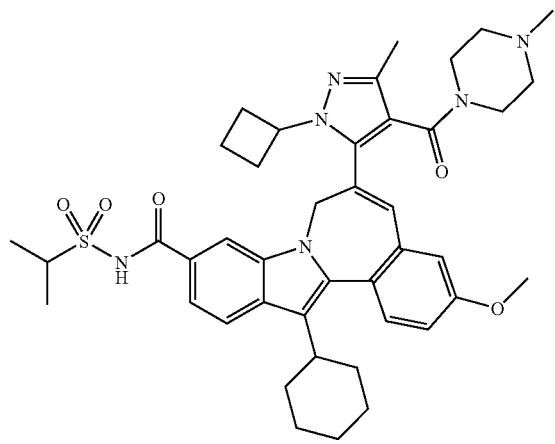 | B | B |
| 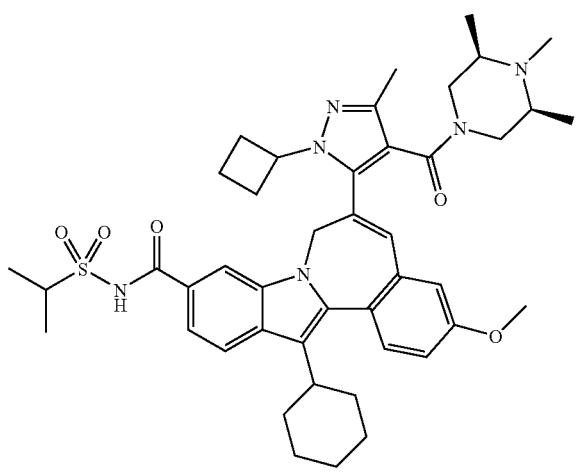 Chiral | B | B |
| 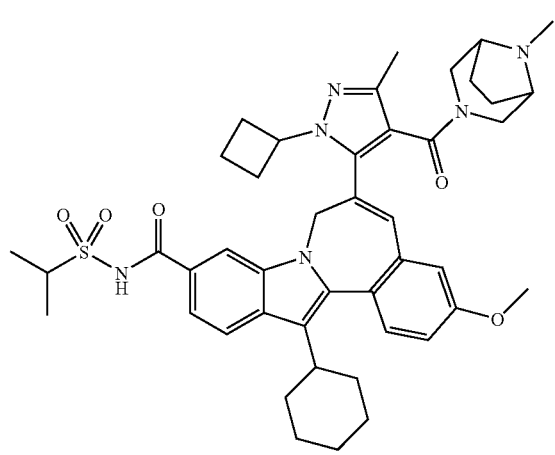 | B | B |

TABLE 1-continued
| Structure | IC$_{50}$ (μM) | EC$_{50}$ (μM) |
|---|---|---|
| Chiral 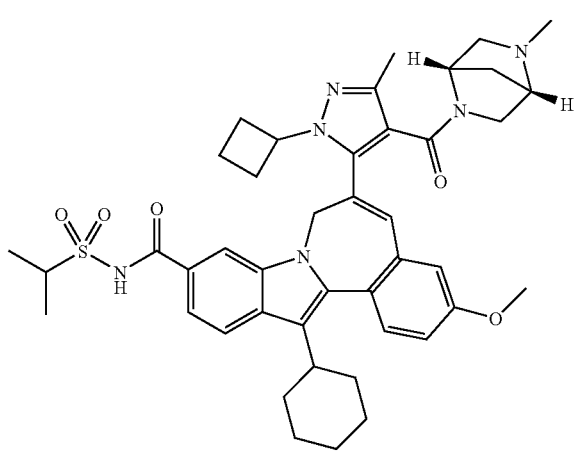 | B | B |
| Chiral 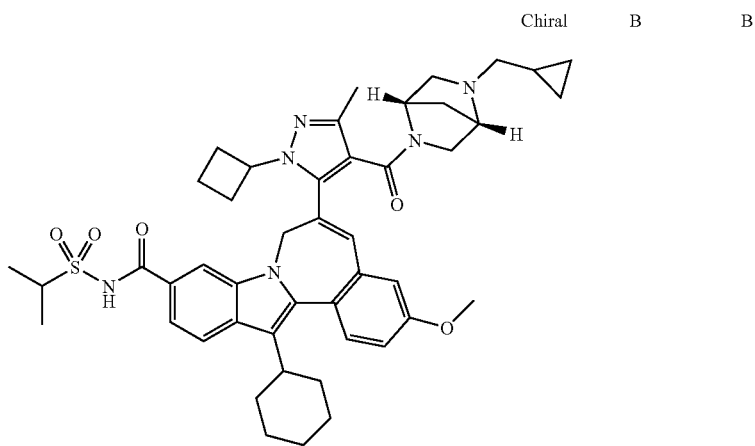 | B | B |
| Chiral 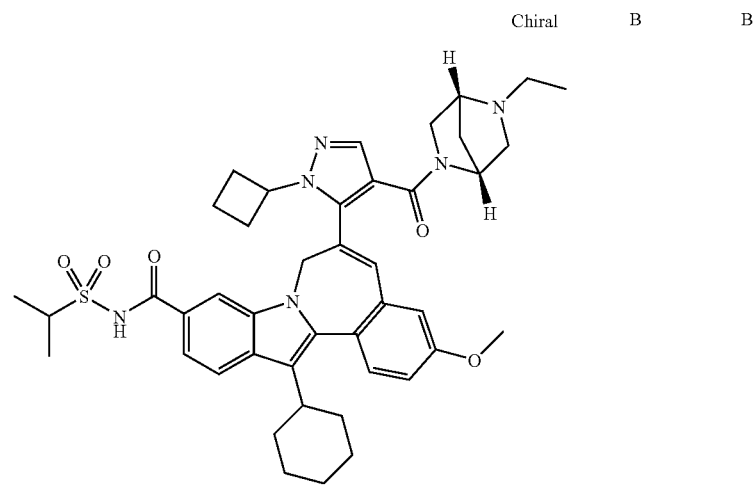 | B | B |

TABLE 1-continued
| Structure | IC$_{50}$ (μM) | EC$_{50}$ (μM) |
|---|---|---|
| 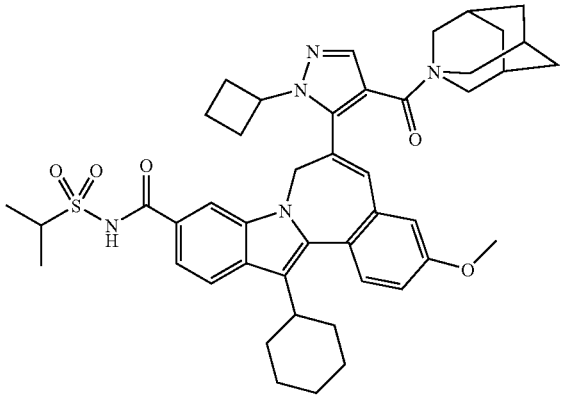 | B | B |
| 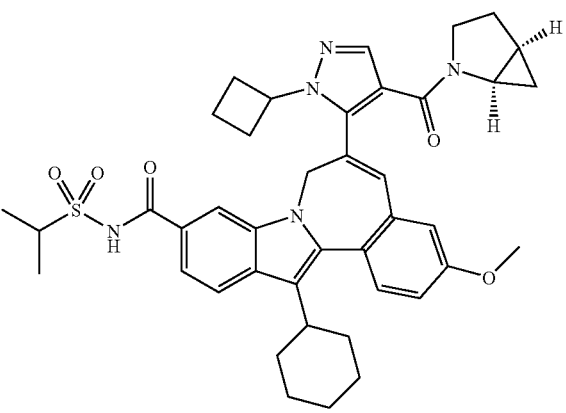 Chiral | B | B |
| 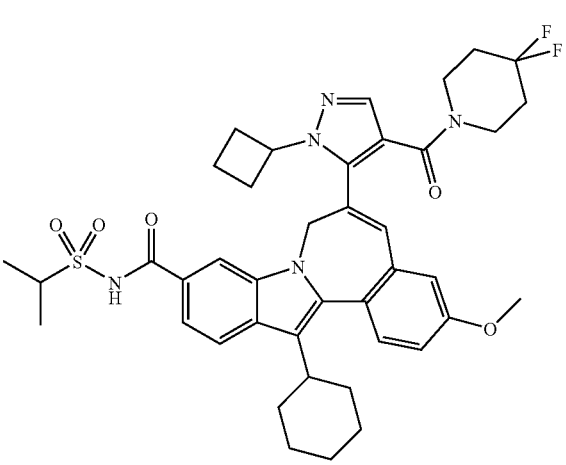 | B | B |

TABLE 1-continued
| Structure | IC$_{50}$ (μM) | EC$_{50}$ (μM) |
|---|---|---|
| 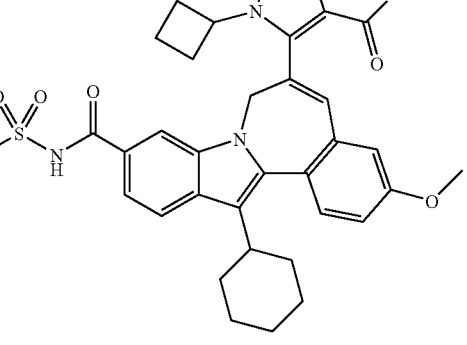 | B | B |
| 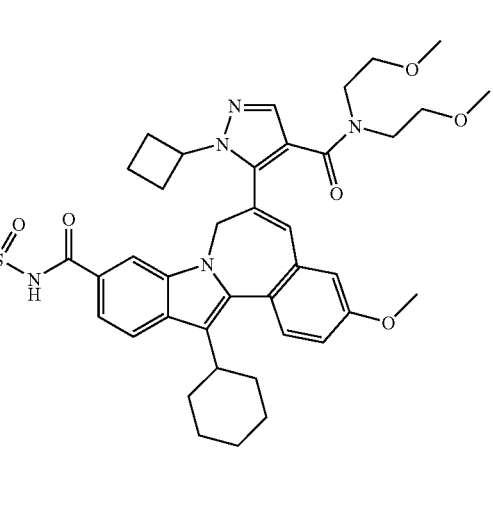 | B | B |
| 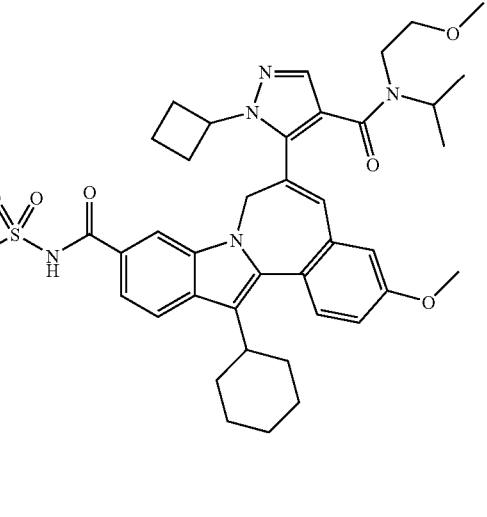 | B | B |

TABLE 1-continued
| Structure | IC$_{50}$ (μM) | EC$_{50}$ (μM) |
|---|---|---|
| 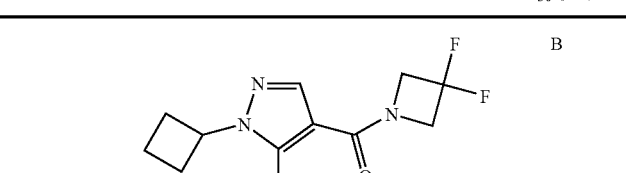 | B | B |
| 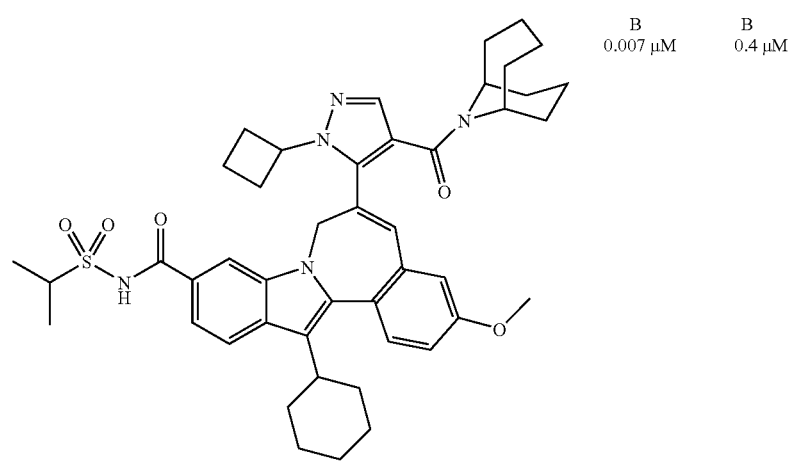 | B 0.007 μM | B 0.4 μM |
| 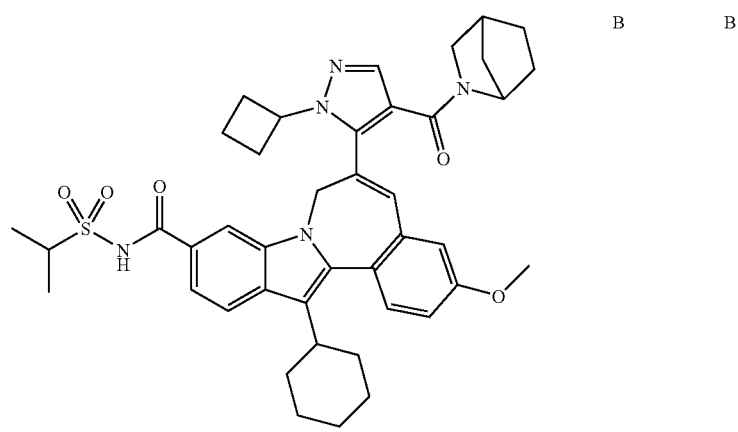 | B | B |

TABLE 1-continued
| Structure | IC$_{50}$ (μM) | EC$_{50}$ (μM) |
|---|---|---|
| 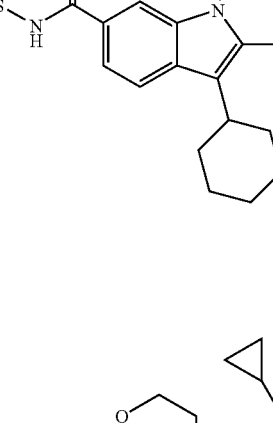 Chiral | B | B |
| 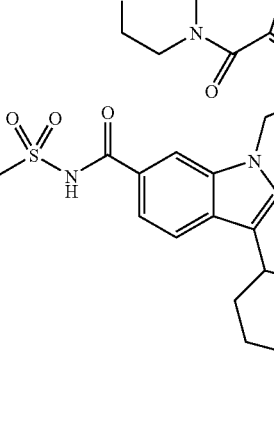 | B 0.0024 μM | B 0.0088 μM |
| 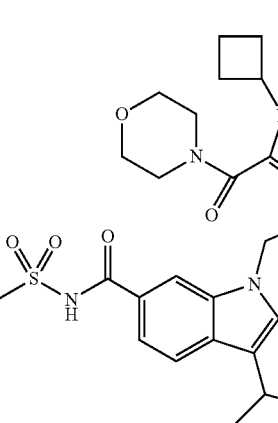 | B 0.0018 μM | B 0.009 μM |

TABLE 1-continued
| Structure | IC$_{50}$ (μM) | EC$_{50}$ (μM) |
|---|---|---|
| 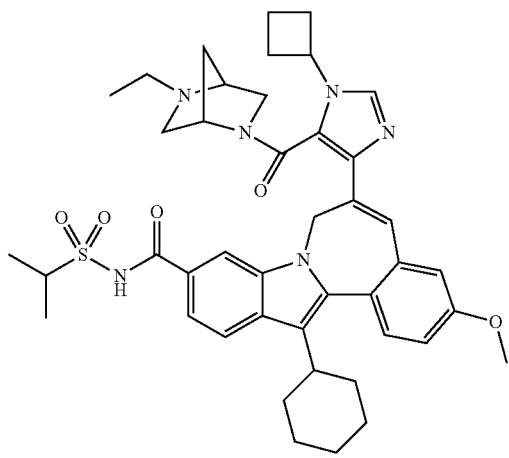 | B | B |
| | B | B |
| 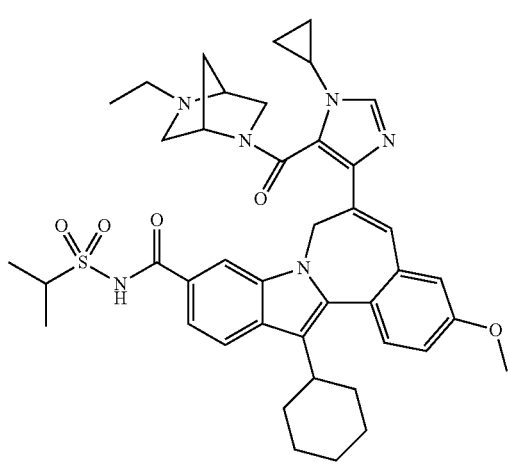 | B | |

TABLE 1-continued
| Structure | IC$_{50}$ (µM) | EC$_{50}$ (µM) |
|---|---|---|
| 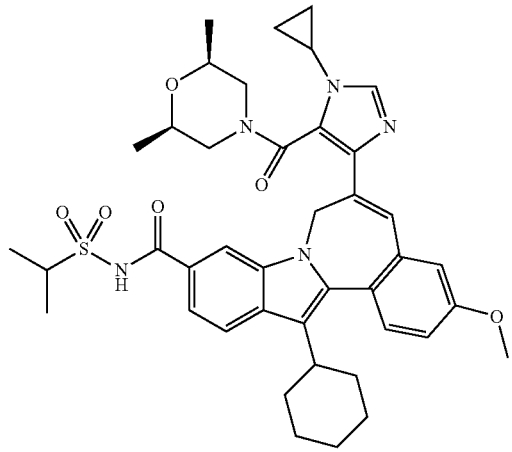 | | B |
| 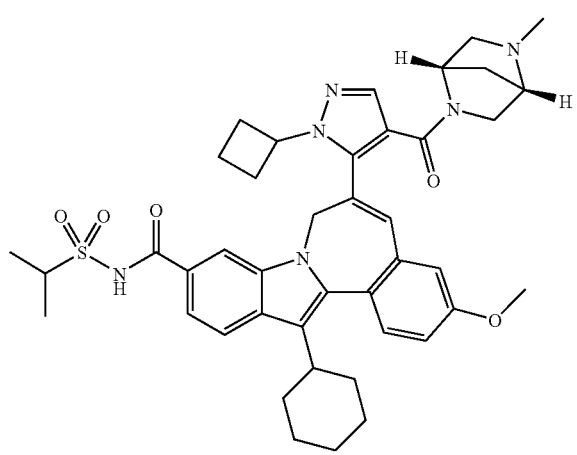 Chiral | B | B |
| | | B |

TABLE 1-continued
| Structure | IC$_{50}$ (μM) | EC$_{50}$ (μM) |
|---|---|---|
| 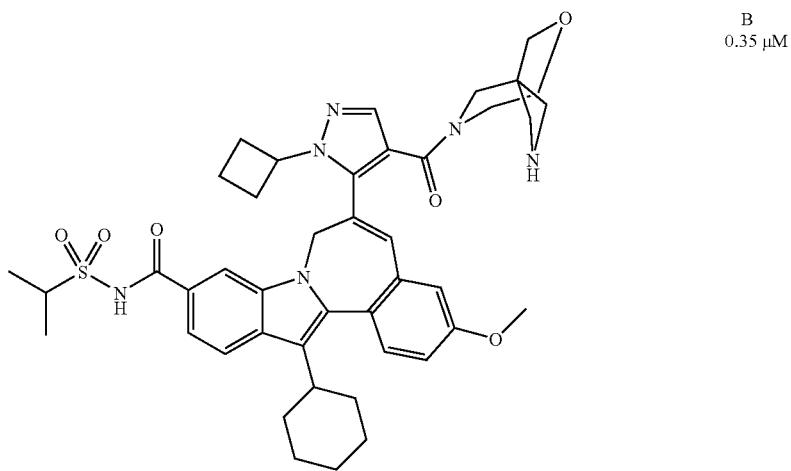 | | B<br>0.35 μM |
| 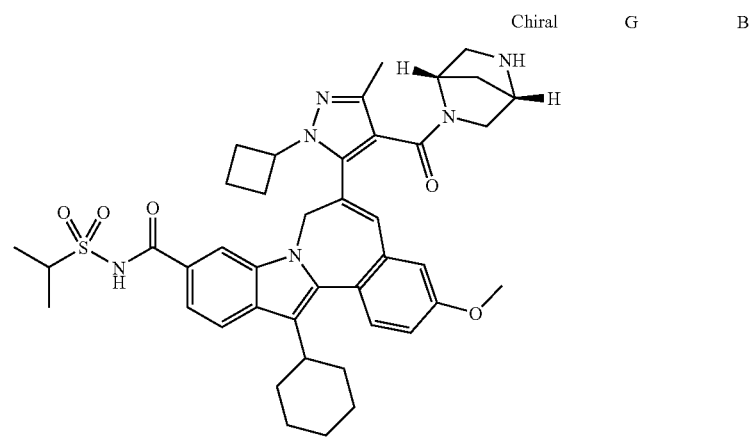 Chiral | G | B |
| 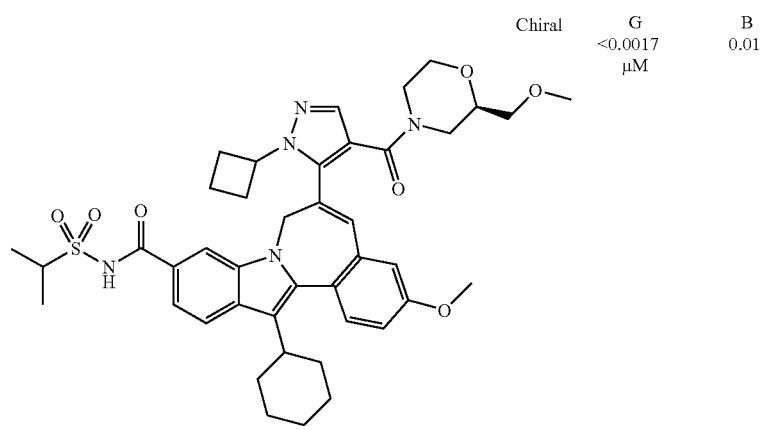 Chiral | G<br><0.0017 μM | B<br>0.01 |

TABLE 1-continued
| Structure | IC$_{50}$ (μM) | EC$_{50}$ (μM) |
|---|---|---|
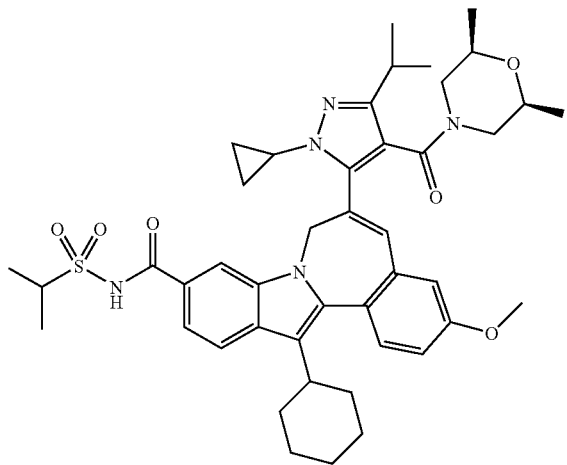
B*
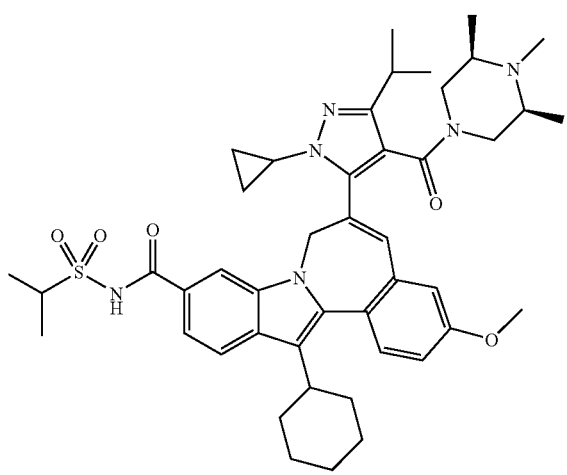
B*
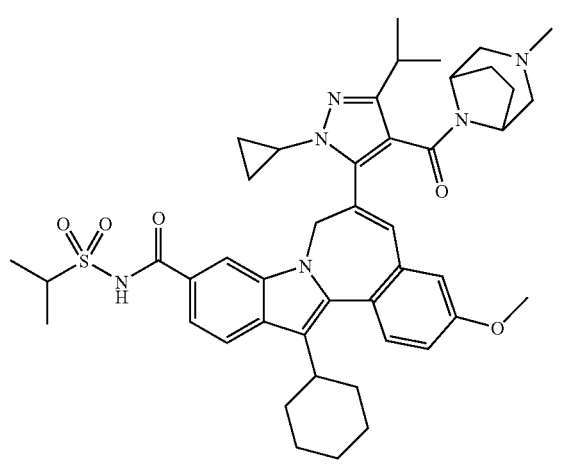
B*

TABLE 1-continued

| Structure | IC$_{50}$ (μM) | EC$_{50}$ (μM) |
|---|---|---|
| | | B* |

A>0.5 μM; B 0.0017 μM-0.5 μM; C<0.02 μM but an exact value was not determined; D>0.04 μM but an exact value was not determined; E<0.07 μM but an exact value was not determined; F>1.0 μM; G<0.0017 μM but an exact value was not determined; * These values were determined similarly but with a 1a replicon. IC$_{50}$ values were determined using the preincubation protocol. EC50 values were determined using one of the methods described in the procedures.

Pharmaceutical Compositions and Methods of Treatment

The compounds demonstrate activity against HCV NS5B and can be useful in treating HCV and HCV infection. Therefore, another aspect of the invention is a composition comprising a compound of formula I, or a pharmaceutically acceptable salt thereof, and a pharmaceutically acceptable carrier.

Another aspect of the invention is the use of a compound of formula I in the manufacture of a medicament for the treatment of hepatitis C.

Another aspect of the invention is a composition further comprising a compound having anti-HCV activity.

Another aspect of the invention is a composition where the compound having anti-HCV activity is an interferon. Another aspect of the invention is where the interferon is selected from interferon alpha 2B, pegylated interferon alpha, consensus interferon, interferon alpha 2A, and lymphoblastoid interferon tau.

Another aspect of the invention is a composition where the compound having anti-HCV activity is a cyclosporin. Another aspect of the invention is where the cyclosporin is cyclosporin A.

Another aspect of the invention is a composition where the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is a composition where the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a composition comprising a compound of formula I, or a pharmaceutically acceptable salt thereof, a pharmaceutically acceptable carrier, and an interferon and ribavirin.

Another aspect of the invention is a method of inhibiting the function of the HCV replicon comprising contacting the HCV replicon with a compound of formula I or a pharmaceutically acceptable salt thereof.

Another aspect of the invention is a method of inhibiting the function of the HCV NS5B protein comprising contacting the HCV NS5B protein with a compound of formula I or a pharmaceutically acceptable salt thereof.

Another aspect of the invention is a method of treating an HCV infection in a patient comprising administering to the patient a therapeutically effective amount of a compound of formula I or a pharmaceutically acceptable salt thereof. In another embodiment the compound is effective to inhibit the function of the HCV replicon. In another embodiment the compound is effective to inhibit the function of the HCV NS5B protein.

Another aspect of the invention is a method of treating an HCV infection in a patient comprising administering to the patient a therapeutically effective amount of a compound of formula I, or a pharmaceutically acceptable salt thereof, in conjunction with (prior to, after, or concurrently) another compound having anti-HCV activity.

Another aspect of the invention is the method where the other compound having anti-HCV activity is an interferon.

Another aspect of the invention is the method where the interferon is selected from interferon alpha 2B, pegylated interferon alpha, consensus interferon, interferon alpha 2A, and lymphoblastoid interferon tau.

Another aspect of the invention is the method where the other compound having anti-HCV activity is a cyclosporin.

Another aspect of the invention is the method where the cyclosporin is cyclosporin A.

Another aspect of the invention is the method where the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is the method where the other compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is the method where the other compound having anti-HCV activity is effective to inhibit the function of target in the HCV life cycle other than the HCV NS5B protein.

"Therapeutically effective" means the amount of agent required to provide a meaningful patient benefit as understood by practitioners in the field of hepatitis and HCV infection. A therapeutically effective amount is that which is needed to provide a meaningful patient benefit.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including for example capsules, tablets, lozenges, and powders as well as liquid suspensions, syrups, elixirs, and solutions. Compositions are made using common formulation techniques, and conventional excipients (such as binding and wetting agents) and vehicles (such as water and alcohols) are generally used for compositions. See, for example, *Remington's Pharmaceutical Sciences,* 17th edition, Mack Publishing Company, Easton, Pa. (1985).

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgment.

The invention also encompasses methods where the compound is given in combination therapy. That is, the compound can be used in conjunction with, but separately from, other agents useful in treating hepatitis and HCV infection. In these combination methods, the compound will generally be given in a daily dose of 1-100 mg/kg body weight daily in conjunction with other agents. The other agents generally will be given in the amounts used therapeutically. The specific dosing regime, however, will be determined by a physician using sound medical judgment.

Some examples of compounds suitable for compositions and methods are listed in Table 2.

TABLE 2

| Brand Name | Type of Inhibitor or Target | Source Company |
|---|---|---|
| Omega IFN | IFN-ω | Intarcia Therapeutics |
| BILN-2061 | serine protease inhibitor | Boehringer Ingelheim Pharma KG, Ingelheim, Germany |
| Summetrel | antiviral | Endo Pharmaceuticals Holdings Inc., Chadds Ford, PA |
| Roferon A | IFN-α2a | F. Hoffmann-La Roche LTD, Basel, Switzerland |
| Pegasys | PEGylated IFN-α2a | F. Hoffmann-La Roche LTD, Basel, Switzerland |
| Pegasys and Ribavirin | PEGylated IFN-α2a/ribavirin | F. Hoffmann-La Roche LTD, Basel, Switzerland |
| CELLCEPT ® | HCV IgG immunosuppressant | F. Hoffmann-La Roche LTD, Basel, Switzerland |
| Wellferon | lymphoblastoid IFN-αn1 | GlaxoSmithKline plc, Uxbridge, UK |
| Albuferon-α | albumin IFN-α2b | Human Genome Sciences Inc., Rockville, MD |
| Levovirin | ribavirin | ICN Pharmaceuticals, Costa Mesa, CA |
| IDN-6556 | caspase inhibitor | Idun Pharmaceuticals Inc., San Diego, CA |
| IP-501 | antifibrotic | Indevus Pharmaceuticals Inc., Lexington, MA |
| Actimmune | INF-γ | InterMune Inc., Brisbane, CA |
| Infergen A | IFN alfacon-1 | InterMune Pharmaceuticals Inc., Brisbane, CA |

TABLE 2-continued

| Brand Name | Type of Inhibitor or Target | Source Company |
|---|---|---|
| ISIS 14803 | antisense | ISIS Pharmaceuticals Inc, Carlsbad, CA/Elan Pharmaceuticals Inc., New York, NY |
| JTK-003 | RdRp inhibitor | Japan Tobacco Inc., Tokyo, Japan |
| Pegasys and Ceplene | PEGylated IFN-α2a/immune modulator | Maxim Pharmaceuticals Inc., San Diego, CA |
| Ceplene | immune modulator | Maxim Pharmaceuticals Inc., San Diego, CA |
| Civacir | HCV IgG immunosuppressant | Nabi Biopharmaceuticals Inc., Boca Raton, FL |
| Intron A and Zadaxin | IFN-α2b/α1-thymosin | RegeneRx Biopharmaceuticals Inc., Bethesda, MD/ SciClone Pharmaceuticals Inc, San Mateo, CA |
| Levovirin | IMPDH inhibitor | Ribapharm Inc., Costa Mesa, CA |
| Viramidine | Ribavirin Prodrug | Ribapharm Inc., Costa Mesa, CA |
| Heptazyme | ribozyme | Ribozyme Pharmaceuticals Inc., Boulder, CO |
| Intron A | IFN-α2b | Schering-Plough Corporation, Kenilworth, NJ |
| PEG-Intron | PEGylated IFN-α2b | Schering-Plough Corporation, Kenilworth, NJ |
| Rebetron | IFN-α2b/ribavirin | Schering-Plough Corporation, Kenilworth, NJ |
| Ribavirin | ribavirin | Schering-Plough Corporation, Kenilworth, NJ |
| PEG-Intron/Ribavirin | PEGylated IFN-α2b/ribavirin | Schering-Plough Corporation, Kenilworth, NJ |
| Zadazim | Immune modulator | SciClone Pharmaceuticals Inc., San Mateo, CA |
| Rebif | IFN-β1a | Serono, Geneva, Switzerland |
| IFN-β and EMZ701 | IFN-β and EMZ701 | Transition Therapeutics Inc., Ontario, Canada |
| Batabulin (T67) | β-tubulin inhibitor | Tularik Inc., South San Francisco, CA |
| Merimepodib (VX-497) | IMPDH inhibitor | Vertex Pharmaceuticals Inc., Cambridge, MA |
| Telaprevir (VX-950, LY-570310) | NS3 serine protease inhibitor | Vertex Pharmaceuticals Inc., Cambridge, MA/ Eli Lilly and Co. Inc., Indianapolis, IN |
| Omniferon | natural IFN-α | Viragen Inc., Plantation, FL |
| XTL-6865 (XTL-002) | monoclonal antibody | XTL Biopharmaceuticals Ltd., Rehovot, Israel |
| HCV-796 | NS5B Replicase Inhibitor | Wyeth/Viropharma |
| NM-283 | NS5B Replicase Inhibitor | Idenix/Novartis |
| GL-59728 | NS5B Replicase Inhibitor | Gene Labs/Novartis |
| GL-60667 | NS5B Replicase Inhibitor | Gene Labs/Novartis |
| 2'C MeA | NS5B Replicase Inhibitor | Gilead |
| PSI 6130 | NS5B Replicase Inhibitor | Roche |
| R1626 | NS5B Replicase Inhibitor | Roche |
| SCH 503034 | serine protease inhibitor | Schering-Plough |
| NIM811 | Cyclophilin Inhibitor | Novartis |
| Suvus | Methylene blue | Bioenvision |
| Multiferon | Long lasting IFN | Viragen/Valentis |
| Actilon (CPG10101) | TLR9 agonist | Coley |
| Interferon-β | Interferon-β-1a | Serono |
| Zadaxin | Immunomodulator | SciClone |
| Pyrazolopyrimidine compounds and salts From WO 2005/047288 26 May 2005 | HCV Inhibitors | Arrow Therapeutics Ltd. |
| 2'C Methyl adenosine | NS5B Replicase Inhibitor | Merck |
| GS-9132 (ACH-806) | HCV Inhibitor | Achillion/Gilead |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:

1. A compound of formula I

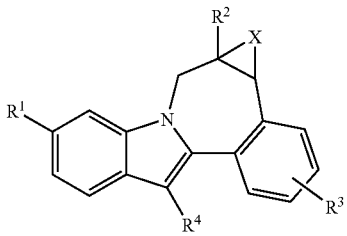

where:
- $R^1$ is $CO_2R^5$ or $CONR^6R^7$;
- $R^2$ is furanyl, pyrrolyl, thienyl, pyrazolyl, isoxazolyl, isothiazolyl, imidazolyl, oxazolyl, thiazolyl, oxadiazolyl, triazolyl, or tetrazolyl; and $R^2$ is substituted with 1 substituent selected from the group consisting of cycloalkyl, tetrahydrofuranyl, tetrahydropyranyl, phenyl, pyrimidinyl, pyrazinyl, pyridinonyl, benzimidazolyl, piperidinyl substituted with 0-1 alkyl substituents, and pyridinyl substituted with 0-1 alkyl substituents; and $R^2$ is substituted with 1 substituent selected from $CO_2R^5$, $CON(R^{12})_2$, and $COR^{13}$; and $R^2$ is substituted with 0-1 substituents selected from oxo, amino, alkyl, and haloalkyl;
- $R^3$ is hydrogen, halo, alkyl, alkenyl, hydroxy, benzyloxy, or alkoxy;
- $R^4$ is cycloalkyl;
- $R^5$ is hydrogen or alkyl;
- $R^6$ is hydrogen, alkyl, alkylSO$_2$, cycloalkylSO$_2$, haloalkylSO$_2$, $(R^9)(R^{10})NSO_2$, or $(R^{11})SO_2$;
- $R^7$ is hydrogen or alkyl;
- $R^8$ is hydrogen, alkyl, cycloalkyl, (cycloalkyl)alkyl, alkylcarbonyl, cycloalkylcarbonyl, haloalkylcarbonyl, alkoxycarbonyl, alkylSO$_2$, cycloalkylSO$_2$, haloalkylSO$_2$, aminocarbonyl, (alkylamino)carbonyl, (dialkylamino)carbonyl, benzyl, benzyloxycarbonyl, or pyridinyl;
- $R^9$ is hydrogen or alkyl;
- $R^{10}$ is hydrogen or alkyl;
- $R^{11}$ is azetidinyl, pyrrolidinyl, piperidinyl, piperazinyl, morpholinyl, thiomorpholinyl, homopiperidinyl, homopiperazinyl, or homomorpholinyl, and is substituted with 0-1 alkyl substituents;
- $R^{12}$ is hydrogen, alkyl, alkoxyalkyl, aminoalkyl, (alkylamino)alkyl, (dialkylamino)alkyl, or $(R^{11})$alkyl;
- $R^{13}$ is azetidinyl, pyrrolidinyl, piperidinyl, piperazinyl, morpholinyl, thiomorpholinyl, homopiperidinyl, homopiperazinyl, or homomorpholinyl, and is substituted with 0-3 substituents selected from halo, alkyl, cycloalkyl, alkoxyalkyl, amino, alkylamino, dialkylamino, $R^{11}$, aminoalkyl, (alkylamino)alkyl, (dialkylamino)alkyl, $(R^{11})$alkyl, or $CO_2R^5$;

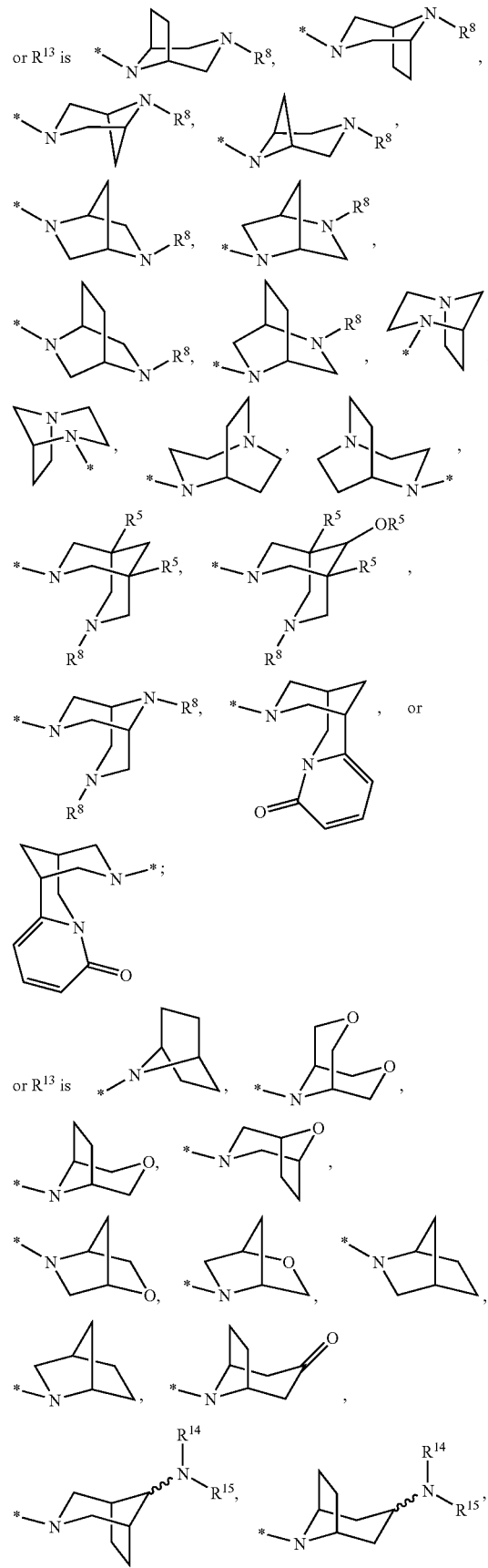

-continued

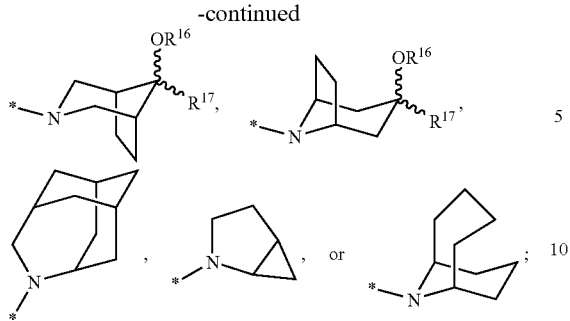

or $R^{13}$ is a [4.3.0] or [3.3.0] bicyclic diamine attached to the carbonyl through one nitrogen, and is substituted with 0-2 $R^8$ substituents;

or $R^{13}$ is

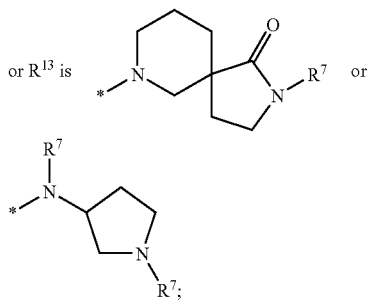

$R^{14}$ is hydrogen, alkyl, cycloalkyl, (cycloalkyl)alkyl, aminoalkyl, (alkylamino)alkyl, (dialkylamino)alkyl, or benzyl;
$R^{15}$ is hydrogen, alkyl, cycloalkyl, (cycloalkyl)alkyl, aminoalkyl, (alkylamino)alkyl, (dialkylamino)alkyl, or benzyl;
or $NR^{14}R^{15}$ taken together is azetidinyl, pyrrolidinyl, piperidinyl, piperazinyl, N-(alkyl)piperazinyl, morpholinyl, thiomorpholinyl, homopiperidinyl, or homomorpholinyl;
$R^{16}$ is hydrogen or alkyl;
$R^{17}$ is hydrogen, alkyl, or cycloalkyl; and
X is methylene, a bond, or absent;
or a pharmaceutically acceptable salt thereof.
2. A compound of claim 1 where:
$R^1$ is $CO_2R^5$ or $CONR^6R^7$;
$R^2$ is pyrazolyl, isoxazolyl, or imidazolyl, and is substituted with 1 substituent selected from the group consisting of cycloalkyl, tetrahydropyranyl, phenyl, pyrimidinyl, pyrazinyl, pyridinonyl, benzimidazolyl, piperidinyl substituted with 1 alkyl substituent, and pyridinyl substituted with 0-1 alkyl substituents; and $R^2$ is substituted with 1 substituent selected from $CO_2R^5$, $CON(R^{12})_2$, and $COR^{13}$; and $R^2$ is substituted with 0-1 alkyl substituents;
$R^3$ is alkoxy;
$R^4$ is cycloalkyl;
$R^5$ is hydrogen or alkyl;
$R^6$ is alkylSO$_2$, cycloalkylSO$_2$, or $(R^9)(R^{10})NSO_2$;
$R^7$ is hydrogen;
$R^8$ is hydrogen, alkyl, or (cycloalkyl)alkyl;
$R^{12}$ is alkyl or alkoxyalkyl;
$R^{13}$ is azetidinyl, piperidinyl, piperazinyl, morpholinyl, homopiperazinyl, or homomorpholinyl, and is substituted with 0-3 substituents selected from halo, alkyl, cycloalkyl, or alkoxyalkyl;

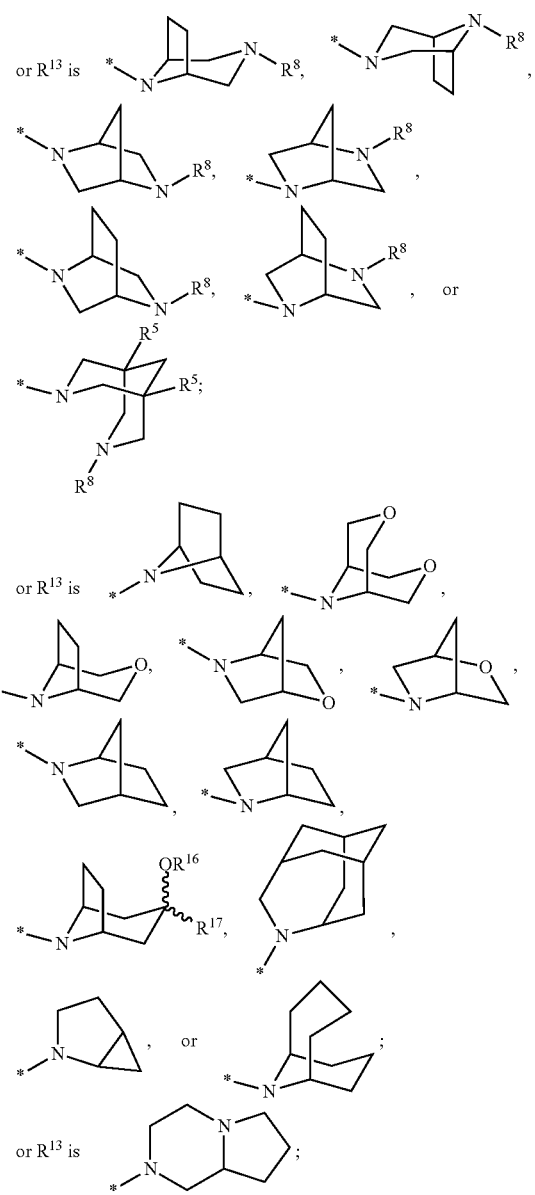

$R^{16}$ is hydrogen;
$R^{17}$ is alkyl; and
X is a bond;
or a pharmaceutically acceptable salt thereof.
3. A compound of claim 2 where:
$R^1$ is $CO_2R^5$ or $CONR^6R^7$;
$R^2$ is pyrazolyl, isoxazolyl, or imidazolyl, and is substituted with 1 substituent selected from cyclopropyl, cyclobutyl, tetrahydropyranyl, phenyl, pyrimidinyl, pyrazinyl, pyridinonyl, benzimidazolyl, N-methylpiperidinyl, pyridinyl or methylpyridinyl; and $R^2$ is substituted with 1 substituent selected from $CO_2R^5$, $CON(R^{12})_2$, and $COR^{13}$; and $R^2$ is substituted with 0-1 methyl substituent;
$R^3$ is methoxy;
$R^4$ is cyclohexyl;
$R^5$ is hydrogen or alkyl;
$R^6$ is isopropylSO$_2$, isobutylSO$_2$, cyclopropylSO$_2$, or Me$_2$NSO$_2$;

R⁷ is hydrogen;

R⁸ is hydrogen, methyl, ethyl, or (cyclopropyl)methyl;

R¹² is isopropyl or methoxyethyl;

R¹³ is difluoroazetidinyl, difluoropiperidinyl, methylpiperazinyl, cyclopentylpiperazinyl, trimethylpiperazinyl, morpholinyl, dimethylmorpholinyl, (methoxymethyl)molpholinyl, N-methylhomopiperazinyl, or homomorpholinyl;

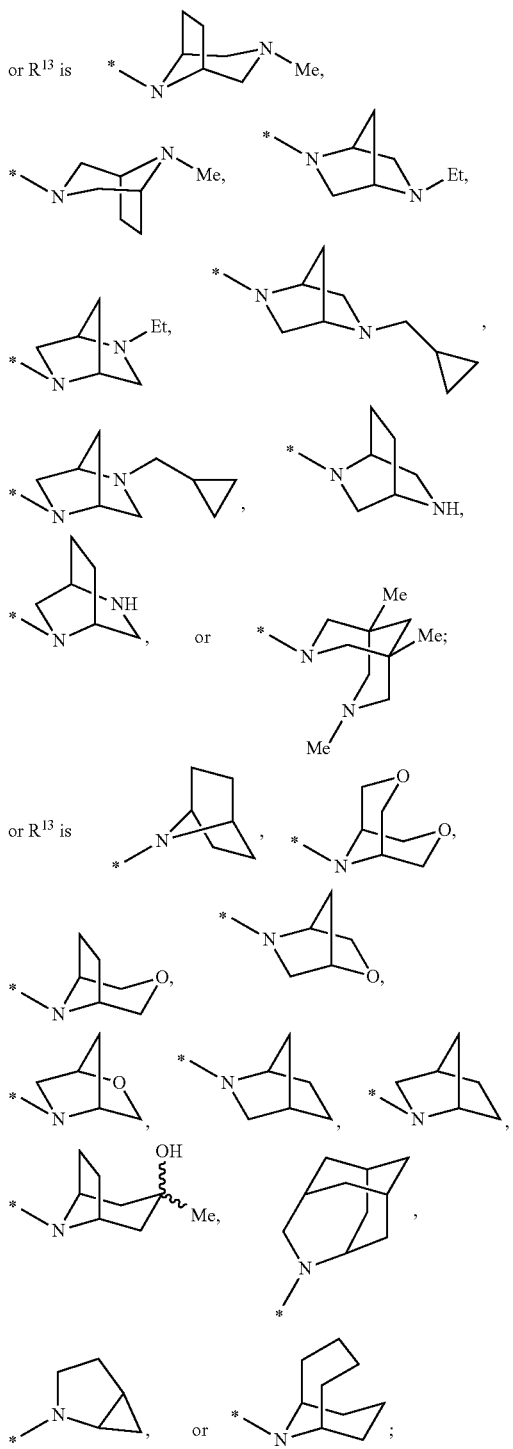

X a bond;

or a pharmaceutically acceptable salt thereof.

4. A compound of claim 1 where:

R¹ is CO₂R⁵ or CONR⁶R⁷;

R² is furanyl, pyrrolyl, thienyl, pyrazolyl, isoxazolyl, isothiazolyl, imidazolyl, oxazolyl, thiazolyl, oxadiazolyl, triazolyl, or tetrazolyl; and R² is substituted with 1 substituent selected from cycloalkyl, tetrahydrofuranyl, tetrahydropyranyl, piperidinyl substituted with 0-1 alkyl substituents, and pyridinyl substituted with 0-1 alkyl substituents; and R² is substituted with 1 substituent selected from CO₂R⁵, CON(R¹²)₂, and COR¹³; and R² is substituted with 0-1 substituents selected from oxo, amino, alkyl, and haloalkyl;

R³ is hydrogen, halo, alkyl, alkenyl, hydroxy, benzyloxy, or alkoxy;

R⁴ is cycloalkyl;

R⁵ is hydrogen or alkyl;

R⁶ is hydrogen, alkyl, alkylSO₂, cycloalkylSO₂, haloalkylSO₂, (R⁹)(R¹⁰)NSO₂, or (R¹¹)SO₂;

R⁷ is hydrogen or alkyl;

R⁸ is hydrogen, alkyl, cycloalkyl, (cycloalkyl)alkyl, alkylcarbonyl, cycloalkylcarbonyl, haloalkylcarbonyl, alkoxycarbonyl, alkylSO₂, cycloalkylSO₂, haloalkylSO₂, aminocarbonyl, (alkylamino)carbonyl, (dialkylamino)carbonyl, benzyl, benzyloxycarbonyl, or pyridinyl;

R⁹ is hydrogen or alkyl;

R¹⁰ is hydrogen or alkyl;

R¹¹ is azetidinyl, pyrrolidinyl, piperidinyl, piperazinyl, morpholinyl, thiomorpholinyl, homopiperidinyl, homopiperazinyl, or homomorpholinyl, and is substituted with 0-1 alkyl substituents;

R¹² is hydrogen, alkyl, alkoxyalkyl, aminoalkyl, (alkylamino)alkyl, (dialkylamino)alkyl, or (R¹¹)alkyl;

R¹³ is azetidinyl, pyrrolidinyl, piperidinyl, piperazinyl, morpholinyl, thiomorpholinyl, homopiperidinyl, homopiperazinyl, or homomorpholinyl, and is substituted with 0-3 substituents selected from alkyl, alkoxyalkyl, amino, alkylamino, dialkylamino, R¹¹, aminoalkyl, (alkylamino)alkyl, (dialkylamino)alkyl, (R¹¹)alkyl, or CO₂R⁵;

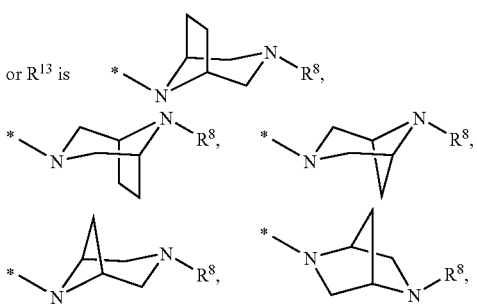

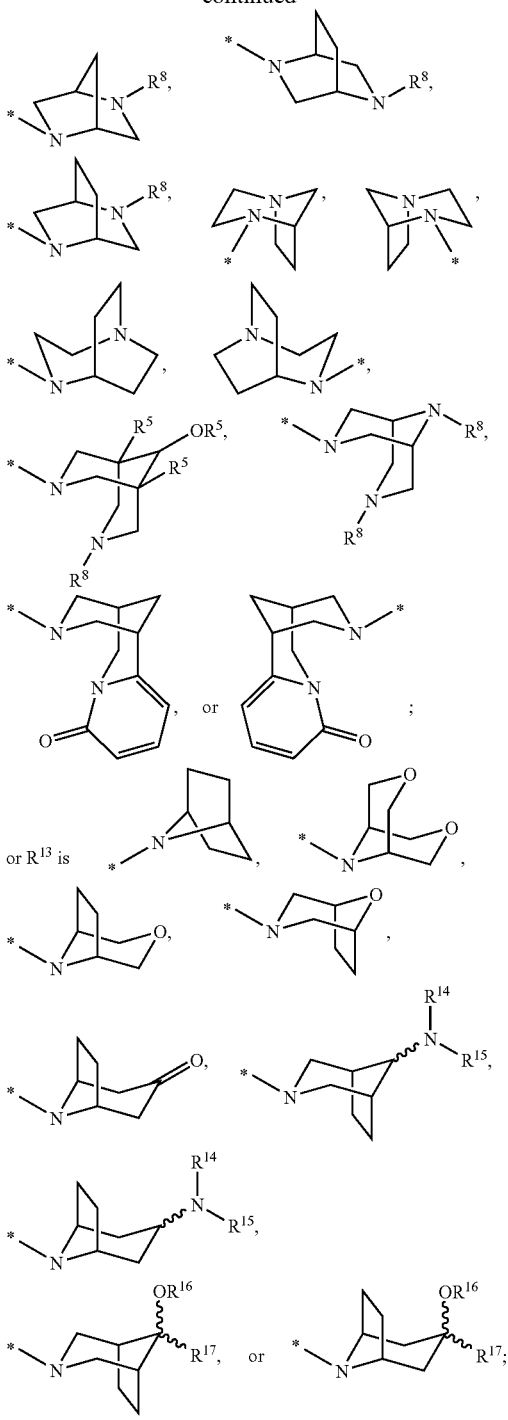

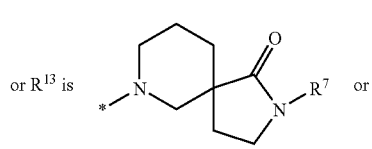

or R$^{13}$ is a [4.3.0] or [3.3.0] bicyclic diamine attached to the carbonyl through one nitrogen, and is substituted with 0-2 R$^8$ substituents;

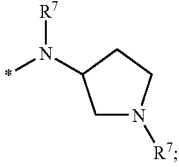

R$^{14}$ is hydrogen, alkyl, cycloalkyl, (cycloalkyl)alkyl, aminoalkyl, (alkylamino)alkyl, (dialkylamino)alkyl, or benzyl;

R$^{15}$ is hydrogen, alkyl, cycloalkyl, (cycloalkyl)alkyl, aminoalkyl, (alkylamino)alkyl, (dialkylamino)alkyl, or benzyl;

or NR$^{14}$R$^{15}$ taken together is azetidinyl, pyrrolidinyl, piperidinyl, piperazinyl, N-(alkyl)piperazinyl, morpholinyl, thiomorpholinyl, homopiperidinyl, or homomorpholinyl;

R$^{16}$ is hydrogen or alkyl;

R$^{17}$ is hydrogen, alkyl, or cycloalkyl; and

X is methylene, a bond, or absent;

or a pharmaceutically acceptable salt thereof.

5. A compound of claim 1 where R$^1$ is CONR$^6$R$^7$; R$^6$ is alkylSO$_2$, cycloalkylSO$_2$, haloalkylSO$_2$, (R$^9$)(R$^{10}$)NSO$_2$, or (R$^{11}$)SO$_2$; and R$^7$ is hydrogen.

6. A compound of claim 1 where R$^2$ is pyrazolyl substituted with 1 substituent selected from cyclopropyl, cyclobutyl, N-alkylpiperidin-4-yl, 3-alkylpyridin-4-yl, and tetrahydropyran-4-yl, 1 substituent selected from CON(R$^{12}$)$_2$ and COR$^{13}$, and 0-1 alkyl substituent.

7. A compound of claim 1 where R$^3$ is hydrogen.

8. A compound of claim 1 where R$^3$ is methoxy.

9. A compound of claim 1 where R$^4$ is cyclohexyl.

10. A compound of claim 1 where X is a bond.

11. A compound of claim 1 selected from the group consisting of 7H-indolo[2,1-a][2]benzazepine-10-carboxamide, 6-[1-cyclobutyl-4-[[(2R,6S)-2,6-dimethyl-4-morpholinyl]carbonyl]-1H-pyrazol-5-yl]-13-cyclohexyl-3-methoxy-N-[(1-methylethyl)sulfonyl];

7H-indolo[2,1-a][2]benzazepine-10-carboxamide, 6-[1-cyclobutyl-4-[[(2S)-2-(methoxymethyl)-4-morpholinyl]carbonyl]-1H-pyrazol-5-yl]-13-cyclohexyl-3-methoxy-N-[(1-methylethyl)sulfonyl]-;

7H-indolo[2,1-a][2]benzazepine-10-carboxamide, 6-[1-cyclobutyl-4-(8-oxa-3-azabicyclo[3.2.1]oct-3-ylcarbonyl)-1H-pyrazol-5-yl]-13-cyclohexyl-3-methoxy-N-[(1-methylethyl)sulfonyl]-;

7H-indolo[2,1-a][2]benzazepine-10-carboxamide, 6-[1-cyclobutyl-4-[[(2R,6S)-2,6-dimethyl-4-morpholinyl]carbonyl]-1H-pyrazol-5-yl]-13-cyclohexyl-N-[(dimethylamino)sulfonyl]-3-methoxy-;

7H-indolo[2,1-a][2]benzazepine-10-carboxamide, 6-[1-cyclobutyl-4-[[(2R,6S)-2,6-dimethyl-4-morpholinyl]carbonyl]-3-methyl-1H-pyrazol-5-yl]-13-cyclohexyl-N-[(dimethylamino)sulfonyl]-3-methoxy-;

7H-indolo[2,1-a][2]benzazepine-10-carboxamide, 6-[1-cyclobutyl-3-methyl-4-(4-morpholinylcarbonyl)-1H-pyrazol-5-yl]-13-cyclohexyl-3-methoxy-N-[(1-methylethyl)sulfonyl]-;

7H-indolo[2,1-a][2]benzazepine-10-carboxamide, 13-cyclohexyl-6-[1-cyclopropyl-3-(1-methylethyl)-4-[[(3R,5S)-3,4,5-trimethyl-1-piperazinyl]carbonyl]-1H-pyrazol-5-yl]-3-methoxy-N-[(1-methylethyl)sulfonyl]-;

7H-indolo[2,1-a][2]benzazepine-10-carboxamide, 6-[1-cyclobutyl-4-[[(2R)-2-(methoxymethyl)-4-morpholinyl]carbonyl]-1H-pyrazol-5-yl]-13-cyclohexyl-3-methoxy-N-[(1-methylethyl)sulfonyl]-;

7H-indolo[2,1-a][2]benzazepine-10-carboxamide, 6-[1-cyclobutyl-4-[[(1S,4S)-5-ethyl-2,5-diazabicyclo[2.2.1]hept-2-yl]carbonyl]-1H-pyrazol-5-yl]-13-cyclohexyl-N-[(dimethylamino)sulfonyl]-3-methoxy-;

7H-indolo[2,1-a][2]benzazepine-10-carboxamide, 6-[1-cyclobutyl-4-[[(1S,4S)-5-ethyl-2,5-diazabicyclo[2.2.1]hept-2-yl]carbonyl]-3-methyl-1H-pyrazol-5-yl]-13-cyclohexyl-N-[(dimethylamino)sulfonyl]-3-methoxy-;

7H-indolo[2,1-a][2]benzazepine-10-carboxamide, 6-[1-cyclobutyl-4-[[(1S,4S)-5-ethyl-2,5-diazabicyclo[2.2.1]hept-2-yl]carbonyl]-3-methyl-1H-pyrazol-5-yl]-13-cyclohexyl-3-methoxy-N-[(1-methylethyl)sulfonyl]-;

7H-indolo[2,1-a][2]benzazepine-10-carboxamide, 6-[1-cyclobutyl-4-[(3-methyl-3,8-diazabicyclo[3.2.1]oct-8-yl)carbonyl]-1H-pyrazol-5-yl]-13-cyclohexyl-N-[(dimethylamino)sulfonyl]-3-methoxy-;

7H-indolo[2,1-a][2]benzazepine-10-carboxamide, 6-[1-cyclobutyl-3-methyl-4-[(3-methyl-3,8-diazabicyclo[3.2.1]oct-8-yl)carbonyl]-1H-pyrazol-5-yl]-13-cyclohexyl-N-[(dimethylamino)sulfonyl]-3-methoxy-;

7H-indolo[2,1-a][2]benzazepine-10-carboxamide, 6-[1-cyclobutyl-3-methyl-4-[(3-methyl-3,8-diazabicyclo[3.2.1]oct-8-yl)carbonyl]-1H-pyrazol-5-yl]-13-cyclohexyl-3-methoxy-N-[(1-methylethyl)sulfonyl]-; and 7H-indolo[2,1-a][2]benzazepine-10-carboxamide, 6-[1-cyclobutyl-3-methyl-4-[[(1S,4S)-5-methyl-2,5-diazabicyclo[2.2.1]hept-2-yl]carbonyl]-1H-pyrazol-5-yl]-13-cyclohexyl-3-methoxy-N-[(1-methylethyl)sulfonyl]-;

or a pharmaceutically acceptable salt thereof.

12. A composition comprising a compound of claim 1, or a pharmaceutically acceptable salt thereof, and a pharmaceutically acceptable carrier.

13. A method of treating hepatitis C infection comprising administering a therapeutically effective amount of a compound of claim 1 to a patient.

* * * * *

UNITED STATES PATENT AND TRADEMARK OFFICE
CERTIFICATE OF CORRECTION

PATENT NO. : 8,133,884 B2  
APPLICATION NO. : 12/434748  
DATED : March 13, 2012  
INVENTOR(S) : Scott W. Martin et al.

It is certified that error appears in the above-identified patent and that said Letters Patent is hereby corrected as shown below:

In the Claims:

Claim 3:

Column 291, line 8, change "molpholinyl," to -- morpholinyl, --.

Column 292, line 8, change "X a" to -- X is a --.

Claim 11:

Column 294, line 37, change "of" to -- of: --.

Column 294, line 41, change "N-[(1-methylethyl)sulfonyl];" to -- N-[(1-methylethyl)sulfonyl]-; --.

Signed and Sealed this  
Fourth Day of March, 2014

Michelle K. Lee  
*Deputy Director of the United States Patent and Trademark Office*